(12) United States Patent
Kangawa et al.

(10) Patent No.: US 9,938,332 B2
(45) Date of Patent: Apr. 10, 2018

(54) MODIFIED GHRELIN PEPTIDES

(75) Inventors: Kenji Kangawa, Minoo (JP);
Masayasu Kojima, Toyonaka (JP);
Hiroshi Hosoda, Minoo (JP); Hisayuki Matsuo, Kobe (JP); Yoshiharu Minamitake, Ohra-gun (JP)

(73) Assignee: Kenji Kanagawa, Osaka (JP)

( * ) Notice: Subject to any disclaimer, the term of this patent is extended or adjusted under 35 U.S.C. 154(b) by 0 days.

(21) Appl. No.: 13/494,673

(22) Filed: Jun. 12, 2012

(65) Prior Publication Data

US 2013/0172251 A1 Jul. 4, 2013

Related U.S. Application Data

(62) Division of application No. 12/010,838, filed on Jan. 30, 2008, now Pat. No. 8,227,570, which is a division
(Continued)

(30) Foreign Application Priority Data

Jul. 23, 1999 (JP) .................................. 1999-210002
Nov. 29, 1999 (JP) .................................. 1999-338841
Apr. 26, 2000 (JP) .................................. 2000-126623

(51) Int. Cl.
*C07K 14/47* (2006.01)
*A61K 38/00* (2006.01)
(Continued)

(52) U.S. Cl.
CPC .......... *C07K 14/575* (2013.01); *A61K 9/0019* (2013.01); *C07K 14/461* (2013.01);
(Continued)

(58) Field of Classification Search
CPC .. A61K 9/0019; C07K 14/575; C07K 14/461; C07K 14/463; C07K 14/465; C07K 14/47; C07K 14/4702
See application file for complete search history.

(56) References Cited

U.S. PATENT DOCUMENTS 5,194,596 A  3/1993  Tischer et al.
5,350,836 A  9/1994  Kopchick et al.
(Continued)

FOREIGN PATENT DOCUMENTS

EP  1 197 496  11/2007
WO  98/42840  10/1998
(Continued)

OTHER PUBLICATIONS

UniProt Entry GHRL_Human, Mar. 2, 2010.
(Continued)

*Primary Examiner* — Cherie M Stanfield
(74) *Attorney, Agent, or Firm* — Wenderoth, Lind & Ponack, L.L.P.

(57) ABSTRACT

The present invention provides a peptide-type compound which induces secretion of growth hormone and which has the activity of increasing the intracellular calcium ion concentration, wherein at least one amino acid is replaced by a modified amino acid and/or a non-amino acid compound, or a pharmaceutically acceptable salt thereof.

57 Claims, 9 Drawing Sheets

Related U.S. Application Data of application No. 09/959,577, filed as application No. PCT/JP00/04907 on Jul. 24, 2000, now Pat. No. 7,385,026.

(51) Int. Cl.
  *A61K 48/00* (2006.01)
  *C07K 14/575* (2006.01)
  *A61K 9/00* (2006.01)
  *C07K 14/46* (2006.01)
  *C07K 14/465* (2006.01)
  *A61K 47/42* (2017.01)

(52) U.S. Cl.
  CPC .......... *C07K 14/463* (2013.01); *C07K 14/465* (2013.01); *C07K 14/47* (2013.01); *C07K 14/4702* (2013.01); *A01K 2217/05* (2013.01); *A61K 38/00* (2013.01); *A61K 47/42* (2013.01); *A61K 48/00* (2013.01)

(56) References Cited

U.S. PATENT DOCUMENTS

| | | | |
|---|---|---|---|
| 5,854,389 A | 12/1998 | Kent et al. | |
| 6,420,521 B1 * | 7/2002 | Sheppard | C07K 7/06 435/198 |
| 2003/0176640 A1 * | 9/2003 | Sheppard | C07K 7/06 530/326 |

FOREIGN PATENT DOCUMENTS

| | | |
|---|---|---|
| WO | 9842840 | 10/1998 |
| WO | 99/63088 | 12/1999 |

OTHER PUBLICATIONS

Gualillo et al., Mol Cell. Endocrin, Aug. 15, 2006: 256(1-2):1-8, Epub Jul. 7, 2006, Review.
Bowie et al., 1990, Science 247:1306-1310.
Wells, 1990, Biochemistry 29:8509-8517.
Benjamin et al., 1998, Development 125:1591-1598.
Vukicevic et al., 1996, PNAS USA 93:9021-9026.
Massague, 1987, Cell 49:437-8.
Pilbeam et al., 1993, Bone 14: 717-720.
Skolnick et al. 2000, Trends in Biotech 18:34-39.
Bork 2000, Genome Research 10:398-400.
Doerks et al., 1998, Trends in Genetics 14:248-250.
Smith et al., 1997, Nature Biotechnology, 15:1222-1223.
Brenner, 1999, Trends in Genetics 15:132-133.
Bork et al., 1996, Trends in Genetics 12:425-427.
Bluet-Pajot, M.-T. et al. "Hypothalamic and hypophyseal regulation of growth hormone secretion", Cellular and Molecular Neurobiology, 1998, pp. 101-104, 109.
Kojima, M., et al., "Ghrelin is a growth-hormone-releasing acylated peptide from stomach," Nature, Dec. 1999, vol. 402 (6762), pp. 656-660.
Hosoda, H., et al., "Purficiation and characterization of rat des -Gin14-Ghrelin, a second endogenous ligand for the growth hormone secretagogue receptor," J. Biol., Chem. May 2000, 275, 29, pp. 21995-22000.
Romano Deghenghi et al., "GH-Releasing Activity of Hexarelin, A New Growth Hormone Releasing Peptide, in Infant and Adult Rats", Life Sciences, vol. 54, No. 18, pp. 1321-1328, 1994.
Vito De Gennaro Colonna et al., "Cardiac Ischemia and Impairment of Vascular Endothelium Function in Hearts from Growth Hormone-Deficient Rats: Protection by Hexarelin", European Journal of Pharmacology, vol. 334, p. 201-207, 1997.
Mitchell S. Akman et al., "Mechanisms of Action of a Second Generation Growth Hormone-Releasing Peptide (Ala-His-D-βNal-Ala-Trp-D-Phe-Lys-NH2) in Rat Anterior Pituitary Cells", Endocrinology, vol. 132, No. 3, pp. 1286-1291, 1993.
Andrew D. Howard et al., "A Receptor in Pituitary and Hypothalamus That Functions in Growth Hormone Release", Science, vol. 273, pp. 974-977, Aug. 16, 1996.
Mickle JE et al., "Genotype-phenogype relationships in cystic fibrosis", Med Clin North Am. May 2000;84(3):597-607.
Voet et al., Biochemistry, 1990, John Wiley & Sons, Inc., pp. 126-128 and 228-234.
Yan et al., Two-amino acid molecular switch in an epithelial morphogen that regulates binding to two distinct receptors. Science 290:523-527, 2000.
Bulet-Pajot et al., Cell and Mol Neurobio Feb. 18, 1998(1): 101-123.
UniProt Q9QYH7 (GHRL_RAT), May 1, 2000.

\* cited by examiner a

| | | | |
|---|---|---|---|
| Human | 1 | MPSPGTVCSLLLLGMLWLDLAMAGSSFLSP | 30 |
| Rat | 1 | MVSSATICSLLLLSMLWMDMAMAGSSFLSP | 30 |
| Human | 31 | EHQRVQQRKESKKPPAKLQPRALAGWLRPE | 60 |
| Rat | 31 | EHQKAQQRKESKKPPAKLQPRALEGWLHPE | 60 |
| Human | 61 | DGGQAEGAEDELEVRFNAPFDVGIKLSGVQ | 90 |
| Rat | 61 | DRGQAEEAEEELEIRFNAPFDVGIKLSGAQ | 90 |
| Human | 91 | YQQHSQALGKFLQDILWEEAKEAPADK | 117 |
| Rat | 91 | YQQHGRALGKFLQDILWEEVKEAPANK | 117 | b

MODIFIED GHRELIN PEPTIDES

This application is a divisional of Ser. No. 12/010,838, filed Jan. 30, 2008, now U.S. Pat. No. 8,227,570 now allowed, which is a divisional of Ser. No. 09/959,577, filed Oct. 30, 2001, now U.S. Pat. No. 7,385,026, which is a 371 U.S. national stage of International Application No. PCT/JP00/04907 filed Jul. 24, 2000, herein incorporated by reference in their entirety.

TECHNICAL FIELD

The present invention relates to a novel peptide having the action of increasing the intracellular calcium concentration or the activity of inducing secretion of growth hormone, wherein an amino acid in the peptide is modified. Further, the present invention relates to a method for obtaining said novel peptide and a method for producing the same, a gene coding said peptide or a precursor of said peptide, and a method for producing said peptide or a precursor of said peptide by use of said gene. Further, the present invention relates to a structural analogue of the novel modified peptide disclosed in the present invention, which binds to a receptor for a growth hormone secretion-inducing compound thereby exhibiting the action of increasing the intracellular calcium concentration or the activity of inducing secretion of growth hormone, as well as a method for producing the same. Further, the present invention relates to a pharmaceutical composition or a growth promoter for animals comprising said peptide or said peptide analogue as an active ingredient, as well as an antibody to said peptide or a method of utilizing the same.

BACKGROUND ART

Growth hormone (abbreviated hereinafter to GH) is a proteinous hormone synthesized in adenohypophysis and indirectly promotes growth of bone and differentiation of adipocytes and chondrocytes, and its secretion is promoted by growth hormone-releasing hormone (GHRH) and inhibited by somatostatin [J. Kendrew, et al., Eds., The Encyclopedia of Molecular Biology (Blackwell Science Ltd., London, 1994), p. 462]. GH has not only a growth-promoting action but also actions such as promotion of protein synthesis in various tissues, stimulation of transfer of depot fats and elevation of glycogen content in muscles, and a reduction in GH secretion induces dwarfism, while excessive secretion thereof induces gigantism or acromegaly [Iwanami's Dictionary of Biology, fourth edition, edited by Ryuichi Yasugi, et al. (Iwanami Syoten, Tokyo, 1997), p. 757].

Since human GH has been produced by genetic engineering, GH is used not only for treatment of dwarfism [J. O. Jorgensen, Endocr. Rev. 12, 189 (1991)], but also for treatment of other diseases, and its various effects were found [J. O. Jorgensen, et al., Horm. Res. 42, 235 (1994)]. For example, such effects include activation of reconstitution of osteoblasts and bone in the normal [K. Brixen, et al., Miner. Res. 5, 609 (1990)], enhancement of muscular strength and muscular amount in GH-deficient adults [R. C. Cuneo, et al., J. Appl. Physiol. 70, 688 (1991)], improvement of motility in GH-deficient adults [R. C. Cuneo, et al., J. Appl. Physiol. 70, 695 (1991)], remedy of heavy burns in children [D. N. Herndon, et al., Ann. Surg. 212, 424 (1990)], its combined use with gonadotropins in induction of ovulation [R. Homburg, et al., Clin. Endocrinol. (Oxf). 32, 781 (1990)], prevention of metabolic disorder by administration of prednisone [F. F. Horber and M. W. Haymond, J. Clin. Invest. 86, 265 (1990)], promotion of T cell "education" in heavy immune disorder [W. J. Murphy, et al., Proc. Natl. Acad. Sci. U.S. A. 89, 4481 (1992)], and the effect of inhibiting reduction of the body weight of the aged and the effect of enlarging adipose fat tissues and preventing dermal atrophy [D. Rudman, et al, N. Engl. J. Med. 323, 1 (1990)].

Administration of recombinant GH is effective for promotion of growth in children and normalization of defects in metabolism and functions accompanying GH-deficiency in adults, but there are problems that GH has dose-restricting side effects, cannot be orally administered and is expensive [B. A. Lefker, et al., in Growth Hormone Secretagogues in Clinical Practice, B. B. Bercu and R. F. Walker, Eds. (Marcel Dekker, Inc., New York, 1998), pp. 107-108]. Many adult patients suffer from side effects such as arthralgia and a carpal tunnel syndrome considered to be attributable to pool of excess sodium and humor, so that GH administration cannot be continued [E. Corpas, et al., Endocr. Rev. 14, 20 (1993)]. These side effects are correlated with a non-physiological pattern of hormone secretion by GH administration, and in GH administration, the pulsatility of normal GH secretion cannot be imitated [B. A. Lefker, et al., in Growth Hormone Secretagogues in Clinical Practoce, B. B. Bercu and R. F. Walker, Eds. (Marcel Dekker, Inc., New York, 1998), pp. 107-108].

The pulsatility of in vivo GH secretion is established basically by interaction between two regulating factors derived from hypothalamus; that is, GHRH and somatostatin act on pituitary gland to regulate GH secretion [G. S. Tannenbaum and N. Ling, Endocrinology 115, 1952 (1984), R. G. Clark and I. C. Robinson, Endocrinology 122, 2675 (1988)]. The normal pattern of GH secretion differs during the day and night, and during the night, a larger amount of GH is released more frequently. The amplitude of GH release pulse is further regulated by feedback by various steroid hormones, neurotransmitters, GH and insulin-like growth factor, by nutritional status, sleep and motility [J. S. Strobl and M. J. Thomas, Pharmacol. Rev. 46, 1 (1994)].

To overcome the side effects caused by GH administration, a large number of compounds having a GH secretion-inducing action were synthesized, and as growth hormone secretagogue (GHS), their structural activity correlation, their pharmacology and clinical applications were extensively studied. First, peptides such as GHRP-6 (Growth Hormone-Releasing hexapeptide) were synthesized and developed as therapeutic agents for treating disorders attributable to deficiency or reduction in GH [C. Y. Bowers, et al., Endocrinology 114, 1537-1545 (1984)]. However, because these peptide compounds could demonstrate their effect through intravenous injection only, non-peptide compounds having low-molecular weight capable of oral administration were developed [R. G. Smith, et al., Science 260, 1640-1643 (1993)] and some of them have advanced to a phase II clinical test [A. A. Patchett, et al., Proc. Natl. Acad. Sci. U.S.A. 92, 7001-7005 (1995)].

A series of information transfer from signal reception of receptor to functional expression is called signal transduction, and the signal transduction system coupled with G protein proceeds in the following mechanism [Iwanami's Dictionary of Biology, fourth edition, ed. by Ryuichi Yasugi, et al., pp. 555-556 (Iwanami Syoten, Tokyo, 1997)]. This G protein coupled system has a receptor with seven transmembrane domains and is divided into a cAMP system for producing cAMP as a second messenger and inositol-1,4,5-triphosphoric acid (IP3) and diacylglycerol (DG) inositol phospholipid information transduction system. The cAMP activates cAMP-dependent kinase (A kinase), to cause phosphorylation of serine and threonine residues in functional protein to modify its activity. On the other hand, IP3 binds to IP3 receptor on endoplasmic reticulum to promote release of calcium ions, while DG activates C kinase to promote the action of hormones etc.

The mechanism of increasing the intracellular calcium ion concentration in the signal transduction system with IP3 or DG as second messenger [J. Kendrew, et al., Eds., The Encyclopedia of Molecular Biology (Blackwell Science Ltd., London, 1994), p. 136-137] is as follows: When a ligand binds to the receptor, phospholipase C is activated via G protein, to covert PIP2 into IP3. By IP3, calcium ions pooled in endoplasmic reticulum (ER) as intracellular granule are released into cytoplasm, thus increasing calcium ion levels in the cytoplasm. If IP3 or calcium ions are present in the cytoplasm, the calcium is incorporated again into the endoplasmic reticulum, thus lowering calcium ion levels in the cytoplasm. That is, the binding of the ligand to the receptor causes a transient increase in calcium ion levels in the cytoplasm.

Since GHS acts synergistically on the GH secretion and increase of intracellular cAMP levels by GHRH [K. Cheng, et al., Endocrinology 124, 2791-2798 (1989)] and the binding of GHRH to the receptor induces production of cAMP as second messenger while GHS induces an increase in the intracellular calcium ion concentration, it was suggested that the working mechanism of GHS is different from that of GHRH [J. Herrington and B. Hille, Endocrinology 135, 1100-1108 (1994).], and GHS was supposed to bind to a receptor different than GHRH receptor. Actually, a gene for a receptor to which GHS is bound was cloned, and from the result of Northern analysis, it was found that GHS receptor (GHS-R) is expressed in hypothalamus and brain pituitary gland, and that there is 90% or more homology between the amino acid sequences of porcine- and human-derived GHS receptors [A. D. Howard, et al., Science 273, 974-977 (1996)]. However, an endogenous ligand that binds to GHS-R has not been isolated, and this GHS-R was an orphan receptor whose ligand was not evident.

In some cases, fatty acids such as myristic acid, geranic acid, palmitoyl acid or farnesyl acid are bound to the amino-terminal of a certain protein or to side chains of its amino acid residues, and the role of these fatty acids is anchoring such fatty acid-modified protein to cell membrane [J. Kendrew, et al., Eds., The Encyclopedia of Molecular Biology (Blackwell Science Ltd., London, 1994), p. 616]. In such fatty acid-modified protein, the fatty acid binds to a cysteine residue via S-acyl linkage, and neither an amino acid having fatty acid bound to serine residue via O-acyl linkage, such as the endogenous GHS disclosed in the present invention, nor protein or peptide containing such fatty acid-modified amino acid, is known. Neither is it known for which the peptide containing such fatty acid-modified amino acid functions as a ligand for any receptor.

DISCLOSURE OF INVENTION

Before the present invention is described in detail, terms are defined as follows:

The term "peptide" refers to a compound comprising a plurality of amino acids linked therein via peptide linkages. Here, the amino acid (also called an amino acid residue) includes naturally occurring amino acids represented by formula: $NH_2$—$CH(R')$—$COOH$, wherein R' is a naturally occurring substituent group, as well as its D, L-optical isomers etc.

There is also a peptide, wherein a certain naturally occurring amino acid is replaced by a modified amino acid (also called a modified amino acid residue). The modified amino acid includes the amino acids of the above formula wherein the substituent group R' is further modified, its D, L-optical isomers thereof, and non-natural amino acids wherein e.g. various substituent groups are bound to the substituent group R' of the above formula via or not via an ester, ether, thioester, thioether, amide, carbamide or thiocarbamide linkage. The modified amino acid also includes non-natural amino acids whose amino groups are replaced by lower alkyl groups.

The terms "peptide analogue" refer to a compound wherein at least one amino acid in a peptide is replaced by a non-amino acid compound, and thus at least one linkage of said substituent compound to the peptide analogue is not a peptide linkage.

Further, those compounds derived from these peptides and peptide analogues by modifying the amino-terminal and/or carboxyl-terminal thereof are referred to as derivatives. And the peptides, peptide analogues and derivatives thereof are referred collectively to as "peptide-type compound".

In the amino acid sequence set forth in SEQ ID NO: 2, an amino acid sequence of amino acids 1 to 4 refers to Gly Ser Ser Phe, an amino acid sequence of amino acids 1 to 5 refers to Gly Ser Ser Phe Leu, an amino acid sequence of amino acids 1 to 6 refers to Gly Ser Ser Phe Leu Ser, an amino acid sequence of amino acids 1 to 7 refers to Gly Ser Ser Phe Leu Ser Pro, an amino acid sequence of amino acids 1 to 8 refers to Gly Ser Ser Phe Leu Ser Pro Glu, an amino acid sequence of amino acids 1 to 9 refers to Gly Ser Ser Phe Leu Ser Pro Glu His, and an amino acid sequence of amino acids 1 to 10 refers to Gly Ser Ser Phe Leu Ser Pro Glu His Gln.

The discovery of an endogenous ligand (endogenous GHS) which binds to GHS receptor to exhibit an activity for increasing the intracellular calcium ion concentration or for inducing GH secretion has been desired together with a method of utilizing the same. Further, a compound has been desired, which is a structural analogue of said endogenous GHS and has an activity for increasing the intracellular calcium ion concentration or for inducing GH secretion. Further, a pharmaceutical composition or a composition for promoting animal growth has been desired, which comprises said endogenous GHS or its structural analogous inducing pulsatile GH secretion thereby eliminating side effects by GH administration, as well as a therapeutic application using said composition.

The present inventors focused their attention on the fact that binding of the ligand to GHS receptor (GHS-R) causes a transient increase in the intracellular calcium ion concentration with inositol phospholipid as second messenger, and they screened extracts of various organs and tissues by using the activity of increasing the intracellular calcium ion concentration (Ca-releasing activity) as an indicator in CHO cells (CHO-GHSR62) expressing GHS-R. As a result, the inventors found that stomach extracts of rat has a strong Ca-releasing activity, and successfully purified a substance having a strong Ca-releasing activity from the above extracts by various kinds of chromatography, and found that said substance is a novel peptide modified with fatty acid, having a molecular weight of about 3,000. Further, they confirmed that said novel peptide promotes specific secretion of GH from cells of anterior pituitary, and found that said novel peptide is an endogenous ligand for GHS-R, that is, an endogenous GH secretagogue (endogenous GHS). That is, the first aspect of the present invention is directed to an endogenous GH secretion-inducing peptide having the activity of increasing the intracellular calcium ion concentration or the activity of inducing GH secretion, wherein a certain constituent amino acid residue is modified with fatty acid, as well as a method for preparing said peptide.

The present inventors precisely analyzed the structure of the endogenous GH secretion-inducing peptide, and found that said peptide is a peptide consisting of the amino acid sequence set forth in SEQ ID NO: 2, wherein the side-chain hydroxyl group of 3rd serine from the Amino-terminal has been acylated with fatty acid. Further, a human-derived GH secretion-inducing peptide was also purified from human stomach extract having a strong Ca-releasing activity similar to that of rat stomach extract and analyzed for its structure in the same manner as for rat-derived GH secretion-inducing peptide, and as a result the inventors found that the human-derived endogenous GH secretion-inducing peptide consists of the amino acid sequence set forth in SEQ ID NO: 3, wherein the side-chain hydroxyl group of 3rd serine from the amino-terminal has been acylated with fatty acid. Comparison between the amino acid sequences of the rat- and human-derived endogenous GH secretion-inducing peptides revealed homology as high as 89% as a whole.

Specifically, the rat- and human-derived peptides are identical in an amino acid sequence of amino acids 1 to 10 from amino-terminal and in an amino acid sequence of amino acids 13 to 28 from amino-terminal, but are different in amino acids 11 and 12 which are lysine and alanine in the rat peptide, which are replaced by arginine and valine in the human peptide, respectively. The rat-derived endogenous GH secretion-inducing peptide was cleaved with various proteases and its purified peptide fragments were measured for Ca-releasing activity, and as a result, a peptide consisting of amino acids 1 to 7 from amino-terminal was the minimum peptide having the Ca-releasing activity.

By measurement of the Ca-releasing activity of chemically synthesized peptides, the inventors found that the core sequence essential for eliciting the Ca-releasing activity is a sequence consisting of 4 amino acids set forth in SEQ ID NO: 8. Further, the sequence consisting of 10 amino acids set forth in SEQ ID NO: 9 was conserved in non-rat endogenous GH secretion-inducing peptides (each consisting of 28 amino acids) separated from human, porcine and bovine, as well as in endogenous GH secretion-inducing peptides (each consisting of 27 amino acids) wherein one glutamine was deleted from the above peptides.

That is, the second aspect of the present invention is directed to a fatty acid-modified peptide comprising the amino acid sequence set forth in SEQ ID NO: 8, preferably the amino acid sequence set forth in SEQ ID NO: 1 and more preferably the amino acid sequence set forth in SEQ ID NO: 9 as the core sequence essential for eliciting the Ca-releasing activity.

Endogenous GH secretion-inducing peptides were also isolated from chicken, eel and frog, and these peptides were found to have a core sequence consisting of 4 amino acids set forth in SEQ ID NO: 8.

In addition, an endogenous GH secretion-inducing peptide very similar to the rat endogenous GH secretion-inducing peptide was also isolated from frog.

Further, endogenous GH secretion-inducing peptides were also isolated from *Xenopus laevis*, rainbow trout (*Oncorhynchus mykiss*), and dog. From rainbow trout, ghrelin-23 consisting of 23 amino acids and ghrelin-20 consisting of 20 amino acids were isolated respectively.

The carboxyl-terminal amino acid of eel ghrelin, rainbow trout ghrelin-23 and ghrelin-20 was amidated.

Because an amino acid residue at the 3rd position from the amino-terminal in the endogenous GH secretion-inducing peptide from *Xenopus laevis* is threonine, the present invention also relates to a fatty acid-modified peptide, which contains, as the core sequence essential for exhibiting the Ca-releasing activity, a peptide wherein the amino acid residue 3rd serine was replaced by threonine in the amino acid sequence set forth in SEQ ID NO: 8, preferably the amino acid sequence set forth in SEQ ID NO: 1 and more preferably the amino acid sequence set forth in SEQ ID NO: 9.

The endogenous fatty acid-modified peptide having GH secretion-inducing activity or the fatty acid-modified peptide consisting of said core sequence, disclosed in the present invention, also provides a guideline for designing a compound having Ca-releasing activity.

That is, in the third aspect of the present invention, a novel compound having Ca-releasing activity is obtained by synthesizing a structural analogue of said fatty acid-modified peptide by confirming the Ca-releasing activity of the resulting structural analogue. Accordingly, the present invention also encompasses a peptide or peptide analogue having the activity of increasing the intracellular calcium ion concentration, wherein a certain constituent amino acid is replaced by a modified amino acid or non-amino acid compound.

A cDNA coding the endogenous GH secretion-inducing peptide was obtained in a usual manner. Each of rat and human cDNAs consists of 117 amino acids as shown in the amino acid sequences in SEQ ID NOS: 4 and 5, and the amino acid sequences of rat and human endogenous GH secretion-inducing peptides were identical in a sequence of 28 amino acids from the 24th to 51st positions from the amino-terminal, respectively. That is, it was revealed that the endogenous GH secretion-inducing peptide is synthesized as a precursor peptide consisting of 117 amino acids, then a signal peptide consisting of amino-terminal 23 amino acids is cleaved off and further carboxyl-terminal 56 amino acids are cleaved off, whereby the fatty acid-modified peptide having GH secretion-inducing activity is formed. In addition, a cDNA coding a precursor of the endogenous GH secretion-inducing peptide consisting of 28 amino acids was also found in porcine.

Further, a cDNA coding a precursor for the endogenous GH secretion-inducing peptide consisting of 27 amino acids was found in porcine.

Further, a partial cDNA coding a precursor for the endogenous GH secretion-inducing peptide consisting of 27 amino acids was found in bovine.

Further, a cDNA coding a precursor of the endogenous GH secretion-inducing peptide was also found in eel, *Xenopus laevis* and rainbow trout. From rainbow trout, a cDNA coding a precursor of ghrelin-23 consisting of 23 amino acids and a cDNA coding a precursor of ghrelin-20 of 20 amino acids were isolated respectively.

Accordingly, the fourth aspect of the present invention lies in a cDNA coding a precursor of the endogenous GH secretion-inducing peptide, as well as a method for producing a peptide as a starting material of the fatty acid-modified peptide or peptide analogue having Ca-releasing activity, which comprises using said cDNA.

In purification of the endogenous GH secretion-inducing peptide (ghrelin) composed of 28 amino acids from rat stomach extract, a peptide recovered as a minor fraction was analyzed, and as a result a peptide consisting of 27 amino acids (ghrelin-27), which is a peptide of ghrelin from which glutamine 13 or 14 had been deleted, was found. Ghrelin-27 has completely the same Ca-releasing activity and GH secretion-inducing activity as those of ghrelin consisting of 28 amino acids, and ghrelin-27 is an endogenous GH secretion-inducing peptide, and thus ghrelin-27 also falls under the scope of the present invention.

The nucleotide sequence coding glutamine residues 13 and 14 in ghrelin is gca gca, which is a terminal exon sequence to be subjected to mRNA splicing, thus suggesting the possibility of formation of a cDNA from which one of two codons for glutamine residues was deleted by different splicing. Actually, a cDNA coding a precursor peptide of ghrelin-27 consisting of 27 amino acids was found in screening of rat and human cDNA libraries.

That is, it was revealed that rat and human ghrelin-27 peptide is synthesized as a precursor peptide consisting of 116 amino acids set forth in SEQ ID NO: 12 or 13, then a signal peptide consisting of amino-terminal 23 amino acids is cleaved off and further carboxyl-terminal 56 amino acids are cleaved off, whereby a fatty acid-modified peptide consisting of 27 amino acids having GH secretion-inducing activity (ghrelin-27) is formed.

Further, a cDNA coding a precursor of ghrelin-27 peptide was found in porcine and bovine, and the presence of ghrelin-27 and its precursor was confirmed in these animals.

That is, the present invention also encompasses ghrelin-27 peptide consisting of an amino acid sequence set forth in SEQ ID NOS: 10, 11, 17 and 22, a ghrelin-27 precursor peptide having an amino acid sequence set forth in SEQ ID NOS: 12, 13, 19 and 23, and a cDNA coding said precursor peptide which comprises a nucleotide sequence set forth in SEQ ID NOS: 14, 15, 21 and 24.

The fatty acid-modified peptide having Ca-releasing activity and the peptide-type compound such as peptide analogue having Ca-releasing activity as disclosed in the present invention also provide a pharmaceutical composition for treating diseases attributable to defect or decrease in GH. Said pharmaceutical composition can be used to treat any diseases against which the GH administration is effective, and various side effects caused by GH administration can be overcome. Further, said pharmaceutical composition can also be used as an animal drug such as a growth-promoting agent for animals.

Because the peptide-type compound of the present invention has an appetite-promoting action by administration into ventricle and intravenous administration, and thus it can be used as an appetite promoting agent for treating loss of appetite or sitophobia. In addition, the present peptide-type compound has a stomach motility- and gastric acid secretion-promoting action, and thus it can also be used as an agent for treating stomach functional diseases such as non-ulcer indigestion, sudden light stomach atony, functional indigestion, and reflux esophagitis. Further, the present peptide-type compound exhibits a cell growth-promoting action in bone marrow, duodenum and jejunum by intravenous administration, and thus it can be used as an agent for protecting mucous membrane on intestinal tract, an agent for preventing damage to mucous membrane on small intestine during intravenous nutrition and an agent for treating osteoporosis.

The present invention also encompasses an antibody prepared by using the fatty acid-modified peptide having Ca-releasing activity disclosed in the present invention as an antigen, a method for measuring the endogenous GH secretion-inducing peptide by use of said antibody, and a measurement kit comprising said antibody.

Further, the present invention encompasses an assay method for separating and quantifying ghrelin modified with a fatty acid and ghrelin from which the fatty acid was eliminated, which comprises using two antibodies built up to N- and carboxyl-terminal peptides from ghrelin, the former antibody capable of recognizing fatty acid-modified 3rd serine, as well as an assay kit comprising a combination of the antibodies against N- and carboxyl-terminal peptides from ghrelin.

That is, the present invention provides a novel peptide hormone having a novel modified amino acid i.e. acylated serine, and also provides a guideline for novel design of a compound having Ca-releasing activity with the structure of said peptide as a fundamental skeleton.

Further, the elucidation of the mechanism of induction of GH secretion by the fatty acid-modified peptide disclosed in the present invention or by GH releasing hormone and somatostatin is suggested to be extendable not only to the mechanism of induction of GH secretion but also to the mechanism of regulating secretion of other hormones. The present invention discloses various functions of the fatty acid-modified peptide as a regulatory factor in the circulatory system and the metabolic system, and the effect of the present invention extends to the elucidation of a new biological regulatory mechanism.

Specifically, the present invention relates to:

(1) A peptide-type compound, wherein in a peptide having the activity of increasing the intracellular calcium ion concentration, at least one amino acid is replaced by a modified amino acid and/or a non-amino acid compound, or a pharmaceutically acceptable salt thereof;

(2) The peptide-type compound according to item (1), which comprises (a) an amino acid sequence set forth in SEQ ID NO: 2 or (b) an amino acid sequence having any one of amino acid sequences selected from the group consisting of (1) amino acid sequence of amino acids 1 to 4,
(2) amino acid sequence of amino acids 1 to 5,
(3) amino acid sequence of amino acids 1 to 6,
(4) amino acid sequence of amino acids 1 to 7,
(5) amino acid sequence of amino acids 1 to 8,
(6) amino acid sequence of amino acids 1 to 9, and
(7) amino acid sequence of amino acids 1 to 10 from the amino-terminal in the sequence (a) and at least one amino acid deleted, replaced and/or added in a part outside said amino acid sequences, or a pharmaceutically acceptable salt thereof;

(3) The peptide-type compound according to item (2) above, which comprises one amino acid sequence selected from the group consisting of amino acid sequences set forth in SEQ ID NOS: 3, 4, 5, 8, 9, 10, 11, 12, 13, 16, 17, 18, 19, 22 and 23, or a pharmaceutically acceptable salt thereof;

(4) The peptide-type compound according to item (2) above, which comprises one amino acid sequence selected from the group consisting of amino acid sequences set forth in SEQ ID NOS: 25, 26, 29, 30, 31, 32, 34 and 35, or a pharmaceutically acceptable salt thereof;

(5) A peptide-type compound, wherein in a peptide having the activity of increasing the intracellular calcium ion concentration and the activity of inducing secretion of growth hormone, (a) constitutional amino acids are modified or not modified and (b) at least one amino acid is replaced or not replaced by a non-amino acid compound, or a pharmaceutically acceptable salt thereof;

(6) The peptide-type compound according to item (1) or (5) which comprises amino acid sequences set forth in SEQ ID NOS: 27, 28 and 33, or a pharmaceutically acceptable salt thereof;

(7) The peptide-type compound according to item (5), which comprises (a) an amino acid sequence set forth in SEQ ID NO: 2 or (b) an amino acid sequence having any one of amino acid sequences selected from the group consisting of
(1) amino acid sequence of amino acids 1 to 4,
(2) amino acid sequence of amino acids 1 to 5,
(3) amino acid sequence of amino acids 1 to 6,
(4) amino acid sequence of amino acids 1 to 7,
(5) amino acid sequence of amino acids 1 to 8,
(6) amino acid sequence of amino acids 1 to 9, and
(7) amino acid sequence of amino acids 1 to 10
from the amino-terminal in the sequence (a) and at least one amino acid deleted, replaced and/or added in a part outside said amino acid sequences, or a pharmaceutically acceptable salt thereof;

(8) The peptide-type compound according to item (7) above, which comprises one amino acid sequence selected from the group consisting of amino acid sequences set forth in SEQ ID NOS: 3, 4, 5, 8, 9, 10, 11, 12, 13, 16, 17, 18, 19, 22 and 23, or a pharmaceutically acceptable salt thereof;

(9) The peptide-type compound according to item (7) above, which comprises one amino acid sequence selected from the group consisting of amino acid sequences set forth in SEQ ID NOS: 25, 26, 29, 30, 31, 32, 34 and 35, or a pharmaceutically acceptable salt thereof;

(10) The peptide-type compound according to item (1) or (5) above, whose amino-terminal amino acids 1 to 4 are represented by formula:

A-B-C-D- wherein the symbol A is either an amino acid or a non-amino acid compound, or is missing, and the symbol B is either an amino acid or a non-amino acid compound, or is missing, provided that the length of the A+B molecular chain is a dipeptide length, and the symbol C or the symbol D may be the same or different and represents (a) a modified amino acid, (b) an amino acid having a hydrophobic residue, or (c) an amino acid having a basic side chain, or a pharmaceutically acceptable salt thereof;

(11) The peptide-type compound according to item (10), wherein the symbol C is a modified amino acid in which (a) a saturated or unsaturated alkyl chain containing one or more carbon atoms was introduced at the α carbon atom of the amino acid via or not via an alkylene group containing one or more carbon atoms and via an ester, ether, thioether, amide or disulfide linkage, or (b) a saturated or unsaturated alkyl chain containing one or more carbon atoms was introduced at the α carbon atom of the amino acid, and the symbol D is an amino acid having a hydrophobic residue, or a pharmaceutically acceptable salt thereof;

(12) A peptide-type compound, wherein in one amino acid sequence selected from the group consisting of amino acid sequences set forth in SEQ ID NOS: 2, 3, 9, 10, 11, 16, 17, 22, 25, 26, 27, 28, 29, 30 and 31, an amino acid sequence of amino-terminal amino acids 1 to 4 is replaced by the structure of the peptide-type compound described in item (10) or (11), or a pharmaceutically acceptable salt thereof;

(13) The peptide-type compound according to item (1), (2), (3), (5), (7) or (8) above, wherein the modified amino acid is an amino acid at the 3rd position from the amino-terminal, or a pharmaceutically acceptable salt thereof;

(14) The peptide-type compound according to item (13), wherein the amino acid in the modified amino acid is serine or cysteine, or a pharmaceutically acceptable salt thereof;

(15) The peptide-type compound according to item (1), (2), (3), (5), (7) or (8) above, which comprises a modified amino acid in which (a) a saturated or unsaturated alkyl chain containing one or more carbon atoms was introduced at the α carbon atom of the amino acid via or not via an alkylene group containing one or more carbon atoms and via an ester, ether, thioester, thioether, amide or carbamide linkage, or (b) H or a saturated or unsaturated alkyl chain containing one or more carbon atoms was introduced at the α carbon atom of the amino acid, or a pharmaceutically acceptable salt thereof;

(16) The peptide-type compound according to item (1), (2), (4), (5), (6), (7), (9), (10) or (12) above, wherein the modified amino acid is an amino acid in which, (a) a saturated or unsaturated alkyl chain containing one or more carbon atoms was introduced at the α carbon atom via or not via an alkylene group containing one or more carbon atoms and via an ester, ether, thioester, thioether, disulfide, amide, carbamide or thiocarbamide linkage, or (b) a saturated or unsaturated alkyl chain containing one or more carbon atoms was introduced at the a carbon, or a pharmaceutically acceptable salt thereof;

(17) The peptide-type compound according to item (1), (2), (3), (5), (7) or (8) above, which comprises a modified amino acid modified with an ester linkage, or a pharmaceutically acceptable salt thereof;

(18) The peptide-type compound according to item (1), (2), (4), (5), (6), (7), (9), (10), (11) or (12) above, which comprises a modified amino acid modified by conversion of a functional group in a side chain of said amino acid into an ester linkage, or a pharmaceutically acceptable salt thereof;

(19) The peptide-type compound according to item (17) above, which comprises an amino acid having a fatty acid bound via an ester linkage to a side-chain hydroxyl group of said amino acid, or a pharmaceutically acceptable salt thereof;

(20) The peptide-type compound according to item (18) above, which comprises an amino acid having a fatty acid bound via an ester linkage to a side-chain hydroxyl group of said amino acid or via a thioester linkage to a side-chain mercapto group of said amino acid, or a pharmaceutically acceptable salt thereof;

(21) The peptide-type compound according to item (19) above, which comprises an amino acid to which a fatty acid containing 2 to 35 carbon atoms was bound, or a pharmaceutically acceptable salt thereof;

(22) The peptide-type compound according to item (20) above, wherein the fatty acid contains 2 to 35 carbon atoms, or a pharmaceutically acceptable salt thereof;

(23) The peptide-type compound according to item (21) above, which comprises an amino acid to which a fatty acid selected from the group consisting of fatty acids containing 2, 4, 6, 8, 10, 12, 14, 16 and 18 carbon atoms was bound, or a pharmaceutically acceptable salt thereof;

(24) The peptide-type compound according to item (22) above, wherein the fatty acid is a fatty acid selected from the group consisting of fatty acids containing 2, 4, 6, 8, 10, 12, 14, 16 and 18 carbon atoms, or a pharmaceutically acceptable salt thereof;

(25) The peptide-type compound according to item (23) above, wherein the bound fatty acid is octanoic acid, a monoene fatty acid thereof or a polyene fatty acid thereof, or a pharmaceutically acceptable salt thereof;

(26) The peptide-type compound according to item (24) above, wherein the fatty acid is octanoic acid, a monoene fatty acid thereof or a polyene fatty acid thereof, or a pharmaceutically acceptable salt thereof;

(27) The peptide-type compound according to item (23) above, wherein the bound fatty acid is decanoic acid, a monoene fatty acid thereof or a polyene fatty acid thereof, or a pharmaceutically acceptable salt thereof;

(28) The peptide-type compound according to item (24) above, wherein the fatty acid is decanoic acid, a monoene fatty acid thereof or a polyene fatty acid thereof, or a pharmaceutically acceptable salt thereof;

(29) A peptide-type compound comprising a basic amino acid bound to the carboxyl-terminal of a peptide-type compound described in items (1) to (28) above;

(30) The peptide-type compound according to items (1), (2), (3), (5), (7), (8), (13), (14), (15), (17), (19), (21), (23), (25) and (27) above, wherein the amino-terminal is modified with a saturated or unsaturated alkyl or acyl group containing one or more carbon atoms, and/or a hydroxyl group of the carboxyl-terminal carboxyl group is OZ or NR2R3 wherein Z is a pharmaceutically acceptable cation or a lower branched or linear alkyl group, and R2 and R3 are the same or different and represent H or a lower branched or linear alkyl group;

(31) The peptide-type compound according to items (1), (2), (4), (5), (6), (7), (9), (10), (11), (12), (16), (18), (20), (22), (24), (26), (28) and (29) above, wherein the amino-terminal amino group is modified by introduction of a saturated or unsaturated alkyl or acyl group containing one or more carbon atoms, and/or a hydroxyl group of the carboxyl-terminal carboxyl group is OZ or NR2R3 wherein Z is a pharmaceutically acceptable cation or a lower branched or linear alkyl group, and R2 and R3 are the same or different and represent H or a lower branched or linear alkyl group;

(32) A peptide-type compound comprising a basic group introduced into a carboxyl-terminal amide derivative of a peptide-type compound described in item (30) or (31) above;

(33) A pharmaceutical composition comprising a peptide-type compound described in items (1) to (32) above or a pharmaceutically acceptable salt thereof as an active ingredient;

(34) A pharmaceutical composition for treatment of diseases attributable to a defect or decrease in growth hormone, which comprises a peptide-type compound described in items (1) to (32) above or a pharmaceutically acceptable salt thereof as an active ingredient;

(35) A pharmaceutical composition for treatment of diseases not attributable to a defect or decrease in growth hormone, which comprises an agent for treating diseases not attributable to a defect or decrease in growth hormone and a peptide-type compound described in items (1) to (32) above or a pharmaceutically acceptable salt thereof;

(36) A pharmaceutical composition according to items (33) to (35) above, which is applied to animals other than human beings;

(37) A method for treatment of diseases attributable to a defect or decrease in growth hormone, which comprises administering a pharmaceutical composition comprising a peptide-type compound described in items (1) to (32) above or a pharmaceutically acceptable salt thereof as an active ingredient;

(38) A method for treatment of diseases not attributable to a defect or decrease in growth hormone, which comprises administering an agent for treating diseases not attributable to a defect or decrease in growth hormone and a peptide-type compound described in items (1) to (32) above or a pharmaceutically acceptable salt thereof;

(39) The treatment method according to items (37) or (38), which is applied to animals other than human beings;

(40) A DNA coding an amino acid sequence of a peptide-type compound described in items (1) to (32) above, which comprises a nucleotide sequence coding a peptide containing an amino acid sequence recognizing at least one modifiable amino acid in the amino acid sequence encoded by said DNA;

(41) The DNA according to item (40) above, wherein the nucleotide sequence is one nucleotide sequence selected from the group consisting of nucleotide sequences set forth in SEQ ID NOS: 6, 7, 14, 15, 20, 21, 24, 36, 37, 38 and 39;

(42) The DNA according to item (40) above, wherein the nucleotide sequence is an amino acid-coding nucleotide sequence in one nucleotide sequence selected from the group consisting of nucleotide sequences set forth in SEQ ID NOS: 6, 7, 14, 15, 20, 21, 24, 36, 37, 38 and 39;

(43) A vector comprising a DNA described in items (40) to (42) above;

(44) Cells comprising the vector described in item (43) above;

(45) Cells comprising a DNA described in items (40) to (42) above, wherein a peptide-type compound having an amino acid sequence encoded by said DNA can be produced as a peptide-type compound having at least one amino acid modified in said amino acid sequence;

(46) An antibody against a peptide-type compound described in items (1) to (32) above;

(47) A method for assaying a peptide-type compound described in items (1) to (32) above, which comprises using the antibody described in item (46) above to detect the peptide-type compound described in items (1) to (32) above;

(48) A kit for detecting a peptide-type compound described in items (1) to (32) above, which comprises using the antibody described in item (46) above to detect the peptide-type compound described in items (1) to (32) above;

(49.) A method for producing a peptide-type compound described in items (1) to (32) above by genetic recombination technology, which comprises transforming a vector containing a DNA described in items (40) to (42) above into host cells capable of modifying a side chain of at least one amino acid in said peptide, then culturing the resulting transformed cells and recovering the desired peptide-type compound from the culture;

(50) A method for producing a peptide-type compound described in items (1) to (32) above by genetic recombination technology, which comprises transforming a vector containing a DNA described in items (40) to (42) above into host cells, then culturing the resulting transformed cells and recovering the desired peptide-type compound from the culture, followed by chemically modifying an arbitrary amino acid thereof;

(51) A method for producing a peptide-type compound described in items (19) to (28) above by genetic recombination technology, which comprises using cells having the activity of binding a fatty acid via an ester linkage to a side-chain hydroxyl group of an amino acid or via a thioester linkage to a side-chain mercapto group of an amino acid in the peptide-type compound;

(52) A method for producing a peptide-type compound described in items (19) to (28) above, which comprises using cells having the serine acylation activity of binding a fatty acid via an ester linkage to a side-chain hydroxyl group of serine in the amino acid sequence set forth in SEQ ID NO: 8;

(53) A process for producing a peptide-type compound described in items (19) to (28) above, which comprises using cells having the acylation activity of binding a fatty acid via an ester linkage to a side-chain hydroxyl group of threonine in the amino acid sequence set forth in SEQ ID NO: 28;

(54) A pharmaceutical composition for gene therapy for treatment of diseases attributable to a defect or decrease in growth hormone, which comprises integrating a vector containing a DNA coding an amino acid sequence of a peptide-type compound described in items (1) to (32) above into cells in a living body and expressing a peptide with at least one modified amino acid, the peptide having the activity of increasing the intracellular calcium ion concentration;

(55) A method for treatment of diseases attributable to a defect or decrease in growth hormone, which comprises integrating a vector containing a DNA coding an amino acid sequence of a peptide-type compound described in items (1) to (32) above into cells in a living body enabling a peptide having an amino acid sequence encoded by said DNA to be produced as a peptide having an amino acid sequence recognizing at least one modifiable amino acid in said amino acid sequence, whereby a peptide having the activity of inducing growth hormone is expressed;

(56) A pharmaceutical composition for gene therapy for treatment of diseases not attributable to a defect or decrease in growth hormone, which comprises integrating a vector containing a DNA coding an amino acid sequence of a peptide-type compound described in items (1) to (32) above into cells in a living body and expressing a peptide with at least one modified amino acid, the peptide having the activity of increasing the intracellular calcium ion concentration;

(57) A method for treatment of diseases not attributable to a defect or decrease in growth hormone, which comprises integrating a vector containing a DNA coding an amino acid sequence of a peptide-type compound described in items (1) to (32) above into cells in a living body enabling a peptide having an amino acid sequence encoded by said DNA to be produced as a peptide having an amino acid sequence recognizing at least one modifiable amino acid in said amino acid sequence, whereby a peptide having the activity of inducing growth hormone is expressed.

Specifically, the present invention also relates to:

(1) A peptide-type compound, wherein in a peptide having the activity of increasing the intracellular calcium ion concentration, at least one amino acid is replaced by a modified amino acid and/or a non-amino acid compound, or a pharmaceutically acceptable salt thereof;

(2) The peptide-type compound according to item (1) above, which comprises (a) an amino acid sequence set forth in SEQ ID NO: 2 or (b) an amino acid sequence having any one of amino acid sequences selected from the group consisting of
(1) amino acid sequence of amino acids 1 to 4,
(2) amino acid sequence of amino acids 1 to 5,
(3) amino acid sequence of amino acids 1 to 6,
(4) amino acid sequence of amino acids 1 to 7,
(5) amino acid sequence of amino acids 1 to 8,
(6) amino acid sequence of amino acids 1 to 9, and
(7) amino acid sequence of amino acids 1 to 10
from the amino-terminal in the sequence (a) and at least one amino acid deleted, replaced and/or added in a part outside said amino acid sequences, or a pharmaceutically acceptable salt thereof;

(3) The peptide-type compound according to item (2) above, which comprises one amino acid sequence selected from the group consisting of amino acid sequences set forth in SEQ ID NOS: 3, 4, 5, 8, 9, 10, 11, 12, 13, 16, 17, 18, 19, 22, 23, 25 and 26, or a pharmaceutically acceptable salt thereof;

(4) A peptide-type compound wherein in a peptide having the activity of increasing the intracellular calcium ion concentration and the activity of inducing secretion of growth hormone, (a) constitutional amino acids are modified or not modified and (b) at least one amino acid is replaced or not replaced by a non-amino acid compound, or a pharmaceutically acceptable salt thereof;

(5) The peptide-type compound according to item (1) or (4) which comprises an amino acid sequence set forth in SEQ ID NO: 27, or a pharmaceutically acceptable salt thereof;

(6) The peptide-type compound according to item (4) above, which comprises (a) an amino acid sequence set forth in SEQ ID NO: 2 or (b) an amino acid sequence having any one of amino acid sequences selected from the group consisting of
(1) amino acid sequence of amino acids 1 to 4,
(2) amino acid sequence of amino acids 1 to 5,
(3) amino acid sequence of amino acids 1 to 6,
(4) amino acid sequence of amino acids 1 to 7,
(5) amino acid sequence of amino acids 1 to 8,
(6) amino acid sequence of amino acids 1 to 9, and
(7) amino acid sequence of amino acids 1 to 10
from the amino-terminal in the sequence (a) and at least one amino acid deleted, replaced and/or added in a part outside said amino acid sequences, or a pharmaceutically acceptable salt thereof;

(7) The peptide-type compound according to item (6) above, which comprises one amino acid sequence selected from the group consisting of amino acid sequences set forth in SEQ ID NOS: 3, 4, 5, 8, 9, 10, 11, 12, 13, 16, 17, 18, 19, 22, 23, 25 and 26, or a pharmaceutically acceptable salt thereof;

(8) The peptide-type compound according to item (1) or (4) above, whose amino-terminal amino acids 1 to 4 are represented by formula:

wherein the symbol A is either an amino acid or a non-amino acid compound, or is missing, and the symbol B is either an amino acid or a non-amino acid compound, or is missing, provided that the length of the A+B molecular chain is a dipeptide length, and the symbol C or the symbol D may be the same or different and represents (a) a modified amino acid, (b) an amino acid having a hydrophobic residue or (c) an amino acid having a basic side chain, or a pharmaceutically acceptable salt thereof;

(9) A peptide-type compound, wherein in one amino acid sequence selected from the group consisting of amino acid sequences set forth in SEQ ID NOS: 2, 3, 8, 9, 10, 11, 16, 17, 22, 25 and 26, an amino acid sequence of amino-terminal amino acids 1 to 4 is s replaced by the structure of the peptide-type compound described in item (8) above, or a pharmaceutically acceptable salt thereof.

(10) The peptide-type compound according to items (1) to (9) above, wherein the modified amino acid is an amino acid in which (a) a saturated or unsaturated alkyl chain containing one or more carbon atoms was introduced at the α carbon atom of the amino acid via or not via an alkylene group containing one or more carbon atoms and via an ester, ether, thioester, thioether, disulfide, amide, carbamide or thiocarbamide linkage, or (b) a saturated or unsaturated alkyl chain containing one or more carbon atoms was introduced at the α carbon atom of the amino acid, or a pharmaceutically acceptable salt thereof;

(11) The peptide-type compound according to items (1) to (10) above, which comprises a modified amino acid modified by conversion of a functional group in a side chain of said amino acid into an ester linkage, or a pharmaceutically acceptable salt thereof;

(12) The peptide-type compound according to item (11) above, which comprises an amino acid having a fatty acid bound via an ester linkage to a side-chain hydroxyl group or mercapto group of said amino acid, or a pharmaceutically acceptable salt thereof;

(13) The peptide-type compound according to item (12) above, wherein the fatty acid contains 2 to 35 carbon atoms, or a pharmaceutically acceptable salt thereof;

(14) The peptide-type compound according to item (12) above, wherein the fatty acid is a fatty acid selected from the group consisting of fatty acids containing 2, 4, 6, 8, 10, 12, 14, 16 and 18 carbon atoms, or a pharmaceutically acceptable salt thereof;

(15) The peptide-type compound according to item (12) above, wherein the fatty acid is octanoic acid, a monoene fatty acid thereof or a polyene fatty acid thereof, or a pharmaceutically acceptable salt thereof;

(16) The peptide-type compound according to item (12) above, wherein the fatty acid is decanoic acid, a monoene fatty acid thereof or a polyene fatty acid thereof, or a pharmaceutically acceptable salt thereof;

(17) The peptide-type compound according to items (1) to (16) above, wherein the amino-terminal amino group is modified by introduction of a saturated or unsaturated alkyl or acyl group containing one or more carbon atoms, and/or a hydroxyl group of the carboxyl-terminal carboxyl group is OZ or NR2R3 wherein Z is a pharmaceutically acceptable cation or a lower branched or linear alkyl group, and R2 and R3 are the same or different and represent H or a lower branched or linear alkyl group;

(18) A peptide-type compound comprising a basic amino acid bound to the carboxyl-terminal of a peptide-type compound described in items (1) to (16) above;

(19) A peptide-type compound comprising a basic group introduced into a carboxyl-terminal amide derivative of the peptide-type compound described in items (1) to (16) or (18) above;

(20) A pharmaceutical composition comprising a peptide-type compound described in items (1) to (19) above or a pharmaceutically acceptable salt thereof as an active ingredient;

(21) A pharmaceutical composition for treatment of diseases attributable to a defect or decrease in growth hormone, which comprises a peptide-type compound described in items (1) to (19) above or a pharmaceutically acceptable salt thereof as an active ingredient;

(22) A pharmaceutical composition for treatment of diseases not attributable to a defect or decrease in growth hormone, which comprises an agent for treating diseases not attributable to a defect or decrease in growth hormone and a peptide-type compound described in items (1) to (19) above or a pharmaceutically acceptable salt thereof;

(23) A pharmaceutical composition according to items (20) to (22), which is applied to animals other than human beings;

(24) A method for treatment of diseases attributable to a defect or decrease in growth hormone, which comprises administering a pharmaceutical composition comprising a peptide-type compound described in items (1) to (19) above or a pharmaceutically acceptable salt thereof as an active ingredient;

(25) A method for treatment of diseases not attributable to a defect or decrease in growth hormone, which comprises administering an agent for treating diseases not attributable to a defect or decrease in growth hormone and a peptide-type compound described in items (1) to (19) above or a pharmaceutically acceptable salt thereof;

(26) A method according to item (24) or (25), which is applied to animals other than human beings;

(27) A DNA coding an amino acid sequence of a peptide-type compound described in items (1) to (19) above, which comprises a nucleotide sequence coding a peptide containing an amino acid sequence recognizing at least one modifiable amino acid in the amino acid sequence encoded by said DNA;

(28) The DNA according to item (27) above, wherein the nucleotide sequence is one nucleotide sequence selected from the group consisting of nucleotide sequences set forth in SEQ ID NOS: 6, 7, 14, 15, 20, 21 and 24;

(29) The DNA according to item (27) above, wherein the nucleotide sequence is an amino acid-coding nucleotide sequence in one nucleotide sequence selected from the group consisting of nucleotide sequences set forth in SEQ ID NOS: 6, 7, 14, 15, 20, 21 and 24;

(30) A vector comprising a DNA described in items (27) to (29) above;

(31) Cells comprising the vector described in item (30) above;

(32) Cells comprising a DNA described in items (27) to (29) above, wherein a peptide-type compound having an amino acid sequence encoded by said DNA can be produced as a peptide-type compound having at least one amino acid modified in said amino acid sequence;

(33) An antibody against a peptide-type compound described in items (1) to (19) above;

(34) A method for assaying a peptide-type compound described in items (1) to (19) above, which comprises using the antibody described in item (33) above to detect the peptide-type compound described in items (1) to (19) above;

(35) A kit for detecting a peptide-type compound described in items (1) to (19) above, which comprises using the antibody described in item (33) above to detect the peptide-type compound described in items (1) to (19) above;

(36) A method for producing a peptide-type compound described in items (1) to (19) above by genetic recombination technology, which comprises transforming a vector containing a DNA described in items (27) to (29) above into host cells capable of modifying a side chain of at least one amino acid in said peptide, then culturing the resulting transformed cells and recovering the desired peptide-type compound from the culture;

(37) A method for producing a peptide-type compound described in items (1) to (19) above by genetic recombination technology, which comprises transforming a vector containing a DNA described in items (27) to (29) above into host cells, then culturing the resulting transformed cells and recovering the desired compound from the culture, followed by chemically modifying an arbitrary amino acid thereof;

(38) A method for producing a peptide-type compound described in items (12) to (16) above by genetic recombination technology, which comprises using cells having the activity of binding a fatty acid via an ester linkage to a side-chain hydroxyl group or a side-chain mercapto group of an amino acid in the peptide-type compound;

(39) A method for producing a peptide-type compound described in items (12) to (16) above, which comprises using cells having the serine acylation activity of binding a fatty acid via an ester linkage to a side-chain hydroxyl group of serine in the amino acid sequence set forth in SEQ ID NO: 8;

(40) A pharmaceutical composition for gene therapy for treatment of diseases attributable to a defect or decrease in growth hormone, which comprises integrating a vector containing a DNA coding an amino acid sequence of a peptide-type compound described in items (1) to (19) above into cells in a living body and expressing a peptide with at least one modified amino acid, the peptide having the activity of increasing the intracellular calcium ion concentration;

(41) A method for treatment of diseases attributable to a defect or decrease in growth hormone, which comprises integrating a vector containing a DNA coding an amino acid sequence of a peptide-type compound described in items (1) to (19) above into cells in a living body enabling a peptide having an amino acid sequence encoded by said DNA to be produced as a peptide having an amino acid sequence recognizing at least one modifiable amino acid in said amino acid sequence, whereby a peptide having the activity of inducing growth hormone is expressed;

(42) A pharmaceutical composition for gene therapy for treatment of diseases not attributable to a defect or decrease in growth hormone, which comprises integrating a vector containing a DNA coding an amino acid sequence of a peptide-type compound described in items (1) to (19) above into cells in a living body and expressing a peptide with at least one modified amino acid, the peptide having the activity of increasing the intracellular calcium ion concentration;

(43) A method for treatment of diseases not attributable to a defect or decrease in growth hormone, which comprises integrating a vector containing a DNA coding an amino acid sequence of a peptide-type compound described in items (1) to (19) above into cells in a living body enabling a peptide having an amino acid sequence encoded by said DNA to be produced as a peptide having an amino acid sequence recognizing at least one modifiable amino acid in said amino acid sequence, whereby a peptide having the activity of inducing growth hormone is expressed.

Specifically, the present invention also relates to:

(1) A peptide-type compound having the activity of increasing the intracellular calcium ion concentration, wherein at least one amino acid is replaced by a modified amino acid and/or a non-amino acid compound, or a pharmaceutically acceptable salt thereof;

(2) The peptide-type compound according to item (1) above, which comprises (a) an amino acid sequence set forth in SEQ ID NO: 2 or (b) an amino acid sequence having any one of amino acid sequences selected from the group consisting of
(1) amino acid sequence of amino acids 1 to 4,
(2) amino acid sequence of amino acids 1 to 5,
(3) amino acid sequence of amino acids 1 to 6,
(4) amino acid sequence of amino acids 1 to 7,
(5) amino acid sequence of amino acids 1 to 8,
(6) amino acid sequence of amino acids 1 to 9, and
(7) amino acid sequence of amino acids 1 to 10
from the amino-terminal in the sequence (a) and at least one amino acid deleted, replaced and/or added in a part outside said amino acid sequences, or a pharmaceutically acceptable salt thereof;

(3) The peptide-type compound according to item (2) above, which comprises one amino acid sequence selected from the group consisting of amino acid sequences set forth in SEQ ID NOS: 3, 4, 5, 8, 9, 10, 11, 12, 13, 16, 17, 18, 19, 22 and 23, or a pharmaceutically acceptable salt thereof;

(4) A peptide-type compound having the activity of increasing the intracellular calcium ion concentration and the activity of inducing secretion of growth hormone, wherein (a) constitutional amino acids are modified or not modified and (b) at least one amino acid is replaced or not replaced by a non-amino acid compound, or a pharmaceutically acceptable salt thereof;

(5) The peptide-type compound according to item (4) above, which comprises (a) an amino acid sequence set forth in SEQ ID NO: 2 or (b) an amino acid sequence having any one of amino acid sequences selected from the group consisting of
(1) amino acid sequence of amino acids 1 to 4,
(2) amino acid sequence of amino acids 1 to 5,
(3) amino acid sequence of amino acids 1 to 6,
(4) amino acid sequence of amino acids 1 to 7,
(5) amino acid sequence of amino acids 1 to 8,
(6) amino acid sequence of amino acids 1 to 9, and
(7) amino acid sequence of amino acids 1 to 10
from the amino-terminal in the sequence (a) and at least one amino acid deleted, replaced and/or added in a part outside said amino acid sequences, or a pharmaceutically acceptable salt thereof;

(6) The peptide-type compound according to items (4) or (5) above, which comprises one amino acid sequence selected from the group consisting of amino acid sequences set forth in SEQ ID NOS: 3, 4, 5, 8, 9, 10, 11, 12, 13, 16, 17, 18, 19, 22 and 23, or a pharmaceutically acceptable salt thereof;

(7) The peptide-type compound according to items (1) to (6) above, wherein the modified amino acid is an amino acid at the 3rd position from the amino-terminal thereof, or a pharmaceutically acceptable salt thereof;

(8) The peptide-type compound according to item (7) above, wherein the amino acid in the modified amino acid is serine or cysteine, or a pharmaceutically acceptable salt thereof;

(9) The peptide-type compound according to items (1) to (6) above, which comprises a modified amino acid in which (a) a saturated or unsaturated alkyl chain containing one or more carbon atoms was introduced at the α carbon atom of the amino acid via or not via an alkylene group containing one or more carbon atoms and via an ester, ether, thioester, thioether, amide or carbamide linkage, or (b) H or a saturated or unsaturated alkyl chain containing one or more carbon atoms was introduced at the α carbon atom of the amino acid, or a pharmaceutically acceptable salt thereof;

(10) The peptide-type compound according to items (1) to (6) above, which comprises a modified amino acid modified with an ester linkage, or a pharmaceutically acceptable salt thereof;

(11) The peptide-type compound according to item (10) above, which comprises an amino acid to which a fatty acid was bound, or a pharmaceutically acceptable salt thereof;

(12) The peptide-type compound according to item (11) above, which comprises an amino acid to which a fatty acid containing 2 to 35 carbon atoms was bound, or a pharmaceutically acceptable salt thereof;

(13) The peptide-type compound according to item (12) above, which comprises an amino acid to which a fatty acid selected from the group of consisting fatty acids containing 2, 4, 6, 8, 10, 12, 14, 16 and 18 carbon atoms was bound, or a pharmaceutically acceptable salt thereof;

(14) The peptide-type compound according to item (13) above, wherein the bound fatty acid is octanoic acid, a monoene fatty acid thereof or a polyene fatty acid thereof, or a pharmaceutically acceptable salt thereof;

(15) The peptide-type compound according to item (13) above, wherein the bound fatty acid is decanoic acid, a monoene fatty acid thereof or a polyene fatty acid thereto, or a pharmaceutically acceptable salt thereof;

(16) The peptide-type compound according to items (1) to (15) above, wherein the amino-terminal is modified with a saturated or unsaturated alkyl or acyl group containing one or more carbon atoms, and/or a hydroxyl group of the carboxyl-terminal carboxyl group is OZ or NR2R3 wherein Z is a pharmaceutically acceptable cation or a lower branched or linear alkyl group, and R2 and R3 are the same or different and represent H or a lower branched or linear alkyl group;

(17) A pharmaceutical composition comprising a peptide-type compound described in items (1) to (16) above or a pharmaceutically acceptable salt thereof as an active ingredient;

(18) A pharmaceutical composition for treatment of diseases attributable to a defect or decrease in growth hormone, which comprises a peptide-type compound described in items (1) to (16) above or a pharmaceutically acceptable salt thereof as an active ingredient;

(19) A pharmaceutical composition for treatment of diseases not attributable to a defect or decrease in growth hormone, which comprises an agent for treating diseases not attributable to a defect or decrease in growth hormone and a peptide-type compound described in items (1) to (16) above or a pharmaceutically acceptable salt thereof;

(20) A pharmaceutical composition according to items (17) to (19), which is applied to animals other than human beings;

(21) A method for treatment of diseases attributable to a defect or decrease in growth hormone, which comprises administering a pharmaceutical composition comprising a peptide-type compound described in items (1) to (16) above or a pharmaceutically acceptable salt thereof as an active ingredient;

(22) A method for treatment of diseases not attributable to a defect or decrease in growth hormone, which comprises administering an agent for treating diseases not attributable to a defect or decrease in growth hormone and a peptide-type compound described in items (1) to (16) above or a pharmaceutically acceptable salt thereof;

(23) A method for treatment according to items (21) to (22), which is applied to animals other than human beings;

(24) A DNA for a peptide-type compound described in items (1) to (16) above, which comprises a nucleotide sequence coding a peptide containing an amino acid sequence recognizing at least one modifiable amino acid in the amino acid sequence encoded by said DNA;

(25) The DNA according to item (24) above, which comprises one nucleotide sequence selected from the group consisting of nucleotide sequences set forth in SEQ ID NOS: 6, 7, 14, 15, 20, 21 and 24;

(26) The DNA according to item (24) above, which comprises an amino acid-coding nucleotide sequence in one nucleotide sequence selected from the group consisting of nucleotide sequences set forth in SEQ ID NOS: 6, 7, 14, 15, 20, 21 and 24;

(27) A vector comprising a DNA described in items (24) to (26) above;

(28) Cells comprising the vector described in item (27) above;

(29) Cells comprising a vector containing a DNA described in items (24) to (26) above, wherein a peptide-type compound having an amino acid sequence encoded by said DNA can be produced as a peptide-type compound having at least one amino acid modified in said amino acid sequence;

(30) An antibody against a peptide-type compound described in items (1) to (16) above;

(31) A method for assaying a peptide-type compound described in items (1) to (16) above, which comprises using the antibody described in item (30) above to detect the peptide-type compound described in items (1) to (16) above;

(32) A kit for detecting a peptide-type compound described in items (1) to (16) above, which comprises using the antibody described in item (30) above to detect said peptide-type compound;

(33) A method for producing a peptide-type compound described in items (1) to (16) above by genetic recombination technology, which comprises transforming a vector containing a DNA described in items (24) to (26) above into host cells capable of modifying a side chain of at least one amino acid in said peptide, then culturing the resulting transformed cells and recovering the desired peptide-type compound from the culture;

(34) A method for producing a peptide-type compound described in items (1) to (16) above by genetic recombination technology, which comprises transforming a vector containing a DNA described in items (24) to (26) above into host cells, then culturing the resulting transformed cells and recovering the desired peptide-type compound from the culture, followed by chemically modifying an arbitrary amino acid thereof;

(35) A method for producing the peptide-type compound described in items (11) to (15) above by genetic recombination technology, wherein the peptide-type compound can be produced as a peptide having a fatty acid bound to a serine residue in the amino acid sequence set forth in SEQ ID NO: 8;

(36) A method for producing a peptide-type compound having the activity of increasing the intracellular calcium ion concentration and the activity of inducing secretion of growth hormone, which comprises transforming a vector containing a DNA coding a peptide-type compound described in items (4) to (6) above into host cells, and culturing the resulting transformed cells and recovering the desired compound from the culture;

(37) A pharmaceutical composition for gene therapy for treatment of diseases attributable to a defect or decrease in growth hormone, which comprises integrating a vector containing a DNA coding a peptide-type compound described in items (1) to (16) above into cells in a living body and expressing a peptide with at least one modified amino acid, the peptide having the activity of increasing the intracellular calcium ion concentration.

(38) A method for treatment of diseases attributable to a defect or decrease in growth hormone, which comprises integrating a vector containing a DNA coding a peptide-type compound described in items (1) to (16) above into cells in a living body enabling a peptide having an amino acid sequence encoded by said DNA to be produced as a peptide having an amino acid sequence recognizing at least one modifiable amino acid in said amino acid sequence, whereby a peptide having the activity of inducing growth hormone is expressed;

(39) A pharmaceutical composition for gene therapy for treatment of diseases not attributable to a defect or decrease in growth hormone, which comprises integrating a vector containing a DNA coding a peptide-type compound described in items (1) to (16) above into cells in a living body and expressing a peptide with at least one modified amino acid, the peptide having the activity of increasing the intracellular calcium ion concentration;

(40) A method for treatment of diseases not attributable to a defect or decrease in growth hormone, which comprises integrating a vector containing a DNA coding a peptide-type compound described in items (1) to (16) above into cells in a living body enabling a peptide having an amino acid sequence encoded by said DNA to be produced as a peptide having an amino acid sequence recognizing at least one modifiable amino acid in said amino acid sequence, whereby a peptide having the activity of inducing growth hormone is expressed.

Specifically, the present invention also relates to:

(1) A peptide-type compound having the activity of increasing the intracellular calcium ion concentration, wherein at least one amino acid is replaced by a modified amino acid and/or a non-amino acid compound, or a pharmaceutically acceptable salt thereof;

(2) The peptide-type compound according to item (1) above, which comprises an amino acid sequence set forth in SEQ ID NO: 1, or a pharmaceutically acceptable salt thereof;

(3) The peptide-type compound according to item (1) above, which comprises an amino acid sequence set forth in SEQ ID NO: 2 or an amino acid sequence wherein in SEQ ID NO: 2, at least one amino acid is deleted, replaced and/or added in a part outside a sequence of amino acids 1 to 7 from the amino-terminal thereof, or a pharmaceutically acceptable salt thereof;

(4) An analogue or derivative of the peptide described in item (1) above, which comprises an amino acid sequence set forth in SEQ ID NO: 3 or an amino acid sequence wherein in SEQ ID NO: 3, at least one amino acid is deleted, replaced and/or added in a part outside a sequence of amino acids 1 to 7 from the amino-terminal thereof, or a pharmaceutically acceptable salt thereof;

(5) A precursor peptide-type compound of the peptide compound described in (3) above, which comprises an amino acid sequence set forth in SEQ ID NO: 4 or an amino acid sequence wherein in SEQ ID NO: 4, at least one amino acid is deleted, replaced and/or added in a part outside a sequence of amino acids 1 to 28 from the amino-terminal thereof;

(6) A precursor peptide-type compound of the peptide compound described in item (4) above, which comprises an amino acid sequence set forth in SEQ ID NO: 5 or an amino acid sequence wherein in SEQ ID NO: 5, at least one amino acid is deleted, replaced and/or added in a part outside a sequence of amino acids 1 to 28 from the amino-terminal thereof;

(7) A peptide-type compound having the activity of increasing the intracellular calcium ion concentration and the activity of inducing secretion of growth hormone, or a pharmaceutically acceptable salt thereof;

(8) The peptide-type compound according to item (7) above, which has the activity of increasing the intracellular calcium ion concentration and the activity of inducing secretion of growth hormone and has at least one amino acid replaced by a non-amino acid compound, or a pharmaceutically acceptable salt thereof;

(9) The peptide-type compound according to items (7) to (8) above, which comprises an amino acid sequence set forth in SEQ ID NO: 1, or a derivative thereof or a pharmaceutically acceptable salt thereof;

(10) The peptide compound described in items (7) to (8) above, which comprises an amino acid sequence set forth in SEQ ID NO: 2 or an amino acid sequence wherein in SEQ ID NO: 2, at least one amino acid is deleted, replaced and/or added in a part outside a sequence of amino acids 1 to 7 from the amino-terminal thereof, or a derivative thereof or a pharmaceutically acceptable salt thereof;

(11) The peptide compound described in items (7) to (8) above, which comprises an amino acid sequence set forth in SEQ ID NO: 3 or an amino acid sequence wherein in SEQ ID NO: 3, at least one amino acid is deleted, replaced and/or added in a part outside a sequence of amino acids 1 to 7 from the amino-terminal thereof, or a derivative thereof or a pharmaceutically acceptable salt thereof;

(12) A precursor peptide-type compound of the peptide-type compound described in item (10) above, which comprises an amino acid sequence set forth in SEQ ID NO: 4 or an amino acid sequence wherein in SEQ ID NO: 4, at least one amino acid is deleted, replaced and/or added in a part outside a sequence of amino acids 1 to 28 from the amino-terminal thereof;

(13) A precursor peptide-type compound of the peptide-type compound described in item (11) above, which comprises an amino acid sequence set forth in SEQ ID NO: 5 or an amino acid sequence wherein in SEQ ID NO: 5, at least one amino acid is deleted, replaced and/or added in a part outside a sequence of amino acids 1 to 28 from the amino-terminal thereof;

(14) The peptide-type compound according to items (1) to (6) above, wherein the modified amino acid is an amino acid at the 3rd position from the amino-terminal thereof, or a pharmaceutically acceptable salt thereof;

(15) The peptide-type compound according to item (14), wherein the amino acid in the modified amino acid is serine or cysteine, or a pharmaceutically acceptable salt thereof;

(16) The peptide-type compound according to items (1) to (6) above, wherein the modification in the modified amino acid indicates the modification at the α carbon of said amino acid by (a) a saturated or unsaturated alkyl chain containing one or more carbon atoms which binds in a mode of linkage selected from the group consisting of ester, ether, thioester, thioether, amide or carbamide via or not via an alkyl chain, containing one or more carbon atoms, or (b) H or a saturated or unsaturated alkyl chain containing one or more carbon atoms, or a pharmaceutically acceptable salt thereof;

(17) The peptide-type compound according to item (1) above, which comprises a modified amino acid modified with an ester linkage, or a pharmaceutically acceptable salt thereof;

(18) The peptide-type compound according to item (17) above, which comprises an amino acid to which a fatty acid is bound, or a pharmaceutically acceptable salt thereof;

(19) The peptide-type compound according to item (18) above, which comprises an amino acid to which a fatty acid containing 2 to 35 carbon atoms is bound, or a pharmaceutically acceptable salt thereof;

(20) The peptide-type compound according to item (18) above, wherein the bound fatty acid is caprylic acid, a monoene fatty acid thereof or a polyene fatty acid thereof, or a pharmaceutically acceptable salt thereof;

(21) The peptide-type compound according to item (18) above, wherein the bound fatty acid is capric acid, a monoene fatty acid thereof or a polyene fatty acid thereof, or a pharmaceutically acceptable salt thereof;

(22) The peptide-type compound according to item (18) above, wherein the bound fatty acid is lauric acid, a monoene fatty acid thereof or a polyene fatty acid thereof, or a pharmaceutically acceptable salt thereof;

(23) The peptide-type compound according to items (1) to (22) above, wherein the amino-terminal is modified with a saturated or unsaturated alkyl or acyl group containing one or more carbon atoms, and/or the carboxyl-terminal is OZ or NR2R3 wherein Z is a pharmaceutically acceptable cation or a lower branched or linear alkyl group, and R2 and R3 are the same or different and represent H or a lower branched or linear alkyl group;

(24) A pharmaceutical composition for treatment of diseases attributable to a defect or decrease in growth hormone, which comprises a peptide-type compound described in items (1) to (6) above or a pharmaceutically acceptable salt thereof as an active ingredient;

(25) A pharmaceutical composition for treatment of diseases not attributable to a defect or decrease in growth hormone, which comprises an agent for treating diseases not attributable to a defect or decrease in growth hormone and a peptide-type compound described in items (1) to (6) above or a pharmaceutically acceptable salt thereof;

(26) A pharmaceutical composition according to items (24) to (25), which is applied to animals other than human beings;

(27) A method for treatment of diseases attributable to a defect or decrease in growth hormone, which comprises administering a pharmaceutical composition comprising a peptide-type compound described in items (1) to (6) above or a pharmaceutically acceptable salt thereof as an active ingredient;

(28) A method for treatment of diseases not attributable to a defect or decrease in growth hormone, which comprises administering an agent for treating diseases not attributable to a defect or decrease in growth hormone and a peptide-type compound described in items (1) to (6) above or a pharmaceutically acceptable salt thereof;

(29) The treatment method according to items (27) to (28), which is applied to animals other than human beings;

(30) A DNA for a peptide-type compound described in items (1) to (6), which comprises a DNA sequence coding a peptide having a amino acid sequence recognizing at least one modifiable amino acid in said amino acid sequence;

(31) The cDNA according to item (30) above, which comprises a DNA sequence set forth in SEQ ID NO: 6 (including NCR);

(32) The cDNA according to item (30) above, which comprises a DNA sequence of bases 31 to 381 in a DNA sequence set forth in SEQ ID NO: 6 (not including NCR);

(33) The cDNA according to item (30) above, which comprises a DNA sequence set forth in SEQ ID NO: 7 (including NCR);

(34) The cDNA according to item (30) above, which comprises a DNA sequence of bases 34 to 385 in a DNA sequence set forth in SEQ ID NO: 7 (not including NCR);

(35) A vector comprising a DNA described in items (30) to (34) above;

(36) Cells comprising the vector described in item (35) above;

(37) Cells comprising a vector containing a DNA described in items (30) to (34) above, wherein a peptide-type compound having an amino acid sequence encoded by said DNA can be produced as a peptide-type compound having an amino acid sequence recognizing at least one modifiable amino acid in said amino acid sequence;

(38) An antibody against a peptide-type compound described in items (1) to (23) above;

(39) A method for assaying a peptide-type compound described in items (1) to (23) above, which comprises using the antibody described in item (38) above to detect the peptide-type compound;

(40) A kit for detecting a peptide-type compound described in items (1) to (23) above, which comprises using the antibody described in item (38) above to detect the peptide-type compound;

(41) A method for producing a peptide-type compound described in items (1) to (6) above by genetic recombination technology, which comprises transforming a vector containing a DNA described in item (30) above into host cells capable of modifying a side chain of at least one amino acid in said peptide, then culturing the resulting transformed cells and recovering the desired peptide-type compound from the culture;

(42) A method for producing a peptide-type compound described in items (1) to (6) above by genetic recombination technology, which comprises transforming a vector containing a DNA described in item (30) above into host cells, then culturing the resulting transformed cells and recovering the desired peptide-type compound from the culture, followed by chemically modifying an arbitrary amino acid thereof;

(43) A method for producing a peptide-type compound described in items (18) to (22) above by genetic recombination technology, which comprises using cells enabling the peptide-type compound to be produced as a peptide having a fatty acid bound to a serine residue in the amino acid sequence set forth in SEQ ID NO: 1;

(44) A method for producing a peptide-type compound having the activity of increasing the intracellular calcium ion concentration and the activity of secreting growth hormone, which comprises transforming a vector containing a DNA coding a peptide-type compound described in items (7) to (13) above into host cells, culturing the resulting transformed cells and recovering the desired compound from the culture;

(45) A pharmaceutical composition for gene therapy for treatment of diseases attributable to a defect or decrease in growth hormone, which comprises integrating a vector containing a DNA coding an amino acid sequence of a peptide-type compound described in items (1) to (6) above into cells in a living body and expressing a peptide with at least one modified amino acid, the peptide having the activity of increasing the intracellular calcium ion concentration;

(46) A method for treatment of diseases attributable to a defect or decrease in growth hormone, which comprises integrating a vector containing a DNA coding an amino acid sequence of a peptide-type compound described in items (1) to (6) above into cells in a living body enabling a peptide having an amino acid sequence encoded by said DNA to be produced as a peptide having an amino acid sequence recognizing at least one modifiable amino acid in said amino acid sequence, whereby a peptide having the activity of inducing growth hormone is expressed;

(47) A pharmaceutical composition for gene therapy for treatment of diseases not attributable to a defect or decrease in growth hormone, which comprises integrating a vector containing a DNA coding an amino acid sequence of a peptide-type compound described in items (1) to (6) above into cells in a living body and expressing a peptide with at least one modified amino acid having the activity of increasing the intracellular calcium ion concentration;

(48) A method for treatment of diseases not attributable to a defect or decrease in growth hormone, which comprises integrating a vector containing a DNA coding an amino acid sequence of a peptide-type compound described in items (1) to (6) above into cells in a living body enabling a peptide having an amino acid sequence encoded by said DNA to be produced as a peptide having an amino acid sequence recognizing at least one modifiable amino acid in said amino acid sequence, whereby a peptide having the activity of inducing growth hormone is expressed.

In the present invention, the amino acid encompasses every amino acid such as L-amino acid, D-amino acid, α-amino acid, β-amino acid, γ-amino acid, natural amino acid and synthetic amino acid or the like.

In the present invention, the modified amino acid refers to an amino acid wherein an arbitrary group thereof is chemically modified. In particular, a modified amino acid chemically modified at the α-carbon atom in an α-amino acid is preferable. That is, when the α-amino acid is represented by formula (1):

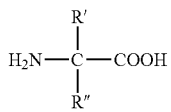

R' and R" in the chemically modified amino acid may be H or an arbitrary group; in short, the modified amino acid may be any chemically modified natural amino acid. Either R' or R" may also be H.

An amino acid wherein as the substituent group represented by R' and R", a substituent group present in the natural amino acid is replaced by a substituent group not present in the natural amino acid or in its corresponding D-amino acid is referred to as the modified amino acid.

When the naturally occurring amino acid contains e.g. —OH, —SH, —NH or —NH$_2$ as a substituent group in a side chain thereof, a group formed by acylating such a substituent group is mentioned as a preferable example of the substituent group mentioned above.

The acyl group therefor includes e.g. groups formed by removing a hydroxyl group from an organic carboxylic acid, organic sulfonic acid and organic phosphoric acid.

The organic carboxylic acid includes e.g. fatty acids, and the number of carbon atoms thereof is preferably 2 to 35, more preferably 6 to 18 and most preferably 8 to 16. Such fatty acids include e.g. octanoic acid (preferably caprylic acid), decanoic acid (preferably capric acid), and dodecanoic acid (preferably lauric acid), as well as monoene or polyene fatty acids thereof.

In the organic sulfonic acid or organic phosphoric acid, the number of carbon atoms thereof is preferably 2 to 35.

Further, the modified amino acid may be an amino acid wherein the group represented by R' and/or R" is replaced, for example, by:

—(CH$_2$)$_n$—P-Q (wherein n is an integer of 0 to 10, P is —CO—O—, —O—CO—, —O—, —CO—S—, —CS—S—, —S—CO—, —S—, —CO—NH—, —NH—CO— or —CO—NH—CO—, Q is H or C$_{1-35}$ preferably C$_{1-20}$ alkyl.) Further, P may be —CO—.

In addition, P may be —S—S— or —NH—CS—. In every —NH— described above, H may be replaced by a C$_{1-35}$ saturated or unsaturated alkyl group, a C$_{6-20}$ aryl group, or a C$_{7-13}$ aralkyl group.

In the case where the α-amino acid is represented by the formula (1) above, the modified amino acid wherein R' or R" is replaced by the above group —(CH$_2$)$_n$—P-Q is a preferable embodiment. In particular, said modified amino acid is preferably modified serine wherein a substituent group represented by the above formula —(CH$_2$)$_n$—P-Q is bound to the α-carbon of serine, as shown in the formula:

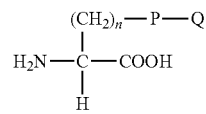

wherein n, P and Q have the same meanings as defined above.

The mode of linkage selected from the group consisting of ester, ether, thioester, thioether, amide and carbamide via or not via an alkyl group containing one or more carbon atoms is described in more detail.

For example, if the amino acid is serine, threonine, tyrosine or oxyproline, the amino acid has a hydroxyl group in the side chain. If the amino acid is cysteine, the amino acid has a mercapto group in the side chain. If the amino acid is lysine, arginine, histidine, tryptophan, proline or oxyproline, it has an amino group or imino group in the side chain.

The hydroxyl group, mercapto group, amino group and imino group described above may have been chemically modified. That is, the hydroxyl group or mercapto group may be etherized, esterified, thioetherified or thioesterified. The imino group may have been iminoetherified, iminothioetherified or alkylated. The amino group may have been amidated, thioamidated or carbamidated.

Further, the mercapto group may have been disulfidated, the imino group may have been amidated or thioamidated, and the amino group may have been alkylated or thiocarbamidated.

The thus chemically modified hydroxyl group or mercapto group can be represented for example by:

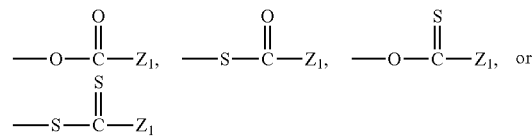

The amidated or thioamidated amino group or imino group can be represented by:

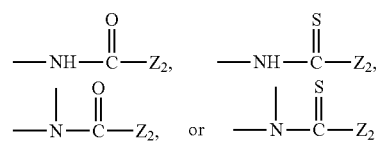

The etherified hydroxyl group or mercapto group can be represented by:

—O—Z$_3$, or

—S—Z$_3$

The iminoetherified or iminothioetherified imino group can be represented by:

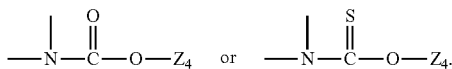

The alkylated amino group can be represented by:

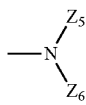

The alkylated imino group can be represented by:

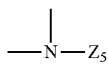

The carbamidated or thiocarbamidated imino group can be represented by:

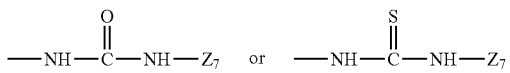

The disulfidated mercapto group can be represented by: 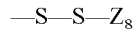

In the formulae above, $Z_1$, $Z_2$, $Z_3$, $Z_4$, $Z_5$, $Z_6$, $Z_7$ and $Z_8$ may be any substituent groups for chemical modification insofar as they are not against the sprit of the present invention, but because substituent groups used conventionally in a pharmaceutical field or for chemical modification of peptides are well known in patent literatures or scientific literatures, such known substituent groups for modification can be used and according to such known methods, chemical modification can be performed in the present invention.

In the above formulae, $Z_1$ may be a hydrogen atom or a linear-chain, branched or cyclic alkyl group, and such alkyl group may be saturated or unsaturated. The number of carbon atoms thereof is usually $C_{1-50}$, preferably $C_{6-20}$.

$Z_2$, $Z_3$, $Z_4$, $Z_5$, $Z_6$, $Z_7$ or $Z_8$ may be a hydrogen atom or a straight-chain, branched or cyclic alkyl group, and such alkyl group may be saturated or unsaturated. The number of carbon atoms thereof is usually $C_{1-10}$, preferably $C_{1-6}$.

The alkyl groups represented by $Z_1$, $Z_2$, $Z_3$, $Z_4$, $Z_5$, $Z_6$, $Z_7$, or $Z_8$ may be substituted with substituent groups such as hydroxyl group, amino group, halogen, nitro and $C_{1-3}$ alkoxy group, which are used conventionally for chemical modification of peptides.

In the above, if $Z_1$—CO— is a residue of the fatty acid $Z_1$—COOH, this is one example of the amino acid to which the fatty acid was bound. The fatty acid in this case includes e.g. saturated fatty acid such as caprylic acid, capric acid, lauric acid, butyric acid, caproic acid, undecylic acid, palmitic acid, decanoic acid, nonadecanoic acid, behenic acid, montanic acid and lacceric acid and unsaturated fatty acid such as acrylic acid, oleic acid, linolic acid, linolenic acid and aatearolic acid. The unsaturated fatty acid may be a monoene or a polyene.

Further, the modified amino acid may also be an α-amino acid formed by replacing a group (excluding a carboxyl group and an amino group constituting a peptide linkage) binding to the α-carbon atom of the α-amino acid by a hydrogen atom or a saturated or unsaturated alkyl group.

In the present invention, the modified amino acid may also be an amino acid formed by introducing a $C_{1-6}$ saturated or unsaturated alkyl group onto the amino group of the amino acid.

The non-natural amino acid in the present invention is the one having amino group and carboxyl group in both terminals of the molecule, and includes e.g. $NH_2$—$(CH_2)_3$CH($CH_2$OH)—COOH, $NH_2$—$(CH_2)_4$—COOH, $NH_2$—C($CH_3)_2$—$(CH_2)_3$—COOH, and $NH_2$—CH($CH_3$)—$(CH_2)_2$—CH($CH_3$)—COOH. The length of their molecular chain corresponds to the length of a dipeptide, but the non-natural amino acid in the present invention also includes those having the length of a peptide.

Further, the non-amino acid compound in the present invention includes e.g. $NH_2$—CH($CH_2$OH)—$CH_3$, $CH_3$—CH(R)—COOH, $CH_3$—CH(R)—$CH_3$ wherein the length of their molecule corresponds to the length of a peptide, or $NH_2$—$(CH_2)_3$CH($CH_2$OH)—$CH_3$ and $NH_2$—$(CH_2)_3$CH(R)—$CH_3$ wherein the length of their molecule corresponds to the length of a dipeptide.

Here, R represents a substituent group on a side chain of the natural amino acid or on the α-carbon in the aforementioned modified amino acid.

BRIEF DESCRIPTION OF DRAWINGS

FIG. 1a shows a profile in Sephadex G-50 (fine) gel filtration of an SP-III fraction prepared from 40 g rat stomach, to indicate that the molecular weight of the active fractions is about 3,000 Dalton. FIG. 1b is a graph shows a profile in secondary CM ion-exchange HPLC, and the active fractions eluted at retention times of 55 to 56 minutes were further purified by reversed-phase HPLC.

FIG. 2a shows the result of analysis of 2 μg each of natural ghrelin (upper) and synthetic ghrelin and synthetic de-acylated ghrelin (lower) by reversed-phase HPLC. FIG. 2b is a graph showing changes in the intracellular calcium ion concentration in CHO-GHSR62 cells by natural ghrelin (solid line), synthetic ghrelin (small broken line) and synthetic de-acylated ghrelin (large solid line). FIG. 2c shows ghrelin modified with N-octanoyl (SEQ ID NO: 2).

FIG. 3a is a graph showing changes in the intracellular calcium ion concentration in CHO-GHSR62 cells by ghrelin, GHRP-6 and GRF (GHRH), respectively. Fig. b is a graph showing changes in the intracellular calcium ion concentration in CHO-GHSR62 cells by ghrelin in the presence (○) or absence (●) of [D-Lys-3]-GRP-6, and a change in the intracellular calcium ion concentration by GRF (GHRH) (black triangle) is also shown.

FIG. 4a shows comparison between the amino acid sequences of rat- and human-derived ghrelin precursors (SEQ ID NO:4 and SEQ ID NO:5, respectively), where the same amino acid is shaded, a signal peptide is indicated by the broken line, a cleavage site of the signal peptide is indicated by the shaded triangle, a cleavage site at the side of carboxyl-terminal is indicated by the triangle, a matured ghrelin moiety is boxed, and a modification with n-octanoic acid is indicated by *. FIG. 4b shows the analysis result of expression of ghrelin in a wide variety of rat tissues by Northern blotting.

FIG. 5a is a graph showing a change in fluorescence intensity by a change in the intracellular calcium ion concentration in rat pituitary cultured cells at an initial stage, where the change upon addition of ghrelin is indicated by the solid line and the change upon addition of de-acylated ghrelin by the broken line. FIG. 5b is a graph showing the secretion of pituitary hormones, where the black bar and white bar show the concentrations of pituitary hormone levels in the presence and absence of ghrelin, respectively. FIG. 5c is a graph showing a time course of pituitary hormone concentration in plasma after ghrelin was injected intravenously to male rats. In FIGS. 5b and 5c, GH is growth hormone, ACTH is adrenocorticotropin, FSH is follicle-stimulating hormone, LH is luteinizing hormone, PRL is prolactin, and TSH is thyroid-stimulating hormone.

FIG. 6a shows that the error range for the effect of ghrelin is less than 0.0001.

FIG. 8A shows typical waves of stomach motility upon administration of physiological saline and rat ghrelin (rGhrelin), and Fig. B is a graph showing an average value from 4 rats along with the standard error. At the arrowed point, the drug was administered.

FIG. 9a is a graph showing the binding inhibition, by various ghrelins, of $^{125}$I-labeled rat ghrelin to an antibody against a amino-terminal ghrelin fragment, and FIG. 9b is a graph showing the binding inhibition, by various ghrelins, of $^{125}$I-labeled rat ghrelin to an antibody against a carboxyl-terminal ghrelin fragment. The amount of various ghrelins/reaction tube is shown on the abscissa, while the ratio (%) of the amount (B) of rat ghrelin bound in the presence of various ghrelins to the amount thereof ($B_0$) in the absence of various ghrelins is shown on the ordinate. Symbols in the graphs are as follows: Rat ghrelin (○); human ghrelin (●); rat ghrelin-27 (□); [Ser3 (decanoyl)]-rat ghrelin (◇); [Ser3 (hexanoyl)]-rat ghrelin (Δ); and de-fatty acid rat ghrelin (▼).

BEST MODE FOR CARRYING OUT THE INVENTION

Figure 1:
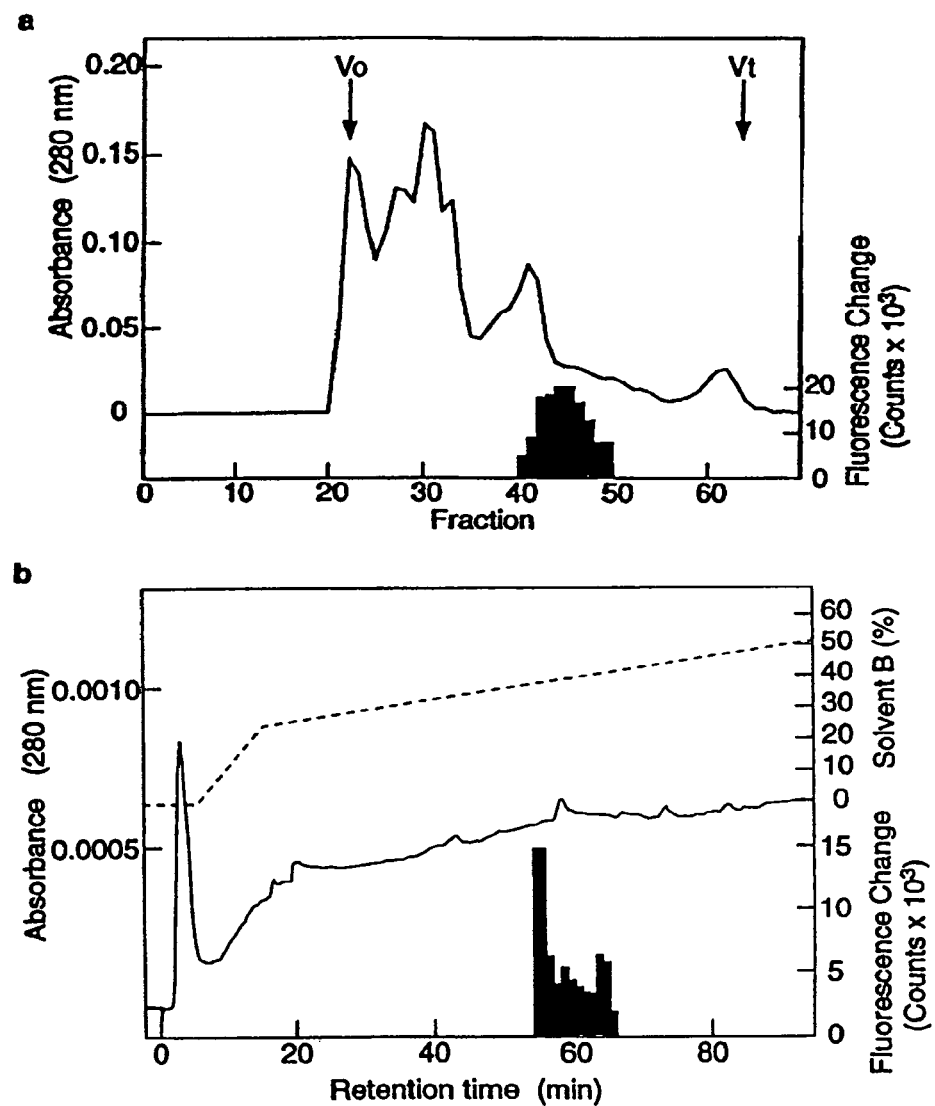
FIG. 1 shows purification of ghrelin from rat stomach extract, and the change in fluorescence intensity by an increase in the intracellular calcium ion concentration in CHO-GHSR62 cells is shown by the black bar.

For a peptide serving as an endogenous ligand for GHS receptor (GHS-R), the distribution of the endogenous ligand in organs or tissues can be known by adding an extract from various organs or tissues to cells expressing GHS-R and measuring the intracellular calcium ion concentration.

The cells expressing GHS-R include strains derived from the hypothalamus and pituitary gland known to express GHS-R constantly and their tissues, but the cells are preferably those transformed cells having GHS-R gene introduced into suitable cells such as CHO cells, and expressing the gene.

The strong Ca-releasing activity of the endogenous GHS peptide of the present invention was found not in the hypothalamus and pituitary gland expressing the peptide, but in an extract from stomach as an organ in the digestive organ system. It is therefore necessary to examine not only tissues and organs expressing said receptor but also a wide variety of other tissues and organs in order to find the desired endogenous ligand for the orphan receptor.

The intracellular calcium ion concentration can be measured by any method known in the art, preferably by means of FLIPR (Fluorometric Imaging Plate Reader, Molecular Devices Co., Ltd.) utilizing the change in the fluorescent intensity of Fluo-4 AM (Molecular Probe Co., Ltd.) caused by a change in the concentration of calcium ions.

To obtain the desired endogenous GHS peptide from tissues and organs confirmed to exhibit the Ca-releasing activity, any purification method known in the art can be used.

As the method of purifying the peptide, it is effective to use a combination of gel filtration, ion exchange and reversed-phase chromatographic techniques after a wide variety of fractionation methods or use them separately, but it is possible to use not only such chromatographic techniques but also any means effective for purification of the peptide.

For isolation and purification of the peptide from the tissues and organs, inactivation of proteases in the tissues and organs by heat treatment thereof in boiling water is desired to prevent degradation of the desired peptide by the action of the proteases. Heat treatment and removal of the tissues and organs under cooling on ice are also effective for extraction and purification of the desired peptide.

To confirm that the purified peptide having the Ca-releasing activity has a GH secretion-inducing activity in vitro and in vivo, a known method can be utilized.

For example, GH secreted into a medium of pituitary grand cell culture confirmed to secrete GH and express GHS-R can be measured in vitro in radioimmunoassays by adding anti-GH antibody to the cells. By using an antibody against other hormone in place of the anti-GH antibody in radioimmunoassays, the amount of said hormone secreted can also be measured.

Further, the GH secretion-inducing activity in vivo can be confirmed by injecting the peptide having the Ca-releasing activity into a peripheral vein of an animal and then measuring the concentration of GH in serum.

For analyzing the structure of the purified peptide, a known method can be used.

For determining the amino acid sequence of the peptide, there is a method wherein amino acid residues are released sequentially from the carboxyl-terminal by Edman degradation followed by identification of the released amino acids by high performance liquid chromatography (HPLC), as well as an automated version thereof by an amino acid sequencer.

There is also a method for determining the amino acid sequence thereof by measuring the molecular weights of ionized fragments thereof by GC-MASS.

For the peptide containing modified amino acids in one aspect of the present invention, the modified amino acid is identified as "unknown amino acid" upon determination of the amino acid sequence.

In this case, the modified peptide is decomposed into amino acid units from which the modified amino acid is separated and purified, and the structure of the modified amino acid is determined in a usual manner for determining the structure of the compound, whereby the entire structure of the peptide can be known. Alternatively, there is a method wherein the peptide is obtained from a cDNA coding the modified peptide, then a peptide having the amino acid sequence of the resulting peptide is chemically synthesized, and the molecular weight and physical properties of the synthetic unmodified peptide are compared with those of the modified peptide in order to estimate the structure of the modified group.

A partial amino acid sequence (core sequence) which in the peptide thus structurally determined, is essential for the Ca-releasing activity is revealed by measuring the Ca-releasing activity of each peptide fragment formed by cleaving said peptide with a protease.

The used protease shall be a protease highly specific to the amino acid sequence of the peptide to be cleaved, but a low specific protease can also be used under conditions for partial digestion to prepare various peptide fragments from said peptide.

By measuring the Ca-releasing activity of each peptide fragment thus prepared, a core sequence essential for the Ca-releasing activity can be known.

In the endogenous GH secretion-inducing peptide, serine 3 from the amino-terminal has been acylated with a fatty acid, and it is also possible to chemically be synthesized a peptide fragment having a part of the amino acid sequence of the endogenous GH secretion-inducing peptide, as well as a fatty acid-modified peptide comprising a fatty acid bound via an ester linkage to the serine side chain in said peptide fragment.

Using said peptide fragment, the endogenous GH secretion-inducing peptide can be analyzed in detail. Simultaneously, the type of fatty acid necessary for the Ca-releasing activity can be determined by comparing the peptide fragments modified with various fatty acids.

For example, in the endogenous GH secretion-inducing peptide derived from some species of *Xenopus Laevis*, an amino acid residue at the 3rd position from the amino-terminal is not serine but threonine, and such threonine has been acylated with a fatty acid, and this peptide-type compound can also be synthesized and said compound can be analyzed in detail.

By comparing the amino acid sequences of those peptides having a GH secretion-inducing activity in vertebrates, a region preserved widely in vertebrates can be found, and from the amino acid sequence of said region, a core sequence essential for the GH secretion-inducing activity can be found.

A DNA having a nucleotide sequence deduced from the amino acid sequence of the endogenous GH secretion-inducing peptide is chemically synthesized, and this DNA is used as a probe for screening a cDNA library prepared from mRNA in cells expressing said peptide, whereby a cDNA coding said peptide can be obtained.

However, a codon corresponding to an amino acid is degenerated thus increasing the number of nucleotide sequences deduced from the amino acid sequence of the peptide, so that the screening by using a certain synthetic DNA consisting of various types of such nucleotide sequences as a probe can be difficult.

In this case, if a sequence in accordance with the amino acid sequence of said peptide is present in amino acid sequences deduced from the nucleotide sequence of an expressed sequence tag (EST) disclosed in a sequence data base, a DNA consisting of a part of the nucleotide sequence of the EST can be synthesized and used to screen the above cDNA library.

Further, a genomic DNA can be obtained in a usual manner from the cDNA.

From the nucleotide sequence of the cDNA thus obtained, the amino acid sequence of a precursor polypeptide of the endogenous GH secretion-inducing peptide is revealed.

By analyzing said amino acid sequence, a signal peptide, the endogenous GH secretion-inducing peptide, other peptide moieties and cleavage sites of these peptides are revealed, thus revealing the mechanism of formation of the endogenous GH secretion-inducing peptide.

Other aspects of the present invention, that is, a partial amino acid sequence of the endogenous GH secretion-inducing peptide, the amino acid sequence of a precursor polypeptide of said peptide, and the nucleotide sequence of a DNA coding said polypeptide are disclosed in International Appln. Disclosure WO 98/42840, but the peptide disclosed therein is a peptide consisting of 14 amino acids having a motilin-like activity, and there is no description therein of the activity of increasing Ca concentration and the activity of inducing GH secretion disclosed in the present invention.

The peptide-type compound of the present invention refers to a peptide having the activity of increasing the intracellular calcium ion concentration, which is represented by formula (2) below wherein at least one amino acid is replaced by a modified amino acid; a peptide analogue thereof wherein at least one amino acid is replaced by a non-amino acid; and a peptide derivative thereof wherein amino-terminal and/or carboxyl-terminal is modified.

In the present invention, the peptide, peptide analogue and peptide derivative described above are referred to collectively as the peptide-type compound.

In the peptide-type compound, a plurality of amino acids may be replaced by modified amino acids and/or non-amino acids. In the amino acid sequence set forth in SEQ ID No:2, it is preferable in the present invention that usually one or more amino acids of amino acids 1 to 10 from the amino-terminal, preferably amino acids 1 to 4 or amino acids 1 to 5 from the amino-terminal are replaced by modified amino acids and/or non-amino acids. It is particularly preferable that amino acids 1 to 5 are replaced by modified amino acids and/or non-amino acids.

In the amino acid sequence set forth in SEQ ID NO: 2, one or more amino acids outside of amino acids 1 to 4, preferably amino acids 1 to 6 and more preferably amino acids 1 to 10 from the amino-terminal may be added or deleted.

The peptide-type compound of the present invention is preferably a peptide compound which has the activity of increasing the intracellular calcium ion concentration and induces secretion of growth hormone in vivo, wherein at least one amino acid is replaced by a modified amino acid and/or a non-amino acid compound.

That is, the peptide-type compound of the present invention is a peptide-type compound having the activity of increasing the intracellular calcium ion concentration and/or the action of inducing secretion of growth hormone in vivo, wherein an amino acid in the peptide chain is replaced by a modified amino acid and/or a non-amino acid compound.

Examples of the compound include those compounds wherein in the peptide shown in SEQ ID NO: 1, 2 or 3, a hydroxyl group of the amino acid Ser 3 is acylated, those compounds wherein in the peptide shown in SEQ ID NO: 4 or 5, a hydroxyl group of the amino acid Ser 25 is acylated, or pharmaceutically acceptable salts thereof.

Other examples include those compounds wherein in the peptide shown in SEQ ID NO: 10, 11, 16 or 17, a hydroxyl group of the amino acid Ser 3 is acylated, or pharmaceutically acceptable salts thereof.

Still other examples include those compounds wherein in the peptide shown in SEQ ID NO: 22, 25, 26 or 27, a hydroxyl group of the amino acid Ser 3 is acylated, or pharmaceutically acceptable salts thereof.

Still other examples include those compounds wherein in the peptide shown in SEQ ID NO: 29, 30 or 31, a hydroxyl group of the amino acid Ser 3 is acylated, or pharmaceutically acceptable salts thereof.

Still other examples include those compounds wherein in the peptide shown in SEQ ID NO: 28, a hydroxyl group of the amino acid Thr 3 is acylated, or pharmaceutically acceptable salts thereof.

The acyl group introduced into a hydroxyl group by acylation in the present invention is a group formed by removing a hydroxyl group from e.g. an organic carboxylic acid, an organic sulfonic acid or an organic phosphoric acid.

The organic carboxylic acid includes e.g. fatty acids, and the number of carbon atoms thereof is preferably about 2 to 35, more preferably about 6 to 18, and most preferably about 8 to 16. Such fatty acids include e.g. octanoic acid (preferably caprylic acid), decanoic acid (preferably capric acid), and dodecanoic acid (preferably laurylic acid [sic: lauric acid]), as well as their monoene or polyene fatty acids thereof.

In the organic sulfonic acid or organic phosphoric acid, the number of carbon atoms thereof is preferably about 2 to 35.

Any peptide-type compounds or pharmaceutically acceptable salts thereof, including the amino acid sequence set forth in SEQ ID NO: 1 wherein a hydroxyl group of Ser 3 is acylated, are also preferable embodiments of the present invention.

That is, in the second aspect of the present invention, any peptide-type compounds or pharmaceutically acceptable salts thereof, including fatty acid-modified peptides wherein a hydroxyl group of Ser 3 is acylated in the amino acid sequence set forth in SEQ ID NO: 8, preferably the amino acid sequence set forth in SEQ ID NO: 1 and more preferably the amino acid sequence set forth in SEQ ID NO: 9, are also preferable embodiments of the present invention.

Further, any peptide compounds or pharmaceutically acceptable salts thereof, including fatty acid-modified peptides wherein a hydroxyl group of Thr 3 is acylated in the amino acid sequence set forth in SEQ ID NO: 8, preferably the amino acid sequence set forth in SEQ ID NO: 1 and more preferably an amino acid sequence wherein in the amino acid sequence set forth in SEQ ID NO: 9, the amino acid residue serine at the 3rd position from the amino-terminal is converted into threonine, are also preferable embodiments of the present invention.

Further, a preferable embodiment of the present invention is a compound or pharmaceutically acceptable salts represented by formula (2):

X-AA1-AA2-AA3-Y    (2)

wherein X is a moiety corresponding to a hydrogen atom in an amino group of the amino-terminal amino acid and represents H or a saturated or unsaturated alkyl or acyl group containing one or more carbon atoms; Y is a moiety corresponding to a hydroxyl group in an α-carboxyl group of the carboxyl-terminal amino acid and represents OH, OZ or NR6R7 whereupon Z is a pharmaceutically acceptable cation or a lower branched or linear alkyl group; and R6 and R7 may be the same or different and represent H or a lower branched or linear alkyl group.

Here, AA1 represents:

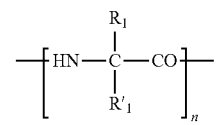

wherein n is 1 or 2, $R_1$ and $R_1'$ may be the same or different and represent hydrogen or a substituent group, provided that when n is 2, the two substituent groups $R_1$ may be the same or different; this also applies to $R_1'$.

Examples of the substituent group include (1) a saturated or unsaturated alkyl chain containing one or more carbon atoms which binds in a mode of linkage selected from the group consisting of ester, ether, thioester, thioether, amide and carbamide via or not via an alkyl chain containing one or more carbon atoms, (2) H or a saturated or unsaturated alkyl chain containing one or more carbon atoms, and (3) a side chain of natural amino acid.

Further, the substituent group may be a saturated or unsaturated alkyl chain containing one or more carbon atoms, which is bound via a disulfide or thiocarbamide linkage via or not via an alkyl chain containing one or more carbon atoms.

AA2 represents:

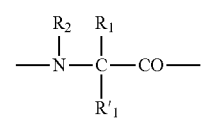

wherein $R_1$ and $R_1'$ have the same meanings as defined above, and $R_2$ represents H or a saturated or unsaturated alkyl group containing 1 to 6 carbon atoms, or AA2 represents —$CH_2$—$CH(R_1)$—$CH_2$— or —$CH_2$—$CH(R_1)$—CO— whereupon $R_1$ has the same meaning as defined above.

AA3 represents:

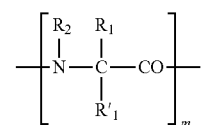

wherein m is an integer of 1 or more, and $R_1$, $R_1'$ and $R_2$ have the same meanings as defined above, provided that when m is an integer of 2 or more, the two substituent groups $R_1$ may be the same or different; this also applies to $R_1'$ and $R_2$.

The saturated or unsaturated alkyl containing one or more carbon atoms, which is represented by X, is preferably $C_{1-20}$ alkyl such as methyl, ethyl, n-propyl, i-propyl, n-butyl, s-butyl, t-butyl, n-heptyl, n-hexyl, n-decyl, vinyl, propanyl or hexenyl.

The acyl represented by X includes $C_{2-10}$ carboxylic acid acyl such as formyl, acetyl, propionyl or benzoyl; or $C_{7-13}$ sulfonic acid acyl such as benzenesulfonyl naphthalene sulfonyl or the like.

The group represented by $R_1$ or $R_1'$ is preferably a group represented by e.g. formula (2):

(wherein n is an integer of 0 to 10, P is —CO—O—, —O—CO—, —O—, —CO—S—, —CS—S—, —S—CO—, —S—, —CO—NH—, —NH—CO— or —CO—NH—CO—, Q is H or $C_{1-20}$ alkyl represented by X described above.) Further, P may also be —CO—.

In addition, P may be —S—S— or —NH—CS—. In every —NH— described above, H may be replaced by a $C_{1-25}$ saturated or unsaturated alkyl group, a $C_{6-20}$ aryl group, or a $C_{7-23}$ aralkyl group.

More preferably, P is:
—CO—O—, —CO—, —O—, —S—, —S—S—, —CO—S—, —CO—NH—, —NH—CO— or —NH—CS—.

The group represented by $R_1$ or $R_1'$ may be a group having Q bound to —$(CH_2)_n$ directly not via P.

It is preferable that the lower alkyl group represented by Z, R6 or R7 is $C_{2-6}$ alkyl such as methyl, ethyl, n-propyl, i-propyl, n-butyl, s-butyl, t-butyl, i-butyl, n-pentyl or n-hexyl.

Hereinafter, preferable embodiments of the peptide compounds according to the present invention are described.
(1) Preferable embodiments of AA1: (A) amino acids or peptides such as Ser, Gly-Ser or —NH—$(CH_2)_3$CH$(CH_2OH)$CO— where a peptide linkage moiety between two amino acid residues is —$(CH_2)_2$— and (B) primary amines, for example —NH— $(CH_2)_3$CH$(CH_2OH)CH_2$— where a peptide linkage moiety between two amino acids is —$(CH_2)_2$—; —NH— $(CH_2)_3$CH$(R_1)CH_2$— where a peptide linkage moiety between two amino acids is —$(CH_2)_2$—, wherein $R_1$, has the same meanings as defined above; and —NH—CH$(CH_2OH)CH_2$—.

As (A) amino acids or peptides, $NH_2$—$(CH_2)_4$—COOH, $NH_2$—$C(CH_3)_2$—$(CH_2)_3$—COOH and $NH_2$—CH$(CH_3)$—$(CH_2)_2$—CH$(CH_3)$—COOH— can also be exemplified
(2) Preferable embodiments of AA2: (A) amino acids such as Ser, homoSer, Cys, homoCys, Asp, Glu, Lys, Ala, Val, Leu, homoLeu, Ile, homoIle, ornithine, aminoadipic acid, methionine, ethionine, butionine, and S-methyl cysteine, among which Ser is particularly preferable, and (B) structures other than amino acid residues; for example, there can be mentioned —$CH_2$—CH$(R_1)$—CO—, —$CH_2$—CH$(R_3)$—$CH_2$—, etc. wherein $R_1$ has the same meanings as defined above.

In particular, amino acids (a) with a hydrophobic side chain, such as leucine, valine, norleucine, homoleucine, homoisoleucine, naphthyl alanine or its analogues thereof, tryptophan, phenylalanine, cyclohexylalanine etc. or N-methylamino acids thereof are preferable. Further, amino acids (b) with a side chain having a functional group capable of modification with acyl group, alkyl group, alkenyl group or aralkyl group, such as serine, homoserine, threonine, cysteine, homocysteine, aspartic acid, glutamic acid, adipic acid, lysine, ornithine etc. and N-methylamino acids thereof are preferable.

An acyl group, alkyl group, alkenyl group or aralkyl group etc. are bound to side chains of the amino acids (b) via an ester, amide, disulfide, ether, thioether, thioester, carbamide or thiocarbamide linkage. Further, an alkyl or aralkyl group may be bound to the α-carbon of the amino acid.
(3) Preferable embodiments of AA3: Amino acids or peptides such as Phe or a peptide having an amino acid sequence of from Phe at the 4th position to Arg at the 28th position from the amino-terminal in the amino acid sequence set forth in SEQ ID NO: 2 or 3, or peptides having an amino acid sequence wherein in the amino acid sequence set forth in SEQ ID NO: 2 or 3, one amino acid is sequentially deleted starting from the carboxyl-terminal amino acid until Leu at the 5th position from the amino-terminal. For example, AA3 includes:

```
Phe Leu,

Phe Leu Ser,

Phe Leu Ser Pro,

Phe Leu Ser Pro Glu,

Phe Leu Ser Pro Glu His,

Phe Leu Ser Pro Glu His Gln,

Phe Leu Ser Pro Glu His Gln Arg,

Phe Leu Ser Pro Glu His Gln Lys Ala,

Phe Leu Ser Pro Glu His Gln Lys Ala Gln,

Phe Leu Ser Pro Glu His Gln Lys Ala Gln Gln,

Phe Leu Ser Pro Glu His Gln Lys Ala Gln Gln Arg,

Phe Leu Ser Pro Glu His Gln Lys Ala Gln Gln Arg Lys,

Phe Leu Ser Pro Glu His Gln Lys Ala Gln Gln Arg Lys Glu,

Phe Leu Ser Pro Glu His Gln Lys Ala Gln Gln Arg Lys Glu Ser,

Phe Leu Ser Pro Glu His Gln Lys Ala Gln Gln Arg Lys Glu Ser Lys,

Phe Leu Ser Pro Glu His Gln Lys Ala Gln Gln Arg Lys Glu Ser Lys Lys,
```

-continued

```
Phe Leu Ser Pro Glu His Gln Lys Ala Gln Gln Arg Lys Glu Ser Lys

Lys Pro,

Phe Leu Ser Pro Glu His Gln Lys Ala Gln Gln Arg Lys Glu Ser Lys

Lys Pro Pro,

Phe Leu Ser Pro Glu His Gln Lys Ala Gln Gln Arg Lys Glu Ser Lys

Lys Pro Pro Ala,

Phe Leu Ser Pro Glu His Gln Lys Ala Gln Gln Arg Lys Glu Ser Lys

Lys Pro Pro Ala Lys,

Phe Leu Ser Pro Glu His Gln Lys Ala Gln Gln Arg Lys Glu Ser Lys

Lys Pro Pro Ala Lys Leu,

Phe Leu Ser Pro Glu His Gln Lys Ala Gln Gln Arg Lys Glu Ser Lys

Lys Pro Pro Ala Lys Leu Gln,

Phe Leu Ser Pro Glu His Gln Lys Ala Gln Gln Arg Lys Glu Ser

Lys Lys Pro Pro Ala Lys Leu Gln Pro,
and

Phe Leu Ser Pro Glu His Gln Lys Ala Gln Gln Arg Lys Glu Ser Lys

Lys Pro Pro Ala Lys Leu Gln Pro Arg.
```

As a matter of course, the amino acids exemplified as AA3 may be L-amino acids or D-amino acids. Further, in the amino acid sequences exemplified as AA3, one to several amino acids (preferably up to about ⅓ of the amino acid sequence) may be replaced by non-natural amino acid units or non-amino acid units, for example:
—NH—(CH$_2$)$_3$CH(CH$_2$OH)—
—NH—(CH$_2$)$_3$CH(CH$_2$OH)CO—
—NH—CH(CH$_2$OH)CH$_2$—
—NH—(CH$_2$)$_3$CH(R$_1$)CH$_2$—
—CH$_2$—CH(R$_1$)—CO—, or
—CH$_2$—CH(R$_1$)—CH$_2$— wherein R$_1$ has the same meanings as defined above. When AA3 contains a plurality of groups represented by the above formulae and a plurality of groups represented by R$_1$, these groups are the same or different.

Further, any amino acids exemplified as AA3 may have substituent groups represented by R$_1$ described above. When a plurality of R$_1$ groups are present in a group represented by AA3, these R$_1$ groups may be the same or different.

When amino acids constituting the peptide have hydroxyl group, mercapto group, imino group or amino group in their side chains, preferable examples of such side chains are shown below. In the following examples, R8 is a saturated or unsaturated alkyl group containing one or more carbon atoms. Such alkyl chain may have the same meanings as defined for the above-described alkyl chain shown by X.

A) Side chain of Ser; —CH$_2$—O—CO—R8 or —CH$_2$—O—R8,
B) Side chain of homoSer; —CH$_2$—CH$_2$—O—CO—R8 or —CH$_2$—CH$_2$—O—R8,
C) Side chain of Cys; —CH$_2$—S—CO—R8 or —CH$_2$—S—R8,
D) Side chain of homoCys; —CH$_2$—CH$_2$—S—CO—R8 or —CH$_2$—CH$_2$—S—R8,
E) Side chain of Asp; —CH$_2$—COO—R8 or —CH$_2$—CO—NH—R8,
F) Side chain of Glu; —CH$_2$—CH$_2$—COO—R8 or —CH$_2$—CH$_2$—CO—NH—R8
G) Side chain of Lys; —(CH$_2$)$_4$—NH—CO—R8,
H) Side chain of aminoadipic acid; —CH$_2$—CH$_2$—CH$_2$—COO—R8 or CH$_2$—CH$_2$—CH$_2$—CO—NH—R8,
I) Side chain of ornithine; —(CH$_2$)$_3$—NH—CO—R8.
J) An alkyl side-chain in an amino acid such as Ala, Val, Leu, homoleucine, Ile, homoisoleucine, S-methyl cysteine, methionine, ethionine, or butionine may be a modified alkyl group shown in the formula (2) as described above.

Further, the present invention encompasses, as preferable embodiments, an agent for increasing the intracellular calcium ion concentration or an agent for inducing GH secretion, which comprises a partial peptide consisting of amino acids of from the amino-terminal to 13th, 14th or 15th position in the amino acid sequence of SEQ ID NO: 2 or 3. In this case, it is not always necessary that the respective amino acid units constituting the partial peptide are chemically modified.

Further, a preferable embodiment of the present invention is the following peptide-type compound.

A ghrelin derivative refers to a peptide-type compound wherein the chemical structure of natural ghrelin is partially modified, and short-chain ghrelin refers to a peptide consisting of less than 27 or 28 amino acids, which is derived from natural ghrelin of 27 to 28 amino acids by deleting some of the amino acids. Further, an amino acid residue at the n-position refers to an amino acid residue at the n-position from the amino-terminal.

The amino-terminal amino acid of ghrelin or its short-chain ghrelin derivative may be any amino acid (the amino-terminal amino acid of natural ghrelin is glycine) insofar as the α-amino group of said amino acid is not protected, or may be either D- or L-amino acid, but it is preferably alanine, valine, aminoisobutanoic acid or butanoic acid.

The 2nd residue may be any amino acid (e.g. serine in the natural ghrelin), preferably an amino acid having a small side-chain, such as alanine, serine, histidine, norvaline or a non-amino acid compound.

The 1st and 2nd residues may be a δ-amino acid corresponding to two amino acids, for example, 5-aminopentanoic acid, 5-amino-5-dimethylpentanoic acid, 2,5-diaminopentanoic acid etc. exemplified in the Examples.

The amino acid residues selected at the 3rd and 4th positions may be D- or L-amino acids, D- or L-N-methylamino acids, or a combination of these amino acids. In particular, it is preferable that the amino acid at the 3rd positions is an L-amino acid or both the amino acids at the 3rd and 4th positions are L-amino acids.

The steric configuration of the amino acid residues selected at the 3rd and 4th positions can be suitably selected depending on the sequence of amino acids at 1st and 2nd positions. That is, both the 3rd and 4th positions residues are preferably L-amino acids in the case of the amino acid sequence Gly-Ser at the 1st and 2nd positions in natural ghrelin, whereas both the 3rd and 4th positions residues may be D-amino acids in the case of another amino acid sequence such as Aib-His. Further, if the residues at the 1st and 2nd positions are an δ-amino acid (e.g., aminopentanoic acid) having a length of 2 amino acids, the residues at the 3rd and 4th positions may be L- or D-amino acids.

The amino acid residues selected at the 3rd and 4th positions are preferably D- or L-amino acids such as leucine, valine, norleucine, homoleucine, homoisoleucine, naphthyl alanine and its homologues thereof, tryptophan, phenylalanine and cyclohexyl alanine or D- or L-N-methylamino acids thereof.

The amino acid residues selected at the 3rd and 4th positions are more preferably aromatic hydrophobic amino acids such as naphthyl alanine and its homologues thereof, tryptophan, phenylalanine and cyclohexyl alanine, among the hydrophobic amino acids described above.

Further, the amino acid residues selected at the 3rd and 4th positions are preferably basic amino acids such as lysine, arginine and histidine. Especially, lysine is preferable.

The ghrelin molecule is to be basic by these basic amino acids, thus further improving the Ca-releasing activity.

The amino acid residues selected at the 3rd and 4th positions are preferably those having functional groups in their side chains, which can be modified with an acyl group (alkanyl group, alkenonyl group or aryl alkanyl group), an alkyl group or an aralkyl group, and preferable examples of such amino acids residues include serine, homoserine, threonine, cysteine, homocysteine, aspartic acid, glutamic acid, adipic acid, lysine, ornithine etc.

The amino acids having these reactive side chains may be either D- or L-amino acids or their corresponding D- or L-N-methyl amino acids, but it is particularly preferable that the 3rd position residue is an L-amino acid or both the 3rd and 4th positions residues are L-amino acids.

Further, to side chains of these amino acids may be bound an acyl group such as alkanyl group (the number of carbon atoms thereof is 2 to 35, preferably 6 to 18, more preferably 8 to 12), an alkenonyl group (the number of carbon atoms thereof is 2 to 35, preferably 6 to 18, more preferably 8 to 12), an aryl alkanyl group (benzoyl, phenacetyl, phenyl butyryl, naphthoyl, naphthyl acetyl or naphthyl propionyl group etc.), an alkyl group (the number of carbon atoms thereof is 2 to 35, preferably 6 to 18, more preferably 8 to 12), or an aralkyl group (benzyl, phenetyl, phenyl propyl, phenyl butyl, phenyl pentyl, naphthyl methyl group etc.) via a carbamate, thiocarbamate, ester, amide, disulfide, ether, thioether or thioester linkage. Further, the aforementioned alkyl and aralkyl groups may be bound not via the linkage to the α-carbon atoms of amino acids at the 3rd and 4th positions.

The combination of amino acid residues selected at the 3rd and 4th positions is preferably a combination of an amino acid having a hydrophobic side chain as the 3rd position amino acid residue and a hydrophobic amino acid as the 4th position amino acid residue.

The 3rd position amino acid residue having a hydrophobic side chain is preferably a modified amino acid into the α carbon of which (a) a saturated or unsaturated alkyl chain containing one or more carbon atoms was introduced via or not via an alkylene group containing one or more carbon atoms and via an ester, ether, thioether, amide or disulfide linkage, or (b) a saturated or unsaturated alkyl chain containing one or more carbon atoms was introduced. In particular, a modified amino acid into the α-carbon of which a saturated alkyl chain containing one or more carbon atoms was introduced is more preferable.

The carboxyl group of amino acid at the 4th position may be an amide, an alkyl amide (e.g. methyl amide or ethyl amide), a benzyl amide, or an aralkyl amide (e.g. adamantane amide or adamantane alkyl amide).

Further, a basic group such as amino group or guanidido group may be bound to the alkyl or aralkyl amide. The basic group includes e.g. —CONH—CH$_2$CH$_2$—NH$_2$, —CONH—CH$_2$NHCH$_3$, —CONH—CH$_2$CH$_2$CH$_2$—NH—C(NH$_2$)=NH, and —CONHCH$_2$Ph-NH$_2$.

A basic amino acid such as arginine, lysine and histidine may be added to the carboxyl group of amino acid at the 4th position, and this basic amino acid may be a D- or L-amino acid, a racemate, or D- or L-N-methyl amino acid.

The carboxyl group of the amino acid may be an alkyl or aralkyl amide as described above. Further, a basic group such as amino group or guanidido group may be added to the alkyl or aralkyl amide. The basic group includes those exemplified above.

As an amino acid sequence of amino acid at the 5th position and subsequent amino acids, a sequence of any length consisting of leucine at the 5th position and subsequent amino acids up to amino acid at the 28th position in human or rat ghrelin may be added to amino acid at the 4th position.

Such amino acid sequences are preferably ghrelin (1-5), ghrelin (1-6), ghrelin (1-7), ghrelin (1-8), ghrelin (1-9), ghrelin (1-10), and ghrelin (1-11) where ghrelin (m-n) refers to a peptide having an amino acid sequence at the m- to n-positions from the amino-terminal in ghrelin. In particular, ghrelin (1-5) is preferable.

The carboxyl-terminal thereof is preferably an alkyl or aralkyl amide as described above.

Further, a basic group such as amino group or guanidido group may be bound to the alkyl or aralkyl amide. The basic group includes those exemplified above.

Further, a basic amino acid such as arginine, lysine and histidine may be added to the carboxyl-terminal amino acid of a carboxyl-terminal-deleted ghrelin derivative wherein an amino acid sequence of any length consisting of amino acid 5 and subsequent amino acids up to amino acid 28 was added to the carboxyl-terminal of ghrelin (1-4).

This basic amino acid may be a D- or L-amino acid, a racemate, or D- or L-N-methyl amino acid.

The carboxyl group of the basic amino acid may be an alkyl or aralkyl amide as described above. Further, a basic group such as amino group or guanidido group may be bound to the alkyl or aralkyl amide. The basic group includes those exemplified above.

In a particularly preferable embodiment, the carboxyl-terminal amino acid of ghrelin (1-5), ghrelin (1-6) and ghrelin (1-7) is a D- or L-amino acid or its corresponding D- or L-N-methyl amino acid.

Further, basic amino acids such as arginine, lysine and histidine may be added to resides at the 5th, 6th and 7th position, and these basic amino acids may be D- or L-amino acids, racemates, or D- or L-N-methyl amino acids.

The carboxyl group of such a basic amino acid may be an alkyl or aralkyl amide as described above. Further, a basic group such as amino group or guanidido group may be bound to the alkyl or aralkyl amide. The basic group includes those exemplified above.

In a preferable embodiment in the present invention, the peptide compound of the present invention in the case where the carboxyl-terminal is an alkyl or aralkyl amide as described above may be an amide derivative wherein an amino group is further bound to the alkyl or aralkyl group. Specifically, a peptide compound wherein the carboxyl-terminal is e.g. aminoethyl amide can be mentioned.

The peptide-type compound of the present invention wherein the carboxyl-terminal is an amide or an amide derivative as described above is a useful compound because of its resistance to decomposition by enzymes such as carboxy peptidases in vivo.

Similarly, the peptide-type compound of the present invention including N-methyl amino acid is also a useful compound because of its resistance to enzymes.

The peptide-type compound of the present invention can be obtained in a usual manner. For example, it can be isolated from a natural source or produced by recombinant DNA technology and/or chemical synthesis. Further, when a modification (e.g., acylation) in the amino acid residues is necessary, the peptide compound can be subjected to a modification reaction by well-known methods in the art.

Specifically, the peptide-type compound of the present invention can be obtained by culturing host cells transformed with an expression vector harboring a DNA coding the peptide of the present invention and then recovering the desired peptide from the culture.

By selecting the host cells, a compound having the desired peptide modified by e.g. acylation in the cells can be obtained. When said peptide is not modified, a modification reaction such as acylation can be conducted as necessary by well-known methods in the art. For the acylation reaction, enzymes such as lipase can also be used.

The vector in which the gene is to be integrated includes e.g. E. coli vectors (pBR322, pUC18, pUC19 etc.), Bacillus subtilis vectors (pUB110, pTP5, pC194 etc.), yeast vectors (YEp type, YRp type, YIp type), or animal cell vectors (retrovirus, vaccinia virus etc.), but any other vectors capable of maintaining the desired gene stably in host cells can also be used. The vector is introduced into suitable host cells. For integrating the desired gene into a plasmid and introducing the plasmid into host cells, methods described in Molecular Cloning (Sambrook et al., 1989) can be used.

To express the desired peptide gene in the above plasmid, a promoter is linked operatively upstream of said gene.

The promoter used in the present invention may be any suitable promoter compatible with host cells used for expression of the desired gene. For example, lac promoter, trp promoter, lpp promoter, λPL promoter, recA promoter etc. can be used in the genus *Escherichia* as host cells to be transformed; SP01 promoter, SP02 promoter etc. can be used in the genus *Bacillus*; GAP promoter, PH05 promoter, ADH promoter etc. can be used in yeasts; and SV40-derived promoter, retrovirus-derived promoter etc. can be used in animal cells.

The desired gene-containing vector obtained in this manner is used to transform host cells. The host cells include microorganisms (for example, the genus *Escherichia*, the genus *Bacillus* etc.), yeast (the genus *Saccharomyces*, the genus *Pichia*, the genus *Candida* etc.), animal cells (CHO cells, COS cells etc.) etc. The medium for culture is preferably a liquid medium, and particularly preferably the medium containing a carbon source, a nitrogen source etc. necessary for growth of the transformed cells to be cultured. If desired, vitamins, growth promoters, serum etc. can be added.

For directly producing the fatty acid-modified peptide, the cells are preferably those having the activity of a processing protease capable of cutting a suitable site in a precursor polypeptide of said peptide and the activity of acylating the serine residue in said peptide. Host cells having such processing protease activity and serine-acylating activity can be obtained by transforming host cells with an expression vector containing a cDNA coding said precursor polypeptide and then selecting the transformed cells by confirming whether or not they produce the fatty acid-modified peptide having a Ca-releasing activity or a GH secretion-inducing activity.

After culture, the peptide of the present invention is separated and purified from the culture in a usual manner. To extract the desired product from the cultured microorganisms or cells, for example, the microorganisms or cells after culture are collected and suspended in a buffer containing a protein denaturant (e.g. guanidine hydrochloride) and the microorganisms or cells are disrupted by sonication etc. and then centrifuged. To purify the desired product from the supernatant, separation and purification methods such as gel filtration, ultrafiltration, dialysis, SDS-PAGE, various chromatographic techniques can be suitably combined in consideration of the molecular weight, solubility, charge (isoelectric point), affinity etc. of the desired product.

The peptide compound of the present invention can be chemically synthesized in a usual manner. For example, amino acids having protective groups are condensed by a liquid phase method and/or a solid phase method to extend a peptide chain, then all protective groups are removed therefrom by an acid, and the resulting crude product is purified by the above purification techniques to give the desired peptide compound. An amino acid residue at the desired site can be acylated selectively by an acylase or acyl transferase.

Various methods have been well established for production of peptides, and the peptide-type compound of the present invention can also be easily produced by such known methods. For example, the peptide-type compound may be synthesized by the classical peptide synthesis method or by the solid phase method.

Hereinafter, a process for producing the peptide compound of the present invention by a combination of recombinant DNA technology and chemical synthesis is described by reference to examples.

Active esters of amino-terminal peptides, for example, (1) Boc-Gly-Ser(Bu)-Ser(R10)-Osu, (2) Boc-Gly-Ser(Bu)-Ser(R10)-Phe-Osu, and (3) Boc-Gly-Ser(Bu)-Ser(R10)-Phe-Leu-Osu, are chemically synthesized and then bound to carboxyl-terminal peptides produced by recombinant DNA technology, that is, (4) FLSPEHQRVQQRKESKKPPAK-LQPR, (5) LSPEHQRVQQRKESKKPPAKLQPR, and (6) SPEHQRVQQRKESKKPPAKLQPR, respectively; that is, (1) is bound to (4), (2) to (5), and (3) to (6), whereby peptide compounds each consisting of 28 amino acids are obtained respectively. Specifically, XXXXZSPEHQRVQQRKESK-KPPAKLQPR is expressed in *E. coli* followed by protection of its amino groups with Boc2(O) to give Boc-XXXXZSPE-HQRVQQRK(Boc)K(Boc)PPAK(Boc)LQPR. Then, the resulting peptide is converted into $NH_2$-SPE-HQRVQQRK(Boc)ESK(Boc)K(Boc)PPAK(Boc)LQPR by cleavage with an enzyme selective for the carboxyl-terminal of amino acid Z. This compound is mixed with Boc-Gly-Ser(Bu)-Ser(R10)-Phe-Leu-Osu in an aqueous neutral to weak alkaline solution, and the resulting BocGlySer(Bu)Ser(R10)FLSPEHQRVQQRK(Boc)ESK(Boc)K(Boc)PPAK(Boc)LQPR is treated with trifluoroacetic acid, whereby the desired product can be obtained.

The above one-letter notation of amino acid is in accordance with a description in Cellular Molecular Biology, 3rd edition published on Dec. 10, 1997 by Newton Press Co., Ltd.

In addition, Boc represents t-butyloxycarbonyl, Osu represents a residue derived from N-hydroxysuccinimide by eliminating hydrogen from the hydroxyl group thereof, Bu represents a butyl group, and R10 represents the substituent group of the modified amino acid according to the present invention.

Salts of the peptide-type compound of the present invention are preferably pharmaceutically acceptable salts including, for example, salts with inorganic bases, salts with organic bases, salts with inorganic acids, salts with organic acids, and salts with basic or acidic amino acids.

Preferable examples of the salts with inorganic bases include alkali metal salts such as sodium salts, potassium salts etc.; alkaline earth metal salts such as calcium salts, magnesium salts etc.; and aluminum salts, ammonium salts etc.

Preferable examples of the salts with organic bases include salts with trimethylamine, triethylamine, pyridine, picoline, ethanolamine, diethanolamine, triethanolamine, dicyclohexyl amine, N,N'-dibenzylethylene diamine etc.

Preferable examples of the salts with inorganic acids include salts with hydrochloric acid, hydrobromic acid, nitric acid, sulfuric acid, phosphoric acid etc.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.

Preferable examples of the salts with basic amino acids include salts with arginine, lysine, ornithine etc., and suitable examples of the salts with acidic amino acids include salts with aspartic acid, glutamic acid etc.

Among these salts, sodium salts and potassium salts are most preferable.

The peptide-type compound of the present invention or pharmaceutically acceptable salts thereof are low toxic and have a GH-secretion inducing action, and they can be administered as such or after mixed with known, pharmaceutically acceptable carriers, excipients, vehicles augmentors etc., to a mammal (for example, human being, mouse, rat, rabbit, dog, cat, bovine, horse, porcine, monkey etc.). In the case of intravenous injection into an adult, the daily dose is 0.01 to 5 mg/kg, preferably 0.04 to 1.5 mg/kg. This dose is administered desirably once to thrice every day. The peptide-type compound of the present invention is compounded with pharmaceutically acceptable carriers and can be orally or parenterally as solid pharmaceutical preparations such as tablets, capsules, granules, powders etc. or as liquid pharmaceutical preparations such as syrups, injections etc.

The pharmaceutically acceptable carriers include a wide variety of organic or inorganic carriers which are customarily used as pharmaceutical materials, and these are compounded as vehicles, lubricants, binders, disintegrant in solid pharmaceutical preparations or as solvents, adjuvant, suspending agents, isotonicity-conferring agents, buffers and soothing agents in liquid pharmaceutical preparations.

As necessary, pharmaceutical additives such as preservatives, antioxidants, coloring agents, sweeteners etc. can also be used.

Preferable examples of the vehicles include e.g. lactose, white sugar, D-mannitol, starch, crystalline cellulose, light anhydrous silicic acid etc. Preferable examples of the lubricants include magnesium stearate, calcium stearate, talc, colloidal silica etc.

Preferable examples of the binders include crystalline cellulose, white sugar, D-mannitol, dextrin, hydroxypropyl cellulose, hydroxypropylmethyl cellulose, polyvinyl pyrrolidone etc.

Preferable examples of the disintegrant include starch, carboxymethyl cellulose, carboxymethyl cellulose calcium, croscalomelose sodium, carboxymethyl starch sodium etc.

Preferable examples of the solvents include water for injection, alcohol, propylene glycol, macrogol, sesame oil, corn oil etc.

Preferable examples of the solubilizers include polyethylene glycol, propylene glycol, D-mannitol, benzyl benzoate, ethanol, trisaminomethane, cholesterol, triethanolamine, sodium carbonate, sodium citrate etc.

Preferable examples of the suspending agents include surfactants such as stearyl triethanolamine, sodium lauryl sulfate, lauryl aminopropionic acid, lecithin, benzalconium chloride, benzethonium chloride and glycerin monostearate, and hydrophilic polymers such as polyvinyl alcohol, polyvinyl pyrrolidone, carboxymethyl cellulose sodium, methyl cellulose, hydroxymethyl cellulose, hydroxyethyl cellulose and hydroxypropyl cellulose.

Preferable examples of the isotonicity-conferring agents include sodium chloride, glycerine, D-mannitol etc.

Preferable examples of the buffers include buffer solutions such as phosphates, acetates, carbonates, citrates etc.

Preferable examples of the soothing agents include benzyl alcohol etc.

Preferable examples of the preservatives include p-oxyesterbenzoates, chlorobutanol, benzyl alcohol, phenetyl alcohol, dehydroacetic acid, sorbic acid etc.

Preferable examples of the antioxidants include sulfites, ascorbic acid etc.

The above pharmaceutical composition brings about an effect equal to or higher than the effect of GH upon administration and can reduce various side effects caused by administration of GH.

As diseases attributable to deficiency or reduction in GH, the diseases to which the pharmaceutical composition can be applied or the effects of the pharmaceutical composition include, but are not limited to, activation of osteoblasts and re-constitution of bone in people with dwarfism and normal human beings, enhancement of muscular strength and muscular amount in GH-deficient adults, improvement of motility in GH-deficient adults, remedy of heavy burns in children, its combined use with gonadotropins in induction of ovulation, prevention of abnormalities in protein metabolism by administration of prednisone, promotion of T cell "education" in heavy immune disorder, the effect of inhibiting reduction of the body weight of the aged and the effect of enlarging adipose tissues and preventing dermal atrophy.

Further, the diseases or effects not directly correlated with deficiency or reduction in GH include e.g. the effect of increasing pulsatile flow as shown in Example 7, and thus it is effective for treatment of cardiac diseases such as cardiac failure etc.

The effect of the pharmaceutical composition is not restricted to human beings. That is, it has an effect on growth promotion for animals, reduction of fat in meat, etc., which is equal to or higher than administered GH.

For example, as shown in Example 13, the pharmaceutical composition of the present invention exhibits an appetite-promoting action upon administration into ventricle or intravenous administration, so it can be used as an appetite promoter for treating anorexia or sitophobia.

In addition, as shown in Example 14, the pharmaceutical composition of the present invention has a stomach motility- and gastric acid secretion-promoting action, and thus it can also be used as an agent for treating stomach functional diseases such as non-diabrotic dyspepsia, sudden light stomach atony, functional dyspepsia, and reflux esophagitis.

Further, as shown for example in Example 15, the pharmaceutical composition of the present invention exhibits a cell growth-promoting action in bone marrow, duodenum and jejunum by intravenous administration, and thus it can be used as an agent for protecting small intestine tunica mucosa, an agent for preventing damage to small intestine tunica mucosa during intravenous nutrition and an agent for treating osteoporosis.

Further, the pharmaceutical composition described above has an effect for treating the diseases or for improving the physical conditions described below.

For example, it can be used for stimulative treatment for release of growth hormones in the aged, prevention of catabolic side effects of sugar corticoids, prevention and treatment of osteoporosis, stimulation at immune system, promotion of remedy of damages, promotion of repair of broken bone, treatment of growth delay, treatment of renal insufficiency or functional insufficiency attributable to growth delay, treatment of insufficient conditions correlated with physiological insufficient conditions including growth hormone-deficient children and chronic diseases, treatment of obesity and growth delay correlated with obesity, treatment of growth delay correlated with Plauda-Villi syndrome and Taner syndrome, promotion of recovery of burn patient and reduction in hospitalization, treatment of intrauterine growth delay, skeleton mulformation, hypercorticoid disease and Cusshing syndrome, induction of release of pulsatile growth hormone, replacement of growth hormone in stressed patients, cartilage mulformation, Noonan syndrome, schizophrenia, depression, Alzheimer's disease, remedy of delayed repair of damage and physicosocial deprivation, treatment of pulmonary insufficiency and respiratory organ dependence, decrease of catabolic reaction of protein after major operation, reduction of protein loss and cachexia caused by chronic diseases such as cancer and AIDS, treatment of hyperinsulinism including pancreas nesidioblastosis, adjuvant therapy for induction of ovulation, and treatment of patients with immune repression, improvement of muscular strength and motility, maintenance of thickness of skin in the aged, metabolic homeostasis and renal homeostasis, stimulation of osteoblast, re-formation of bone and stimulation of cartilage growth, in order to stimulate growth of thymus and to prevent deterioration in thymic functions accompanying aging.

Further, the following effects on animals are also expected. For example, mention is made of an increase in the rate of animal growth, an increase in production of milk and fur in animals, stimulation of the immune system in pet animals, treatment of diseases caused by advanced age in pet animals, growth promotion of domestic animals, and an increase in fur in sheep.

An antibody whose antigen is fatty acid-modified peptide of the present invention having a Ca-releasing activity or a GH secretion-inducing activity can be obtained by a method known in the art. The antibody may be a monoclonal or polyclonal antibody, and can be obtained by a method known in the art. Further, a method for measuring the fatty acid-modified peptide using said antibody and a measuring kit using said measuring method can also make use of a method known in the art. As described in Example 17, antibodies to amino- and carboxyl-terminal peptides from ghrelin are prepared respectively, and since the former recognizes fatty acid-modified serine at the 3rd position, both the antibodies can be used to separate and quantify ghrelin modified with a fatty acid and ghrelin from which the fatty acid was eliminated.

The antibodies to amino- and carboxyl-terminal peptides in ghrelin can be obtained in a known method, and they may be monoclonal or polyclonal antibodies.

For the present peptide-type compound having a modified amino acid at the 3rd position from the amino-terminal or a pharmaceutically acceptable salt thereof, an antibody which specifically recognizes a side chain of 3rd amino acid residue (preferably a fatty acid) and binds to an amino-terminal partial peptide of the peptide-type compound can also be produced in the same manner. In addition, for the peptide-type compound of the present invention or a pharmaceutically acceptable salt thereof, an antibody which binds specifically to the peptide having a modified amino acid can also be produced in the same manner.

The present invention also encompasses an examination kit comprising a combination of an antibody specifically recognizing a side chain of the modified amino acid and an antibody recognizing amino acids (or a peptide) excluding the modified amino acid and/or a non-amino acid compound, preferably an antibody to a carboxyl-terminal partial peptide of the peptide-type compound of the present invention or of a pharmaceutically acceptable salt thereof, as described above.

Further, the present invention encompasses an assay method wherein the peptide-type compound of the present invention having a modified amino acid, preferably an acylated amino acid, or a pharmaceutically acceptable salt thereof, and the peptide-type compound of the present invention not containing a modif ied amino acid, or a pharmaceutically acceptable salt thereof, are separated and detected by use of said examination kit.

Hereinafter, the assay method and examination kit described above are described by reference to their embodiments, which however are not intended to limit the present invention.

That is, the assay method includes, for example, (i) a method of quantifying the peptide-type compound etc. of the present invention in a test solution, which comprises allowing a test material in a test solution and the labeled peptide-type compound etc. of the present invention to react competitively with an antibody to the peptide-type compound etc. of the present invention and then determining the ratio of the labeled peptide-type compound etc. of the present invention bound to said antibody, and (ii) a method of quantifying the proteins etc. of the present invention in a test solution, which comprises allowing a test solution to react with the antibody of the present invention insolubilized on a carrier and another labeled antibody of the present invention simultaneously or successively and then measuring the activity of the labeling agent on the insolubilizing carrier and/or the activity of the labeling agent not captured on the insolubilizing carrier. In the quantification methods (i) and (ii), it is preferable that one antibody is an antibody recognizing an amino-terminal region of the protein etc. of the present invention, while the other antibody is an antibody reacting to a carboxyl-terminal region of the protein etc. of the present invention.

In the method of assaying the peptide-type compound etc. of the present invention, the monoclonal antibody against said compound (also referred hereinafter to as the anti-protein antibody) can be used not only for quantifying the protein etc. of the present invention, but also for detection thereof by tissue staining etc.

For these purposes, either the antibody molecule itself or an F(ab')$_2$, Fab' or Fab fraction of the antibody molecule may be used.

The method of quantifying the peptide-type compound etc. of the present invention by use of said antibody is not particularly limited as long as the method comprises detecting the amount of the antibody corresponding to the amount of the antigen (e.g., the amount of the protein), the antigen or an antigen-antibody conjugate in a test solution, by chemical or physical means and calculating it on the basis of a standard curve prepared using standard solutions containing known amounts of the antigen. For example, nephelometry, the competitive method, the immunometric method and the sandwich method are preferably used, but the sandwich method described later is particularly preferably used in respect of sensitivity and specificity.

For a measurement method using a label in the assay method of the present invention, the label includes e.g. a radioisotope, an enzyme, a fluorescent material and a luminescent material.

The radioisotope includes, for example, $^{125}$I, $^{131}$I, $^{3}$H, $^{14}$C etc.

The enzyme is preferably a stable enzyme with high specific activity, which includes, for example, β-galactosidase, β-glucosidase, alkali phosphatase, peroxidase and malate dehydrogenase.

The fluorescent material includes, for example, fluorescamine and fluorescein isocyanate.

The luminescent material includes, for example, luminol, luminol derivatives, luciferin, and lucigenin.

Further, a biotin-avidin system can also be used for binding the label to the antibody or antigen.

Hereinafter, the present invention is described in more detail by reference to the Examples. Unless otherwise specified, the genetic manipulation means were in accordance with Molecular Cloning (Sambrook et al., 1989).

Example 1. Creation of a Cell Strain Expressing GHS-R and Measurement of Ca-Releasing Activity To assay an increase in the intracellular calcium ion concentration (Ca-releasing activity) occurring upon binding of a GH secretagogue (GHS) to GHS-receptor (GHS-R), a cell strain expressing rat GHS-R was created in the following manner. A full-length cDNA for rat GHS-R was obtained by RT-PCR (reverse Example 1. Creation of a Cell Strain Expressing GHS-R and Measurement of Ca-Releasing Activity To assay an increase in the intracellular calcium ion concentration (Ca-releasing activity) occurring upon binding of a GH secretagogue (GHS) to GHS-receptor (GHS-R), a cell strain expressing rat GHS-R was created in the following manner. A full-length cDNA for rat GHS-R was obtained by RT-PCR (reverse transcriptase-polymerase chain reaction) where a cDNA derived from rat brain was used as template. From the nucleotide sequence of known rat GHS-R [K. K. Mckee, et al, Molecular Endocrinology 11, 415-423 (1997)], sense and antisense primers consisting of the following nucleotide sequences were synthesized.

```
Sense primer:      5'-ATGTGGAACGCGACCCCCAGCGA-3'

Antisense primer:  5'-ACCCCCAATTGTTTCCAGACCCAT-3'
```

The amplified cDNA was ligated to vector pcDNAIII (Invitrogen) to construct expression vector GHSR-pcDNAIII. CHO cells were transformed via the expression vector, and the transformed cells stably expressing GHS-R were selected in a medium containing 1 µg/ml G418. The selected cell strain CHO-GHSR62 responded to $10^{-10}$ to $10^{-9}$ M GHRP-6 (Growth Hormone-Releasing hexapeptide). A change in the intracellular calcium ion concentration (Ca-releasing activity) was measured by an FLIPR system (Molecular Device). Before this measurement, $4 \times 10^4$ CHO-GHSR62 cells were put to a 96-well microplate with black wall (Corning Co., Ltd) and cultured for 12 to 15 hours. Then, the cells were incubated with 4 µM fluorescent Fluo4 (Molecular Probe Co., Ltd) for 1 hour and washed four times with Hank's BSS (Hank's Balanced Salt Solution) containing 20 mM Hepes ([N-2-hydroxyethyl]-piperazine-N-[2-ethanesulfonic acid]) and 2.5 mM probenecid, and the Ca-releasing activity was assayed by adding a sample and measuring a change in the fluorescence.

Example 2. Purification of an Endogenous GH Secretion-Inducing Peptide

Using the CHO-GHSR62 cells described in Example 1, a wide variety of rat-derived tissues and organs were examined for their Ca-releasing activity, and as a result, it was found that a peptide extract derived from rat stomach has a strong Ca-releasing activity even in a small amount of 5 mg. Accordingly, a peptide having the Ca-releasing activity was purified from a rat stomach extract by several kinds of chromatography.

40 g fresh rat stomach was boiled for 5 minutes in 5-fold boiling water to inactivate proteases present in it. After cooling, the boiled sample was placed in 1M AcOH-20 mM followed by extracting the peptide by a Polytron mixer. The extract was centrifuged at 11,000 rpm for 30 min., and the supernatant was concentrated into about 40 ml in an evaporator. The concentrate was precipitated with acetone by adding acetone thereto at a concentration of 66%, and after the formed precipitates were removed, the acetone in the supernatant was evaporated. The supernatant was applied to 10 g Sep-Pak C18 cartridge (Waters Co., Ltd) previously equilibrated with 0.1% TFA (trifluoroacetic acid), washed with 10% CH$_3$CN/0.1% TFA and then eluted with 60% CH$_3$CN/0.1% TFA. After the solvent in the eluate was evaporated, the sample was lyophilized. The lyophilized sample was dissolved in 1 M AcOH and absorbed onto SP-Sephadex C-25 (H$^+$ type) previously equilibrated with 1 M AcOH. The sample was eluted stepwise with 1 MAcOH, then with 2 M pyridine, and finally with 2 M pyridine-AcOH (pH 5.0), whereby 3 fractions, that is, SP-I, SP-II and SP-III were obtained respectively. The SP-III fraction was applied to a Sephadex G-50 gel filtration column, and an aliquot of each fraction was assayed for Ca-releasing activity by use of the CHO-GHSR62 cells. A profile in Sephadex G-50 column chromatography is shown in FIG. 1a, and active fractions (fractions 43 to 48 in FIG. 1a) having molecular weights of about 3,000 were fractionated by high performance liquid chromatography (HPLC) by CM-ion exchange on TSK CM-2SW column (4.6×250 mm, Tosoh Corp.) at pH 6.4. The active fractions by CM-HPLC were secondarily fractionated by CM-HPLC on the same column at pH 4.8 (FIG. 1b). The active fractions (elution time of 55 to 56 minutes in FIG. 1b) were purified to homogeneity by reverse phase HPLC on µBondasphere C-18 column (3.9×150 mm, Waters Co., Ltd). From 40 g of the rat stomach, 16 µg peptide having a Ca-releasing activity was purified and designated as ghrelin.

Example 3. Structural Analysis of as Ghrelin

The amino acid sequence of the purified ghrelin derived from rat was determined by a peptide sequencer (ABI 494, Applied Biosysytems Co., Ltd). The ghrelin was a peptide composed of 28 amino acid residues consisting of the following sequence: Gly Ser Xaa Phe Leu Ser Pro Glu His Gln Lys Ala Gln Gln Arg Lys Glu Ser Lys Lys Pro Pro Ala Lys Leu Gln Pro Arg (SEQ ID NO: 40) where Xaa is an unidentified amino acid. On the basis of the nucleotide sequence of the rat cDNA, Xaa was estimated to be Ser, indicating a certain modification on Ser in the peptide.

Accordingly, unmodified ghrelin wherein serine at the 3rd position from the amino-terminal was chemically synthesized by a peptide synthesizer (ABI 433A, Applied Biosystems Co., Ltd). Because the elution time of the unmodified synthetic ghrelin in reverse phase HPLC was significantly different from that of natural ghrelin (FIG. 2a), the unmodified synthetic ghrelin was found to be more significantly hydrophilic than natural ghrelin.

From the above result, it was found that in natural ghrelin, serine at the 3rd position from the amino-terminal (3rd serine) has been modified with a hydrophobic residue.

To reveal the modifying group on 3rd serine, the purified ghrelin was analyzed by electrospray ionization mass spectrometry (ESI-MS). The found molecular weight (3314.9±0.7) of natural ghrelin was greater by 126 than the molecular weight (3188.5) of the unmodified ghrelin peptide which was estimated from the nucleotide sequence of the cDNA. From the above result, it was found that the hydroxyl group of 3rd serine in natural ghrelin has been modified with n-octanoyl (C8:0) fatty acid.

Figure 2:
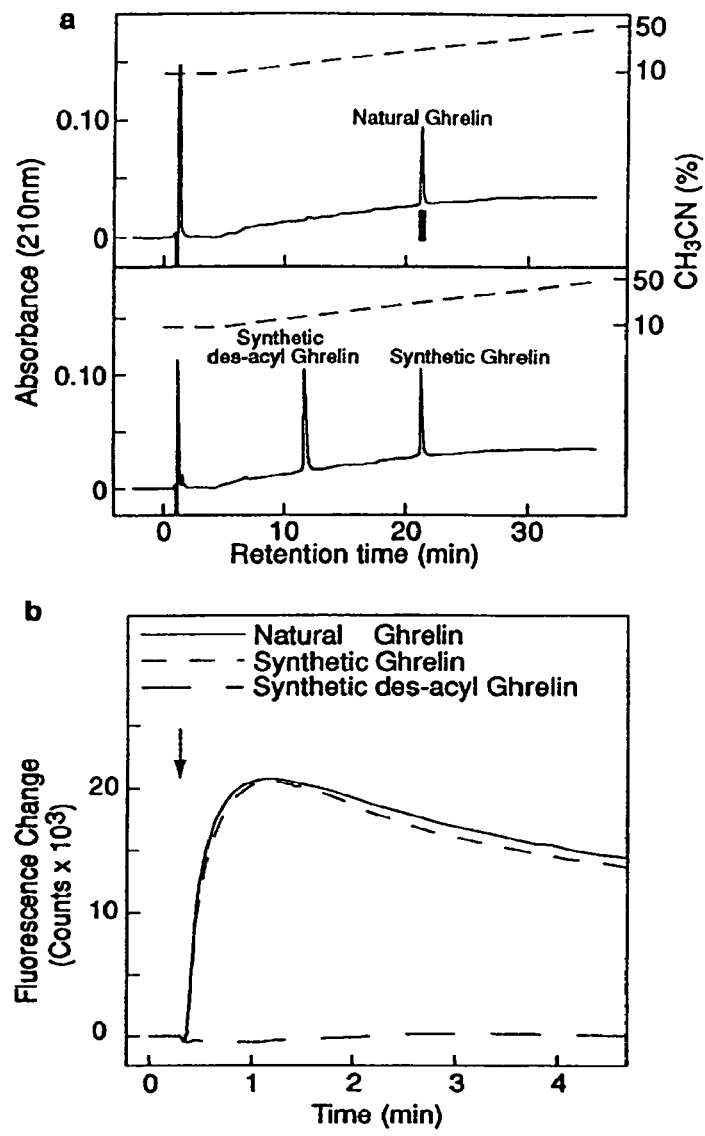
FIG. 2 shows that the modification of ghrelin with n-octanoyl was identified.

To confirm this, the n-octanoyl (C8:0) ghrelin peptide was chemically synthesized and examined for its elution time in reverse phase HPLC. In chemical synthesis of the n-octanoyl (C8:0) peptide, the peptide wherein all functional groups except for the hydroxyl group of 3rd serine were protected was synthesized by the Fmoc solid phase method using a peptide synthesizer (ABI 433A, Applied Biosystems Co., Ltd), and then the desired peptide was obtained by acylation of the hydroxyl group of 3rd serine with n-octanoic acid and ethyl-3-(3-dimethylaminopropyl) carbodiimide in the presence of 4-(dimethylamino)pyridine. The synthetic n-octanoyl peptide indicated the same elution time as that of the purified natural ghrelin (FIG. 2a). Further, the synthetic n-octanoyl peptide and a peptide fragment at the 1st to 4th positions from the amino-terminal (Gly 1-Phe 4) which was obtained by treating natural ghrelin with chymotrypsin showed the same retention time in reverse phase HPLC.

From the above result, it was concluded that the natural ghrelin derived from rat has the amino acid sequence set forth in SEQ ID NO: 2, wherein the hydroxyl group of 3rd serine has been acylated with n-octanoic acid (caprylic acid) (FIG. 2c).

Figure 4:
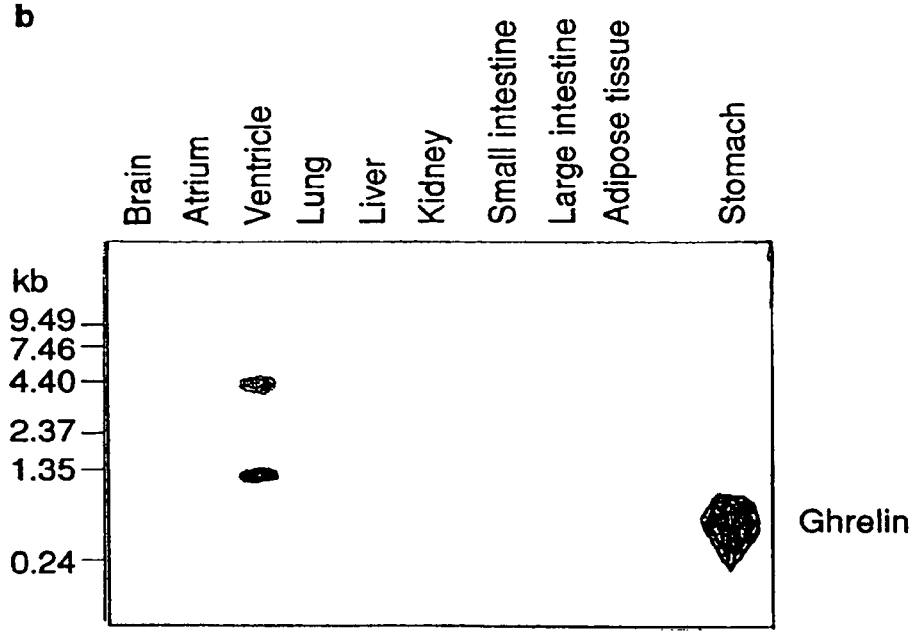
FIG. 4 shows the amino acid sequences of rat- and human-derived ghrelin precursors, as well as the analysis result of expression of these precursors in various tissues.

Further, human ghrelin was purified from a human stomach extract, and it was found that its structure has the amino acid sequence set forth in SEQ ID NO: 3, wherein the side-chain hydroxyl group of 3rd serine has been acylated with n-octanoic acid (caprylic acid) (FIG. 4a).

The structures of the rat- and human-derived ghrelins were determined using those purified as the first-peak fractions (elution time of 55 to 56 minutes) out of the active fractions in FIG. 1b, and after purification, the structure of the other active fractions in FIG. 1b was also analyzed in the same manner, indicating the presence of not only caprylic acid (C8:1) but also its monoene acid (C8:1), capric acid (C10:0) and its monoene acid (C10:1), and lauric acid (C12:0) and its monoene acid (C12:1) as the modifying fatty acid on 3rd serine.

Further, chicken, eel and frog ghrelins were purified from stomach extracts in the same manner as in Example 2 and analyzed for their structure in the same manner as in Example 3. It was found that the chicken ghrelin has the amino acid sequence shown in SEQ ID NO: 25, the eel ghrelin has the amino acid sequence shown in SEQ ID NO: 26, and the frog ghrelin has the amino acid sequence shown in SEQ ID NO: 27, and in all of the ghrelins, the side-chain hydroxyl group of 3rd serine has been acylated with n-octanoic acid (caprylic acid).

Further, frog (*Xenopus Laevis*), fish (rainbow trout) and canine ghrelins were purified from stomach extracts in the same manner as in Example 2 and analyzed for their structure in the same manner as in Example 3.

It was found that the frog ghrelin has the amino acid sequence shown in SEQ ID NO: 28, the rainbow trout ghrelin has the amino acid sequence shown in SEQ ID NO: 29 and 30, and the canine ghrelin has the amino acid sequence shown in SEQ ID NO: 31, and in all of the ghrelins, the side-chain hydroxyl group of 3rd serine or threonine has been acylated with n-octanoic acid (caprylic acid).

From the rainbow trout, ghrelin-23 consisting of 23 amino acid residues shown in SEQ ID NO: 29 and ghrelin-20 consisting of 20 amino acid residues shown in SEQ ID NO: 30 were obtained.

Example 4. Ca-Releasing Activity of Ghrelin

The natural ghrelin and n-octanoyl-modified synthetic ghrelin had a Ca-releasing activity, but the unmodified synthetic ghrelin did not show a significant Ca-releasing activity (FIG. 2b). Further, because n-octanoic acid or a mixture of n-octanoic acid and the unmodified synthetic ghrelin did not show a significant Ca-releasing activity, it was found that the n-octanoic acid residue in the natural ghrelin constitutes an important structure for the Ca-releasing activity. Hereinafter, ghrelin refers to [O-n-octanoyl-serine 3]-ghrelin (FIG. 2c).

Figure 3:
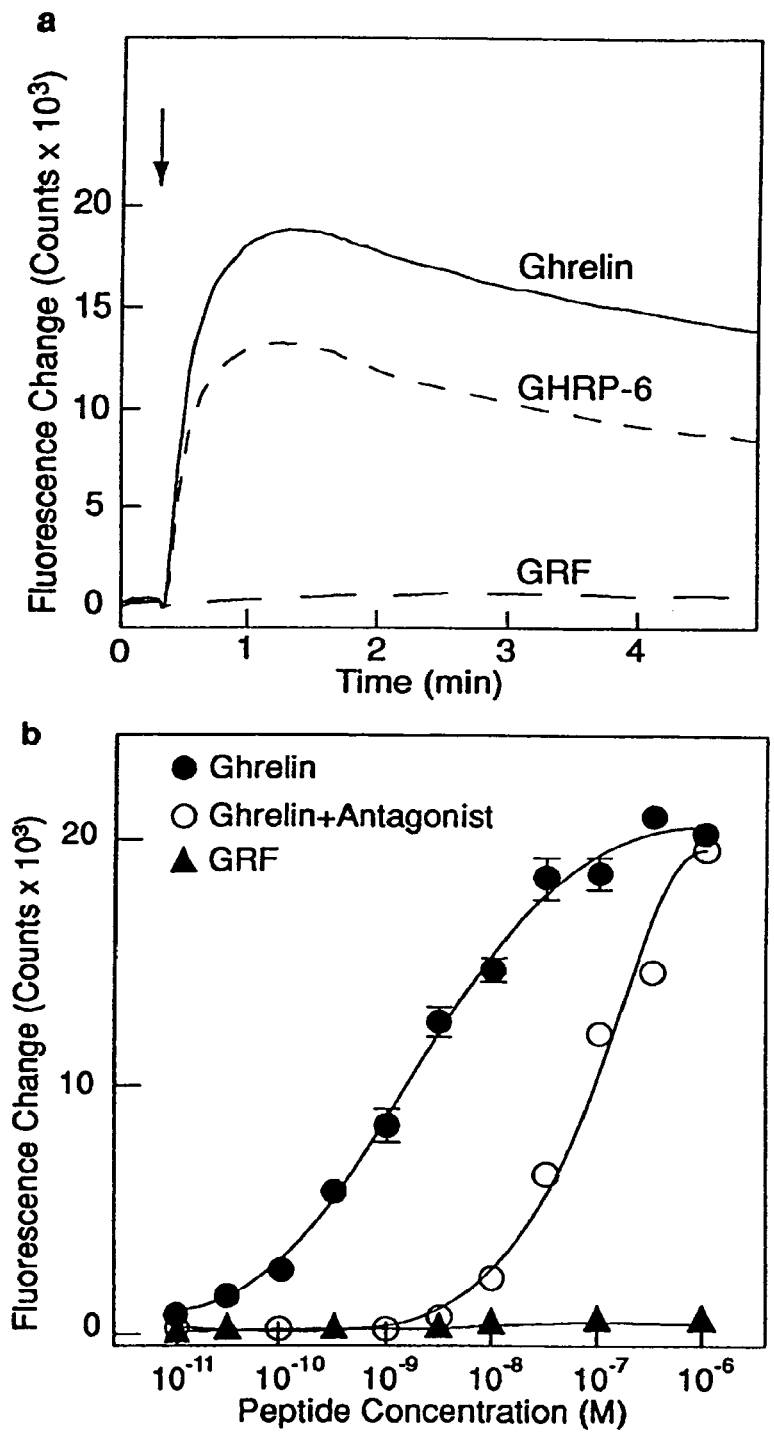
FIG. 3 is a graph showing specific interaction of ghrelin with CHO-GHSR62 cells, and ghrelin was added at the arrowed point.

In CHO-GHSR62 cells, the ghrelin exhibited a higher activity of increasing the intracellular calcium ion concentration (Ca-releasing activity) than that by GHRP-6, while GHRH (GH releasing hormone, expressed as GRF in FIG. 3a) did not exhibit the Ca-releasing activity (FIG. 3b). The Ca-releasing activity of ghrelin was recognized at a concentration of $10^{-11}$ M or more, and its $EC_{50}$ was 2.5 nM. The Ca-releasing activity of ghrelin was inhibited in the presence of $10^{-4}$ M specific antagonist ([D-Lys 3]-GHRP-6) for GHS-R [R. G. Smith, et al., Science 260, 1640-1643 (1993)], and the Ca-releasing activity was restored at a high concentration of ghrelin in the absence of the antagonist (FIG. 3b). The above result indicates that the Ca-releasing activity of ghrelin is 10 inhibited antagonistically by the specific antagonist for GHS-R.

Example 5. A cDNA for a Ghrelin Precursor and Expression Thereof in Various Organs The amino acid sequence of the ghrelin had no homology with the amino acid sequences of any known peptides, but as a result of homology examination in the GenBank data base, the same sequence was found in a rat EST (Expressed Sequence Tag) sequence (GenBank acceptation No. AI549172). On the basis of this EST sequence, the following PCR primers were synthesized:

```
                                            (SEQ ID NO: 41)
Sense primer:       5'-TTGAGCCCAGAGCACCAGAAA-3'

(SEQ ID NO: 42)
Antisense primer:   5' -AGTTGCAGAGGAGGCAGAAGCT-3'.
```

These 2 primers were used in RT-PCR where a rat stomach-derived cDNA was used as template. PCR conditions utilized 35 cycles each consisting of 98° C. for 10 seconds, 55° C. for 30 seconds and 72° C. for 1 minute. The amplified DNA fragment was used as a probe for screening a rat stomach cDNA library. By screening about $2 \times 10^5$ recombinant phages, a full-length cDNA coding the rat-derived ghrelin was obtained.

The rat ghrelin cDNA was composed of 501 bases shown in SEQ ID NO: 6, coding a ghrelin precursor (prepro-ghrelin) consisting of 117 amino acids (FIG. 4a). The amino-terminal 23 amino acid residues in the ghrelin precursor had properties as a signal peptide. The ghrelin starts from glycine 24, and the last 2 amino acids (Pro-Arg) in the mature ghrelin was a sequence undergoing cleavage with a protease.

Using the rat ghrelin cDNA, a human stomach cDNA library was screened under low-stringency conditions to obtain a full-length human ghrelin cDNA. The human stomach cDNA library was prepared from human gastric poly(A)+ RNA (Clontech Co., Ltd) by use of a cDNA synthesis kit (Pharmacia Co., Ltd). The full-length human ghrelin cDNA thus obtained was composed of 511 bases shown in SEQ ID NO: 7, coding a human ghrelin precursor (prepro-ghrelin) consisting of 117 amino acids (FIG. 4a). Homology at the amino acid sequence level between the rat- and human-derived ghrelin precursors was 82.9%, revealing that ghrelins are highly conserved between species.

To known the distribution of ghrelin in tissues, poly(A)+ RNA isolated from various rat tissues was analyzed (FIG. 4b). By Northern blotting analysis of the rat tissues, 0.62 kb ghrelin precursor mRNA was recognized in stomach. Two faint bands were also recognized in ventricle, and these were 6.2 kb and 1.2 kb mRNAs which were larger than the mRNA in stomach, thus suggesting different mRNA splicing from that in stomach. From the above result, it was found that a major expression site for ghrelin is stomach.

Example 6. Effect of Ghrelin on Secretion of Pituitary Hormones

Whether ghrelin has GH secretion-inducing activity or not was examined in vitro and in vivo. First, the effect of ghrelin on primary cultured cells of anterior pituitary was examined for assay in vitro. Anterior pituitaries were collected from 4-week-old male SD rats and dispersed by treatment with collagenase, and the cells were collected, washed twice with DMEM medium (Dulbecco's modified Eagle's medium) containing 10% FCS (fetal bovine serum) and an antibiotic, and suspended in DMEM medium to prepare the primary cultured cells of anterior pituitary at an initial stage. The $5 \times 10^4$ cells were inoculated onto a 96-well cell culture plate coated with poly-D-lysine, and cultured for 3 to 4 days. The culture medium was exchanged with DMEM medium containing 0.1 ml sample, and maintained at 37° C. for 15 minutes. An aliquot of the culture medium was collected and measured by radioimmunoassay for the concentrations of various pituitary hormones in the culture medium. Out of the pituitary hormones, GH, FSH, LH, PRL and TSH were measured by using a kit produced by Biotrak/Amersham Co., Ltd, and ACTH was measured by using a high-sensitivity EIA kit produced by Peninsula Laboratories.

Figure 5:
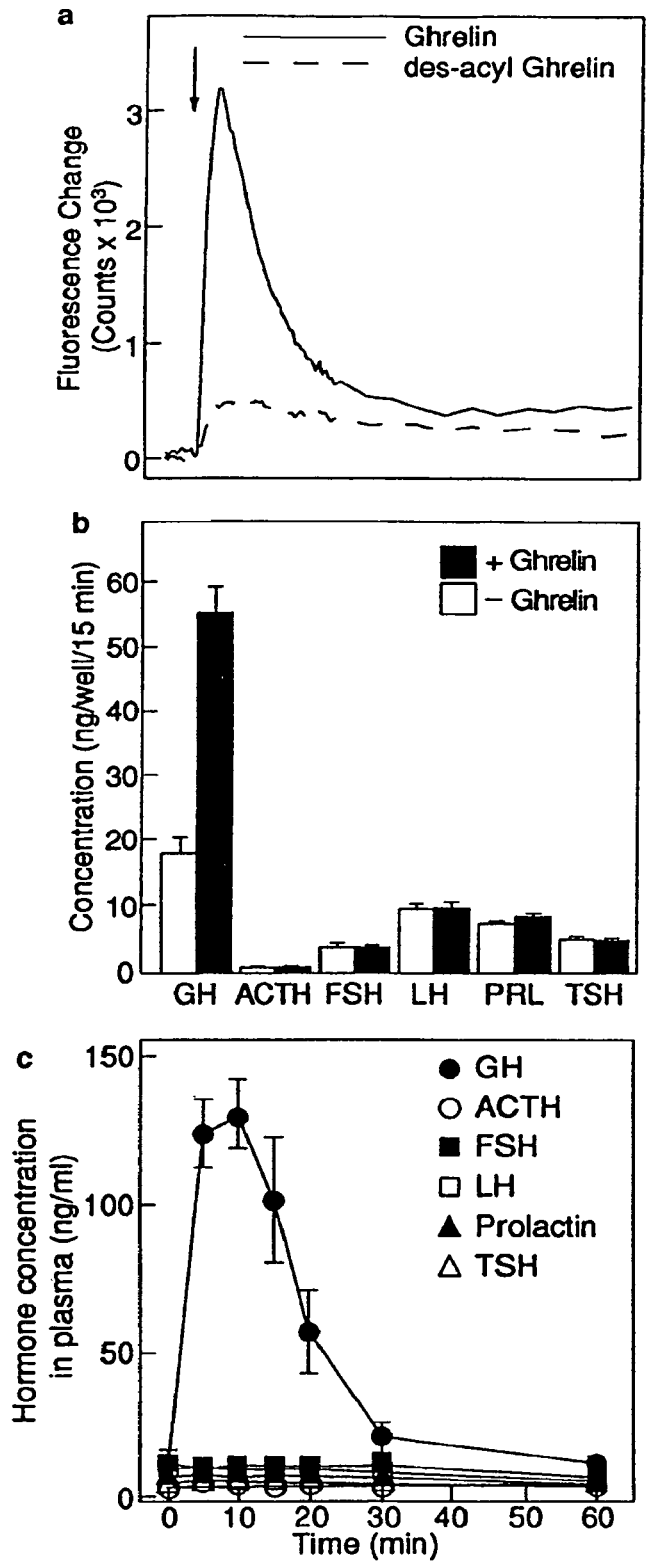
FIG. 5 is a graph showing the effect of ghrelin in vitro and in vivo on secretion of pituitary hormones.

When ghrelin was added to the primary anterior pituitary, an increase in the intracellular calcium ion concentration was recognized, while unmodified synthetic ghrelin also showed an slightly increased Ca-releasing activity (FIG. 5a). This result indicates that both ghrelin and unmodified ghrelin act directly on pituitary cells. Then, the GH secretion-inducing activity of ghrelin was examined using the primary cultured of anterior pituitary cells at an initial stage, and by addition of $10^{-6}$ M ghrelin, the concentration of GH in the culture was increased, but no increase in the concentrations of other pituitary hormones (FSH, LH, PRL, TSH) was observed (FIG. 5b).

The GH secretion-inducing activity of ghrelin was examined in vivo. After 10 μg of synthetic ghrelin was injected intravenously into a male rat (250 g), the blood was collected periodically for up to 60 minutes to measure the concentration of the pituitary hormones in plasma by radioimmunoassay. Out of the pituitary hormones, only GH was released into blood and reached the maximum level in 5 to 10 minutes after intravenous injection of ghrelin. From this result, it was found that ghrelin released from stomach to blood act on cells of anterior pituitary and release GH into blood, and it was confirmed that the ghrelin is an unidentified specific endogenous GH-secretion-inducing substance.

Example 7. Increase in Cardiac Output in Rat

The effect of bolus administration of ghrelin into a rat under anesthesia on the cardiovascular system was examined. Wistar male rats (Carerie) each weighing 220 to 250 g were divided at random into 4 groups (as groups given 10, 1, 0.5, and 0.2 μg ghrelin respectively) in order to examine the effect of acute administration of ghrelin on the cardiovascular system. Ghrelin was diluted with physiological saline and then rapidly administered in a dose of 10, 1, 0.5, or 0.2 μg/rat/120 μl via an injection tube (PE50) which had been inserted into the right common jugular vein for measuring cardiac output.

As a dynamic indicator, systemic blood pressure and cardiac output were measured, and peripheral vascular resistance was calculated. The rats were anesthetized with pentobarbital and fixed with dorsal position. For measurement of average blood pressure, a polyethylene canula (PE50) filled with heparin was inserted into the right femoral artery. The cardiac output was measured using a thermal dilution-type cardiac output meter (CARDIOTHER M500R). An injection tube (PE50) filled with physiological saline was inserted into the right common jugular vein in the rat and retained in the right ventricle. A micro-catheter was inserted into from the right common carotid artery in the rat and retained in the initiating part of the aorta. The infusion made use of 100 µl physiological saline at room temperature (25° C.). By pushing a MEASURE switch of the thermal dilution-type cardiac output meter and simultaneously injecting the infusion (100 µl physiological saline), measurement of cardiac output was initiated. Cardiac output was measured 5 times to determine average cardiac output. Average blood pressure and cardiac output were determined in 1, 5, 15, and 30 minutes before and after administration of ghrelin. Peripheral vascular resistance was determined by dividing average blood pressure by cardiac output.

TABLE 1

| | Body weight | Cardiac output (ml/min/kg) after administration of 1 µg ghrelin | | | | |
|---|---|---|---|---|---|---|
| | (g) | 0 min. | 1 min. | 5 min. | 15 min. | 30 min. |
| Mean | 230 | 347 | 382 | 367 | 341 | 338 |
| SEM | 3.7 | 14.3 | 10.2 | 11.5 | 7.9 | 8.8 |

In the table, SEM is standard error means.

TABLE 2

| | Body weight | Cardiac output (ml/min/kg) after administration of 10 µg ghrelin | | | | |
|---|---|---|---|---|---|---|
| | (g) | 0 min. | 1 min. | 5 min. | 15 min. | 30 min. |
| Mean | 237 | 350 | 390 | 392 | 370 | 344 |
| SEM | 1.0 | 8.5 | 7.4 | 15.8 | 14.7 | 13.8 |

In the Table, SEM is standard error means.

In the group given 1 µg ghrelin (Table 1) and the group given 10 µg ghrelin (Table 2), an increase in cardiac output was recognized in 1 to 5 minutes after administration.

Example 8. Isolation of Ghrelin and Ghrelin-27 from Various Origins

From rat stomach extract, ghrelin was purified using Ca-releasing activity as an indicator in the method described in Example 2. The active fraction (elution time of 59 minutes in FIG. 1b) in secondary CM-HPLC was purified to homogeneity by reverse phase HPLC on µBondasphere C-18 column (3.9×150 mm, produced by Waters Co., Ltd). This fraction was analyzed by electrospray ionization mass spectrometry (ESI-MS), indicating a peak of the molecular weight (3187.2±0.9) which was smaller by about 126 than that of natural ghrelin modified with octanoic acid (C8) consisting of 28 amino acids. Determination of the amino acid sequence of this peptide by a peptide sequencer (ABI 494, manufactured by Applied Biosysytems Co., LTd) revealed that it is a peptide composed of the following 27 amino acid residues (SEQ ID NO: 43): Gly Ser Xaa Phe Leu Ser Pro Glu His Gln Lys Ala Gln Arg Lys Glu Ser Lys Lys Pro Pro Ala Lys Leu Gln Pro Arg (Xaa is an unidentified amino acid). That is, this peptide was composed of an amino acid sequence wherein in ghrelin consisting of 28 amino acids, glutamine 13 or 14 was deleted. Since the Ca-releasing activity of this peptide was similar to that of ghrelin of 28 amino acids as shown in Example 9, this peptide was designated as ghrelin-27. From human stomach extract, human ghrelin-27 was isolated in the same manner as for rat ghrelin, and confirmed to consist of the amino acid sequence set forth in SEQ ID NO: 11. Peak fractions with retention times of 64 to 65 minutes in secondary CM-HPLC were purified and analyzed by electrospray ionization mass spectrometry (ESI-MS), indicating a peak of the molecular weight (3341.4±0.9). Because this fatty acid-modified peptide was composed of 28 amino acids, it was revealed to be a peptide wherein in ghrelin (28 amino acids), 3rd serine was modified with decanoic acid (C10).

From the rat stomach cDNA library prepared in Example 5, a cDNA coding a precursor of ghrelin-27 was cloned by plaque hybridization where the PCR-amplified DNA fragment prepared in Example 5 was used as a probe. The nucleotide sequence of the cDNA was determined and confirmed to code the precursor of ghrelin-27. The resulting cDNA for the rat ghrelin-27 precursor was composed of the nucleotide sequence set forth in SEQ ID NO: 14, coding the ghrelin-27 precursor having the amino acid sequence (116 amino acids) set forth in SEQ ID NO: 12. A cDNA for the human ghrelin-27 precursor was also cloned in the same manner as described above, and revealed to consist of the nucleotide sequence set forth in SEQ ID NO: 15, coding the human ghrelin-27 precursor having the amino acid sequence (116 amino acids) set forth in SEQ ID NO: 13.

A cDNA coding a precursor of porcine-derived ghrelin or ghrelin-27 was cloned from a porcine cDNA library in the method described in Example 5 by plaque hybridization where the PCR-amplified DNA fragment described in Example 5 was used as a probe. The nucleotide sequence of the resulting cDNA clone was determined and confirmed to code a porcine ghrelin precursor or a porcine ghrelin-27 precursor. The resulting cDNA for the porcine ghrelin precursor was composed of the nucleotide sequence set forth in SEQ ID NO: 20, coding a ghrelin precursor having the amino acid sequence (118 amino acids) set forth in SEQ ID NO: 18. The cDNA for the porcine ghrelin-27 precursor was composed of the nucleotide sequence set forth in SEQ ID NO: 21, coding the ghrelin-27 precursor having the amino acid sequence (117 amino acids) set forth in SEQ ID NO: 19. Accordingly, the porcine ghrelin (28 amino acids) and the porcine ghrelin-27 (27 amino acids) are composed of the amino acid sequences set forth in SEQ ID NOS: 16 and 17, respectively.

A cDNA coding a ghrelin precursor derived from eel, *Xenopus Laevis* or rainbow trout was cloned from various cDNA libraries in the method described in Example 5 by plaque hybridization where the PCR-amplified DNA fragment described in Example 5 was used as a probe. The nucleotide sequence of the resulting cDNA clone was determined and confirmed to code the ghrelin precursor.

The resulting cDNA for the eel ghrelin precursor was composed of the nucleotide set forth in SEQ ID NO: 36, the cDNA for the frog ghrelin precursor was composed of the nucleotide set forth in SEQ ID NO: 37, and the cDNA for the rainbow trout ghrelin precursor was composed of the nucleotide set forth in SEQ ID NO: 38 or 39.

From rainbow trout, the cDNA coding the ghrelin-23 precursor set forth in SEQ ID NO: 38 and the cDNA coding the ghrelin-20 precursor set forth in SEQ ID NO: 39 were obtained.

From the nucleotide sequences of the above cDNAs, it was found that the eel ghrelin precursor has the amino acid sequence set forth in SEQ ID NO: 32, the frog ghrelin precursor has the amino acid sequence set forth in SEQ ID NO: 33, and the rainbow trout ghrelin precursor has the amino acid sequence set forth in SEQ ID NO: 34 or 35.

From rainbow trout, the amino acid sequence of ghrelin-23 precursor set forth in SEQ ID NO: 34 and the amino acid sequence of ghrelin-20 precursor in SEQ ID NO: 35 were found.

A cDNA for a bovine ghrelin precursor was cloned by the PCR method. That is, PCR was carried out where synthetic DNA having nucleotide sequences designed on the basis of amino acid sequences conserved among the rat, human and porcine-derived ghrelins and ghrelins-27 were used as primer and a bovine stomach cDNA library as template. The DNA fragment thus amplified had the nucleotide sequence set forth in SEQ ID NO: 24, coding a part of bovine ghrelin-27 precursor set forth in SEQ ID NO: 23. Accordingly, the bovine ghrelin-27 has the amino acid sequence set forth in SEQ ID NO: 22. In the DNA fragment amplified by the above PCR using the bovine stomach cDNA library as template, there was no DNA coding a ghrelin (28 amino acids) precursor.

The amino acids of the rat-, human- and porcine-derived ghrelins and the rat-, human-, porcine- and bovine-derived ghrelins-27 were very similar, and in particular, the amino acid sequences of amino acids 1 to 10 in the 7 ghrelins described above were completely identical with one another.

Example 9. Comparison of Activity Among Various Ghrelin Derivatives

Peptide fragments obtained by partially digested the rat- and human-derived ghrelins by various proteases, or chemically synthesized peptides, were examined for their Ca releasing activity in order to determine a core amino acid sequence and the optimum chain length of a modifying fatty acid necessary for Ca-releasing activity. The Ca-releasing activity of ghrelin was expressed in terms of 50% effective concentration ($EC_{50}$, nM) at which 50% of the maximum activity is achieved. Accordingly, lower $EC_{50}$ values are indicative of higher activity.

TABLE 3

Comparison of the activity among various ghrelin derivatives

| Origin | SEQ ID NO. | Amino acids | Fatty acid modification | Ca-releasing activity ($EC_{50}$, nM) | Remark |
|---|---|---|---|---|---|
| human | 3 | 1-28 | Acyl (C:8) | 2.6 | natural ghrelin |
| human | 3 | 1-15 | Acyl (C:8) | 7.0 | |
| human | 3 | 1-11 | Acyl (C:8) | 15 | |
| rat | 2 | 1-28 | Acyl (C:8) | 2.9 | natural ghrelin |
| rat | 2 | 1-15 | Acyl (C:8) | 8.6 | |
| rat | 2 | 1-11 | Acyl (C:8) | 15 | |
| rat | 2 | 1-10 | Acyl (C:8) | 19 | |
| rat | 2 | 1-9 | Acyl (C:8) | 38 | |
| rat | 2 | 1-8 | Acyl (C:8) | 100 | |
| rat | 2 | 1-4 | Acyl (C:8) | 480 | |
| rat | 2 | 16-28 | Acyl (C:8) | >10000 | |
| rat | 2 | (1-28) + (14-28) | Acyl (C:8) | 2.8 | ghrelin-27 |
| rat | 2 | 1-28 | Acyl (C:16) | 3.1 | |
| rat | 2 | 1-28 | Acyl (C:10) | 2.6 | |
| rat | 2 | 1-28 | Acyl (C:6) | 16 | |
| rat | 2 | 1-28 | Acyl (C:4) | 280 | |
| rat | 2 | 1-28 | Acyl (C:2) | 780 | |

The Ca-releasing activity of ghrelin is present in the side of the amino-terminal. A peptide of from the amino-terminal to amino acid 4 has a sufficient Ca-releasing activity, and a peptide of from the amino-terminal to amino acid 10 shows a strong Ca-releasing activity near to that of natural ghrelin. When the chain length of modifying fatty acid is C:2 (acetyl group), a sufficient activity is brought about, and when the chain length is C:8 (octanoyl group), the maximum Ca-releasing activity is achieved, and even if the number of carbon atoms of fatty acid is further increased to C:10 (decanoyl group) or to C:16, the strong Ca-releasing activity does not change. That is, when the fatty acid for modifying 3rd serine from the amino-terminal contains 8 or more carbon atoms, the strongest Ca-releasing activity is brought about.

Example 10. Synthesis of Various Ghrelin Derivatives (1) Synthesis of Peptide Derivatives Amino acid derivatives other than Fmoc-$^D$Ser ($C_8H_{17}$) and Fmoc-Ser ($C_8H_{17}$), and synthesis reagents, were purchased from Perkin Elmer, Novabiochem or Watanabe Kagaku Co., Ltd. Peptide chain extension was performed by mainly using Applied Biosystem 433A synthesizer produced by Perkin Elmer, and a protected peptide derivative-resin was constructed by the Boc or Fmoc method. The protected peptide resin obtained by the Boc method was deprotected with anhydrous hydrogen fluoride (HF) in the presence of p-cresol thereby releasing the peptide, which was then purified. The protected peptide resin obtained by the Fmoc method was deprotected with trifluoroacetic acid (TFA) or dilute TFA containing various scavengers, and the released peptide was purified. Purification was performed in reversed phase HPLC on a C4 or C18 column. The purity of the purified product was confirmed by reverse phase HPLC, and its structure was confirmed by amino acid composition analysis and mass spectrometry.

The peptide of the present invention is produced by a conventional peptide synthesis method. For example, it can be produced by a method described, in chapter 2 and 3 of "Biochemical Experimental Course 1, Protein Chemistry IV" (Tokyo KagakuDojin) or in "Development of Medicines, a second series, Vol. 14, Peptide Synthesis (Hirokawa Shoten Co., Ltd). Accordingly, typical examples of the peptide of the present invention are shown below. Specifically, synthesis of acylated or alkylated peptides is exemplified below. Further, human-derived ghrelin (which may be abbreviated hereinafter to hGhrelin) or rat-derived ghrelin (which may be abbreviated hereinafter to rGhrelin) was reacted with trypsin or chymotrypsin or both the enzymes successively to give the following ghrelin fragments: 19. Ghrelin (16-28), 20. hGhrelin (1-15), 21. rGhrelin (1-15), 23. hGhrelin (1-11), 24. rGhrelin (1-11), 25. Ghrelin (1-10), 26. Ghrelin (1-9), 27. Ghrelin (1-8), and 30. Ghrelin (1-4). Then, these fragments were isolated by analytical HPLC and measured for their activity. 41. [N-Acetyl]-Ghrelin (1-10) was prepared in a usual manner by treating Ghrelin (1-10) with N-acetylsuccinimide. Compound No. 2 (rat ghrelin) made use of a natural material, and 10. [Ser$^3$(Butyryl)]-rGhrelin, 11. [Ser$^3$(Hexanoyl)]-rGhrelin, 12. [Ser$^3$(Decanoyl)]-rGhrelin, 13. [Ser$^3$(Lauroyl)]-rGhrelin, and 14. [Ser$^3$(Palmitoyl)]-rGhrelin were synthesized in the same manner as in synthesis of Compound 1 (hGhrelin) and then measured for their activity.

Main Abbreviations

HMP resin; 4-hydroxymethyl-phenoxymethyl resin
Fmoc amide resin; 4-(2',4'-dimethoxyphenyl-Fmoc-aminomethyl) phenoxyacetamido-ethyl resin
PAM resin; phenylacetoamidomethyl resin HBTU; 2-(1H-benzotriazole-1-yl)-1,1,3,3-tetramethyluronium hexafluorophosphate
TBTU; 2-(1H-benzotriazole-1-yl)-1,1,3,3-tetramethyluronium tetrafluoroborate
HOBt; 1-hydroxybenzotriazole
DCC; dicyclohexylcarbodiimide
DIPCI; diisopropylcarbodiimide
TFA; trifluoroacetic acid
DIPEA; diisopropylethylamine
TIPS; triisopropylsilane
Fmoc; fluorenylmethoxycarbonyl
Boc; t-butyloxycarbonyl
Trt; trityl
$Bu^t$; t-butyl
Pmc; 2,2,5,7,8-pentamethylchroman-6-sulfonyl
Prl; propionyl
PhPrl; phenylpropionyl
Bzl; benzyl
Bom; benzyloxymethyl
Tos; toluenesulfonyl
Cl-Z; 2-chloro-benzyloxycarbonyl
Pis; 2-phenylisopropyl
Mtt; 4-methyltrityl
DMF; N,N-dimethylformamide
NMP; N-methylpyrrolidone
DMAP; 4-dimethylaminopyridine
HOSu; N-hydroxysucciniimide
Adod; 2-aminododecanoic acid
Aib; 2-aminoisobutylic acid
Ape; 5-aminopentanoic acid
Cha; cyclohexylalanine
Dap; 2,3-diaminopropionic acid
Nal; naphtylalanine
Nle; norleucine
[Protecting Amino Acids Used in Synthesis]
Fmoc Method:
Boc-Gly, Fmoc-Gly, Fmoc-Ser ($Bu^t$), Fmoc-Ser (Trt), Fmoc-Glu (OBu$^t$), Fmoc-His (Boc), Fmoc-Gln (Trt), Fmoc-Arg (Pmc), Fmoc-Lys (Boc), Fmoc-Pro, Fmoc-Leu, Fmoc-Ala, Fmoc-Val, Fmoc-Phe, Fmoc-$^D$Phe, Fmoc-Ser (n-$C_8H_{17}$), Fmoc-$^D$Ser (n-$C_8H_{17}$), Fmoc-Cys (n-$C_8H_{17}$), Fmoc-Asp (OPis), Fmoc-Ser (Bzl), Fmoc-Cys (Trt), Fmoc-Dap (Octanoyl), Fmoc-2-$^L$Nal, Fmoc-2-$^D$Nal, Fmoc-Nle, Fmoc-Lys (Mtt), Fmoc-Aib-OH, Fmoc-Asp (O—$C_7H_{15}$)
Boc Method:
Boc-Gly, Boc-Ser (Bzl), Boc-Ser (Ac), Boc-Ser (Prl), Boc-Glu (OBzl), Boc-His (Bom), Boc-Gln, Boc-Arg (Tos), Boc-Lys (Cl-Z), Boc-Pro, Boc-Leu, Boc-Ala, Boc-Val, Boc-Phe, Boc-Cys (n-$C_8H_{17}$), Boc-Ape Boc-Ser (n-$C_8H_{17}$)
[Units Used]
(a) Analytical HPLC System
Unit: Shimadzu LC-10A System
Column: YMC PROTEIN-RP (4.6 mmφ×150 mm)
Column temperature: 40° C.
Eluent: A linear gradient of from 0 to 50% acetonitrile for 20 minutes in 0.1% trifluoroacetic acid
Flow rate: 1 mL/min.
Detection: UV (210 nm)
Injection volume: 10 to 100 µl
(b) Preparative HPLC System
Unit: Waters 600 Multisolvent Delivery System
Columns: YMC-Pack-ODS-A (5 µm, 20 mm×250 mm)
  YMC-Pack-PROTEIN-RP (5 µm, C4, 10 mm×250 mm)
  YMC-Pack. PROTEIN-RP (5 µm, C4, 20 mm×250 mm)
  YMC PROTEIN-RP (4.6 mmφ×150 mm)
Eluent: A suitable linear gradient of acetonitrile concentration in 0.1% trifluoroacetic acid
Flow rate: 10 mL/min. (for the column of an inner diameter of 20 mm), 3 mL/min. (for the column of an inner diameter of 10 mm), 1 mL/min. (for the column of an inner diameter of 4.6 mm)
Detection: 210 nm, 260 nm
Injection: 10 to 2000 µl (2000 µl or more was injected via a pump)
(c) Mass Spectrometer
Unit: Finigan MAT TSQ700
Ion source: ESI
Detection ion mode: Positive
Spray voltage: 4.5 kV
Capillary temperature: 250° C.
Mobile phase: A mixture of 0.2% acetic acid and methanol (1:1)
Flow rate: 0.2 mL/min.
Scan range: m/z 300 to 1,500
(d) Analysis of Amino Acid Sequence
Unit: Applied Biosystem 477A, 492 model sequencer manufactured by Perkin Elmer
(e) Analysis of Amino Acid Composition
Unit: L-8500 model amino acid analyzer manufactured by Hitachi Co., Ltd.
Sample: Unless otherwise specified, the sample was hydrolyzed with 6 M HCl at 110° C. for 24 hours in a sealed tube.
(2) Example of Synthesis of a Derivative Having Acyl Serine or Acyl Threonine (Fmoc Method, Carboxyl-Terminal Amide Derivatives)

Compound 1 hGhrelin: GSS(CO—$C_7H_{15}$) FLSPEHQRVQQRKESKKPPAKLQPR

Fmoc-Arg (Pmc)-HMP-resin (403 mg, 0.25 mmol, ABI Co., Ltd) was treated with 20% piperazine for 20 minutes and subjected repeatedly to introduction of Fmoc-amino acid by HBTU/HOBt and elimination of Fmoc by piperazine sequentially to construct Fmoc-Ser(Bu$^t$)-Ser(Trt)-Phe-Leu-Ser(tBu)-Pro-Glu(OBu$^t$)-His(Boc)-Gln(Trt)-Arg(Pmc)-Val-Gln(Trt)-Gln(Trt)-Arg (Pmc)-Lys(Boc)-Glu(OBu$^t$)-Ser(Bu$^t$)-Lys(Boc)-Lys(Boc)-Pro-Pro-Ala-Lys(Boc)-Leu-Gln(Trt)-Pro-Arg(Pmc)-resin. After Boc-Gly was finally introduced by DCC/HOBt, the resulting protected peptide resin (1.3 g) was treated with 1% TFA-5% TIPS-methylene chloride solution (15 mL) for 30 minutes. The peptide resin was filtrated, washed several times with methylene chloride (30 mL), and washed with 5% DIEA (10 mL) and then with methylene chloride (30 mL). The resulting de-Trt peptide resin (about 1.3 g) was swollen with NMP (10 mL), and octanoic acid (144.2 mg, 1.0 mmol) and DIPCI (126.2 mg, 1.0 mmol) were added thereto in the presence of DMAP (61.1 mg, 0.5 mmol) and allowed to react for 8 hours. The resin was recovered by filtration and washed with NMP and then with methylene chloride, followed by drying under vacuum to give about 1.2 g protected peptide resin wherein the serine 3rd residue was octanoylated. To this product was added a de-protecting reagent (10 mL) consisting of 88% TFA-5% phenol-2% TIPS-5% H$_2$O, and the mixture was stirred at room temperature for 2 hours. The resin was removed by filtration, and the filtrate was concentrated followed by adding ether to the resulting residues to form precipitates. The precipitates were recovered by filtration and dried to give about 550 mg crude peptide. 200 mg of this product was dissolved in 10 mL water and applied to YMC-Pack PROTEIN-RP (C4, 20 mm×250 mm) and eluted with a linear gradient (flow rate: 10 mL/min.) for 60 minutes of from 0 to 54% acetonitrile in 0.1% trifluoroacetic acid. The desired fractions were collected and lyophilized to give about 120 mg of the desired product.

(3) Example of Synthesis of a Derivative Having Acyl Serine or Acyl Threonine (Fmoc Method, Carboxyl-Terminal Amide Derivative)

Compound 3 Ghrelin (1-9)-NH$_2$; GSS(CO—C$_7$H$_{15}$)FL-SPEH-NH$_2$

Fmoc-amide-resin (403 mg, 0.25 mmol, ABI Co., Ltd) was treated with 20% piperazine for 20 minutes and subjected repeatedly to introduction of Fmoc-amino acid by HBTU/HOBt and elimination of Fmoc by piperazine sequentially to construct Fmoc-Ser(Bu$^t$)-Ser(Trt)-Phe-Leu-Ser(Bu$^t$)-Pro-Glu(OBu$^t$)-His(Boc)-resin. After Boc-Gly was finally introduced by DCC/HOBt, the resulting protected peptide resin (about 550 mg) was treated with 1% TFA-5% TIPS-methylene chloride solution (10 mL) for 30 minutes. The peptide resin was recovered by filtration, washed several times with methylene chloride (30 mL), and washed with 5% DIEA (10 mL) and then with methylene chloride (30 mL). The resulting de-Trt peptide resin (about 750 mg) was swollen with NMP (10 mL), and octanoic acid (144.2 mg, 1.0 mmol) and DIPCI (126.2 mg, 1 mmol) were added thereto in the presence of DMAP (61.1 mg, 0.5 mmol) and allowed to react for 4 hours. The resin was recovered by filtration and washed with NMP and then with methylene chloride, followed by drying under vacuum to give about 800 mg protected peptide resin wherein the 3rd serine residue was octanoylated. TFA (10 mL) was added to this product and stirred at room temperature for 30 minutes. The resin was removed by filtration, and the filtrate was concentrated followed by adding ether to the resulting residues to form precipitates. The precipitates were recovered by filtration and dried to give about 250 mg crude peptide. About 200 mg of this product was dissolved in 10 mL of 30% aqueous acetic acid and applied to YMC-Pack PROTEIN-RP (C4, 20 mm×250 mm) and eluted with a linear gradient (flow rate: 10 mL/min.) for 60 minutes of from 0 to 54% acetonitrile in 0.1% trifluoroacetic acid. The desired fractions were collected and lyophilized to give about 150 mg of the desired product.

(4) Example of Synthesis of a Derivative Having Acyl Serine or Acyl Threonine (Boc Method)

Compound 9 (Ser$^3$(Propionyl)-rGhrelin (1-28); GSS(CO—CH$_2$CH$_3$) FLSPEHQKAQQRKESKKPPAKLQPR Protected rat ghrelin resin (4-28) was constructed from Boc-Arg (Tos)-Pam resin (0.75 g, 0.5 mmol) by Boc chemistry, and Boc-Ser (CO—CH$_2$CH$_3$)—OH, Boc-Ser (Bzl)-OH and Boc-Gly-OH were condensed with a half (1.4 g) of the resin. The resulting resin, 1.5 g, was treated with a mixture of HF and p-cresol (8.5 mL: 1.5 mL) at 0° C. for 1 hour, and the HF was evaporated. Ether was added to the residues, whereby 671 mg crude peptide was obtained. This sample was dissolved in 50% acetic acid (AcOH) and applied to a preparative column YMC-Pack-ODS-A (5 μm, 20 mm×250 mm) and eluted at a rate of 10 mL/min. by a gradient of from 0 to 95% acetonitrile concentration in 0.1% TFA solution for 75 minutes. Those fractions containing the desired product were lyophilized to give 135.8 mg crude peptide. A part (0.5 mg) of this product was applied to YMC-A-302 column (C18, 4.6 mm×150 mm) and eluted at a flow rate of 1 mL/min. by a gradient of from 15 to 19 concentration acetonitrile. This purification procedure was repeated and the desired fractions were combined to give 0.41 mg of the desired product.

The following peptide derivatives having acyl serine or acyl threonine were produced in the same manner as in production of Compound 3 or 9 described above.

The results of the mass spectrometry and amino acid composition analysis of the peptide derivatives having acyl serine or acyl threonine are summarized below.

Compound 1. hGhrelin
ESI-MS 3371.0 (theoretical: 3370.9), amino acid composition: Ser; 3.53 (4), Glx; 5.91 (6), Gly; 1.02 (1), Ala; 1.00 (1), Val; 0.96 (1), Leu; 2, Phe; 1.06 (1), Lys; 3.90 (4), His; 0.97 (1), Arg; 2.87 (3), Pro; 3.87 (4)

Compound 3. Ghrelin (1-9)-amide
ESI-MS [M+H]; 1085.7 (theoretical: 1085.2), amino acid composition: Ser; 2.45 (3), Glx; 0.98 (1), Gly; 0.99 (1), Leu; 1, Phe; 0.99 (1), His; 1.08 (1), Pro; 0.97 (1).

Compound 4. [Ser$^2$(Octanoyl), Ser$^3$]-Ghrelin (1-9)-amide
ESI-MS (M+H); 1085.8 (theoretical: 1085.2), amino acid composition: Ser; 2.46 (3), Glx; 0.98 (1), Gly; 0.99 (1), Leu; 1, Phe; 1.01 (1), His; 1.09 (1), Pro; 0.97 (1)

Compound 5. [Ser$^2$(Octanoyl)]-Ghrelin (1-9)-amide
ESI-MS [M+H]; 1211.7 (theoretical: 1211.4), amino acid composition: Ser; 2.48 (3), Glx; 1.00 (1), Gly; 1.01 (1), Leu; 1, Phe; 1.00 (1), His; 1.11 (1), Pro; 0.98 (1)

Compound 8. [Ser$^3$(Acetyl)]-rGhrelin
ESI-MS 3231.0 (theoretical: 3230.7), amino acid composition: Ser; 3.50 (4), Glx; 5.90 (6), Gly; 0.98 (1), Ala; 2.00 (2), Leu; 2, Phe; 1.01 (1), Lys; 4.97 (5), His; 0.99 (1), Arg; 1.99 (2), Pro; 3.99 (4)

Compound 9. [Ser$^3$(Propionyl)]-rGhrelin
ESI-MS 3245.0 (theoretical: 3242.8), amino acid composition: Ser; 3.42 (4), Glx; 5.93 (6), Gly; 1.00 (1), Ala; 2.00 (2), Leu; 2, Phe; 1.10 (1), Lys; 4.97 (5), His; 0.99 (1), Arg; 1.99 (2), Pro; 3.83 (4)

Compound 15. [Ser$^3$(3-Phenylpropionyl)]-hGhrelin
ESI-MS 3377.0 (theoretical: 3376.9), amino acid composition: Ser; 3.06 (4), Glx; 5.92 (6), Gly; 0.93 (1), Ala; 0.98 (1), Val; 0.99 (1), Leu; 2, Phe; 1.13 (1), Lys; 4.03 (4), His; 1.08 (1), Arg; 3.00 (3), Pro; 3.76 (4)

Compound 16. [Ser$^3$(3-Octenoyl)]-hGhrelin
ESI-MS 3369.0 (theoretical: 3368.9), amino acid composition: Ser; 3.59 (4), Glx; 5.91 (6), Gly; 1.00 (1), Ala; 1.02 (1), Val; 0.99 (1), Leu; 2, Phe; 1.15 (1), Lys; 3.97 (4), His; 0.98 (1), Arg; 2.93 (3), Pro; 3.88 (4)

Compound 28. Ghrelin (1-8)-amide
ESI-MS [M+H] 948.5 (theoretical: 948.1), amino acid composition: Ser; 2.45 (3), Glx; 0.97 (1), Gly; 0.99 (1), Leu; 1, Phe; 1.00 (1), Pro; 0.97 (1)

Compound 29. Ghrelin (1-7)-amide
ESI-MS [M+H] 819.6 (theoretical: 819.0), amino acid composition: Ser; 2.52 (3), Gly; 1.01 (1), Leu; 1, Phe; 1.02 (1), Pro; 1.09 (1)

Compound 30. Ghrelin (1-6)-amide
ESI-MS [M+H]; 722.4 (theoretical: 721.8), amino acid composition: Ser; 2.47 (3), Gly; 0.99 (1), Leu; 1, Phe; 1.00 (1)

Compound 31. Ghrelin (1-5)
ESI-MS [M+H] 636.5 (theoretical: 635.8), amino acid composition: Ser; 1.78 (2), Gly; 0.99 (1), Leu; 1, Phe; 1.02 (1)

Compound 32. Ghrelin (1-5)-amide
ESI-MS [M+H] 635.4 (theoretical: 634.8), amino acid composition: Ser; 1.67 (2), Gly; 1.01 (1), Leu; 1, Phe; 1.01 (1)

Compound 33-2. Ghrelin (1-4)-amide
ESI-MS [M+H] 522.2 (theoretical: 521.6), amino acid composition: Ser; 1.65 (2), Gly; 0.99 (1), Phe; 1

Compound 34. Ghrelin (1-3)-amide
ESI-MS [M+H] 375.2 (theoretical: 374.4), amino acid composition: Ser; 1.66 (2), Gly; 1 Compound 35. [Lys$^8$]-Ghrelin (1-8)-amide ESI-MS [M+H] 947.9 (theoretical: 947.1), amino acid composition: Ser; 2.70 (3), Gly; 1.00 (1), Leu; 1, Phe; 1.00 (1), Lys; 0.99 (1), Pro; 1.00 (1)

Compound 36. [Arg$^8$]-Ghrelin (1-8)-amide

ESI-MS [M+H] 975.8 (theoretical: 975.2), amino acid composition: Ser; 2.70 (3), Gly; 1.00 (1), Leu; 1, Phe; 1.01 (1), Arg; 0.99 (1), Pro; 1.00 (1)

Compound 37. [Lys$^6$]-Ghrelin (1-6)-amide

ESI-MS [M+H] 763.6 (theoretical: 762.9), amino acid composition: Ser; 1.80 (2), Gly; 1.00 (1), Leu; 1, Phe; 1.01 (1), Lys; 1.00 (1)

Compound 38. [Lys$^5$]-Ghrelin (1-5)-amide

ESI-MS [M+H] 650.5 (theoretical: 649.8), amino acid composition: Ser; 1.79 (2), Gly; 0.99 (1), Phe; 1, Lys; 0.99 (1)

Compound 39. [$^D$Phe$^4$, Lys$^5$]-Ghrelin (1-5)-amide

ESI-MS [M+H] 650.5 (theoretical: 649.8), amino acid composition: Ser; 1.79 (2), Gly; 0.99 (1), Phe; 1, Lys; 0.99 (1)

Compound 40. [N-Aminopentanoyl]-Ghrelin (3-7)-amide

ESI-MS [M+H] 774.7 (theoretical: 774.0), amino acid composition: Ser; 1.80 (2), Leu; 1, Phe; 1.01 (1), Pro; 1.00 (1)

Compound 43. [N-Glycyl]-Ghrelin (3-7)-amide

ESI-MS [M+H]; 732.7 (theoretical: 731.9), amino acid composition: Ser; 1.80 (2), Gly; 1.00 (1), Leu; 1, Phe; 1.01 (1), Pro; 1.00 (1)

Compound 44. [Leu$^2$]-Ghrelin (1-7)-amide

ESI-MS [M+H]; 845.7 (theoretical: 845.1), amino acid composition: Ser; 1.80 (2), Gly; 1.01 (1), Leu; 2, Phe; 1.02 (1), Pro; 0.99 (1)

Compound 45. [His$^2$]-Ghrelin (1-7)-amide

ESI-MS [M+H]; 869.7 (theoretical: 869.0), amino acid composition after hydrolysis with propionic acid.hydrochloric acid (50/50) at 150° C. for 2 hours: Ser; 1.02 (2), Gly; 1.00 (1), Leu; 1, Phe; 1.00 (1), His; 0.95 (1), Pro; 0.99 (1)

Compound 46. [Lys$^2$]-Ghrelin (1-7)-amide

ESI-MS [M+H]; 860.7 (theoretical: 860.1), amino acid composition after hydrolysis with propionic acid.hydrochloric acid (50/50) at 150° C. for 2 hours: Ser; 1.04 (2), Gly; 1.00 (1), Leu; 1, Phe; 1.00 (1), Lys; 1.00 (1), Pro; 1.00 (1)

Compound 47. [Gly$^2$]-Ghrelin (1-7)-amide

ESI-MS [M+H]; 789.5 (theoretical: 788.9), amino acid composition after hydrolysis with propionic acid.hydrochloric acid (50/50) at 150° C. for 2 hours: Ser; 1.14 (2), Gly; 2.01 (2), Leu; 1, Phe; 1.00 (1), Pro; 1.00 (1)

Compound 59. [Thr$^2$(Octanoyl)]-hGhrelin

ESI-MS M; 3384.0 (theoretical: 3384.9), amino acid composition: Ala; 1.02 (1) Arg; 2.99 (3), Glx; 5.91 (6), Gly; 1.02 (1), His; 1.00 (1), Leu; 2 (2), Lys; 4.05 (4), Phe; 1.00 (1), Pro; 4.06 (4), Ser; 2.66 (3), Thr; 0.94 (1), Val; 0.96 (1)

Compound 60. [Leu$^2$, Thr$^3$(Octanoyl)]-hGhrelin

ESI-MS M; 3410.0 (theoretical: 3411.0), amino acid composition: Ala; 1.01 (1), Arg; 2.95 (3), Glx; 5.92 (6), Gly; 1.01 (1), His; 1.01 (1), Leu; 3 (3), Lys; 4.02 (4), Phe; 1.01 (1), Pro; 4.00 (4), Ser; 1.81 (2), Thr; 0.96 (1), Val; 0.97 (1)

Compound 69. [Ser$^2$(4-Methylpentanoyl)]-hGhrelin

ESI-MS M; 3343.0 (theoretical: 3342.9), amino acid composition: Ala; 1.00 (1), Arg; 2.97 (3), Glx; 5.86 (6), Gly; 1.02 (1), His; 1.01 (1), Leu; 2, Lys; 4.00 (4), Phe; 1.01 (1), Pro; 3.99 (4), Ser; 3.54 (4), Val; 0.98 (1)

Compound 75. [Lys$^7$]-Ghrelin (1-7)-amide

ESI-MS [M+H]; 850.5 (theoretical: 850.0), amino acid composition: Ser; 2.67 (3), Gly; 1.00 (1), Leu; 1, Phe; 1.00 (1), Lys; 1.00 (1)

(5) Example of Synthesis of an Amino-Terminal Acylated Derivative

Compound 6. [N-Octanoyl, Ser$^3$]-Ghrelin (1-9)-amide; C$_7$H$_{15}$CO-GSSFLSPEH-NH$_2$ Fmoc-amide resin (403 mg, 0.25 mmol, ABI Co., Ltd) was treated with 20% piperazine for 20 minutes and subjected repeatedly to introduction of Fmoc-amino acid by HBTU/HOBt and elimination of Fmoc by piperazine sequentially to construct Fmoc-Gly-Ser(Bu$^r$)-Ser(Bu$^r$)-Phe-Leu-Ser(tBu)-Pro-Glu(OBu$^r$)-His(Boc)-resin. After treatment with piperazine, the resulting resin (550 mg) was washed with NMP, and DIPCI (126.2 mg, 1 mmol) and octanoic acid (144.2 mg, 1.0 mmol) were added thereto in the presence of HOBt (135.1 mg, 1 mmol) and allowed to react for 4 hours. The resin was recovered by filtration, washed with NMP and then with methylene chloride, and dried under vacuum to give about 600 mg protected peptide resin wherein the amino group in amino-terminal Gly was octanoylated. This product was deprotected with TFA (10 ml) (treatment for 30 minutes), to give 200 mg crude peptide. The whole of the sample was applied to YMC-Pack PROTEIN-RP (5 μm, C4, 20 mm×250 mm) and eluted with a linear gradient (flow rate: 10 mL/min) for 60 minutes of from 0 to 54% acetonitrile in 0.1% trifluoroacetic acid. About 180 mg of the desired product was obtained.

Measured values: ESI-MS [M+H]; 1085.6 (theoretical: 1085.2), amino acid composition: Ser; 2.47 (3), Glx; 0.98 (1), Gly; 1.00 (1), Leu; 1, Phe; 1.02 (1), His; 1.09 (1), Pro; 0.96 (1)

(6) Example of Synthesis of a Derivative Containing Serine Having an Alkyl Side-Chain Compound 50. [Ser$^3$(Octyl)]-Ghrelin (1-7)-amide; GSS(C$_8$H$_{17}$) FLSP-NH$_2$ Fmoc-Ser (C$_8$H$_{17}$)

Under cooling on ice, sodium hydride (3.19 g, 133 mmol) was added to a solution of Boc-Ser (12.3 g, 53.9 mmol) in DMF (300 ml) and stirred at room temperature for 1.5 hours. Octane iodide (11.0 ml, 60.9 mmol) was added thereto and stirred at room temperature for 16 hours. After water (40 ml) was added dropwise to the reaction solution under cooling on ice, the solvent was evaporated under vacuum. The resulting residues were purified by applying them to silica gel column chromatography (gel; Art9385, Merck Co., Ltd, eluent; dichloromethane:methanol:acetic acid=120:10:1), to give 6.88 g Boc-Ser (C$_8$H$_{17}$) (yield, 36.2%) as pale yellow oily matter. Trifluoroacetic acid (120 ml) was added to this product, Boc-Ser (C$_8$H$_{17}$) (6.88 g, 21.7 mmol), under cooling on ice and stirred for 0.5 hour at room temperature. After the trifluoroacetic acid was evaporated, the resulting residues were dissolved in diethyl ether (120 ml), and 4N HCl-dioxane (22 ml) was added thereto and stirred for 1 hour under cooling on ice. The precipitated crystals were recovered by filtration to give 5.23 g H-Ser (C$_8$H$_{17}$).HCl (yield, 96.3%) as colorless crystals. After triethylamine (1.40 ml, 10 mmol) was added to a suspension (50 ml) of this product H-Ser (C$_8$H$_{17}$).HCl (2.54 g, 10.0 mmol) in 10 sodium hydrogen carbonate, a solution of Fmoc-Osu (5.00 g, 14.8 mmol) in 1,2-dimethoxyethane (20 ml) was added dropwise thereto over the period of 10 minutes and stirred at room temperature for 16 hours. The insolubles were filtered off, then dichloromethane was added to the filtrate, and the organic phase was separated and washed with 13% NaCl solution. The organic phase was dried over anhydrous sodium sulfate, and the solvent was evaporated. The resulting residues were purified by applying them to silica gel column chromatography (gel; BW-300, Fuji Silicia Co., Ltd, eluent; dichloromethane:methanol=93:7), to give 2.75 g Fmoc-Ser (C$_8$H$_{17}$) (yield: 62.6%) as colorless crystals. Rf=0.45 (CHCl$_3$: MeOH=9:1, Silica gel 60F$_{254}$, MERCK Co., Ltd). Fmoc-$^D$Ser(C$_8$H$_{17}$): Rf=0.45 (CHCl$_3$: MeOH=9: 1, Silica gel 60F$_{254}$, MERCK Co., Ltd).

Fmoc-amide resin (400 mg, 0.25 mmol, ABI Co., Ltd) was treated with 20% piperazine for 20 minutes and subjected repeatedly to introduction of Fmoc-amino acid by HBTU/HOBt and elimination of Fmoc by piperazine sequentially to construct Fmoc-Ser(Bu$^t$)-Ser(C$_8$H$_{17}$)-Phe-Leu-Ser(Bu$^t$)-Pro-resin. After Boc-Gly was finally introduced by DCC/HOBt, a part (250 mg) of the resulting protected peptide resin was treated with TFA (10 mL) for 30 minutes. The resin was removed by filtration, and the filtrate was concentrated followed by adding ether to the resulting residues to give about 120 mg crude peptide as precipitates. This product was dissolved in 5% AcOH (10 mL) and applied to YMC-Pack-ODS-A (5 μm, 20 mm×250 mm) and eluted with a linear gradient (flow rate: 10 mL/min.) for 60 minutes of from 0 to 60% acetonitrile in 0.1% trifluoroacetic acid. The desired fractions were collected and lyophilized to give about 40 mg of the desired product.

Compound 84. [N-Aminopentanoyl, Ser$^3$(Octyl)]-Ghrelin (3-5)-benzyl amide;
H-Ape-Ser(C$_8$H$_{17}$)-Phe-Leu-NH—CH$_2$-Ph Oxime resin (230 mg/0.25 mmol, Novabiochem Co., Ltd) was placed in a reaction vessel equipped with a glass filter, and Boc-Leu-OH.H$_2$O (190 mg, 0.75 mmol) previously dissolved in methylene chloride (DCM) and dried over MgSO$_4$, DCC (160 mg, 0.75 mmol), and 5 ml DCM were added thereto and shaken overnight. The reaction product was washed several times with a suitable amount of DCM, DCM/EtOH (1:1) and DCM in this order. After introduction of Leu, <1> 10 ml of 25% TFA/DCM was added thereto and shaken for 30 minutes, and the resin was washed several times with DCM, isopropyl alcohol (iPrOH), DCM and DMF in this order, and <2> a solution prepared by dissolving 0.75 mmol (3 equivalents) of Boc-amino acid, 0.75 mmol (3 equivalents) of TBTU and 0.75 mmol (3 equivalents) of HOBt and then adding 1.25 mmol (5 equivalents) of DIPEA thereto in 5 mL DMF in an Erlenmeyer flask was introduced into the reaction vessel and shaken for 1 hour; this operation was repeatedly carried out to condense amino acids sequentially. Finally, Boc-NH—(CH$_2$)$_4$—CO-Ser (C$_8$H$_{17}$)-Phe-Leu-Oxime resin, 370 mg, was obtained. The resin was suspended in about 5 mL DMF, and benzylamine hydrochloride (180 mg, 1.25 mmol), triethylamine (173 μL, 1.25 mmol) and acetic acid (72 μL, 1.25 mmol) were added thereto, and the mixture was stirred. After 24 hours, the resin was filtered off, and the filtrate was evaporated, and the resulting Boc-protected peptide was precipitated in 10 mL of 1N HCl. This product was washed with water and dried, and 5 mL TFA was added thereto and reacted for 30 minutes thereby eliminate the Boc. The TFA was evaporated, and the product was precipitated with ether (Et$_2$O), whereby the desired product (N-Aminopentanoyl, Ser$^3$(Octyl)-Ghrelin (3-5)-benzylamide, 110 mg, was obtained. Compounds 82, 83 and 85 were synthesized in the same manner.

The following peptide derivatives having alkyl serine, except for Compounds 82 to 85, were produced in the same manner as in production of Compound 50 described above.

The results of the mass spectrometry and amino acid composition analysis of the peptide derivatives having alkyl serine are summarized below.

Compound 17. [Ser$^3$(Octyl)]-hGhrelin
ESI-MS; 3357.0 (theoretical: 3356.9), amino acid composition: Ser; 2.92 (3+1), Glx; 5.94 (6), Gly; 1.00 (1), Ala; 0.98 (1), Val; 0.99 (1), Leu; 2, Phe; 1.13 (1), Lys; 4.04 (4), His; 1.09 (1), Arg; 3.01 (3), Pro; 3.89 (4)

Compound 50. [Ser$^3$(Octyl)]-Ghrelin (1-7)-amide
ESI-MS [M+H]; 805.5 (theoretical: 805.0), amino acid composition after hydrolysis with propionic acid.hydrochloric acid (50/50) at 150° C. for 2 hours: Ser; 0.86 (2+1), Gly; 1.01 (1), Leu; 1, Phe; 1.06 (1), Pro; 0.95 (1)

Compound 51. [Ser$^3$(Octyl), $^D$Phe$^4$]-Ghrelin (1-7)-amide
ESI-MS [M+H]; 805.4 (theoretical: 805.0), amino acid composition after hydrolysis with propionic acid.hydrochloric acid (50/50) at 150° C. for 2 hours: Ser; 0.97 (2+1), Gly; 1.00 (1), Leu; 1, Phe; 1.05 (1), Pro; 1.16 (1)

Compound 52. [$^D$Ser$^3$ (Octyl)]-Ghrelin (1-7)-amide
ESI-MS [M+H]; 805.4 (theoretical: 805.0), amino acid composition after hydrolysis with propionic acid.hydrochloric acid (50/50) at 150° C. for 2 hours: Ser; 1.51 (2+1), Gly; 1.00 (1), Leu; 1, Phe; 1.00 (1), Pro; 1.00 (1)

Compound 53. [$^D$Ser$^3$(Octyl), $^D$Phe$^4$]-Ghrelin (1-7)-amide
ESI-MS [M+H]; 805.5 (theoretical: 805.0), amino acid composition after hydrolysis with propionic acid.hydrochloric acid (50/50) at 150° C. for 2 hours: Ser; 1.51 (2+1), Gly; 1.00 (1), Leu; 1, Phe; 1.00 (1), Pro; 1.01 (1)

Compound 67. [Ser$^3$(Bzl)]-hGhrelin
ESI-MS M; 3335.0 (theoretical: 3334.8), amino acid composition: Ala; 1.00 (1), Arg; 2.96 (3), Glx; 5.92 (6), Gly; 1.00 (1), His; 1.01 (1), Leu; 2 (2), Lys; 4.00 (4), Phe; 1.02 (1), Pro; 4.08 (4), Ser; 3.58 (4), Val; 0.98 (1)

Compound 76. [N-Aminopentanoyl, Ser$^3$(Octyl), Lys$^5$]-Ghrelin (3-5)-amide
ESI-MS [M+H]; 591.5 (theoretical: 590.8), amino acid composition: Ser; 0.45 (1), Phe; 1, Lys; 1.00 (1)

Compound 77. [N-Aminopentanoyl, $^D$Ser$^3$(Octyl), $^D$Phe$^4$, Lys$^5$]-Ghrelin (3-5)-amide
ESI-MS [M+H]; 591.5 (theoretical: 590.8), amino acid composition: Ser; 0.45 (1), Phe; 1, Lys; 1.01 (1)

Compound 78. [Aib$^1$, His$^2$, Ser$^3$(Octyl), Lys$^5$]-Ghrelin (1-5)-amide
ESI-MS [M+H]; 714.6 (theoretical: 713.9), amino acid composition: Ser; 0.45 (1), Phe; 1, His; 1.01 (1), Lys; 1.00 (1)

Compound 79. [Aib$^1$, His$^2$, $^D$Ser$^3$(Octyl), $^D$Phe$^4$, Lys$^5$]-Ghrelin (1-5)-amide
ESI-MS [M+H]; 714.5 (theoretical: 713.9), amino acid composition: Ser; 0.44 (1), Phe; 1, His; 1.00 (1), Lys; 1.01 (1)

Compound 81. [N-Aminopentanoyl, Ser$^3$(Octyl)]-Ghrelin (3-5)-amide
ESI-MS [M+H]; 576.5 (theoretical: 575.8), amino acid composition: Ser; 0.49 (1), Leu; 1, Phe; 0.99 (1)

Compound 82. [N-Aminopentanoyl, Ser$^3$(Octyl)]-Ghrelin (3-5)-methylamide
ESI-MS [M+H]; 590.6 (theoretical: 589.8), amino acid composition: Ser; 0.49 (1), Leu; 1, Phe; 0.99 (1)

Compound 83. [N-Aminopentanoyl, Ser$^3$(Octyl)]-Ghrelin (3-5)-ethylamide
ESI-MS [M+H]; 604.3 (theoretical: 603.8), amino acid composition: Ser; 0.50 (1), Leu; 1, Phe; 0.99 (1)

Compound 84. [N-Aminopentanoyl, Ser$^3$(Octyl)]-Ghrelin (3-5)-benzylamide
ESI-MS [M+H]; 666.5 (theoretical: 665.9), amino acid composition: Ser; 0.46 (1), Leu; 1, Phe; 0.98 (1)

Compound 85. [N-Aminopentanoyl, Ser$^3$(Octyl)]-Ghrelin (3-5)-aminoethylamide
ESI-MS [M+H]; 619.6 (theoretical: 618.9), amino acid composition: Ser; 0.47 (1), Leu; 1, Phe; 0.99 (1)

(7) Example of Synthesis of a Derivative Containing Cysteine Having an Alkyl Side-Chain Compound 48. [Cys$^3$(Octyl)]-Ghrelin (1-7)-NH$_2$; GSC(C$_8$H$_{17}$)FLSP-NH$_2$ Fmoc-amide-resin (403 mg, 0.25 mmol, ABI Co., Ltd) was treated with 20% piperazine for 20 minutes and subjected repeatedly to introduction of Fmoc-amino acid by HBTU/HOBt and elimination of Fmoc by piperazine sequentially to construct Fmoc-Ser(Bu$^t$)-Cys(C$_8$H$_{17}$)-Phe-Leu-Ser(Bu$^t$)-Pro resin. After Boc-Gly was finally introduced by DCC/HOBt, the resulting protected peptide resin (550 mg) was treated with TFA (10 mL) for 30 minutes. The resin was removed by filtration, and the filtrate was concentrated followed by adding ether to the resulting residues to give about 120 mg crude peptide as precipitates. This product was dissolved in 10 mL of 5% acetic acid and applied to YMC-Pack-ODS-A (5 µm, 20 mm×250 mm) and eluted with a linear gradient (flow rate: 10 mL/min.) for 60 minutes of from 0 to 60% acetonitrile in 0.1% trifluoroacetic acid. The desired fractions were collected and lyophilized to give about 44 mg of the desired product.

Compound 68. [Cys$^3$(Trt)]-hGhrelin; GSC(C-Ph$_3$)FLSPE-HQRVQQRKESKKPPAKLQPR

Fmoc-Arg (Pmc)-resin (403 mg, 0.25 mmol, ABI Co., Ltd) was treated with 20% piperazine for 20 minutes and subjected repeatedly to introduction of Fmoc-amino acid by HBTU/HOBt and elimination of Fmoc by piperazine sequentially to construct Fmoc-Ser(Bu$^t$)-Cys(Trt)-Phe-Leu-Ser(tBu)-Pro-Glu(OBu$^t$)-His(Boc)-Gln(Trt)-Arg(Pmc)-Val-Gln(Trt)-Gln(Trt)-Arg(Pmc)-Lys(Boc)-Glu(OBu$^t$)-Ser(Bu$^t$)-Lys(Boc)-Lys(Boc)-Pro-Pro-Ala-Lys(Boc)-Leu-Gln(Trt)-Pro-Arg(Pmc)-HMP resin. After Boc-Gly was finally introduced by DCC/HOBt, the resulting protected peptide resin (1.4 g) was recovered. TFA (15 mL) was added to a part (400 mg) of the resulting resin and stirred at room temperature for 1 hour. The resin was removed by filtration, and the filtrate was concentrated followed by adding ether to the resulting residues to form precipitates. About 90 mg of the precipitates were dissolved in 40 mL water, then applied to YMC-Pack PROTEIN-RP (C4, 20 mm×250 mm) and eluted with a linear gradient (flow rate: 10 mL/min.) for 60 minutes of from 0 to 54% acetonitrile in 0.1% trifluoroacetic acid. The desired fractions were collected and lyophilized to give about 60 mg of the desired product.

The following peptide derivatives having alkyl cysteine were produced in the same manner as in production of Compound 48 or 68 described above.

The results of the mass spectrometry and amino acid composition analysis of the peptide derivatives having alkyl cysteine are summarized below.

Compound 18. [Cys$^3$(Octyl)]-rGhrelin

ESI-MS; 3317.0 (theoretical: 3316.9), amino acid composition: Ser; 2.69 (3), Glx; 5.90 (6), Gly; 1.00 (1), Ala; 1.99 (2), Leu; 2, Phe; 1.02 (1), Lys; 4.97 (5), His; 0.99 (1), Arg; 1.98 (2), Pro; 3.87 (4)

Compound 48. [Cys$^3$ (Octyl)]-Ghrelin (1-7)-amide

ESI-MS [M+H]; 821.7 (theoretical: 821.1), amino acid composition after hydrolysis with propionic acid.hydrochloric acid (50/50) at 150° C. for 2 hours: Ser; 0.60 (2), Gly; 1.08 (1), Leu; 1, Phe; 1.06 (1), Pro; 0.96 (1)

Compound 49. [Cys$^3$(Octyl), $^D$Phe$^4$]-Ghrelin (1-7)-amide

ESI-MS [M+H]; 821.6 (theoretical: 821.1), amino acid composition after hydrolysis with propionic acid.hydrochloric acid (50/50) at 150° C. for 2 hours: Ser; 0.58 (2), Gly; 1.02 (1), Leu; 1, Phe; 1.06 (1), Pro; 0.97 (1)

Compound 68. [Cys$^3$(Trt)]-hGhrelin

ESI-MS 3503.0 (theoretical: 3503.1), amino acid composition: Ser; 2.42 (3), Glx; 5.77 (6), Gly; 1.00 (1), Ala; 1.01 (1), Val; 0.94 (1), Leu; 2, Phe; 0.99 (1), Lys; 3.94 (4), His; 0.99 (1), Arg; 2.92 (3), Pro; 3.81 (4)

(8) Example of Synthesis of a Peptide Derivative Containing N-Methyl Amino Acids Compound 86. [N-Aminopentanoyl, Ser$^3$(Octyl), MePhe$^4$, MeLeu$^5$]-Ghrelin (3-5)-amide; NH$_2$— (CH$_2$)$_4$—CO-Ser (C$_8$H$_{17}$)-MePhe-MeLeu-NH$_2$ Fmoc-amide resin (0.40 g, 0.25 mmol) was placed in a reaction vessel equipped with a glass filter, and 15 mL of 20% piperidine in NMP was added thereto and shaken for 20 minutes, thus removing the Fmoc group. Thereafter, 15 mL NMP, 1.0 mmol (4 equivalents) of Fmoc-MeLeu-OH, 1.0 mmol (4 equivalents) of TBTU, 1.0 mmol (4 equivalents) of HOBt and 1.0 mmol (4 equivalents) of DIPEA were added thereto and shaken for 1 hour to condense the Fmoc-MeLeu. Thereafter, the peptide chain was extended by repeatedly carrying out removal of Fmoc group by 20% piperidine and condensation of Fmoc-amino acid (3 equivalents) by bromo-tris-pyrrolidino-phosphonium hexafluorophosphate (3 equivalents) in the presence of 2.25 mmol (9 equivalents) of DIPEA. The conclusion of the condensation reaction was confirmed by deprotecting a small amount of the resin with TFA and examining it by HPLC and mass spectrometry (MS). After Boc-NH—(CH$_2$)$_4$—CO-Ser(O—C$_8$H$_{17}$)-MePhe-MeLeu-resin was obtained, this resin was treated with TFA for 30 minutes, whereby the resin was cleaved to de-protect the peptide. After the TFA was evaporated, the peptide was washed with ether (Et$_2$O) to give 120 mg NH$_2$—(CH$_2$)$_4$—CO-Ser(C$_8$H$_{17}$)-MePhe-MeLeu-NH$_2$. This product was applied to YMC-Pack ODS-A (C18, 20 mm×250 mm) and eluted with a linear gradient (flow rate: 10 mL/min.) for 60 minutes of 0 to 54% acetonitrile in 0.1% trifluoroacetic acid. The desired fractions were collected and lyophilized to give 70 mg of the desired product. After this derivative was hydrolyzed with propionic acid.HCl (50/50) at 150° C. for 2 hours, the amount of the peptide was quantified using the ratio of the peak area of aminopentanoic acid detected in the amino acid analyzer to that of 10 nmol aminopentanoic acid as a standard.

ESI-MS [M+H]; 604.5 (theoretical: 603.8), detected amino acids after hydrolysis with propionic acid.HCl (50/50) at 150° C. for 2 hours: Ser, Ape.

(9) Synthesis of a Mixed-Disulfide Derivative

Compound 57. [Cys$^3$(S-Heptyl)]-hGhrelin; GSC(S—C$_7$H$_{15}$) FLSPEHQRVQQRKESKKPPAKLQPR A de-protecting reagent (15 mL) consisting of 88% TFA-5% phenol-2% TIPS-5% H$_2$O was added to a protected peptide-HMP resin (1 g) obtained by synthesis in the same manner as in production of Compound 68, and then stirred at room temperature for 2 hours. The resin was removed by filtration, and the filtrate was concentrated followed by adding ether to the resulting residues, whereby about 550 mg crude [Cys$^3$]-hGhrelin powder was obtained. This product was applied to YMC-Pack ODS-A (C18, 20 mm×250 mm) and eluted with a linear gradient (flow rate: 10 mL/min.) for 60 minutes of from 0 to 54% acetonitrile in 0.1% trifluoroacetic acid. The desired fractions were collected and lyophilized to give 300 mg [Cys$^3$]-hGhrelin (1-28). 40 mg (11.4 µmol) of this product was dissolved in water (20 mL), and 1 mL solution of 4,4'-dithiodipyridine (7.5 mg, 34.2 µmol) in acetonitrile was added thereto and left for 1 hour. After the conclusion of the reaction was confirmed, the reaction solution was washed several times with chloroform to remove an excess of the 4,4'-dithiodipyridine and pyridone derivative. The aqueous layer (10 mL) containing [thiopyridyl Cys$^3$]-hGhrelin (1-28) was adjusted to pH 7.4 with aq. 5% NH$_3$, and a solution of 1-heptane [sic.] thiol (4.5 mg, 34.2 µmol) in 2 mL acetonitrile was added thereto. After 1 hour, the reaction solution was applied to YMC-Pack ODS-A (C18, 20 mm×250 mm) and eluted with a linear gradient (flow rate: 10 mL/min) for 60 minutes of from 0 to 54% acetonitrile in 0.1% trifluoroacetic acid. The desired fractions were collected and lyophilized to give 15 mg of the desired product.

Compound 57. [Cys$^3$(S-Heptyl)]-hGhrelin

ESI-MS 3391.0 (theoretical: 3391.0), amino acid composition: Ser; 2.76 (3), Glx; 5.81 (6), Gly; 0.99 (1), Ala; 1.01 (1), Val; 0.95 (1), Leu; 2, Phe; 0.99 (1), Lys; 3.95 (4), His; 0.99 (1), Arg; 2.93 (3), Pro; 3.84 (4)

(10) Examples of Synthesis of a Derivative Having an Amide in a Side Chain at the 3rd Position and an Ester in the Reverse Direction Compound 55. [Asp$^3$(NH-Heptyl)]-hGhrelin; GSD(NH—C$_7$H$_{15}$)FLSPEHQRVQQRKESKKPPAKLQPR Fmoc-Arg(Pmc)-HMP-resin (403 mg, 0.25 mmol, ABI Co., Ltd) was treated with 20% piperazine for 20 minutes and subjected repeatedly to introduction of Fmoc-amino acid by HBTU/HOBt and elimination of Fmoc by piperazine sequentially to construct Fmoc-Ser(Bu$^t$)-Asp(OPis)-Phe-Leu-Ser(tBu)-Pro-Glu(OBu$^t$)-His(Boc)-Gln(Trt)-Arg(Pmc)-Val-Gln(Trt)-Gln(Trt)-Arg(Pmc)-Lys(Boc)-Glu(OBu$^t$)-Ser(Bu$^t$)-Lys(Boc)-Lys(Boc)-Pro-Pro-Ala-Lys(Boc)-Leu-Gln(Trt)-Pro-Arg(Pmc)-HMP resin. After Boc-Gly was finally introduced by DCC/HOBt, the resulting protected peptide resin (1.3 g) was treated with 4% TFA-methylene chloride solution (15 mL) for 15 minutes. The peptide resin was recovered by filtration and washed several times with methylene chloride (30 mL), washed with 4% DIEA (10 mL) and then with methylene chloride (30 mL).

The resulting de-Pis peptide resin (about 1.3 g) was swollen with NMP (10 mL), and water-soluble carbodiimide hydrochloride (191.7 mg, 1.0 mmol), HOBt (135.2 mg, 1.0 mmol) and n-heptylamine (115.2 mg, 1.0 mmol) were added thereto and allowed to react for 8 hours.

The resin was recovered by filtration, washed with NMP and methylene chloride, and dried under vacuum to give about 1.2 g protected peptide resin where the Asp 3 residue was heptylamidated. A deprotecting reagent (10 mL) consisting of 88% TFA-5% phenol-2% TIPS-5% H$_2$O was added thereto and stirred at room temperature for 2 hours. The resin was removed by filtration, and the filtrate was concentrated followed by adding ether to the resulting residues to form precipitates. The precipitates were recovered by filtration and dried to give about 550 mg crude peptide.

200 mg of this product was dissolved in 10 mL water and applied to YMC-Pack PROTEIN-RP (C4, 20 mm×250 mm) and eluted with a linear gradient (flow rate: 10 mL/min.) for 60 minutes of from 0 to 54% acetonitrile in 0.1% trifluoroacetic acid. The desired fractions were collected and lyophilized to give about 120 mg of the desired product.

Compound 61. [Lys$^3$(Octanoyl)]-hGhrelin; GSK(CO—C$_7$H$_{15}$) FLSPEHQRVQQRKESKKPPAKLQPR Fmoc-Arg (Pmc)-HMP-resin (403 mg, 0.25 mmol, a product of ABI Co., Ltd) was treated with 20% piperazine for 20 minutes and subjected repeatedly to introduction of Fmoc-amino acid by HBTU/HOBt and elimination of Fmoc by piperazine sequentially to construct Boc-Gly-Ser(tBu)-Lys(Mtt)-Phe-Leu-Ser(tBu)-Pro-Glu(OBu$^t$)-His(Boc)-Gln(Trt)-Arg(Pmc)-Val-Gln(Trt)-Gln(Trt)-Arg(Pmc)-Lys(Boc)-Glu(OBu$^t$)-Ser(Bu$^t$)-Lys(Boc)-Lys(Boc)-Pro-Pro-Ala-Lys(Boc)-Leu-Gln(Trt)-Pro-Arg(Pmc)-HMP resin. About 300 mg of the resulting protected peptide resin was treated with 1% TFA-5% TIPS-methylene chloride solution (15 mL) for 60 minutes.

The peptide resin was recovered by filtration and washed several times with methylene chloride (30 mL), washed with 10% DIEA (10 mL) and then with methylene chloride (30 mL). The resulting de-Mtt peptide resin (about 300 mg) was swollen with NMP (2 mL), and octanoic acid (40 μl, 0.25 mmol) and DCC (52 mg, 0.25 mmol) were added thereto in the presence of HOBt (34 mg, 0.25 mmol) and allowed to react overnight.

The resin was recovered by filtration, washed with NMP and then with methylene chloride, and dried under vacuum to give about 300 mg protected peptide resin where the lysine 3rd residue was octanoylated. A deprotecting reagent (5 mL) consisting of 88% TFA-5% phenol-2% TIPS-5% H$_2$O was added thereto and stirred at room temperature for 2 hours. The resin was removed by filtration, and the filtrate was concentrated followed by adding ether to the resulting residues to form precipitates. The precipitates were separated by filtration and dried to give about 234 mg crude peptide.

This product was dissolved in 6 mL acetic acid and applied to YMC-Pack ODS-A (5 μm, 20 mm×250 mm) and eluted with a linear gradient (flow rate: 10 mL/min.) for 60 minutes of from 0 to 60% acetonitrile in 0.1% trifluoroacetic acid. The desired fractions were collected and lyophilized to give about 100 mg powder. This product was dissolved in 2 mL of 50% acetic acid and applied to YMC-Pack PROTEIN-RP (5 μm, C4, 20 mm×250 mm) and eluted with a linear gradient (flow rate: 10 mL/min.) for 60 minutes of from 0 to 60% acetonitrile in 0.1% trifluoroacetic acid. The desired fractions were collected and lyophilized to give about 52 mg powder.

The following compounds were produced in the same manner as in preparation of Compound 55 or 61 described above.

The results of the mass spectrometry and amino acid composition analysis of the peptide derivatives synthesized by the conventional Fmoc method are summarized below.

Compound 54. [Asp$^3$(O-Heptyl)]-hGhrelin (1-28)

ESI-MS 3371.0 (theoretical: 3370.9), amino acid composition: Asx; 0.99 (1), Ser; 2.70 (3), Glx; 5.87 (6), Gly; 1.01 (1), Ala; 1.01 (1), Val; 0.94 (1), Leu; 2, Phe; 1.00 (1), Lys; 4.02 (4), His; 1.00 (1), Arg; 2.98 (3), Pro; 3.84 (4)

Compound 55. [Asp$^3$(NH-Heptyl)]-hGhrelin (1-28)

ESI-MS 3370.0 (theoretical: 3369.9), amino acid composition: Asx; 0.88 (1), Ser; 2.95 (3), Glx; 5.97 (6), Gly; 1.21 (1), Ala; 1.03 (1), Val; 0.98 (1), Leu; 2, Phe; 1.00 (1), Lys; 3.94 (4), His; 0.92 (1), Arg; 2.91 (3), Pro; 3.99 (4)

Compound 56. [Dap$^3$(Octanoyl)]-hGhrelin

ESI-MS M; 3370.0 (theoretical: 3369.9), amino acid composition: Ala; 1.02 (1), Arg; 2.94 (3), Glx; 5.94 (6), Gly; 1.00 (1), His; 0.91 (1), Leu; 2 (2), Lys; 3.93 (4), Phe; 0.99 (1), Pro; 4.01 (4), Ser; 2.88 (3), Val; 0.98 (1), Dap; N.D.

Compound 58. [Adod$^3$]-hGhrelin (1-28)

ESI-MS M; 3355.0 (theoretical: 3355.0), amino acid composition: Ala; 1.01 (1), Arg; 2.91 (3), Glx; 5.95 (6), Gly; 1.01 (1), His; 0.91 (1), Leu; 2 (2), Lys; 3.94 (4), Phe; 0.99 (1), Pro; 4.02 (4), Ser; 2.88 (3), Val; 0.96 (1)

Compound 61. [Lys$^3$(Octanoyl)]-hGhrelin

ESI-MS M; 3412.0 (theoretical: 3412.0), amino acid composition: Ala; 1.05 (1), Arg; 3.05 (3), Glx; 6.02 (6), Gly; 1.00 (1), His; 1.00 (1), Leu; 2 (2), Lys; 5.11 (5), Phe; 0.97 (1), Pro; 4.20 (4), Ser; 2.68 (3), Val; 1.00 (1)

Compound 62. [Trp$^3$]-hGhrelin

ESI-MS M; 3343.0 (theoretical: 3343.9), amino acid composition: Ala; 1.00 (1), Arg; 3.03 (3), Glx; 5.94 (6), Gly; 1.01 (1), His; 1.01 (1), Leu; 2 (2), Lys; 4.00 (4), Phe; 0.99 (1), Pro; 3.96 (4), Ser; 2.60 (3), Trp; N.D., Val; 0.98 (1)

Compound 63. [Phe³]-hGhrelin
ESI-MS M; 3305.0 (theoretical: 3304.8), amino acid composition: Ala; 0.99 (1), Arg; 2.96 (3), Glx; 5.86 (6), Gly; 1.00 (1), His; 1.00 (1), Leu; 2 (2), Lys; 3.98 (4), Phe; 2.01 (2), Pro; 3.99 (4), Ser; 2.67 (3), Val; 0.98 (1)

Compound 64. [Cha³]-hGhrelin
ESI-MS M; 3411.0 (theoretical: 3410.9), amino acid composition: Ala; 1.02 (1), Arg; 3.01 (3), Glx; 5.92 (6), Gly; 1.01 (1), His+Cha; 2.01 (1+1), Leu; 2 (2), Lys; 4.02 (4), Phe; 1.01 (1), Pro; 4.03 (4), Ser; 2.72 (3), Val; 0.97 (1)

Compound 65. [2-$^L$Nal³]-hGhrelin
ESI-MS M; 3354.0 (theoretical: 3354.9), amino acid composition: Ala; 1.00 (1), Arg; 2.95 (3), Glx; 5.87 (6), Gly; 1.02 (1), His; 1.01 (1), Leu; 2 (2), Lys; 3.98 (4), Phe; 1.01 (1), Pro; 3.94 (4), Ser; 2.73 (3), Val; 0.97 (1), Nal; N.D. (1)

Compound 66. [2-$^D$Nal³]-hGhrelin
ESI-MS M; 3355.0 (theoretical: 3354.9), amino acid composition: Ala; 1.02 (1), Arg; 2.95 (3), Glx; 5.96 (6), Gly; 1.00 (1), His; 0.92 (1), Leu; 2 (2), Lys; 3.94 (4), Phe; 0.99 (1), Pro; 4.02 (4), Ser; 2.91 (3), Val; 0.98 (1), Nal; N.D. (2)

Compound 70. [Leu³]-hGhrelin
ESI-MS M; 3270.0 (theoretical: 3270.8), amino acid composition: Ala; 0.99 (1), Arg; 2.95 (3), Glx; 5.88 (6), Gly; 1.01 (1), His; 1.00 (1), Leu; 3 (3), Lys; 3.96 (4), Phe; 1.00 (1), Pro; 3.89 (4), Ser; 2.65 (3), Val; 0.97 (1)

Compound 71. [Ile³]-hGhrelin
ESI-MS M; 3270.0 (theoretical: 3270.8), amino acid composition: Ala; 0.98 (1), Arg; 2.96 (3), Glx; 5.87 (6), Gly; 0.99 (1), His; 1.01 (1), Ile; 0.98 (1), Leu; 2 (2), Lys; 3.97 (4), Phe; 1.00 (1), Pro; 3.97 (4), Ser; 2.65 (3), Val; 0.98 (1)

Compound 72. [Lys³(Octanoyl)]-hGhrelin
ESI-MS M; 3286.0 (theoretical: 3285.8), amino acid composition: Ala; 1.02 (1), Arg; 2.94 (3), Glx; 5.95 (6), Gly; 0.99 (1), His; 0.92 (1), Leu; 2 (2), Lys; 4.92 (5), Phe; 0.99 (1), Pro; 4.02 (4), Ser; 2.91 (4), Val; 0.99 (1)

Compound 73. [Nle³]-hGhrelin
ESI-MS M; 3270.0 (theoretical: 3270.8), amino acid composition: Ala; 1.01 (1), Arg; 2.98 (3), Glx; 5.92 (6), Gly; 1.02 (1), His; 1.01 (1), Leu; 2 (2), Lys; 4.01°(4), Phe; 1.01 (1), Pro; 4.01 (4), Ser; 2.71 (3), Val; 0.98 (1), Nle; N.D. (1)

Compound 74. [Val³]-hGhrelin
ESI-MS M; 3256.0 (theoretical: 3256.8), amino acid composition: Ala; 0.98 (1), Arg; 2.96 (3), Glx; 5.84 (6), Gly; 1.00 (1), His; 1.01 (1), Leu; 2 (2), Lys; 3.97 (4), Phe; 0.99 (1), Pro; 3.94 (4), Ser; 2.64 (3), Val; 1.97 (2)

Compound 80. [Aib¹, His², $^D$Nal³, $^D$Phe⁴, Lys⁵]-Ghrelin (1-5)-amide; Ipamorelin
ESI-MS [M+H]; 712.5 (theoretical: 711.9), amino acid composition: Phe; 1, His; 1.00 (1), Lys; 1.00 (1)

Example 11. Comparison of Activity Among Ghrelin Derivative Peptide-Type Compounds The Ca-increasing activities of the ghrelin derivative peptide-type compounds synthesized in Example 10 and the natural ghrelin peptide were measured in the same manner as in Example 1.

(1) Modification of a Side Chain of Serine 3
A. Position of Octanoyl Group

The significant structural feature of ghrelin lies in the octanoyl group on the hydroxyl group of serine 3. First, whether or not it is advantageous for exhibiting the activity Example 11. Comparison of Activity Among Ghrelin Derivative Peptide-Type Compounds The Ca-increasing activities of the ghrelin derivative peptide-type compounds synthesized in Example 10 and the natural ghrelin peptide were measured in the same manner as in Example 1.

(1) Modification of a Side Chain of 3rd Serine
A. Position of an Octanoyl Group

The significant structural feature of ghrelin lies in the octanoyl group on the hydroxyl group of 3rd serine. First, whether or not it is advantageous for exhibiting the activity that the position of serine to be octanoylated is the 3rd position was examined. In this examination, the intracellular Ca-releasing activity in CHO cells expressing rat GSH receptor was used as the indicator.

On the basis of ghrelin (1-9) amide (a short-chain ghrelin derivative) whose $EC_{50}$ value was kept at 5.4 nM, [serine² (octanoyl), serine³]-ghrelin (1-9) amide, [serine² (octanoyl)]-ghrelin (1-9) amide, and ($N^α$-octanoyl, serine³)-ghrelin (1-9) amide were synthesized, and their intracellular Ca-releasing activity was examined.

The results are summarized in Table 4.

TABLE 4

Ghrelin derivative activity 1

| Compound Structure | Ca-releasing activity $EC_{50}$ (nM) |
|---|---|
| 1. human Ghrelin<br>GSS(CO—C₇H₁₅)FLSPEHQRVQQRKESKKPPAKLQPR | 1.3 |
| 2. rat Ghrelin<br>GSS(CO—C₇H₁₅)FLSPEHQKAQQRKESKKPPAKLQPR | 1.5 |
| 3. Ghrelin (1-9)-amide<br>H-Gly-Ser-Ser(CO—C₇H₁₅)-Phe-Leu-Ser-Pro-Glu-His-NH₂ | 5.4 |
| 4. [Ser²(Octanoyl), Ser³]-Ghrelin (1-9)-amide<br>H-Gly-Ser(CO—C₇H₁₅)-Ser-Phe-Leu-Ser-Pro-Glu-His-NH₂ | 1,100 |
| 5. [Ser²(Octanoyl)]-Ghrelin (1-9)-amide<br>H-Gly-Ser(CO—C₇H₁₅)-Ser(CO—C₇H₁₅)-Phe-Leu-Ser-Pro-Glu-His-NH₂ | 1,400 |
| 6. [N-Octanoyl, Ser³]-Ghrelin (1-9)-amide<br>C₇H₁₅CO-Gly-Leu-Ser-Phe-Leu-Ser-Pro-Glu-His-NH₂ | >10,000 |

The activity was reduced to about 1/200 by transferring an octanoyl group from 3rd serine to 2nd serine in human ghrelin ($EC_{50}$=1,100 nM).

The derivative having octanoyl groups at both the 2nd and 3rd positions also showed a reduced activity ($EC_{50}$=1,400 nM).

Further, the activity was relatively weakened by N-octanoylation at only the amino-terminal amino group ($EC_{50}$>10,000 nM).

From these results, it was revealed that the position of the amino acid modified with an octanoyl group is particularly preferably the 3rd position in the ghrelin molecule.

B. Chain Length of a Fatty Acid

The intracellular Ca-releasing activity of the des-octanoyl derivative derived from rat ghrelin by eliminating the side-chain octanoyl group of 3rd serine was 3,500 nM as compared with the activity (2.6 nM) of the octanoylated ghrelin, and thus it is evident that the side-chain octanoyl group of 3rd serine plays a very important role in expressing the activity.

Accordingly, the relationship between the activity and the number of carbon atoms in the side-chain acyl group of serine in rat ghrelin was examined using various saturated fatty acids. That is, the intracellular Ca-releasing activities of the ghrelin derivatives wherein the hydroxyl group of 3rd serine was acylated with an acetyl group (CH₃CO—), propionyl group (CH₃CH₂CO—) butyryl group (CH₃(CH₂)₂CO—), hexanoyl group (CH₃(CH₂)₄CO—) decanoyl group ($CH_3(CH_2)_8CO$—), lauroyl group ($CH_3(CH_2)_{10}CO$—), and palmitoyl group ($CH_3(CH_2)_{14}CO$—) were determined.

The results are summarized in Table 5.

TABLE 5

Ghrelin derivative activity 2

| Compound Structure | Ca-releasing activity $EC_{50}$ (nM) |
|---|---|
| 7. [Ser³]-rat Ghrelin<br>GSSFLSPEHQKAQQRKESKKPPAKLQPR | 3,500 |
| 8. [Ser3 (Acetyl)]-rGhrelin<br>GSS(CO—$CH_3$)FLSPEHQKAQQRKESKKPPAKLQPR | 780 |
| 9. [Ser³ (Propionyl)]-rGhrelin<br>GSS(CO—$C_2H_5$)FLSPEHQKAQQRKESKICPPAKLQPR | n. t. |
| 10. [Ser³ (Butyryl)]-rGhrelin<br>GSS(CO—$C_3H_7$)FLSPEHQKAQQRKESKKPPAKLQPR | 280 |
| 11. [Ser³ (Hexanoyl)]-rGhrelin<br>GSS(CO—$C_5H_{11}$) FLSPEHQKAQQRKESKKPPAKLQPR | 16 |
| 12. [Ser³ (Decanoyl)]-rGhrelin<br>GSS(CO—$C_9H_{19}$)FLSPEHQKAQQRKESKKPPAKLQPR | 1.7 |
| 13. [Ser³ (Lauroyl)]-rGhrelin<br>GSS(CO—$C_{11}H_{23}$)FLSPEHQKAQQRKESKKPPAK-LQPR | 2.4 |
| 14. [Ser³(Palmitoyl)]-rGhrelin<br>GSS(CO—$C_{15}H_{31}$)FLSPEHQKAQQRKESKKPPAK-LQPR | 6.5 |

In the Table, "n. t." indicates that the sample was not tested.

The influence of the chain length of fatty acid on the activity was made increasingly significant with an $EC_{50}$ value of 780 nM for the ghrelin derivatives having acetyl group (C2) and an $EC_{50}$ value of 280 nM for the ghrelin derivatives having butanoyl group (C4), and the ghrelin derivatives having the hexanoyl group (C7) brought about a further increase in the Ca-releasing activity ($EO_{50}$ value, 16 nM), and the ghrelin the octanoyl group permitted the Ca-releasing activity to reach a peak ($EO_{50}$ value, 1.5 nM). Even the ghrelin derivatives having the decanoyl group (C10) maintained a similar Ca-releasing activity ($EO_{50}$ value, 1.7 nM) to that of ghrelin, and further the $EC_{50}$ value was 2.4 nM for the ghrelin derivatives having lauroyl group (C12) and 6.5 nM for the ghrelin derivatives having palmitoyl group (C16), thus indicating that the Ca-releasing activity was maintained even if the chain length of fatty acid was increased.

C. Substitution of Various Acyl Groups

Human ghrelin derivatives were prepared by binding 3-phenyl propionic acid (HO—CO—$CH_2CH_2Ph$) as a typical example of aromatic fatty acid, 3-octenoic acid ($OH_3(CH_2)_3CH=CH—CH_2COH$) as a typical example of unsaturated fatty acid or 4-methyl pentanoic acid (($CH_3)_2CH—CH_2CH_2CO_2H$) as a typical example of branched fatty acid, in place of saturated fatty acid, via an ester linkage to the hydroxyl group of 3rd serine, and their activity was examined.

D. Conversion into Alkyl Groups

By converting the chemically instable ester linkage into a chemically stable ether or thioether linkage or the like, chemically stable ghrelin derivatives can be formed. However, it goes without saying that maintenance of the activity is a preposition for this conversion.

Hence, an ether derivative of human ghrelin wherein 3rd serine was octylated ($C_8H_{17}$) and a thioether derivative of rat ghrelin wherein 3rd serine was replaced by cysteine and octylated were examined for their activity.

Further, a derivative of human ghrelin wherein 3rd serine was benzylated (—$CH_2Ph$) and a derivative of human ghrelin wherein 3rd serine was replaced by cysteine and tritylated (—$C(Ph)_3$) were prepared.

The results are summarized in Table 6. The Ca-releasing activities of the derivative of human ghrelin wherein 3rd serine was benzylated (—$CH_2Ph$) and the derivative of human ghrelin wherein 3rd serine was replaced by cysteine and tritylated (—$C(Ph)_3$) are shown as those of Compounds 67 and 68 respectively in Table 13. The Ca-releasing activity of the derivative of human ghrelin wherein 4-methyl pentanoic acid (($CH_3)_2CH$—$CH_2CH_2CO_2H$) was bound via an ester linkage to the hydroxyl group of 3rd serine is also shown as that of Compound 69 in Table 13.

TABLE 6

Ghrelin derivative activity 3

| Compound Structure | Ca-releasing activity $EC_{50}$ (nM) |
|---|---|
| 15. (Ser³(3-Phenylpropionyl)]-hGhrelin<br>GSS(CO—$CH_2CH_2Ph$)FLSPEHQRVQQRKESKKPPAKLQPR | 1.4 |
| 16. (Ser³(3-Octenoyl)]-hGhrelin<br>GSS(CO—$CH_2CH=CH(CH_2)_3CH_3$)<br>FLSPEHQRVQQRKESKKPPAKLQPR | 1.7 |
| 17. (Ser³(Octyl)]-hGhrelin<br>GSS($C_8H_{17}$)FLSPEHQRVQQRKESKKPPAKLQPR | 1.2 |
| 18. [Cys³(Octyl)]-rGhrelin<br>GSC($C_8H_{17}$)FLSPEHQKAQQRKESKKPPAKLQPR | 5.4 |

Introduction of 3-octenoyl group as an example of unsaturated fatty acid into the side-chain of 3rd serine brought about a similar Ca-releasing activity ($EC_{50}$=1.7 nM) to the activity of the ghrelin derivatives having an octanoyl group.

Interestingly, even if a phenyl propionyl group was introduced, the Ca-releasing activity was maintained to be high ($EC_{50}$=1.4 nM), and even if a 4-methylpentanoyl group (C6) as an example of branched fatty acid was introduced, the $EC_{50}$ value was 4.4 nM, indicating that the Ca-releasing activity was maintained (Compound 69 in Table 13), thus revealing that it is not always necessary that the side-chain acyl group in 3rd serine is a linear-chain alkanoyl group.

Further, the $EC_{50}$ values of the ether and thioether derivatives expectable to be chemically stable, wherein 3rd serine or 3rd cysteine were octylated, were maintained to be 1.2 nM and 5.4 nM respectively, thus revealing that it is not always necessary that the side chain of amino acid residue at 3rd position is an acyl group.

Further, the $EC_{50}$ values of ghrelins wherein amino acid residue 3rd position was replaced by Ser (Bzl) [that is, the derivative of human ghrelin wherein 3rd serine was benzylated (—$CH_2Ph$)] or by Cys (Trt) [that is, the derivative of human ghrelin wherein 3rd serine was replaced by cysteine and tritylated (—$C(Ph)_3$)] were 7.6 nM and 20 nM, respectively, thus indicating that the Ca-releasing activity was maintained (Compounds 67 and 68 in Table 13).

(2) Determination of the Active Region

The intracellular Ca-releasing activity of ghrelin (16-28) containing the original carboxyl-terminal region was relatively low ($EC_{50}$>10,000 nM), while the $EC_{50}$ values of human ghrelin (1-15) and rat ghrelin (1-15) both containing the original amino-terminal region were 7.0 nM and 8.6 nM respectively, thus indicating that the intracellular Ca-releasing activity was maintained, and it was thereby revealed that the active site of ghrelin is present in the amino-terminal region (Table 7).

TABLE 7

Ghrelin derivative activity 4

| Compound Structure | Ca-releasing activity $EC_{50}$ (nM) |
|---|---|
| 19. Ghrelin (16-28) H-Lys-Glu-Ser-Lys-Lys-Pro-pro-Ala-lysLeu-Gln-Pro-Arg-OH | >10,000 |
| 20. hGhrelin (1-15) H-Gly-Ser-Ser (CO—$C_7H_{15}$)-Phe-Leu-Ser-Pro-Glu-His-Gln-Arg-Val-Gln-Gln-Arg-OH | 7.0 |
| 21. rGhrelin (1-15) H-Gly-Ser-Ser(CO—$C_7H_{15}$)-Phe-Leu-Ser-Pro-Glu-His-Gln-Lys-Ala-Gln-Gln-Arg-OH | 8.6 |
| 22. (des Gln$^{14}$)-rGhrerin GSS(CO—$C_7H_{15}$)FLSPEHQKAQ_RKESKKPPAKLQPR | 1.5 |

Further, because the activities of human and rat ghrelins (1-15) were almost the same, the amino acid resides 11th and 12th position (arginyl-valyl- in human, and -lysyl-aranyl- in rat) are not limited to these amino acids.

The results of the correlation between structure and activity, obtained using human or rat ghrelin, can be applied to rat and human ghrelins respectively.

Further, [des-glutamine$^{14}$]-rat ghrelin prepared by removing 14th glutamine from the ghrelin exhibited a Ca-releasing activity ($EC_{50}$=1.5 nM) similar to that of rat ghrelin, indicating that the amino acid in the middle of the ghrelin molecule may be deleted.

(3) Peptide Chain Length and Introduction of Basic Group into the Carboxyl-Terminal On the basis of ghrelin (1-15) found to have a relatively strong activity, a derivative was prepared by suitably deleting carboxyl-terminal amino acid residues from the ghrelin (1-15), and their activity was evaluated.

The activities of the short-chain derivatives having carboxylic acid at the carboxyl-terminal and the short-chain derivatives amidated at the carboxyl-terminal are shown in Table 8.

TABLE 8

Ghrelin derivative activity 5

| Compound Structure | Ca-releasing activity $EC_{50}$ (nM) |
|---|---|
| 23. hGhrelin (1-11) H-Gly-Ser-Ser(CO—$C_7H_{15}$)-Phe-Leu-Ser-Pro-Glu-His-Gln-Arg-OH | 15 |
| 24. rGhrelin (1-11) H-Gly-Ser-Ser(CO—$C_7H_{15}$)-Phe-Leu-Ser-Pro-Glu-His-Gln-Lys-OH | 15 |
| 25. Ghrelin (1-10) H-Gly-Ser-Ser(CO—$C_7H_{15}$)-Phe-Leu-Ser-Pro-Glu-His-Gln-OH | 19 |
| 26. Ghrelin (1-9) H-Gly-Ser-Ser(CO—$C_7H_{15}$)-Phe-Leu-Ser-Pro-Glu-His-OH | 38 |
| 27. Ghrelin (1-8) H-Gly-Ser-Ser(CO—$C_7H_{15}$)-Phe-Leu-Ser-Pro-Glu-OH | 100 |
| 28. Ghrelin (1-8)-amide H-Gly-Ser-Ser(CO—$C_7H_{15}$)-Phe-Leu-Ser-Pro-Glu-$NH_2$ | 13 |
| 29. Ghrelin (1-7)-amide H-Gly-Ser-Ser(CO—$C_7H_{15}$)-Phe-Leu-Ser-Pro-$NH_2$ | 2.6 |
| 30. Ghrelin (1-6)-amide H-Gly-Ser-Ser(CO—$C_7H_{15}$)-Phe-Leu-Ser-$NH_2$ | 4.8 |
| 31. Ghrelin (1-5) H-Gly-Ser-Ser(CO—$C_7H_{15}$)-Phe-Leu-OH | 68 |
| 32. Ghrelin (1-5)-amide H-Gly-Ser-Ser(CO—$C_7H_{15}$)-Phe-Leu-$NH_2$ | 6.2 |
| 33-1. Ghrelin (1-4) H-Gly-Ser-Ser(CO—$C_7H_{15}$)-Phe-OH | 480 |
| 33-2. Ghrelin (1-4)-amide H-Gly-Ser-Ser(CO—$C_7H_{15}$)-Phe-$NH_2$ | 160 |
| 34. Ghrelin (1-3)-amide H-Gly-Ser-Ser(CO—$C_7H_{15}$)—$NH_2$ | >10,000 |

The Ca-releasing activity of ghrelin (1-3) amide was relatively low ($EC_{50}$>10,000 nM). The $EC_{50}$ of ghrelin (1-4) added phenylalanine to the ghrelin(1-3) was 480 nM and the $EC_{50}$ of the carboxyl-terminal amide derivative thereof was 160 nM, thus revealing that they have a significant Ca-releasing activity.

Further, the activity of ghrelin (1-5) amide added leucine amide to ghrelin(1-4) was about 26 times ($EC_{50}$=6.2 nM) as high as that of ghrelin(1-4) amide, thus exhibiting a Ca-releasing activity at the same level as that of natural ghrelin.

The highest Ca-releasing activity was found in ghrelin (1-7) amide, and its $EC_{50}$ value was almost equivalent to that of natural ghrelin.

From the above result, the structural factor essential for expressing the ghrelin activity could be attributed to the sequence of 4th amino-terminal residues, but because its affinity for ghrelin receptor or signal transduction is drastically improved by adding a residue such as leucine at the 5th position, a residue such as leucine is preferably added at the 5th position.

As is evident from the above result, the Ca-releasing activity tended to be increased by amidation of carboxyl-terminal carboxylic acid.

For example, the Ca-releasing activity ($EC_{50}$=5.4 nM) of ghrelin (1-9) after amidation was about 7 times as high as the activity ($EC_{50}$=38 nM) before amidation, and the Ca-releasing activity ($EC_{50}$=160 nM) of ghrelin (1-4) after amidation was about 3 times as high as the activity ($EC_{50}$=480 nM) before amidation. Further, the Ca-releasing activity ($EC_{50}$=13 nM) of ghrelin (1-8)amide produced from ghrelin (1-9)amide by removing basic histidine reside 9 was lower than the activity ($EC_{50}$=5.4 nM) of ghrelin (1-9)amide, while the Ca-releasing activity ($EC_{50}$=2.6 nM) of ghrelin (1-7) amide produced by removing glutamic acid 8 as acidic amino acid was higher than the activity ($EC_{50}$=13 nM) before removal.

One effect of amidation is to neutralize the negative charge of carboxylic acid, and the above result indicates that the basicity of carboxyl-terminal amino acid in the short-chain derivative contributes significantly to the increase in activity.

On the basis of this result, derivatives endowed with basicity at the carboxyl-terminal, which are similar to ghrelin (1-7) amide showing high activity, were prepared and their activity was examined.

The results are shown in Table 9.

TABLE 9

Ghrelin derivative activity 6

| Compound Structure | Ca-releasing activity $EC_{50}$ (nM) |
|---|---|
| 35. [Lys$^8$]-Ghrelin (1-8)-amide H-Gly-Ser-Ser (CO—C$_7$H$_{15}$)-Phe-Leu-Ser-Pro-Lys-NH$_2$ | 1.1 |
| 36. [Are$^8$]-Ghrelin (1-8)-amide H-Gly-Ser-Ser (CO—C$_7$H$_{15}$)-Phe-Leu-Ser-Pro-Arg-NH$_2$ | 1.1 |
| 37. [Lys$^6$]-Ghrelin (1-6)-amide H-Gly-Ser-Ser(CO—C$_7$H$_{15}$)-Phe-Leu-Lys-NH$_2$ | 12 |
| 38. [Lys$^5$]-Ghrelin (1-5)-amide H-Gly-Ser-Ser(CO—C$_7$H$_{15}$)-Phe-Lys-NH$_2$ | 10 |
| 39. [$^D$Phe$^4$, Lys$^5$]-Ghrelin (1-5)-amide H-Gly-Ser-Ser(CO—C$_7$H$_{15}$)-$^D$Phe-Lys-NH$_2$ | 1,700 |

The Ca-releasing activity ($EC_{50}$=12 nM) of [lysine$^6$]-ghrelin (1-6) amide having lysine added at the carboxyl-terminal of ghrelin (1-5) was slightly lower than the activity ($EC_{50}$=4.8 nM) of ghrelin (1-5), while the Ca-releasing activity ($EC_{50}$=10 nM) of ghrelin (1-4) having lysine added at the carboxyl-terminal was about 50 times as high as the activity ($EC_{50}$=480 nM) before addition. Further, the Ca-releasing activity ($EC_{50}$=1.1 nM), respectively, of the amide derivative having arginine or lysine added at the carboxyl-terminal of ghrelin (1-7) was very stronger than the activity ($EC_{50}$=2.6 nM) of ghrelin (1-7) amide.

It was revealed that in almost all the cases, the activity is increased by masking of acidity at the carboxyl-terminal and introduction of a basic group.

(4) Amino-Terminal Glycine and 2nd Serine Residue

On the basis of ghrelin (1-7) amide ($EC_{50}$=2.6 nM) [Compound 29 in Table 8] or ghrelin (1-9) amide ($EC_{50}$=5.4 nM) [Compound 3 in Table 4] found to have activity, the influence of amino-terminal glycine and 2nd serine on the activity was examined.

The results are summarized in Table 10.

TABLE 10

Ghrelin derivative activity 7

| Compound Structure | Ca-releasing activity $EC_{50}$ (nM) |
|---|---|
| 40. [N-Aminopentanoyl]-Ghrelin (3-7)-amide NH$_2$—(CH$_2$)$_4$—CO-Ser(CO—C$_7$H$_{15}$)-Phe-Leu-Ser-Pro-NH$_2$ | 3.4 |
| 41. [N-Acetyl]-Ghrelin (1-10) CH$_3$CO-Gly-Ser-Ser(CO-C$_7$H$_{15}$)-Phe-Leu-Ser-Pro-Glu-His-Gln-OH | >10,000 |
| 42. [N-Tyr]-rGhrelin YGSS(CO-C$_7$H$_{15}$)FLSPEHQKAQQRKESKKPPAKLQPR | 120 |
| 43. [N-Glycyl]-Ghrelin (3-7)-amide H-Gly-Ser(CO—C$_7$H$_{15}$)-Phe-Leu-Ser-Pro-NH$_2$ | 380 |
| 44. [Leu$^2$]-Ghrelin (1-7)-amide H-Gly-Leu-Ser(CO—C$_7$H$_{15}$)-Phe-Leu-Ser-Pro-NH$_2$ | 42 |
| 45. [His$^2$]-Ghrelin (1-7)-amide H-Gly-His-Ser(CO—C$_7$H$_{15}$)-Phe-Leu-Ser-Pro-NH$_2$ | 35 |

TABLE 10-continued

Ghrelin derivative activity 7

| Compound Structure | Ca-releasing activity $EC_{50}$ (nM) |
|---|---|
| 46. [Lys$^2$]-Ghrelin (1-7)-amide H-Gly-Lys-Ser (CO—C$_7$H$_{15}$)-Phe-Leu-Ser-Pro-NH$_2$ | 24 |
| 47. [Gly$^2$]-Ghrelin (1-7)-amide H-Gly-Gly-Ser(CO—C$_7$H$_{15}$)-Phe-Leu-Ser-Pro-NH$_2$ | 78 |

The activity of $N^\alpha$-acetyl-ghrelin (1-10) wherein the amino-terminal amino group in the ghrelin(1-10) was blocked was relatively low ($EC_{50}$>10,000 nM). As described above, the activity of ($N^\alpha$-ocatonoyl, serine$^3$)-ghrelin (1-9) amide (Compound 6 in Table 1) was also relatively low ($EC_{50}$>10,000 nM), and thus the amino-terminal amino group is preferably not blocked in order to express the Ca-releasing activity.

On the other hand, the Ca-releasing activity of $N^\alpha$-aminopentanoyl-ghrelin (3-7) amide wherein amino-terminal glycine and 2nd serine were replaced by 5-amino-n-pentanoic acid (NH$_2$—(CH$_2$)$_4$—CO—) having a length of 2nd residues was almost maintained ($EC_{50}$=3.4 nM), the Ca-releasing activity of [$N^\alpha$-glycyl]-ghrelin (3-7) amide from which 2nd serine had been deleted was lower ($EC_{50}$=380 nM), and the Ca-increasing activity of [N-tyrosyl]-rat ghrelin having a tyrosine residue added at the amino-terminal in the rat ghrelin was lower ($EC_{50}$=120 nM) so that it is preferable for stronger activity that the amino-terminal amino group is positioned such that amino-terminal amino acid(s) having a length of 2 residues are present from octanoyl 3rd serine residue to the amino-terminal.

Further, the $EC_{50}$ values of the derivatives of ghrelin (1-7) amide wherein 2nd serine had been replaced by leucine, glycine, histidine and lysine were 42 nM, 78 nM, 35 nM and 24 nM respectively, indicating a slightly lower Ca-releasing activity than that of ghrelin (1-7) amide.

Since this result indicates that the 2nd serine residue (—NH—CH(CH$_2$OH)—CO—) can be replaced by the partial structure —CH$_2$—CH$_2$—CO— in aminopentanoic acid, the 2nd serine residue acts at least as a spacer for separating amino-terminal amino group of ghrelin by a predetermined distance from the octanoyl group at the 3rd position. The reason that the activity was maintained by replacement of the 2nd serine residue by 5-aminopentanoic acid is that the basicity of the amino-terminal was increased by introducing its alkylamine structure.

In summary, the amino group of amino-terminal glycine residue is considered to confer basicity on the amino-terminal of ghrelin molecule, thus expressing the activity of ghrelin, and therefore the amino group at the amino-terminal is preferably not blocked.

Further, the 2nd serine residue is considered to act as a spacer for separating the amino group at the amino-terminal by a predetermined distance from the octanoyl group at the 3rd position, and therefore the 2nd serine residue may be replaced by an amino acid or non-amino acid compound having a relatively less bulky side chain. That is, the position of the octanoyl group in the ghrelin molecule is defined relative to the amino-terminal amino group, and this positional relationship constitutes a part of the active structure of ghrelin.

That is, the side chain of amino acid 2 is preferably relatively less bulky such as in serine, alanine and norvaline rather than an amino acid having a bulky structure, and an amino acid residue not restricting the flexibility of neighboring residues is preferable as the amino acid 2. Further, because the Ca-increasing activity of $N^\alpha$-aminopentanoyl-ghrelin (3-7) amide is almost maintained ($EC_{50}$=3.4 nM), 2nd serine can be replaced by a non-amino acid compound.

(5) Configuration of Amino Acid Residues 3 and 4

On the basis of the structure of ghrelin(1-7) amide, its derivatives wherein 3rd L-serine and 4th L-phenylalanine had been replaced by the corresponding D-amino acids were prepared, and the influence which the configuration of amino acid 3 and 4 have on the Ca-releasing activity was examined. Specifically, on the basis of [serine$^3$ (octyl)]-ghrelin (1-7) amide ($EC_{50}$=5.8 nM) [Compound 50 in Table 11] and [cysteine$^3$ (octyl)]-ghrelin (1-7) amide ($EC_{50}$=7.4 nM) [Compound 48 in Table 11] which maintained a good activity, their derivatives wherein 3rd serine and 4th phenylalanine had been replaced by the corresponding L- or D-amino acids were prepared.

The results are summarized in Table 11. From these results, both amino acids 3 and 4 are preferably L-amino acids.

TABLE 11

Ghrelin derivative activity 8

| Compound structure | Ca-releasing activity $EC_{50}$ (nM) |
|---|---|
| 48. [Cys$^3$(Octyl)]-Ghrelin (1-7)-amide<br>H-Gly-Ser-Cys(C$_8$H$_{17}$)-Phe-Leu-Ser-Pro-NH$_2$ | 7.4 |
| 49. [Cys$^3$(Octyl), $^D$Phe$^4$]-Ghrelin (1-7)-amide<br>H-Gly-Ser-Cys(C$_8$H$_{17}$)-$^D$Phe-Leu-Ser-Pro-NH$_2$ | 3,000 |
| 50. [Ser$^3$(Octyl)]-Ghrelin (1-7)-amide<br>H-Gly-Ser-Ser (C$_8$H$_{17}$)-Phe-Leu-Ser-Pro-NH$_2$ | 5.8 |
| 51. [Ser$^3$(Octyl), $^D$Phe$^4$]-Ghrelin (1-7)-amide<br>H-Gly-Ser-Ser(C$_8$H$_{17}$)-$^D$Phe-Leu-Ser-Pro-NH$_2$ | 2,200 |
| 52. [$^D$Ser$^3$(Octyl)]-Ghrelin (1-7)-amide<br>H-Gly-Ser-$^D$Ser(C$_8$H$_{17}$)-Phe-Leu-Ser-Pro-NH$_2$ | >10,000 |
| 53.[$^D$Ser$^3$(Octyl), $^D$Phe$^4$]-Ghrelin (1-7)-amide<br>H-Gly-Ser-$^D$Ser(C$_8$H$_{17}$)-$^D$Phe-Leu-Ser-Pro-NH$_2$ | >10,000 |

(6) Mode of Linkage of a Side Chain at the 3rd Position

Derivatives of ghrelin wherein the original ester linkage was replaced by an ester in the reverse direction (Compound No. 54), an amide (Compound Nos. 55 and 56), a disulfide (Compound No. 57) and methylene (Compound No. 58) were prepared such that the side chain at the 3rd position became the same length as that of the ghrelin chain ($-CH_2-O-CO-C_7H_{15}$). In addition, ester derivatives having steric hindrance on the β-carbon atom of amino acid at the 3rd position (Compound Nos. 59 and 60) and an amide derivative wherein 3 methylene units had been extended (Compound No. 61) were prepared. The results are summarized in Table 12.

TABLE 12

Ghrelin derivative activity 9

| Compound structure | Activity $EC_{50}$ (nM) |
|---|---|
| 54. [Asp$^3$(O-Heptyl)]-hGhrelin<br>GSD(O—C$_7$H$_{15}$)FLSPEHQRVQQRKESKKPPAKLQPR | 5.1 |
| 55. [Asp$^3$(NH-Heptyl)]-hGhrelin<br>GSD(NH—C$_7$H$_{15}$)FLSPEHQRVQQRKESKKPPAKLQPR | 11 |
| 56. [Dap$^3$(Octanoyl)]-hGhrelin<br>GS—NH—$^L$CH(CH$_2$NHCO—C$_7$H$_{15}$)—CO-FLSPEHQRVQQRKESKKPPAKLQPR | 2.6 |
| 57. [Cys$^3$(S-Heptyl)]-hGhrelin<br>GSC(S—C$_7$H$_{15}$)FLSPEHQRVQQRKESKKPPAKLQPR | 1.4 |
| 58. [Adod$^3$]-hGhrelin<br>GS—NH—CH(n-C$_{10}$H$_{21}$)—CO-FLSPEHQRVQQRKESKKPPAKLQPR | 0.91 |
| 59. [Thr$^3$(Octanoyl)]-hGhrelin<br>GST(CO—C$_7$H$_{15}$)FLSPEHQRVQQRKESKKPPAKLQPR | 10 |
| 60. [Leu$^2$, Thr$^3$(Octanoyl)]-hGhrelin<br>GLT(CO—C$_7$H$_{15}$)FLSPEHQRVQQRKESKKPPAKLQPR | 46 |
| 61. [Lys$^3$(Octanoyl)]-hGhrelin<br>GSK(CO—C$_7$H$_{15}$)FLSPEHQRVQQRKESKKPPAKLQPR | 32 |

The activity of Compound 58, wherein the side chain at the 3rd position had been replaced by methylene units exclusively, showed the strongest activity ($EC_{50}$ value=1 nM or less). The activity of other derivatives was varied depending on the type of linkage, but it was confirmed that the mode of linkage of a side chain of amino acid 3 does not exert a significant influence on the activity.

(7) Hydrophobicity of a Side Chain at the 3rd Position

Derivatives wherein Ser (octanoyl) group 3 had been replaced by a hydrophobic amino acid most of which are natural amino acids was prepared, and their activity was examined. The results are summarized in Table 13.

TABLE 13

10. Activity of Ghrelin derivatives

| Compound Structure | Activity $EC_{50}$ (nM) |
|---|---|
| 62. (Trp$^3$)-hGhrelin<br>GSWFLSPEHQRVQQRKESKKPPAKLQPR | 31 |
| 63. [Phe$^3$]-hGhrelin<br>GSFFLSPEHQRVQQRKESKKPPAKLQPR | 2,000 |
| 64. [Cha$^3$]-hGhrelin<br>GS-Cha-FLSPEHQRVQQRKESKKPPAKLQPR | 19 |
| 65. [2-$^L$Nal$^3$]-hGhrelin<br>GS-$^L$Nal-FLSPEHQRVQQRKESKKPPAKLQPR | 8.2 |
| 66. [2-$^D$Nal$^3$]-hGhrelin<br>GS-$^D$Nal-FLSPEHQRVQQRKESKKPPAKLQPR | >10,000 |
| 67. [Ser$^3$(Bzl)]-hGhrelinGSS(CH$_2$—C$_6$H$_5$)FLSPEHQRVQQRKESKKPPAKLQPR | 7.6 |
| 68. (Cys$^3$(Trityl)]-hGhrelinGSC(C—Ph$_3$)FLSPEHQRVQQRKESKKPPAKLQPR | 20 |
| 69. [Ser$^3$(4-Methylpentanoyl)]-hGhrelin<br>GSS(CO—CH$_2$CH$_2$CH(CH$_3$)$_2$)FLSPEHQRVQQRKESKKPPAKLQPR | 4.4 |
| 70. [Leu$^3$]-hGhrelin<br>GSLFLSPEHQRVQQRKESKKPPAKLQPR | 4,400 |

TABLE 13-continued

10. Activity of Ghrelin derivatives

| Compound Structure | Activity EC$_{50}$ (nM) |
|---|---|
| 71. [Ile$^3$]-hGhrelin<br>GSIFLSPEHQRVQQRKESKKPPAKLQPR | >10,000 |
| 72. [Lys$^3$]-hGhrelin<br>GSKFLSPEHQRVQQRKESKKPPAKLQPR | 120 |
| 73. [Nle$^3$]-hGhrelin<br>GS-Nle-FLSPEHQRVQQRKESKKPPAKLQPR | 2,800 |
| 74. [Val$^3$]-hGhrelin<br>GSVFLSPEHQRVQQRKESKKPPAKLQPR | 1,600 |

The EC$_{50}$ values of the derivatives having an aromatic hydrophobic amino acid such as tryptophan, cyclohexyl alanine or naphthyl alanine at the 3rd position were 31 nM, 19 nM and 8.2 nM respectively, indicating that the Ca-releasing activity was maintained. Unexpectedly, when phenyl alanine was introduced at the 3rd position, the Ca-releasing activity was slightly low, but even if more hydrophobic Ser (Bzl) or Cys (Trityl) was introduced at the 3rd position, the Ca-releasing activity was similarly maintained, and thus it was confirmed that the hydrophobicity of the side chain at the 3rd position is more preferable for expressing the activity.

On one hand, when an aliphatic hydrophobic amino acid such as leucine, isoleucine, norleucine or valine was introduced at the 3rd position, the Ca-releasing activity of the derivatives was generally maintained but slightly lower than the derivatives introducing the aromatic amino acid. The activity of Compound 73 having norleucine at the 3rd position was EC$_{50}$=2,800 nM, whereas the activity of 6-amino-norleucine (lysine; Compound 72) having an amino group added to a side chain of norleucine was increased to 120 nM in terms of EC$_{50}$ values, so it was confirmed that similar to the basicity of carboxyl-terminal described above, the basicity of a side chain at the 3rd position is also preferable (8) Short-Chain Ghrelin Derivatives As described above, it was found that a ghrelin fragment of amino-terminal amino acids 1 to 4 shows significant activity and this activity is further increased by adding leucine at 5th position to said fragment; 3rd amino acid residue is preferably the one having a hydrophobic side chain; the activity is increased by introducing a basic residue; and amino acid residues 1 and 2 may be replaced by a non-amino acid compound having a 2-residue length, such as δ-amino acid. On the basis of these results, various short-chain ghrelin derivatives based on the amino-terminal region (1-5) were prepared as shown in Compound Nos. 76 to 87 in Tables 14 and 15, and their activities were examined. The results are summarized in Tables 14 and 15.

Compound 80 is known (Ipamorerin; K. Raum et al., Eur. J. of Endocrinol., 139: 552-561, 1998).

TABLE 14

Ghrelin derivative activity 11

| Compound structure | Activity EC$_{50}$ (nM) |
|---|---|
| 75. (Lys$^7$]-Ghrelin (1-7)-amide<br>H-Gly-Ser-Ser(CO—C$_7$H$_{15}$)-Phe-Leu-Ser-Lys-NH$_2$ | 11 |
| 76.<br>[N-Aminopentanoyl, Ser$^3$(Octyl), Lys$^5$]-Ghrelin (3-5)-amide<br>NH$_2$—(CH$_2$)$_4$—CO-Ser(C$_7$H$_{17}$)-Phe-Lys-NH$_2$ | 12 |
| 77. [N-Aminopentanoyl, $^D$Ser$^3$(Octyl),$^D$Phe$^4$, Lys$^5$)-Ghrelin (3-5)-amide<br>NH$_2$—(CH$_2$)$_4$—CO-$^D$Ser(C$_8$H$_{17}$)-$^D$Phe-Lys-NH$_2$ | 1,600 |
| 78. [Aib$^1$, His$^2$, Ser$^3$(Octyl), Lys$^5$]-Ghrelin (1-5)-amide<br>H-Aib-His-Ser(C$_8$H$_{17}$)-Phe-Lys-NH$_2$ | 34 |
| 79.<br>[Aib$^1$, His$^2$, $^D$Ser$^3$(Octyl), $^D$Phe$^4$, Lys$^5$]-Ghrelin (1-5)-amide<br>H-Aib-His-$^D$Ser (C$_8$H$_{17}$)-$^D$Phe-Lys-NH$_2$ | 38 |
| 80. [Aib$^1$, His$^2$, $^D$Nal$^3$, $^D$Phe$^4$, Lys$^5$]-Ghrelin (1-5)-amide<br>H-Aib-His-$^D$Nal-$^D$Phe-Lys-NH$_2$ | 2.5 |

Since the Ca-releasing activity of known Compound 80 was high (2.5 nM), the activity of Compound 79 derived from Compound 80 by replacing 2-D-naphthyl alanine at the 3rd position by D-octyl serine was also examined, and as a result, its EC$_{50}$ value was 38 nM, indicating that the activity was maintained. Compound 77 having D-octyl serine and D-phenyl alanine at the 3rd and 4th positions, which has the same amino acid structure as that of Compound 79 except for amino acids 1 and 2, showed a lower activity (1,600 nM), and these results indicates that the sequence or structure of amino acids 1 and 2 also affects the steric configuration of side chains of 3rd and 4th amino acids important for exhibiting the activity.

That is, in the case where amino acids 1 and 2 were replaced by aminopentanoic acid, the activity was kept at 34 nM even if 2-D-naphthyl alanine at the 3rd position and D-phenyl alanine at the 4th position were replaced by their corresponding L-amino acids (Compound 78), and thus the amino acid sequence (Gly-Ser) at the 1st to 2nd positions in ghrelin requires L configuration for amino acids 3 and 4, but even if amino acids 3 and 4 have D configuration, the activity is made significant by introducing another amino acid sequence such as Aib-His. It was also confirmed that regardless of L- or D-configuration at the 3rd and 4th positions, the activity is expressed by introduction of aminopentanoic acid at the 1st and 2nd positions.

TABLE 15

Ghrelin derivative activity 12

| Compound Structure | Activity EC$_{50}$ (nM) |
|---|---|
| 81. [N-Aminopentanoyl, Ser$^3$(Octyl)]-Ghrelin (3-5)-amide<br>NH$_2$—(CH$_2$)$_4$—CO-Ser(C$_8$H$_{17}$)-Phe-Leu-NH$_2$ | 11 |
| 82. (N-Aminopentanoyl, Ser$^3$(Octyl)]-Ghrelin (3-5)-methylamide<br>NH$_2$—(CH$_2$)$_4$—CO-Ser(C$_8$H$_{17}$)-Phe-Leu-NH—CH$_3$ | 12 |
| 83.<br>[N-Aminopentanoyl, Ser$^3$(Octyl)]-Ghrelin (3-5)-ethylamide<br>NH$_2$—(CH$_2$)$_4$—CO-Ser (C$_8$H$_{17}$)-Phe-Leu-NH—C$_2$H$_5$ | 22 |
| 84. [N-Aminopentanoyl, Ser$^3$(Octyl) [-Ghrelin (3-5)-benzylamide<br>NH$_2$—(CH$_2$)$_4$—CO-Ser (C$_8$H$_{17}$)-Phe-Leu-NH—CH$_2$—C$_6$H$_5$ | 98 |
| 85. [N-Aminopentanoyl, Ser$^3$(Octyl)]-Ghrelin (3-5), aminoethylamide<br>NH$_2$—(CH$_2$)$_4$—CO-Ser(C$_8$H$_{17}$)-Phe-Leu-NH—(CH$_2$)$_2$—NH$_2$ | 3.5 |
| 86. [N-Aminopentanoyl, Ser$^3$(Octyl), MePhe$^4$, MeLeu$^5$]-Ghrelin (3-5)-amide<br>NH$_2$—(CH$_2$)$_4$—CO-Ser(C$_8$H$_{17}$)—MePhe-MeLeu-NH$_2$ | 82 |
| 87. [$^D$Leu$^5$]-hGhrelin<br>GSS (CO—C$_7$H$_{15}$)F-$^D$L-SPEHQRVQQRKESKKPPAKLQPR | 220 |

Using [N-Aminopentanoyl, Ser$^3$(Octyl)]-Ghrelin (3-5) based on the amino-terminal region (1-5) of ghrelin, the correlation between activity and structure in the carboxyl-terminal region was examined. The activity of its derivatives wherein carboxyl-terminal leucine at the 5th position had been modified with amide, methyl amide, ethyl amide or benzyl amide was maintained but tended to be decreased as shown by $EC_{50}$ values of 11 nM, 12 nM, 22 nM and 98 nM, respectively. On the other hand, by replacing ethyl amide by aminoethyl amide, the activity was increased as shown by an $EC_{50}$ value of 3.5 nM, thus revealing that impartment of basicity to the carboxyl-terminal of ghrelin molecule is preferable.

These various carboxyl-terminal amide derivatives are useful compounds because of their resistance in vivo to decomposition with carboxy peptidases. Compound 86 ($EC_{50}$=86 nM) containing N-methylamino acid is also an useful compound because of its resistance to the enzymes.

Example 12. GH Releasing Activity of Ghrelin Derivatives in Rat (1) GH-Releasing Activity of Various Long-Chain Ghrelin Derivatives in Rat 18 nmol/kg Compound 17 ([Ser³(Octyl)]-hGhrelin), 30 nmol/kg Compound 18 ([Cys³(Octyl)]-rGhrelin), 100 nmol/kg Compound 65 ([2-$^L$Nal³]-hGhrelin), or 18 nmol/kg Compound 15 ([Ser³(3-Phenylpropinyl)]-hGhrelin) was administered rapidly and intravenously into IGS-SD strain rats (about 7-week-old) under anesthesia with Nembutal for each sample (n=3). Fifteen minutes after administration, plasma was collected, and the concentration of GH in plasma was measured by radioimmunoassay (Biotrak/Amersham). Separately, 0.2% bovine serum albumin (BSA)-physiological saline, 6 nmol/kg rGhrelin and hGhrelin, or 80 nmol/kg Ipamorelin (Compound 80) was administered into other rats as the control, respectively, and the concentrations of GH in plasma in 15 minutes after administration were compared (for each sample, n=3).

The results are shown in Table 13. Compound 17 ([Ser³ (Octyl)]-hGhrelin), Compound 18 ([Cys³ (Octyl)]-rGhrelin) and Compound 15 ([Ser³(3-PhPrl)]-hGhrelin) exhibited a strong GH-releasing activity, and the GH-releasing activity of [2-$^L$Nal³]-hGhrelin showed a good correlation with intracellular Ca-releasing activity.

TABLE 16

GH-releasing activity of various long-chain ghrelin derivatives

| Compound administered | $EC_{50}$ value (nM) | dose (nmol/kg) | GH level in plasma in 15 min. after administration (ng/mL) | | | |
|---|---|---|---|---|---|---|
| | | | Rat 1 | Rat 2 | Rat 3 | M ± S.D. |
| Physiological saline | — | — | 32 | 52 | 59 | 49 ± 12 |
| hGhrelin | 1.3 | 6 | 1802 | 1613 | 2203 | 1873 ± 301 |
| rGhrelin | 1.5 | 6 | 2056 | 1082 | 1205 | 1448 ± 530 |
| Ipamorelin (Compound 80) | 2.5 | 80 | 377 | 260 | 1184 | 607 ± 503 |
| [Ser³(Octyl)]-hGhrelin | 1.2 | 18 | 1626 | 1602 | 1743 | 1657 ± 75 |
| [Cys³(Octyl)]-rGhrelin | 5.4 | 30 | 2786 | 2342 | 2354 | 2494 ± 253 |
| [Ser³(Phenyl-propionyl)]-hGhrelin | 1.4 | 18 | 2119 | 2078 | 1581 | 1926 ± 299 |
| [2-$^L$Nal³]-hGhrelin | 8.2 | 100 | 1637 | 1576 | 1357 | 1524 ± 147 |

(2) Change of GH in Plasma by Administration of [Cys³ (Octyl)]-Rat Ghrelin

After Compound 18 ([Cys(Octyl)]-rat ghrelin) was intravenously administered in a dose of 5 μg/head into Wistar strain male rats (about 260 to 280 g) under anesthesia with Nembutal, GH released to blood was measured. Physiological saline as the control and rat ghrelin (5 μg/head) were also administered and compared with Compound 18.

As shown in Tables 17 to 19, the GH secretion-promoting activity of [Cys³ (Octyl)]-rat ghrelin was equivalent to natural rat ghrelin (that is, $C_{max}$ of secreted GH was about 1,100 ng/ml for both ghrelins), and further the secretion time tended to prolong. The intracellular Ca-releasing activity of Compound 18 was 5.4 nM in terms of $EC_{50}$.

TABLE 17

Change of GH level in plasma by administration of [Cys³(Octyl)]-rat ghrelin

| [Cys(C18)³]-rat ghrelin | | Time (min) | | | | | |
|---|---|---|---|---|---|---|---|
| 5 μg/head | | 0 | 5 | 10 | 15 | 20 | 30 | 60 |
| GH | Rat 1 | 377 | 338 | 687 | 927 | 900 | 469 | 98 |
| level | Rat 2 | 101 | 294 | 258 | 300 | 358 | 245 | 86 |
| in | Rat 3 | 59 | 476 | 949 | 1229 | 1417 | 704 | 133 |
| plasma | Rat 4 | 33 | 530 | 959 | 1451 | 1299 | 800 | 220 |
| (ng/mL) | Rat 5 | 32 | 613 | 1060 | 1561 | 1359 | 726 | 122 |
| | Mean ± S.D. | 120 ± 146 | 450 ± 133 | 783 ± 324 | 1093 ± 506 | 1067 ± 445 | 589 ± 229 | 132 ± 53 |

TABLE 18

Change of GH level in plasma by administration of physiological saline

| Physiological saline | | Time (min) | | | | | |
|---|---|---|---|---|---|---|---|
| | | 0 | 5 | 10 | 15 | 20 | 30 | 60 |
| GH | Rat 1 | 0 | 88 | 129 | 133 | 116 | 107 | 430 |
| level | Rat 2 | 204 | 122 | 118 | 134 | 128 | 69 | 36 |
| in | Rat 3 | 77 | 0 | 0 | 0 | 0 | 0 | 11 |
| plasma | Rat 4 | 0 | 0 | 0 | 0 | 48 | 27 | 110 |

TABLE 18-continued

Change of GH level in plasma by administration of physiological saline

| Physiological saline | Time (min) | | | | | | |
|---|---|---|---|---|---|---|---|
| | 0 | 5 | 10 | 15 | 20 | 30 | 60 |
| (ng/mL) Rat 5 | 0 | 0 | 0 | 0 | 0 | 0 | 210 |
| Mean ± S.D. | 56 ± 89 | 42 ± 58 | 49 ± 67 | 53 ± 73 | 58 ± 61 | 41 ± 47 | 159 ± 170 |

TABLE 19

Change of GH level in plasma by administration of rat ghrelin

| Rat ghrelin 5 μg/head | | Time (min) | | | | | | |
|---|---|---|---|---|---|---|---|---|
| | | 0 | 5 | 10 | 15 | 20 | 30 | 60 |
| GH level in plasma (ng/mL) | Rat 1 | 143 | 186 | 425 | 405 | 215 | 56 | 3 |
| | Rat 2 | 10 | 1396 | 2028 | 1566 | 876 | 242 | 27 |
| | Rat 3 | 838 | 163 | 443 | 681 | 419 | 120 | 36 |
| | Rat 4 | 348 | 556 | 1387 | 1469 | 1293 | 663 | 100 |
| | Rat 5 | 0 | 875 | 1380 | 1009 | 1414 | 452 | 20 |
| Mean ± S.D. | | 268 ± 348 | 635 ± 517 | 1133 ± 690 | 1026 ± 498 | 843 ± 525 | 306 ± 250 | 37 ± 37 |

Figure 6:
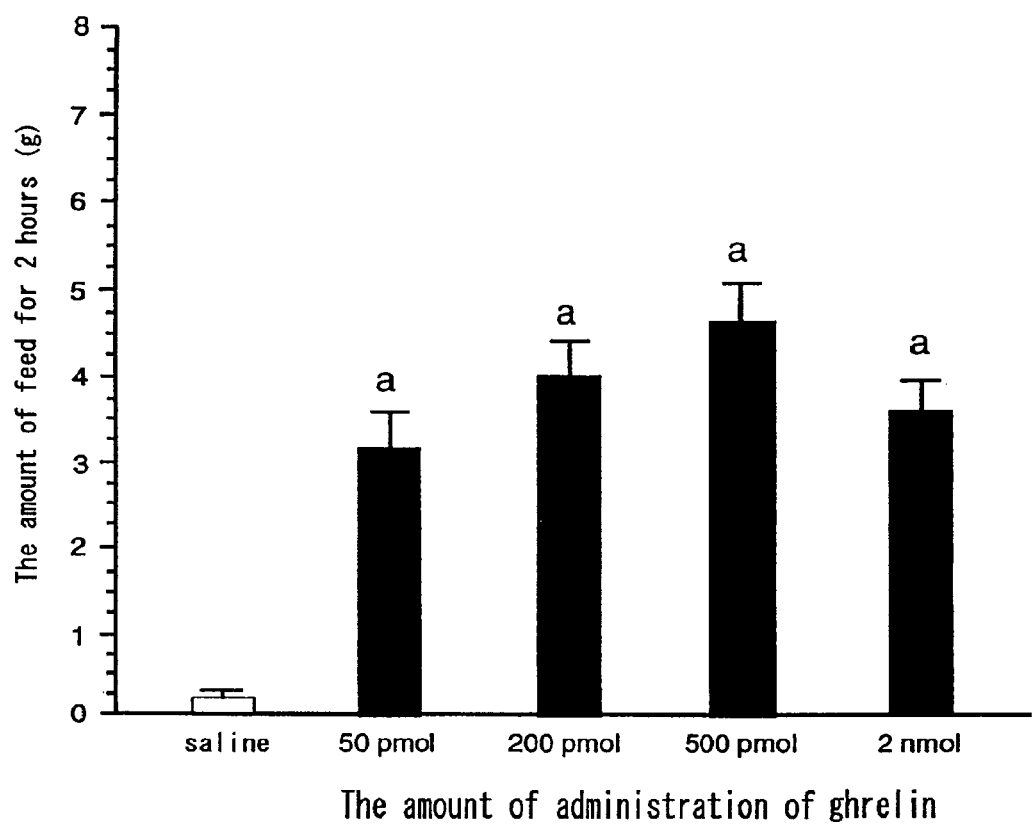
FIG. 6 shows promotion of appetite upon administration of ghrelin into ventricle, where the amount of feed (mean±standard error) for 2 hours after administration of ghrelin is shown.

Example 13. Increasing Action of Ghrelin on Appetite (1) Appetite-Increasing Action by Administration into Ventricle Physiological saline containing rat ghrelin at various concentrations was administered at 8:45 a.m. into cerebral ventricles of male Wistar strain rats (16 to 20 animals per group) each weighing 300 to 325 g. As the control, ghrelin-free physiological saline was administered into ventricles. After administration, the rats were allowed feed ad libitum, and the amount of feed taken for 2 hours after administration was measured. As shown in FIG. 6, an increase in the amount of feed taken was observed in the rats administered 50 μmol ghrelin intracerebroventricularly, and a dose-dependent increase in the amount of feed taken was observed in the rat administered 200 pmol and 500 pmol ghrelin, but the amount of feed taken was decreased in the rats administered 2 nmol ghrelin. Usually, the rat takes feed at night, so that in the morning, the rat is on a full stomach and rarely takes feed (see the rat administered physiological saline as the control in FIG. 6), and thus the increase in the amount of taken feed by administrating ghrelin into cerebral ventricle indicates that ghrelin has an appetite-increasing action.

(2) Appetite-Increasing Action by Intravenous Administration

50 μg/kg rat ghrelin was intravenously administered into tail veins in 9-month-old male SD (Sprague-Dawley) rats (5 animals) and Wister rats (4 animals), and the amount of feed taken for 2 hours after administration was measured (evaluated during 16:00 to 19:00 p.m.). As shown in Table 20, the amount of feed taken was evidently increased by intravenous administration of ghrelin, as compared with the amount of feed taken without administration of rat ghrelin, which was determined using the same animal at the same hour on another day. That is, it was demonstrated that ghrelin has an appetite-increasing action even by intravenous administration.

TABLE 20

| | | Amount of feed taken (g) | |
|---|---|---|---|
| strain | Rat No. | Administration of ghrelin | No administration of ghrelin |
| S-D | 1 | 3.2 | 2.2 |
| | 2 | 3.7 | 1.0 |
| | 3 | 3.2 | 0.1 |
| | 4 | 2.7 | 1.3 |
| | 5 | 2.6 | 0.8 |
| | Mean | 3.1 | 1.1 |
| | S.D. | 0.4 | 0.8 |
| Wister | 6 | 2.3 | 0.2 |
| | 7 | 1.9 | 1.4 |
| | 8 | 1.6 | 0.1 |
| | 9 | 2.1 | 0.3 |
| | Mean | 2.0 | 0.5 |
| | S.D. | 0.3 | 0.6 |

Example 14. Enhancement of Gastric Functions by Ghrelin

To examine the effect of ghrelin on gastric functions, the following experiment was carried out. Male SD strain rats (7- to 8-week-old, weighing 200 to 280 g) were fasted for 20 hours or more and then used in the experiment. The rats were anesthetized by intraperitoneal administration of urethane (1.25 g/kg) and kept warm using a warming pad and a warming light. A tracheal canula was inserted, and the esophagus was ligated by silk thread, and each rat was subjected to the following operation in order to measure gastric acid secretion or gastric motility. In the experiment using conscious animal, the rat was subjected to the operation for measurement of gastric acid secretion or gastric mobility under slight anesthesia by inhalation of ether.

In the experiment for gastric acid secretion under anesthesia with urethane, the operation was conducted according to the method proposed by Ohno et al. [Ohno, T., et al., *Jpn. J. Pharmacol.* 43, 429-439 (1987)]. Briefly, in the supine position the abdomen was incised and the stomach and duodenum were exposed. A polyethylene tube was inserted into a front part of the stomach to prepare acute stomach fistula. Another polyethylene tube was inserted into the stomach after cleaving the duodenum, and the surrounding part of the pylorus was ligated and fixed. The inside of the stomach was infused with physiological saline which was adjusted to pH 7.0 in a reservoir and warmed at 37° C. The flow rate was 1.0 ml/min. The infusion fluid was adjusted to pH 7.0 by titration with 100 mM NaOH using a pH-fixing unit (Hirariuma, Comitite-8). After it was confirmed that a basic amount of gastric acid secretion was stable, the test chemical was intravenously administered, and the rate of secretion of gastric acid was measured at 5-minute intervals. Four rats were used in each group.

In the experiment during arousal, the rat was subjected to the same operation under slight anesthesia by inhalation of ether, and then a small cut was made in the flank, and an infusion tube was taken out from the body. The exposed stomach and duodenum were put back in the abdomen, and the excised site was sutured, and the animal was fastened while lying on the back in a Ballman-type rat-fixing cage, and after it was confirmed that the rat was recovered from anesthesia, the rat was subjected to the experiment. The esophagus was ligated, but a trachea canula was not inserted.

The experiment for measurement of stomach motility under urethane anesthesia, a miniaturized balloon method was used according to the method proposed by Takeuchi & Nobuhara [Takeuchi, K. and Nobuhara, Y., *Digestive Diseases and Sciences* 30, 1181-1188 (1985)]. That is, a balloon filled with water and a supporting catheter were inserted into the stomach after cleavage of a front part of the stomach. It was fixed to lie on a gland of the stomach line, and one end of the catheter was connected to a pressure transducer (LPU-0.1-350-0-II, from Nihon Kohoden Corporation). After it was confirmed that the gastric motility was stable, the test chemical was intravenously administered accumulatively at 60-minute intervals. For the gastric motility, the amplitude of internal pressure in the stomach and the number of shrinking reactions in shrinkage motility having an amplitude of 20 cm $H_2O$ or more were measured at 10-minute intervals. Four animals was used in each group. In the experiment using conscious animals, the rat was subjected to the same operation under light anesthesia by inhalation of ether, and after the excised site was sutured, the animal was fastened in the prone position in a Ballman-type rat-fixing cage. After it was confirmed that the rat was recovered from anesthesia, the animal was subjected to the experiment.

Rat ghrelin and histamine dihydrochloride were dissolved in physiological saline and administered in a dose of 1 ml/kg into tail vein. To examine whether the vagus nerve action is involved in the action of ghrelin, atropine sulfate was subcutaneously administered in 30 minutes before administration of ghrelin, or the cervical vagus nerve bundles were bilaterally cut off. To examine the involvement of histamine $H_2$ receptor in the action of ghrelin, famotidine (Gaster®, produced by Yamanouchi Pharmaceutical Co., Ltd.) was subcutaneously administered 30 minutes before administration of ghrelin. The results are shown in mean±standard error. Statistical analysis was performed using Dunnett's multiple comparison tests. P value <0.05 was judged to be statistically significant.

As shown in FIG. 7A and in Table 21, secretion of gastric acid was promoted in a dose-dependent manner upon intravenous administration of rat ghrelin in a dose of 0.8 to 20 μg/kg into the rat under urethane anesthesia.

Figure 7:
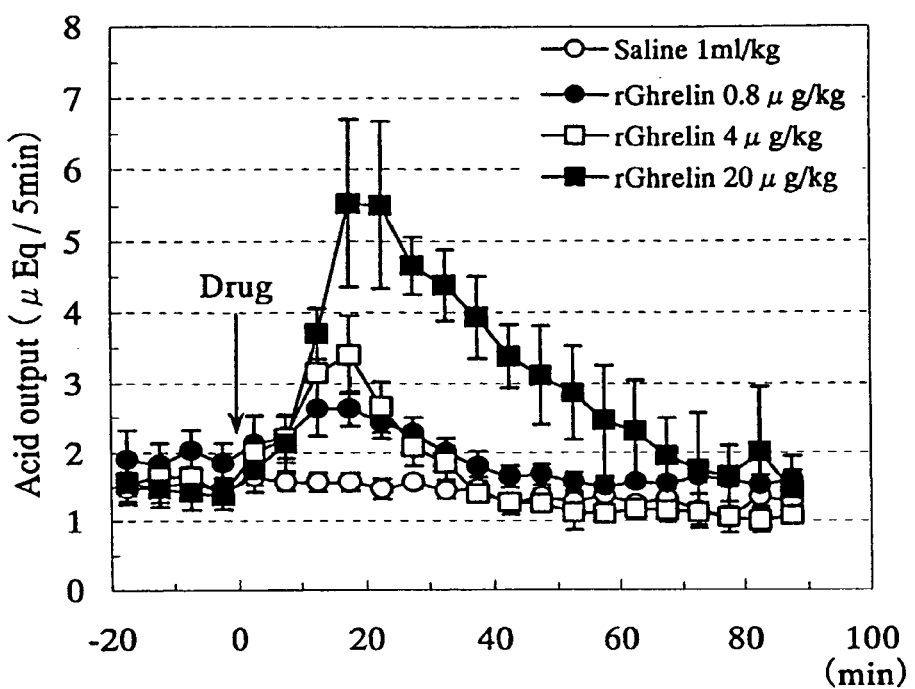
FIG. 7 shows the effect of a drug administered to rat under urethane anesthesia on secretion of gastric acid, where A and B show the results of administration of rat ghrelin (rGhrelin) and histamine, respectively. Each symbol indicates an average value from 4 rats, and the standard error is shown by an error bar. As the control, physiological saline was administered. At the arrowed point, the drug was administered.
Figure 7:
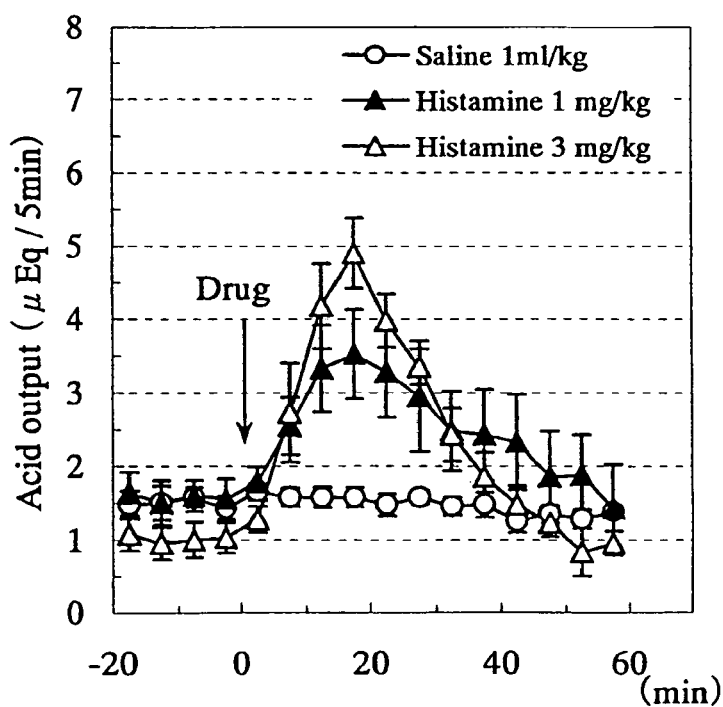
Figure 8:
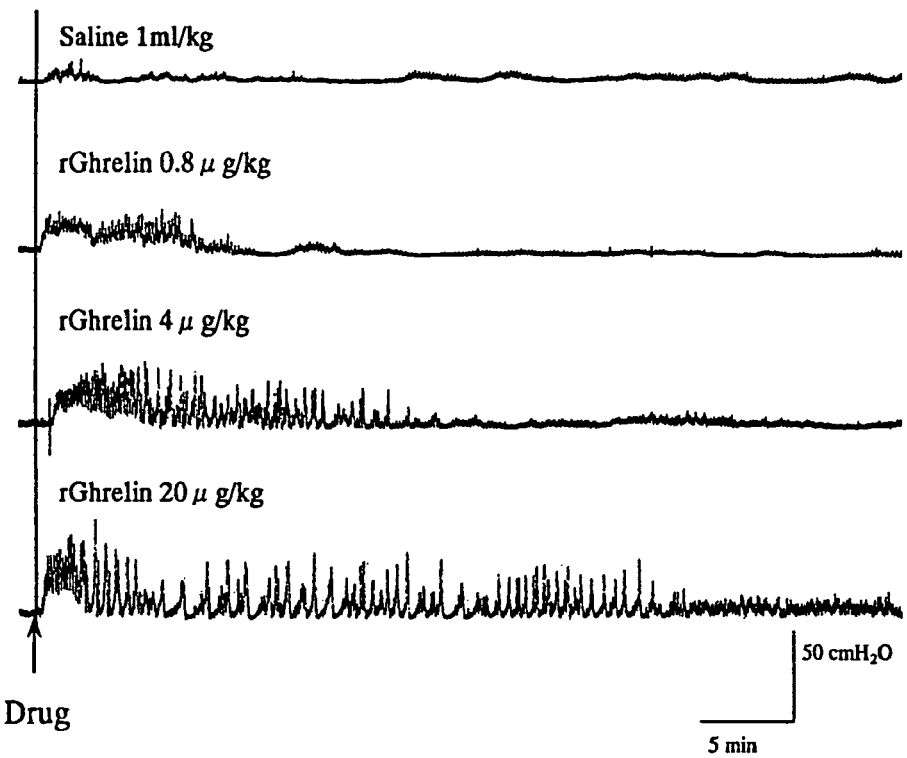
FIG. 8 is a graph showing the action of rat ghrelin on stomach motility in rat under urethane anesthesia.
Figure 8:
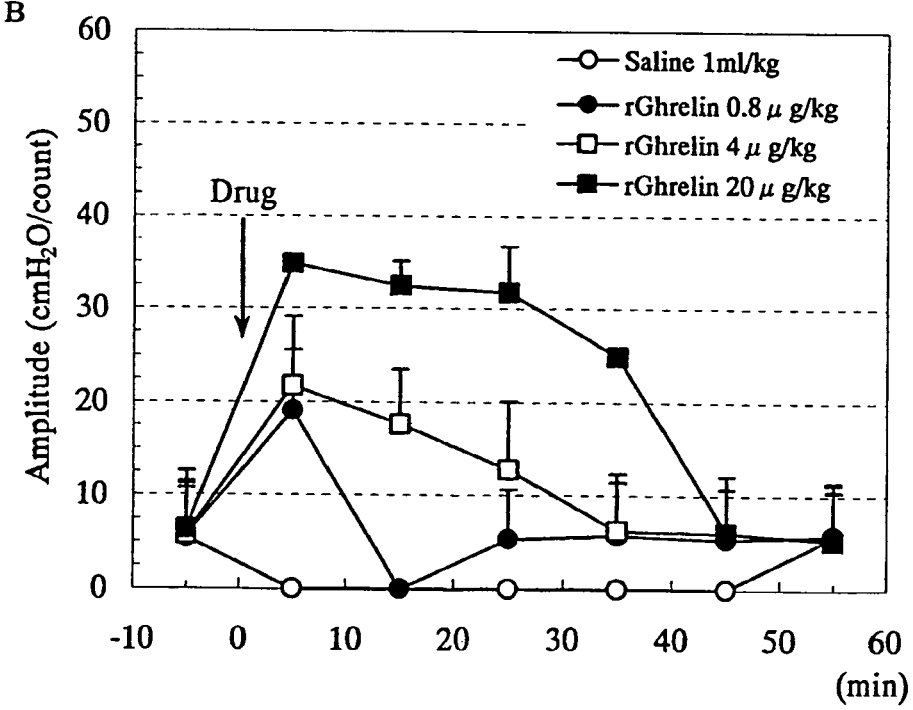

In the rat under anesthesia, the spontaneous motility of stomach was hardly observed before administration of ghrelin. When rat ghrelin was intravenously administered in a dose of 0.8 to 20 μg/kg into the rat in this condition, both the amplitude and frequency of gastric motility were promoted as shown in FIGS. 8A & B and in Table 21. These reactions were observed immediately after administration of rat ghrelin. By administration of 20 μg/kg, secretion of gastric acid was increased and reached to the maximum level within 20 minutes and gradually decreased for 90 minutes after administration. As shown in FIGS. 7 A & B, the maximum reaction in the gastric acid secretion-promoting action by administration of 20 μg/kg rat ghrelin was almost comparable to the reaction induced by intravenous administration of 3 mg/kg histamine. The action of promoting the amplitude of gastric motility reached the maximum reaction within 10 minutes in any dose, and by administration of 20 μg/kg ghrelin, the action was gradually decreased until 50 minutes after administration.

Further, as shown in Table 21, the action of promoting gastric secretion induced by administration of 20 μg/kg rat ghrelin was inhibited almost completely by pretreatment with atropine or bilateral cervical vasotomy, but this action was not affected by pretreatment of subcutaneous administration of 1 mg/kg famotidine i.e. a histamine $H_2$ receptor antagonist. Further, the action of promoting gastric motility induced by administration of rat ghrelin was completely inhibited by pretreatment with atropine or bilateral cervical vagotomy. From these results, it was confirmed that the promoting action of ghrelin on gastric functions is not via histaminergic mechanism but via activation of vagus nerve system.

By intravenous administration of rat ghrelin (4 and 20 μg/kg), secretion of gastric acid was promoted in the conscious rat in the same way as in the rat under urethane anesthesia. As compared with the rat under anesthesia, the conscious rat had spontaneous gastric motility before administration of the test chemical, and even in this condition by administering 0.8 to 20 μg/kg rat ghrelin into the rat, the gastric motility was promoted together with its amplitude and frequency. From the above result, it was confirmed that by intravenous administration of ghrelin, promotion of gastric acid secretion and promotion of gastric motility occur not only in the anesthetized rat but also in the conscious rat.

TABLE 21

| Treatment | | Gastric acid secretion (μ equivalent/ 60 min) | Gastric motility | |
|---|---|---|---|---|
| | | | Frequency (times/ 60 min.) | Amplitude (cm $H_2O$/ 60 min.) |
| Physiological saline | | 17.6 ± 1.2 | 1.3 ± 1.0 | 1.7 ± 1.0 |
| Rat ghrelin | 0.8 μg/kg i.v. injection | 24.5 ± 2.2 | 35.5 ± 18.1 | 6.7 ± 4.4 |
| | 4 μg/kg i.v. injection | 23.5 ± 2.6 | 60.8 ± 25.6 | 11.1 ± 5.3 |
| | 20 μg/kg i.v. injection | 43.3 ± 4.6 (*1) | 100.5 ± 20.4 (*1) | 21.8 ± 2.5 (*1) |
| Intravenous injection of 20 μg/kg rat ghrelin | + atropine 1 mg/kg subcutaneous administration | 26.1 ± 3.9 (*2) | 0 (*3) | 0 (*3) |
| | + removal of vagus nerve | 18.4 ± 3.7 (*3) | 0 (*3) | 0 (*3) |

TABLE 21-continued

| Treatment | Gastric acid secretion (μ equivalent/ 60 min) | Gastric motility | |
|---|---|---|---|
| | | Frequency (times/ 60 min.) | Amplitude (cm H$_2$O/ 60 min.) |
| + famotidine 1 mg/kg subcutaneous administration | 43.0 ± 4.2 | NT | NT |

Symbols in the table indicate:
*1, p < 0.01;
*2, p < 0.05; and
*3, p < 0.01
NT: Not tested.

Example 15. Promoting Action of Ghrelin and Ghrelin Derivatives on Cell Growth

To examine the action of administered ghrelin on promotion of cell growth, the following experiment was conducted. Twenty μg/kg of rat ghrelin or thioether-type rat ghrelin (Compound 18 [Cys$^3$(octyl)]-hGhrelin) was administered into tail veins of Wister male rats (7.5-week-old) respectively. Seventeen hours after administration, $^3$H-thymidine was administered into tail veins, and 1 hour thereafter, duodenum, jejunum and bone marrow were excised. The incorporation of $^3$H-thymidine to DNA fractions of these tissues was measured in order to examine the cell growth-promoting action of ghrelin and ghrelin derivatives. The tissues were cut thin and homogenized using a Polytron homogenizer, and after centrifugation, the supernatant was precipitated with trichloroacetic acid to give a DNA fraction. The radioactivity of the DNA fraction was measured by a liquid scintillation counter.

As shown in Table 22, the incorporation of $^3$H-thymidine into these tissues or organs was increased by intravenous administration of rat ghrelin or thioether-type rat ghrelin, and it was thus confirmed that ghrelin exhibits a cell growth-promoting action in duodenum, jejunum and bone marrow.

The time course of the cell growth-promoting action after intravenous administration of ghrelin was similar to that after administration of GHRH (growth hormone releasing hormone), so it was considered that the cell growth-promoting action of ghrelin occurs via GH (growth hormone) secreted mainly from pituitary. It was considered that the regulation of GH secretion by ghrelin as a physiological factor is reasonable for organism regulation, and there are less adverse effects which could occur by GH administration.

TABLE 22

| | Comparative Example | Rat ghrelin | Thioether-type ghrelin |
|---|---|---|---|
| Bone marrow (in tissues) | 100.0 ± 17.8% | 141.7 ± 30.1% | 144.5 ± 16.5% |
| Duodenum (in DNA fraction) | 100.0 ± 14.2% | 136.0 ± 17.8% | 114.0 ± 11.7% |
| Jejunum (in DNA fraction) | 100.0 ± 6.8% | 159.0 ± 7.5% | 151.0 ± 23.6% |

Numerical values show the ratio (%) of incorporation of radioisotope relative to the mean (in triplicate) of the comparative example (i.e. the group given physiological saline).

Example 16. Quantification of Ghrelin by Anti-Ghrelin Antibody

Using antibodies raised against amino- and carboxyl-terminal rat ghrelin peptides as antigens, ghrelin in various living tissues was quantified by radioimmunoassay (RIA).

Rabbits were immunized with [C-Cys]-rat ghrelin [1-11] (rat ghrelin peptide of amino acids 1 to 11 from amino-terminal having cysteine bound to the carboxyl-terminal thereof) and [C-Cys]-rat ghrelin [13-28] (rat ghrelin peptide of amino acids 13 to 28 from amino-terminal having cysteine bound to the carboxyl-terminal thereof) as antigens, to form amino-terminal antibody (anti-[C-Cys]-rat ghrelin [1-11] antigen) and carboxyl-terminal antibody (anti-[C-Cys]-rat ghrelin [13-28] antigen) respectively.

Figure 9:
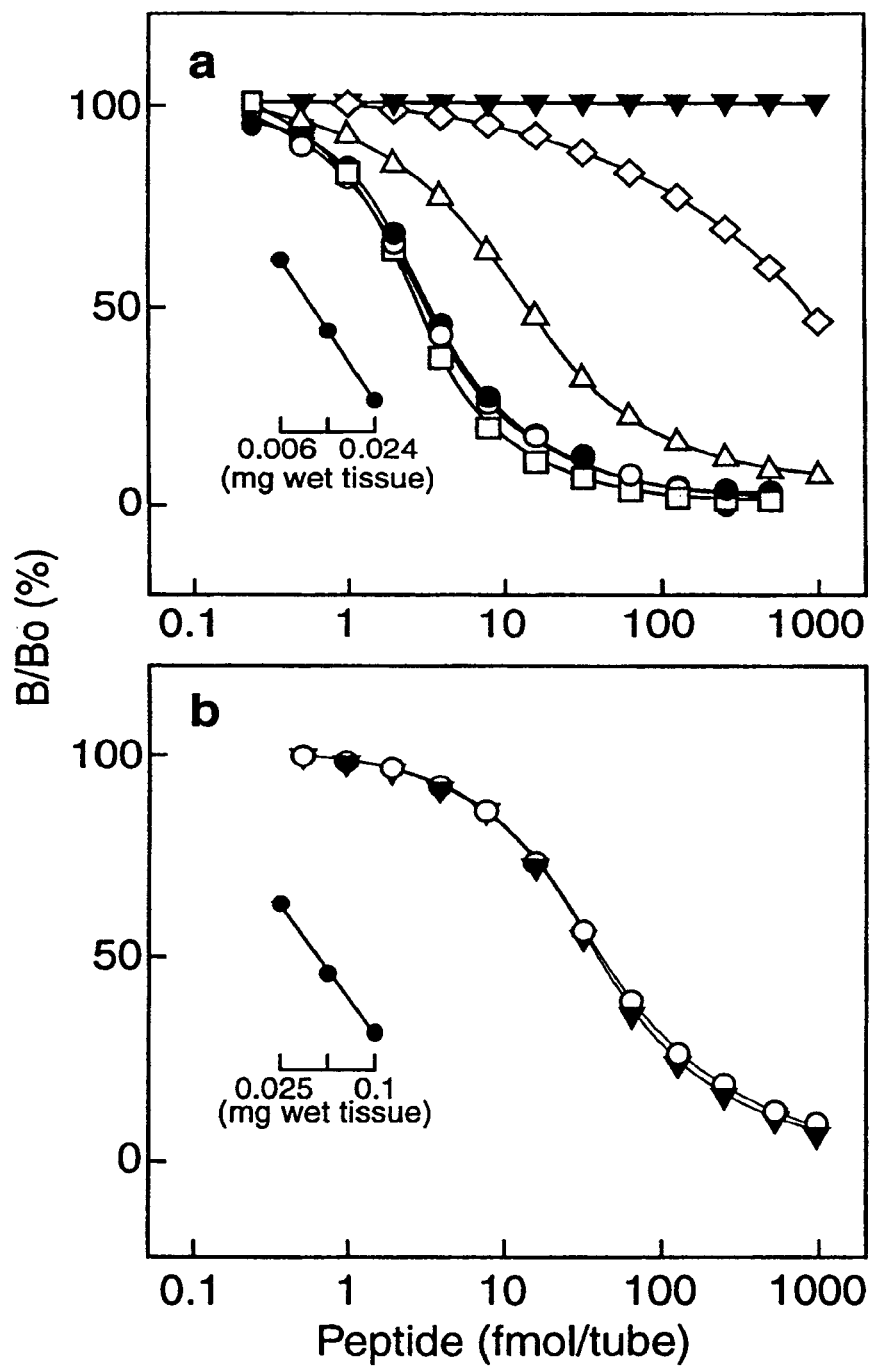
FIG. 9 is a graph showing a standard curve in radioimmunoassays and cross-reactivity with antibody.

As shown in FIG. 9a, the IC$_{50}$ (50% inhibitory concentration) of rat ghrelin was 3.1 fmol in binding between radioisotope-labeled rat ghrelin and the amino-terminal antibody. This amino-terminal antibody, while showing 100% cross-reactivity with chemically synthesized human ghrelin and rat ghrelin, showed only 0.3% cross-reactivity with n-hexanoyl rat ghrelin wherein 3rd serine had been modified with n-hexanoyl group and 20% cross-reactivity with n-decanoyl rat ghrelin wherein 3rd serine had been modified with n-decanoyl group. Further, the amino-terminal antibody did not react with ghrelin from which fatty acid had been released.

The amino-terminal antibody showed similar affinity for rat ghrelin (28 amino acids), human ghrelin (28 amino acids), and ghrelin-27 (ghrelin consisting of 27 amino acids) found in human and rat. Accordingly, it was confirmed that the amino-terminal antibody specifically recognizes natural ghrelin wherein 3rd serine was modified with n-octanoyl group.

As shown in FIG. 9b, natural rat ghrelin modified with n-octanoyl group and rat ghrelin modified by removing n-octanoyl from the natural rat ghrelin showed a similar IC$_{50}$ value of 44 fmol in binding between radioisotope-labeled rat ghrelin and the carboxyl-terminal antibody. That is, it was confirmed that the carboxyl-terminal antibody has the same affinity for ghrelin modified with fatty acid and for ghrelin from which fatty acid was released.

These results revealed that in regard to ghrelins occurring in various tissues in a living body, ghrelin wherein 3rd serine was modified with n-octanoyl group can be quantified by the amino-terminal antibody, while both ghrelin modified with fatty acid and ghrelin from which fatty acid was released can be quantified by the carboxyl-terminal antibody.

Table 23 shows the result of examination of the contents of fatty acid-modified ghrelin and the contents of both fatty acid-modified ghrelin and fatty acid-released ghrelin in various tissues in a living body.

TABLE 23

In the table, C-RIA indicates the result of quantification by radioimmunoassay using the carboxyl-terminal antibody, while N-RIA indicates the result of quantification by the amino-terminal antibody.

| Tissues | Amount of rat ghrelin reacting with antibody (fmol/mg tissues) | |
|---|---|---|
| | C-RIA | N-RIA |
| Hypothalamus | 1.8 ± 0.3 | <0.05 |
| Pituitary | 8.5 ± 3.1 | <0.05 |
| Thyroid | 3.5 ± 2.0 | <0.05 |
| Mandible gland | 8.8 ± 1.3 | <0.05 |
| Thymus | 3.5 ± 0.4 | <0.05 |
| Adrenal gland | 3.1 ± 0.4 | <0.05 |
| Atrium | 2.3 ± 0.2 | 0.07 ± 0.01 |
| Ventricle | 2.1 ± 0.1 | <0.05 |
| Aorta | 2.4 ± 0.7 | 0.14 ± 0.03 |
| Lung | 3.1 ± 0.4 | <0.05 |
| Liver | 2.8 ± 0.5 | <0.05 |
| Pancreas | 2.6 ± 0.6 | 0.15 ± 0.05 |
| Stomach | 1779.8 ± 533.9 | 377.31 ± 55.83 |
| Duodenum | 106.7 ± 7.3 | 20.57 ± 0.69 |
| Jejunum | 60.2 ± 17.2 | 10.73 ± 5.44 |
| Ileum | 20.5 ± 5.1 | 0.16 ± 0.08 |
| Cecum | 15.1 ± 2.5 | 1.70 ± 5.44 |
| Colon | 10.4 ± 0.7 | <0.05 |
| Kidney | 5.4 ± 0.3 | <0.05 |
| Spermary | 2.8 ± 0.2 | <0.05 |
| Plasma (1 mL) | 219.6 ± 71.8 | 4.02 ± 1.91 |

The numerical values in the table indicate "mean±standard deviation".

Example 17. Production of Rat Ghrelin (1-28) by a Semi-Synthesis Method

Synthesis Scheme

In this example, rGhrelin was produced from rGhrelin (6-28) and Ghrelin (1-7) fragments previously prepared by genetic engineering method and chemical synthesis respectively, as follows.

Specifically, β-galactosidase 97S-(QFE-SRHRR)-rGhrelin (6-28), that is, a fusion protein of β-galactosidase 97S and rGhrelin (6-28) between which an amino acid sequence (-QFE-SRHRR-) having a site cleaved by V8 protease and KexII protease occurred was expressed in E. coli. This fusion protein was treated with V8 protease, to cut off SRHRR rGhrelin (6-28). Then, all amino groups of SRHRR rGhrelin (6-28) were protected with Boc groups, and the resulting peptide was treated with KexII protease, to give [Lys (Boc)$^{11, 16, 19, 20, 24}$]-Ghrelin (6-28) from which the amino-terminal amino group of Ser 6 had been isolated. This protected fragment was condensed with [N$^{\alpha}$-Boc]-rGhrelin (1-5)-Osu obtained by chemical synthesis, and the resulting [Lys(Boc)$^{11, 16, 19, 20, 24}$]-rGhrelin was treated with an acid, whereby rGhrelin was produced.

In this example, semi-synthesis of rGhrelin was described, but hGhrelin can also be synthesized by this method.

Further, in this example, fragment (1-5) was condensed with fragment (6-28), but chemically synthesized amino-terminal fragments (1-2), (1-3) and (1-7) can be condensed respectively with carboxyl-terminal fragments (3-28), (4-28) and (8-28) of an arbitrary length consisting of amino acids at the 28th position up to the 3rd position constructed by genetic engineering means, in order to produce ghrelin as a fusion protein. To reduce the number of steps in chemical synthesis, the condensation between (1-2) and (3-28) or between (1-3) and (4-28) is advantageous. From the viewpoint of complete prevention of the racemization caused by condensation, the condensation between (1-7) and (8-28) by using Pro 7 is particularly preferable.

Construction of Expression Vector pG97s rGR and Expression of Ghrelin (6-28) as a Fusion Protein On the basis of the nucleotide sequence of rat ghrelin cDNA, a DNA fragment for rGhrelin (6-28) having an amino acid sequence QFE-SRHRR in the prepro region was obtained by annealing using a total synthetic oligomer.

To insert this DNA fragment into pG97SnPPH34 (JP-A 9-296000), pG97SnPPH34 was treated with SalI and SmaI thereby deleting its human parathyroid hormone precursor gene. The product was treated with alkali phosphatase and ligated by T4 ligase to the rGhrelin derivative gene fragment previously treated with SalI and kinase. The ligated plasmid was transformed into E. coli DH5α strain, to give plasmid pG97s rGR.

The resulting plasmid pG97s rGR was transformed into E. coli M25 (ompT), and the resulting transformant was cultured onto 3 dishes each containing 200 ml Terrific broth liquid medium (1.2% trypton, 2.4% yeast extract, 0.4% glucose) and cultured under shaking at 37° C. When the concentration ($OD_{660}$) of the bacterial cell reached 0.8, isopropyl 1-thio-β-galactopyranoside (IPTG) was added thereto at a final concentration of 2 mM, to express rGhrelin (6-28) fusion protein. Further, the bacterial cell was cultured for 4 hours and then collected by centrifugation. The structure of rGhrelin (6-28) fusion protein is as follows:

rGhrelin 6-28 fusion protein: (β-Galactosidase-97S)-QFE-SRHRR rGhrelin (6-28)

Processing of rGhrelin 6-28 Fusion Protein and Purification of [SRHRR]-rGhrelin (6-28)

20 ml of the resulting bacterial cell was suspended in TE buffer and the bacterial cell was disrupted by a French press. Thereafter, the inclusion body was collected by centrifugation at 3000 rpm for 15 minutes, suspended again in 10 ml TE buffer and deionized water, and centrifuged whereby the inclusion body was washed. The inclusion body was diluted with deionized water such that its $OD_{660}$ was reduced to 50.0, and Tris-HCl (pH 8.2) was added thereto at a final concentration of 50 mM, and the inclusion body was dissolved in urea (final concentration: 3.5 M). To this solution kept at 30° C. was added rV8 protease derivative V8D5 (abbreviated herein after to V8D5) (JP-A 9-47291) at a final concentration of 10 µg/ml, and the solution was treated with the enzyme at 30° C. for 20 minutes. The reaction was terminated by adding 3% acetic acid (AcOH).

1.5-fold excess deionized water was added to the V8D5 enzyme reaction-terminated solution containing the [SRHRR]-rGhrelin (6-28), then this solution was adjusted to pH 5.0 with 5N NaOH, to precipitate the β-galactosidase derivative fragment which was then removed by centrifugation at 5000 rpm for 10 minutes.

The supernatant containing [SRHRR]-rGhrelin (6-28) was applied to TSK-ODS 80Ts column (resin particle diameter of 20 µm, 50 mm I.D.×100 mm, TOSOH Co., Ltd.) previously equilibrated with 0.1% TFA. The desired peptide was eluted by a linear gradient of from 100% buffer A [0.8 ml/min., 1% acetonitrile, 0.1% TFA] to 100% buffer B [50 acetonitrile, 0.095% TFA], which was programmed to be finished in a volume of 5 columns. Fractions containing the desired peptide [SRHRR]-rGhrelin (6-28) were collected (about 50 mg).

Purification of [Boc-SRHRR]-[Lys(Boc)$^{11, 16, 19, 20, 24}$]-rGhrelin (6-28)

6-equivalent mole (19.2 mg, 6×15 µmol) of di-t-butyl bicarbonate was added to 50% aqueous acetonitrile solution containing about 50 mg (15 µmol) of [SRHRR]-rGhrelin (6-28), then adjusted to pH 9 with triethylamine, and left at room temperature for 15 minutes. Acetic acid was added at a final concentration of 0.5% to the reaction solution, and after the acetonitrile was evaporated, the solution was added to EMPORE-Octyl (C8) HD 4 mm/1 ml cartridge previously equilibrated with 10 acetonitrile containing 0.1% TFA, and after the column was washed with the equilibration solution, [Boc-SRHRR]-[Lys (Boc)$^{11, 16, 19, 20, 24}$]-rGhrelin (6-28) was eluted with 90% acetonitrile containing 0.095% TFA. The acetonitrile was evaporated, and 6 ml solution containing about 30 mg of the desired peptide was obtained.

Mass spectrometry indicated mainly two peptides whose molecular weight after Boc modification was higher by 500 (determined molecular weight, 3895) or by 600 (determined molecular weight, 3995) than the molecular weight (determined molecular weight=3396, theoretical molecular weight=3398) before Boc modification.

Cleavage of [Lys (Boc)$^{11, 16, 19, 20, 24}$]-rGhrelin (6-28) by Kex2 Protease and Purification Thereof.

A calcium chloride solution and Tris-HCl, pH 8.2, were added at final concentrations of 0.3 mM and 20 mM respectively to the resulting aqueous solution of [Boc-SRHRR]-[Lys (Boc)$^{11, 16, 19, 20, 24}$]-rGhrelin (6-28) (30 mg, 6 mL). After a solution of Kex2 protease (JP-A 10-229884) was added thereto at a concentration of $1 \times 10^5$ units/ml, the sample was treated with the protease at 30° C. for 60 minutes.

In HPLC, a peak of [Boc-SRHRR]-[Lys (Boc)$^{11, 16, 19, 20, 24}$]-rGhrelin (6-28) disappeared, a peak of [Lys (Boc)$^{11, 16, 19, 20, 24}$]-rGhrelin (6-28) was shifted toward the side of hydrophobicity, and a peak of a hydrophilic fragment corresponding to Boc-SRHRR was observed.

After the disappearance of the starting material was confirmed, the reaction solution was adjusted to pH 3.5 with aqueous acetic acid and applied to reversed-phase chromatography column ODS-80Ts (column volume of 1.66 cc, resin particle diameter 20 µm, TOSOH Co., Ltd.) previously equilibrated with 1.0% acetonitrile containing 1% acetic acid. After the column was washed with the equilibration solution in a volume of 5 columns, [Lys (Boc)$^{11, 16, 19, 20, 24}$]-rGhrelin (6-28) was eluted by a linear gradient of from 1.0% acetonitrile to 90.0% acetonitrile each containing 1% acetic acid, which was programmed to be finished in a volume of 5 columns. Main fractions were lyophilized to give 6.2 mg of the desired protected peptide.

Fragment condensation and de-protection

Triethylamine (51.0 µl, 0.366 mmol) and a solution of di-t-butyl bicarbonate (78.0 mg, 0.0356 mmol) in TFE (4.00 ml) were added respectively to a solution of Ghrelin (1-5) (190 mg, 0.0301 mmol, Compound 31) in trifluoroethanol (TFE) (6.00 ml) and stirred at room temperature for 13 hours. The solvent was evaporated, and ether (20.0 ml) was added to the resulting residues, whereby 180.5 mg (N$^\alpha$-Boc)-rGhrelin (1-5) was obtained.

Then, HOSu (5.20 mg, 0.0452 mmol) was added to a solution of [N$^\alpha$-Boc]-rGhrelin (1-5) (22.0 mg, 0.0301 mmol) in DMF (1.00 ml), and DIPCI (7.30 µl, 0.0466 mmol) was added thereto in a bath at −30° C. After the mixture was stirred in the bath at −30° C. for 1 hour and then at room temperature for 18 hours, the solvent was evaporated, and the resulting residues were converted into powder with ether to give 14.1 mg [N$^\alpha$-Boc]-rGhrelin (1-5)-OSu as a succinimide ester of [N$^\alpha$-Boc]-rGhrelin (1-5).

Then, [N$^\alpha$-Boc]-rGhrelin (1-5)-OSu (3.3 mg, 3.96 µmol) and triethylamine (2.5 µl, 17.9 µmol) were added to a solution in DMF (0.6 ml) of [Lys(Boc)$^{11, 16, 19, 20, 24}$]-rGhrelin (6-28) (6.10 mg, 2.18 µmol) prepared by the recombinant method and stirred at room temperature for 24 hours. The solvent was evaporated, and TFA (2.00 ml) was added directly to the resulting residues under cooling on ice and stirred at room temperature for 1.5 hours. The TFA was evaporated, and ether was added to the residues, whereby 6.2 mg crude peptide containing Ghrelin (1-28) was obtained.

This product was dissolved in 2 ml of 5% acetic acid (AcOH) and applied to YMC-Pack-ODS-A (5 µm, 20 mm×250 mm) and eluted by a linear gradient (flow rate: 10 ml/min.) of from 0 to 95% acetonitrile in 0.1% trifluoroacetic acid for 60 minutes. The desired fractions were collected, lyophilized, applied to YMC-Pack PROTEIN-RP (C4, 10 mm×250 mm) and eluted by a linear gradient (flow rate: 4.7 ml/min.) of from 7.5 to 21.3% acetonitrile in 0.1% trifluoroacetic acid for 30 minutes.

The desired fractions were collected, lyophilized and applied to YMC-Pack PROTEIN-RP (C4, 10 mm×250 mm) and eluted by a linear gradient (flow rate: 4.7 ml/min.) of from 7.5 to 21.3% acetonitrile in 0.1% trifluoroacetic acid for 30 minutes. The desired fractions were collected and lyophilized to give 2.1 mg rGhrelin (1-28). This product showed a retention time agreeing with that of standard rGhrelin (1-28) in analytical HPLC, and had an intracellular Ca-releasing activity of $EC_{50}$=1.5 nM which was equivalent to natural ghrelin.

ESI-MS 3315.0 (theoretical: 3314.8), amino acid composition: Ser; 3.74 (4), Glx; 5.69 (6), Gly; 1.18 (1), Ala; 2.05 (2), Leu; 2, Phe; 0.98 (1), Lys; 4.98 (5), His; 1.03 (1), Arg; 1.96 (2), Pro; 4.01 (4)

Compound 87 [$^D$leu$^5$]-rGhrelin (1-28)

As a by product in succinimide esterification of [N$^\alpha$-Boc]-rGhrelin (1-5) or condensation of the fragments, 0.8 mg [$^D$leu$^5$]-rGhrelin (1-28) was obtained. Its intracellular Ca-releasing activity was $EC_{50}$=220 nM.

ESI-MS 3315.0 (theoretical: 3314.8), amino acid composition: Ser; 3.80 (4), Glx; 5.92 (6), Gly; 1.23 (1), Ala; 2.07 (2), Leu; 2, Phe; 0.97 (1), Lys; 4.92 (5), His; 1.02 (1), Arg; 1.97 (2), Pro; 4.11 (4)

GC-MS analysis of leucine after hydrolysis in $D_2O/DCl$: L-Leu; 1.17 (1), D-Leu; 0.83 (1)

INDUSTRIAL APPLICABILITY

By administering the new peptide-type compound of the present invention or a pharmaceutically acceptable salt thereof into humans or animals, it demonstrates an excellent working effect as a pharmaceutical preparation for promoting growth of children and ameliorating the defect of metabolic functions caused by GH deficiency, by inducing GH secretion without causing substantial side effects, and its antibody demonstrates an excellent working effect as an agent for diagnosis of diseases attributable to GH deficiency and as a research tool in the field of science.

What is claimed is:

1. A DNA coding for an amino acid sequence of a peptide-type compound,
   wherein the amino acid sequence comprises one amino acid sequence selected from the group consisting of amino acid sequences set forth in SEQ ID NOs:2, 10, 16, 17, 22, 25, 26, 27, 28, 29, 30 and 31, wherein one amino acid is deleted, replaced and/or added, and wherein said one amino acid is not deleted, replaced and/or added at the first to fourth amino acid from the amino-terminal in said amino acid sequence,
   provided that a natural product is excluded, and
   wherein the amino acid sequence as modified above is a sequence of a precursor for producing the peptide-type compounds which binds to a growth hormone secretagogue receptor, increases the intracellular calcium ion concentration, or induces growth hormone secretion.

2. An expression vector comprising a desired gene wherein the vector is to express the desired gene, and a promoter is linked operatively upstream of said gene, and the desired gene is DNA of claim 1.

3. An expression vector comprising a desired gene wherein the vector is to express the desired gene, and a promoter is linked operatively upstream of said gene, wherein the desired gene and/or the promoter is heterologous or heterogeneous to the vector, wherein the desired gene is a DNA coding for an amino acid sequence of a peptide-type compound,
  wherein the amino acid sequence consists of one amino acid sequence selected from the group consisting of (A) the amino acid sequence set forth in SEQ ID NOs:1, 2, 3, 8, 9, 10, 11, 16, 17, 22, 25, 26, 27, 28, 29, 30 and 31, (B) a variant of the amino acid sequence set forth in SEQ ID NOs:1, 2, 3, 10, 11, 16, 17, 22, 25, 26, 27, 28, 29, 30 and 31, wherein one amino acid is deleted, replaced and/or added, (C) a variant of the amino acid sequence set forth in SEQ ID NO:8 wherein one amino acid is added, and (D) a variant of the amino acid sequence set forth in SEQ ID NO:9 wherein one amino acid is deleted and/or replaced,
    wherein said one amino acid is not deleted, replaced and/or added at the first to fourth amino acid from the amino-terminal in said amino acid sequence, and
  wherein the amino acid sequence is a sequence of a precursor for producing the peptide-type compounds which binds to a growth hormone secretagogue receptor, increases the intracellular calcium ion concentration, or induces growth hormone secretion.

4. An expression vector comprising a desired gene wherein the vector is to express the desired gene, and a promoter is linked operatively upstream of said gene wherein the desired gene and/or the promoter is heterologous or heterogeneous to the vector, and wherein the desired gene is a DNA consisting of one nucleotide sequence selected from the group consisting of positions 100-183 of SEQ ID NO:6, positions 103-186 of SEQ ID NO:7, positions 100-180 of SEQ ID NO:14, positions 103-183 of SEQ ID NO:15, positions 81-164 of SEQ ID NO:20, positions 81-161 of SEQ ID NO:21, positions 16-96 of SEQ ID NO:24, positions 135-197 of SEQ ID NO:36, positions 119-199 of SEQ ID NO:37, positions 63-131 of SEQ ID NO:38, positions 63-122 of SEQ IDNO:39, positions 103-114 of SEQ ID NO:7, positions 103-123 of SEQ ID NO:7 and positions 103-132 of SEQ ID NO:7, and
  wherein the DNA codes for an amino acid sequence that is a sequence of a precursor for producing a peptide-type compound which binds to a growth hormone secretagogue receptor, increases the intracellular calcium ion concentration, or induces growth hormone secretion.

5. A transformed cell comprising the expression vector of claim 2.

6. A transformed cell comprising the expression vector of claim 3.

7. A transformed cell comprising the expression vector of claim 4.

8. A method for producing a peptide-type compound which comprises culturing the transformed cell of claim 6 in a liquid medium including one or more selected from the group consisting of a carbon source, a nitrogen source, vitamins, growth promoters and serum, and recovering the peptide-type compound from the culture,
  wherein the transformed cell is capable of cutting a suitable site in a precursor polypeptide of said peptide and acylating the serine residue at the third position in said peptide, and
  wherein the recovery step includes separating the peptide-type compound from the culture and purifying the peptide-type compound.

9. The method of claim 8, wherein the transformed cell is capable of binding a fatty acid via an ester linkage to a side-chain hydroxyl group of an amino acid or via a thioester linkage to a side-chain mercapto group of an amino acid in the peptide-type compound, and wherein the recovered peptide-type compound comprises an amino acid with a fatty acid bound via an ester linkage to a side-chain hydroxyl group of the amino acid or an amino acid with a fatty acid bound via a thioester linkage to a side-chain mercapto group of the amino acid.

10. The method of claim 8, wherein the transformed cell is capable of an acylation activity of binding a fatty acid via an ester linkage to a side-chain hydroxyl group of serine, and wherein the recovered peptide-type compound comprises a serine with a fatty acid bound via an ester linkage to a side-chain hydroxyl group of the serine.

11. The method of claim 8, wherein the transformed cell is capable of an acylation activity of binding a fatty acid via an ester linkage to a side-chain hydroxyl group of threonine, and wherein the recovered peptide-type compound comprises a threonine with a fatty acid bound via an ester linkage to a side-chain hydroxyl group of the threonine.

12. The method of claim 8, further comprising acylating with an acyl group containing 2 to 35 carbon atoms an amino acid of the recovered peptide-type compound.

13. The method of claim 8, further comprising acylating with octanoyl an amino acid of the recovered peptide-type compound.

14. The method of claim 8, wherein the second or third amino acid residue from the amino-terminal of the amino acid sequence of the peptide-type compound is a modified amino acid in which:
  (1) one saturated or unsaturated alkyl chain containing 1 to 35 carbon atoms is introduced at the alpha carbon atom of the amino acid by an ester, ether, thioether, thioester, amide, carbamide, thiocarbamide or disulfide linkage;
  (2) one saturated or unsaturated alkyl chain containing 1 to 35 carbon atoms is introduced at the alpha carbon atom of the amino acid by an alkylene group containing 1 to 10 carbon atoms and by an ester, ether, thioether, thioester, amide, carbamide, thiocarbamide or disulfide linkage; or
  (3) one saturated or unsaturated alkyl chain containing 1 to 35 carbon atoms is introduced at the alpha carbon atom of the amino acid, and
  wherein said peptide-type compound or pharmaceutically acceptable salt thereof increases intracellular calcium ion concentration, is produced.

15. The method of claim 14, wherein the second or third amino acid residue from the N-terminal of the amino acid sequence is serine and the serine residue is modified at the side-chain hydroxyl group wherein the peptide-type compound increases intracellular calcium ion concentration.

16. The method of claim 14, wherein the modified amino acid is serine in which the side-chain hydroxy group is converted into a group represented by —OCO—Z1 wherein Z1 is hydrogen or a saturated or unsaturated alkyl chain containing 1 to 50 carbon atoms.

17. The method of claim 14, wherein the modified amino acid residue is one in which a fatty acid is bound to the side-chain hydroxy group via an ester bond.

18. The method of claim 17, wherein the fatty acid contains 2 to 35 carbon atoms.

19. The method of claim 18, wherein the fatty acid is selected from fatty acids containing 2, 4, 6, 8, 10, 12, 14, 16 or 18 carbon atoms.

20. The method of claim 19, wherein the fatty acid is selected from octanoic acid, a monoene fatty acid thereof and a polyene fatty acid thereof.

21. The method of claim 19, wherein the fatty acid is selected from decanoic acid, a monoene fatty acid thereof and a polyene fatty acid thereof.

22. The method of claim 14, in which the side chain hydroxy group of serine at the third position from the amino-terminal in said amino acid sequence is acylated with an acyl group containing 2 to 35 carbon atoms.

23. The method of claim 14, in which the serine at the third position from the amino-terminal in said amino acid sequence is converted into threonine, and in which the side-chain hydroxy group of threonine at the third position from the amino-terminal is acylated with an acyl group containing 2 to 35 carbon atoms.

24. The method of claim 14, in which the side-chain hydroxy group of serine at the third position from the amino-terminal is acylated with octanoyl.

25. The method of claim 14, wherein the compound has additionally an activity of inducing secretion of growth hormone.

26. The method of claim 14, which comprises a basic amino acid bound to the carboxyl-terminal.

27. The method of claim 14, wherein the amino-terminal is modified with a saturated or unsaturated alkyl group or an acyl group containing one or more carbon atoms, and/or the hydroxy group in the carboxyl group at the carboxyl-terminal of said amino acid sequence is OZ or is replaced by $NR_2R_3$ wherein Z is a pharmaceutically acceptable cation or a lower branched or linear alkyl group, and $R_2$ and $R_3$ are the same or different and represent hydrogen or a lower branched or linear alkyl group.

28. The method of claim 27, wherein the carboxyl-terminal of said amino acid sequence is an amide derivative with a substituted basic amino acid.

29. The method of claim 14, wherein the peptide-type compound or a pharmaceutically acceptable salt thereof which consists of an amino acid sequence of SEQ ID NO: 3 or SEQ ID NO: 11 is produced.

30. The method of claim 8, wherein the second or third amino acid residue from the amino-terminal of the amino acid sequence of the peptide-type compound is a modified amino acid selected from
(i) serine, threonine, tyrosine or oxyproline, in which the side-chain hydroxy group is converted into a group represented by —OCO—$Z_1$, —OCS—$Z_1$ or —O—$Z_3$, or
(ii) cysteine in which the side-chain mercapto group is converted into —SCO—$Z_1$, —SCS—$Z_1$, —S—$Z_3$ or —S—S—$Z_8$, or
(iii) lysine or arginine, in which the side-chain amino group is converted into —NH—CO—$Z_2$, —NH—CS—$Z_2$, —N($Z_5$)($Z_6$), —NH—CO—NH—$Z_7$ or —NH—CS—NH—$Z_7$, or
(iv) histidine or tryptophan, in which the side-chain amino group is converted into a group represented by the formula:

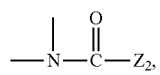

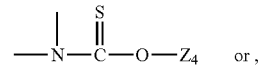

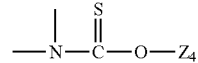

wherein $Z_1$ is hydrogen or a saturated or unsaturated alkyl chain containing 1 to 50 carbon atoms, $Z_2$, $Z_3$, $Z_4$, $Z_5$, $Z_6$, $Z_7$ and $Z_8$ are the same or different and represent hydrogen or a saturated or unsaturated alkyl chain containing 1 to 10 carbon atoms, wherein said peptide-type compound or pharmaceutically acceptable salt thereof increases intracellular calcium ion concentration, is produced.

31. The method of claim 30, wherein the second or third amino acid residue from the N-terminal of the amino acid sequence is serine and the serine residue is modified at the side-chain hydroxyl group wherein the peptide-type compound increases intracellular calcium ion concentration.

32. The method of claim 30, wherein the modified amino acid is serine in which the side-chain hydroxy group is converted into a group represented by —OCO—Z1 wherein Z1 is hydrogen or a saturated or unsaturated alkyl chain containing 1 to 50 carbon atoms.

33. The method of claim 30, wherein the modified amino acid residue is one in which a fatty acid is bound to the side-chain hydroxy group via an ester bond.

34. The method of claim 30, wherein the fatty acid contains 2 to 35 carbon atoms.

35. The method of claim 34, wherein the fatty acid is selected from fatty acids containing 2, 4, 6, 8, 10, 12, 14, 16 or 18 carbon atoms.

36. The method of claim 35, wherein the fatty acid is selected from octanoic acid, a monoene fatty acid thereof and a polyene fatty acid thereof.

37. The method of claim 35, wherein the fatty acid is selected from decanoic acid, a monoene fatty acid thereof and a polyene fatty acid thereof.

38. The method of claim 30, in which the side chain hydroxy group of serine at the third position from the amino-terminal in said amino acid sequence is acylated with an acyl group containing 2 to 35 carbon atoms.

39. The method of claim 30, in which the serine at the third position from the amino-terminal in said amino acid sequence is converted into threonine, and in which the side-chain hydroxy group of threonine at the third position from the amino-terminal is acylated with an acyl group containing 2 to 35 carbon atoms.

40. The method of claim 30, in which the side-chain hydroxy group of serine at the third position from the amino-terminal is acylated with octanoyl.

41. The method of claim 30, wherein the compound has additionally an activity of inducing secretion of growth hormone.

42. The method of claim 30, which comprises a basic amino acid bound to the carboxyl-terminal.

43. The method of claim 30, wherein the amino-terminal is modified with a saturated or unsaturated alkyl group or an acyl group containing one or more carbon atoms, and/or the hydroxy group in the carboxyl group at the carboxyl-terminal of said amino acid sequence is OZ or is replaced by $NR_2R_3$ wherein Z is a pharmaceutically acceptable cation or a lower branched or linear alkyl group, and $R_2$ and $R_3$ are the same or different and represent hydrogen or a lower branched or linear alkyl group.

44. The method of claim 43, wherein the carboxyl-terminal of said amino acid sequence is an amide derivative with a substituted basic amino acid.

45. The method of claim 30, wherein the peptide-type compound or a pharmaceutically acceptable salt thereof which consists of an amino acid sequence of SEQ ID NO: 3 or SEQ ID NO: 11 is produced.

46. The method of claim 8, wherein the peptide-type compound or a pharmaceutically acceptable salt thereof which comprises the amino acid sequence of SEQ ID NO: 3, in which the side-chain hydroxy group of the serine at the third position from the amino-terminal is acylated with n-octanoyl, and said peptide-type compound increases intracellular calcium ion concentration is produced.

47. A method for producing a peptide-type compound which comprises culturing the transformed cell of claim 6 in a liquid medium including one or more selected from the group consisting of a carbon source, a nitrogen source, vitamins, growth promoters and serum, and recovering the peptide-type compound from the culture,
    wherein the recovery step includes separating the peptide-type compound from the culture and purifying the peptide-type compound, and
    chemically modifying an amino acid of the recovered peptide-type compound by acylating the amino acid at the third position of the peptide.

48. A method for producing a peptide-type compound comprising (a) the amino acid sequence set forth in SEQ ID NO: 2 or (b) an amino acid sequence having any one of amino acid sequences selected from the group consisting of
    (1) amino acid sequence of amino acids 1 to 4,
    (2) amino acid sequence of amino acids 1 to 5,
    (3) amino acid sequence of amino acids 1 to 6,
    (4) amino acid sequence of amino acids 1 to 7,
    (5) amino acid sequence of amino acids 1 to 8,
    (6) amino acid sequence of amino acids 1 to 9, and
    (7) amino acid sequence of amino acids 1 to 10
    from the amino-terminal of the amino acid sequence set forth in SEQ ID NO: 2 wherein at least one amino acid is deleted, replaced and/or added in a part outside said amino acid sequences (1) to (7), or a pharmaceutically acceptable salt thereof by genetic recombination technology,
    which comprises transforming the vector of claim 3 into a host cell, wherein the host cell is capable of acylating a side chain of one or more amino acid(s) in said peptide, then culturing the resulting transformed cell in a liquid medium including one or more selected from the group consisting of a carbon source, a nitrogen source, vitamins, growth promoters and serum, and recovering the desired peptide-type compound from the culture wherein the recovery step includes separating the peptide-type compound from the culture and purifying the peptide-type compound.

49. The method of claim 48, wherein the recovered peptide-type compound is further modified in at least one amino acid in positions 1 to 5 from the amino acid terminal as an acylated amino acid in which:
    (a) a saturated or unsaturated alkyl chain containing 1 to 35 carbon atoms is introduced at the α carbon atom of the amino acid by an ester, ether, thioester, thioether, amide, carbamide, thiocarbamide or disulfide linkage;
    (b) a saturated or unsaturated alkyl chain containing 1 to 35 carbon atoms is introduced at the α carbon atom of the amino acid by an alkylene group containing 1 to 10 carbon atoms and by an ester, ether, thioester, thioether, amide, carbamide, thiocarbamide or disulfide, linkage; or
    (c) a saturated or unsaturated alkyl chain containing 1 to 35 carbon atoms is introduced at the α carbon atom of the amino acid.

50. The method of claim 49, wherein the amino acid sequence comprises one amino acid sequence selected from the group consisting of amino acid sequences set forth in SEQ ID NOs: 1, 3, 8, 9, 10, 11, 16, 17, 22, 25, 26, 27, 28, 29, 30 and 31.

51. The method of claim 48, wherein the amino acid sequence comprises one amino acid sequence selected from the group consisting of amino acid sequences set forth in SEQ ID NOs: 1, 3, 8, 9, 10, 11, 16, 17, 22, 25, 26, 27, 28, 29, 30 and 31.

52. A method for producing a peptide-type compound comprising (a) the amino acid sequence set forth in SEQ ID NO: 2 or (b) an amino acid sequence having any one of amino acid sequences selected from the group consisting of
    (1) amino acid sequence of amino acids 1 to 4,
    (2) amino acid sequence of amino acids 1 to 5,
    (3) amino acid sequence of amino acids 1 to 6,
    (4) amino acid sequence of amino acids 1 to 7,
    (5) amino acid sequence of amino acids 1 to 8,
    (6) amino acid sequence of amino acids 1 to 9, and
    (7) amino acid sequence of amino acids 1 to 10
    from the amino-terminal of the amino acid sequence set forth in SEQ ID NO: 2 wherein at least one amino acid is deleted, replaced and/or added in a part outside said amino acid sequences (1) to (7), or a pharmaceutically acceptable salt thereof by genetic recombination technology,
    which comprises transforming the vector of claim 4 into a host cell, wherein the host cell is capable of acylating a side chain of one or more amino acid(s) in said peptide, then culturing the resulting transformed cell in a liquid medium including one or more selected from the group consisting of a carbon source, a nitrogen source, vitamins, growth promoters and serum, and recovering the desired peptide-type compound from the culture wherein the recovery step includes separating the peptide-type compound from the culture and purifying the peptide-type compound.

53. The method of claim 52, wherein the recovered peptide-type compound is further modified in at least one amino acid in positions 1 to 5 from the amino acid terminal as an acylated amino acid in which:
    (a) a saturated or unsaturated alkyl chain containing 1 to 35 carbon atoms is introduced at the α carbon atom of the amino acid by an ester, ether, thioester, thioether, amide, carbamide, thiocarbamide or disulfide linkage;

(b) a saturated or unsaturated alkyl chain containing 1 to 35 carbon atoms is introduced at the α carbon atom of the amino acid by an alkylene group containing 1 to 10 carbon atoms and by an ester, ether, thioester, thioether, amide, carbamide, thiocarbamide or disulfide, linkage; or
(c) a saturated or unsaturated alkyl chain containing 1 to 35 carbon atoms is introduced at the α carbon atom of the amino acid.

54. The method of claim 53, wherein the amino acid sequence comprises one amino acid sequence selected from the group consisting of amino acid sequences set forth in SEQ ID NOs: 1, 3, 8, 9, 10, 11, 16, 17, 22, 26, 28, 29, and 30.

55. The method of claim 52, wherein the amino acid sequence comprises one amino acid sequence selected from the group consisting of amino acid sequences set forth in SEQ ID NOs: 1, 3, 8, 9, 10, 11, 16, 17, 22, 26, 28, 29, and 30.

56. A method for producing a peptide-type compound which comprises culturing the transformed cell of claim 7 in a liquid medium including one or more selected from the group consisting of a carbon source, a nitrogen source, vitamins, growth promoters and serum, and recovering the peptide-type compound from the culture,
wherein the transformed cell is capable of cutting a suitable site in a precursor polypeptide of said peptide and acylating the serine residue at the third position in said peptide, and
wherein the recovery step includes separating the peptide-type compound from the culture and purifying the peptide-type compound.

57. A method for producing a peptide-type compound which comprises culturing the transformed cell of claim 7 in a liquid medium including one or more selected from the group consisting of a carbon source, a nitrogen source, vitamins, growth promoters and serum, and recovering the peptide-type compound from the culture,
wherein the recovery step includes separating the peptide-type compound from the culture and purifying the peptide-type compound, and chemically modifying an amino acid of the recovered peptide-type compound by acylating the amino acid at the third position of the peptide.

* * * * *

SEQUENCE LISTING

<160> NUMBER OF SEQ ID NOS: 43

<210> SEQ ID NO 1
<211> LENGTH: 7
<212> TYPE: PRT
<213> ORGANISM: Artificial Sequence
<220> FEATURE:
<223> OTHER INFORMATION: Amino acid sequence for a core region of
      endogenous peptides of growth hormone secretagogue

<400> SEQUENCE: 1

Gly Ser Ser Phe Leu Ser Pro
1               5

<210> SEQ ID NO 2
<211> LENGTH: 28
<212> TYPE: PRT
<213> ORGANISM: Rattus norvegicus
<220> FEATURE:
<223> OTHER INFORMATION: Amino acid sequence for rat endogenous
      peptides of growth hormone secretagogue

<400> SEQUENCE: 2

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 3
<211> LENGTH: 28
<212> TYPE: PRT
<213> ORGANISM: Homo sapiens
<220> FEATURE:
<223> OTHER INFORMATION: Amino acid sequence for human endogenous
      peptides of growth hormone secretagogue

<400> SEQUENCE: 3

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 117
<212> TYPE: PRT
<213> ORGANISM: Rattus norvegicus
<220> FEATURE:
<223> OTHER INFORMATION: Amino acid sequence for a prepro-form of rat
      endogenous peptides of growth hormone secretagogue

<400> SEQUENCE: 4

Met Val Ser Ser Ala Thr Ile Cys Ser Leu Leu Leu Leu Ser Met Leu
1               5                   10                  15

Trp Met Asp Met Ala Met Ala Gly Ser Ser Phe Leu Ser Pro Glu His
            20                  25                  30

Gln Lys Ala Gln Gln Arg Lys Glu Ser Lys Lys Pro Pro Ala Lys Leu
        35                  40                  45

Gln Pro Arg Ala Leu Glu Gly Trp Leu His Pro Glu Asp Arg Gly Gln
    50                  55                  60

Ala Glu Glu Ala Glu Glu Leu Glu Ile Arg Phe Asn Ala Pro Phe
65                  70                  75                  80

Asp Val Gly Ile Lys Leu Ser Gly Ala Gln Tyr Gln Gln His Gly Arg
                85                  90                  95

```
Ala Leu Gly Lys Phe Leu Gln Asp Ile Leu Trp Glu Glu Val Lys Glu
            100                 105                 110

Ala Pro Ala Asn Lys
        115

<210> SEQ ID NO 5
<211> LENGTH: 117
<212> TYPE: PRT
<213> ORGANISM: Homo sapiens
<220> FEATURE:
<223> OTHER INFORMATION: Amino acid sequence for prepro-form of human
      endogenous peptides of growth hormone secretagogue

<400> SEQUENCE: 5

Met Pro Ser Pro Gly Thr Val Cys Ser Leu Leu Leu Leu Gly Met Leu
 1               5                  10                  15

Trp Leu Asp Leu Ala Met Ala Gly Ser Ser Phe Leu Ser Pro Glu His
             20                  25                  30

Gln Arg Val Gln Gln Arg Lys Glu Ser Lys Lys Pro Pro Ala Lys Leu
         35                  40                  45

Gln Pro Arg Ala Leu Ala Gly Trp Leu Arg Pro Glu Asp Gly Gly Gln
 50                  55                  60

Ala Glu Gly Ala Glu Asp Glu Leu Glu Val Arg Phe Asn Ala Pro Phe
 65                  70                  75                  80

Asp Val Gly Ile Lys Leu Ser Gly Val Gln Tyr Gln Gln His Ser Gln
             85                  90                  95

Ala Leu Gly Lys Phe Leu Gln Asp Ile Leu Trp Glu Glu Ala Lys Glu
            100                 105                 110

Ala Pro Ala Asp Lys
        115

<210> SEQ ID NO 6
<211> LENGTH: 501
<212> TYPE: DNA
<213> ORGANISM: Rattus norvegicus
<220> FEATURE:
<221> NAME/KEY: CDS
<222> LOCATION: (31)...(381)
<223> OTHER INFORMATION: Base sequence of cDNA coding prepro-form of
      rat endogenous peptides of growth hormone secretagogue

<400> SEQUENCE: 6
tccagatcat ctgtcctcac caccaaggcc atg gtg tct tca gcg act              48
                                 Met Val Ser Ser Ala Thr
                                  1               5 atc tgc agt ttg cta ctc ctc agc atg ctc tgg atg gac atg gcc atg      96
Ile Cys Ser Leu Leu Leu Leu Ser Met Leu Trp Met Asp Met Ala Met
                10                  15                  20 gca ggt tcc agc ttc ttg agc cca gag cac cag aaa gcc cag cag aga     144
Ala Gly Ser Ser Phe Leu Ser Pro Glu His Gln Lys Ala Gln Gln Arg
             25                  30                  35 aag gaa tcc aag aag cca cca gct aaa ctg cag cca cga gct ctg gaa     192
Lys Glu Ser Lys Lys Pro Pro Ala Lys Leu Gln Pro Arg Ala Leu Glu
         40                  45                  50 ggc tgg ctc cac cca gag gac aga gga caa gca gaa gag gca gag gag     240
Gly Trp Leu His Pro Glu Asp Arg Gly Gln Ala Glu Glu Ala Glu Glu
 55                  60                  65                  70 gag ctg gaa atc agg ttc aat gct ccc ttc gat gtt ggc atc aag ctg     288
Glu Leu Glu Ile Arg Phe Asn Ala Pro Phe Asp Val Gly Ile Lys Leu
             75                  80                  85 tca gga gct cag tac cag cag cat ggc cgg gcc ctg gga aag ttt ctt     336
Ser Gly Ala Gln Tyr Gln Gln His Gly Arg Ala Leu Gly Lys Phe Leu
```

```
Ser Gly Ala Gln Tyr Gln Gln His Gly Arg Ala Leu Gly Lys Phe Leu
             90                  95                 100 cag gat atc ctc tgg gaa gag gtc aaa gag gcg cca gct aac aag          381
Gln Asp Ile Leu Trp Glu Glu Val Lys Glu Ala Pro Ala Asn Lys
         105                 110                 115 taaccactga caggactggt ccctgtactt tcctcctaag caagaactca catccagctt    441
ctgcctcctc tgcaactccc agcactctcc tgctgactta caaataaatg ttcaagctgt    501

<210> SEQ ID NO 7
<211> LENGTH: 511
<212> TYPE: DNA
<213> ORGANISM: Homo sapiens
<220> FEATURE:
<221> NAME/KEY: CDS
<222> LOCATION: (34)...(384)
<223> OTHER INFORMATION: Base sequence of cDNA coding prepro-form of
      human endogenous peptides of growth hormone secretagogue

<400> SEQUENCE: 7
gcaggcccac ctgtctgcaa cccagctgag gcc atg ccc tcc cca                 45
                                    Met Pro Ser Pro
                                     1 ggg acc gtc tgc agc ctc ctg ctc ctc ggc atg ctc tgg ctg gac ttg      93
Gly Thr Val Cys Ser Leu Leu Leu Leu Gly Met Leu Trp Leu Asp Leu
  5                  10                  15                  20 gcc atg gca ggc tcc agc ttc ctg agc cct gaa cac cag aga gtc cag     141
Ala Met Ala Gly Ser Ser Phe Leu Ser Pro Glu His Gln Arg Val Gln
                 25                  30                  35 cag aga aag gag tcg aag aag cca cca gcc aag ctg cag ccc cga gct     189
Gln Arg Lys Glu Ser Lys Lys Pro Pro Ala Lys Leu Gln Pro Arg Ala
         40                  45                  50 cta gca ggc tgg ctc cgc ccg gaa gat gga ggt caa gca gaa ggg gca     237
Leu Ala Gly Trp Leu Arg Pro Glu Asp Gly Gly Gln Ala Glu Gly Ala
         55                  60                  65 gag gat gaa ctg gaa gtc cgg ttc aac gcc ccc ttt gat gtt gga atc     285
Glu Asp Glu Leu Glu Val Arg Phe Asn Ala Pro Phe Asp Val Gly Ile
 70                  75                  80 aag ctg tca ggg gtt cag tac cag cag cac agc cag gcc ctg ggg aag     333
Lys Leu Ser Gly Val Gln Tyr Gln Gln His Ser Gln Ala Leu Gly Lys
 85                  90                  95                 100 ttt ctt cag gac atc ctc tgg gaa gag gcc aaa gag gcc cca gcc gac     381
Phe Leu Gln Asp Ile Leu Trp Glu Glu Ala Lys Glu Ala Pro Ala Asp
                 105                 110                 115 aag                                                                 434
Lys
tgatcgccca caagccttac tcacctctct ctaagtttag aagcgctcat ctggctttc gcttgcttct gcagcaactc ccacgactgt tgtacaagct caggaggcga    494
ataaatgttc aaactgt                                                  511

<210> SEQ ID NO 8
<211> LENGTH: 4
<212> TYPE: PRT
<213> ORGANISM: Artificial Sequence
<220> FEATURE:
<223> OTHER INFORMATION: Amino acid sequence for a core region of
      endogenous peptides of growth hormone secretagogue

<400> SEQUENCE: 8

Gly Ser Ser Phe
  1

<210> SEQ ID NO 9
```

```
<211> LENGTH: 10
<212> TYPE: PRT
<213> ORGANISM: Artificial Sequence
<220> FEATURE:
<223> OTHER INFORMATION: Amino acid sequence for a core region of
      endogenous peptides of growth hormone secretagogue

<400> SEQUENCE: 9

Gly Ser Ser Phe Leu Ser Pro Glu His Gln
1               5                   10

<210> SEQ ID NO 10
<211> LENGTH: 27
<212> TYPE: PRT
<213> ORGANISM: Rattus norvegicus
<220> FEATURE:
<223> OTHER INFORMATION: Amino acid sequence for rat endogenous peptides
      (27 amino acids) of growth hormone secretagogue

<400> SEQUENCE: 10

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 11
<211> LENGTH: 27
<212> TYPE: PRT
<213> ORGANISM: Homo sapiens
<220> FEATURE:
<223> OTHER INFORMATION: Amino acid sequence for human endogenous
      peptides (27 amino acids) of growth hormone secretagogue

<400> SEQUENCE: 11

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 12
<211> LENGTH: 116
<212> TYPE: PRT
<213> ORGANISM: Rattus norvegicus
<220> FEATURE:
<223> OTHER INFORMATION: Amino acid sequence for a prepro-form of rat
      endogenous peptides (27 amino acids) of growth hormone
      secretagogue

<400> SEQUENCE: 12

Met Val Ser Ser Ala Thr Ile Cys Ser Leu Leu Leu Leu Ser Met Leu
1               5                   10                  15

Trp Met Asp Met Ala Met Ala Gly Ser Ser Phe Leu Ser Pro Glu His
            20                  25                  30

Gln Lys Ala Gln Arg Lys Glu Ser Lys Lys Pro Pro Ala Lys Leu Gln
        35                  40                  45

Pro Arg Ala Leu Glu Gly Trp Leu His Pro Glu Asp Arg Gly Gln Ala
    50                  55                  60

Glu Glu Ala Glu Glu Glu Leu Glu Ile Arg Phe Asn Ala Pro Phe Asp
65                  70                  75                  80

Val Gly Ile Lys Leu Ser Gly Ala Gln Tyr Gln Gln His Gly Arg Ala
                85                  90                  95

Leu Gly Lys Phe Leu Gln Asp Ile Leu Trp Glu Glu Val Lys Glu Ala
            100                 105                 110
```

```
Pro Ala Asn Lys
        115

<210> SEQ ID NO 13
<211> LENGTH: 116
<212> TYPE: PRT
<213> ORGANISM: Homo sapiens
<220> FEATURE:
<223> OTHER INFORMATION: Amino acid sequence for prepro-form of human
      endogenous peptides (27 amino acids) of growth hormone
      secretagogue

<400> SEQUENCE: 13

Met Pro Ser Pro Gly Thr Val Cys Ser Leu Leu Leu Leu Gly Met Leu
  1               5                  10                  15

Trp Leu Asp Leu Ala Met Ala Gly Ser Ser Phe Leu Ser Pro Glu His
             20                  25                  30

Gln Arg Val Gln Arg Lys Glu Ser Lys Lys Pro Pro Ala Lys Leu Gln
         35                  40                  45

Pro Arg Ala Leu Ala Gly Trp Leu Arg Pro Glu Asp Gly Gly Gln Ala
     50                  55                  60

Glu Gly Ala Glu Asp Glu Leu Glu Val Arg Phe Asn Ala Pro Phe Asp
 65                  70                  75                  80

Val Gly Ile Lys Leu Ser Gly Val Gln Tyr Gln Gln His Ser Gln Ala
                 85                  90                  95

Leu Gly Lys Phe Leu Gln Asp Ile Leu Trp Glu Ala Lys Glu Ala
            100                 105                 110

Pro Ala Asp Lys
        115

<210> SEQ ID NO 14
<211> LENGTH: 498
<212> TYPE: DNA
<213> ORGANISM: Rattus norvegicus
<220> FEATURE:
<221> NAME/KEY: CDS
<222> LOCATION: (31)...(375)
<223> OTHER INFORMATION: Base sequence of cDNA coding prepro-form of rat
      endogenous peptides (27 amino acids) of growth hormone
      secretagogue

<400> SEQUENCE: 14
tccagatcat ctgtcctcac caccaaggcc atg gtg tct tca gcg act              48
                                 Met Val Ser Ser Ala Thr
                                  1               5 atc tgc agt ttg cta ctc ctc agc atg ctc tgg atg gac atg gcc atg      96
Ile Cys Ser Leu Leu Leu Leu Ser Met Leu Trp Met Asp Met Ala Met
             10                  15                  20 gca ggt tcc agc ttc ttg agc cca gag cac cag aaa gcc cag aga aag     144
Ala Gly Ser Ser Phe Leu Ser Pro Glu His Gln Lys Ala Gln Arg Lys
         25                  30                  35 gaa tcc aag aag cca cca gct aaa ctg cag cca cga gct ctg gaa ggc     192
Glu Ser Lys Lys Pro Pro Ala Lys Leu Gln Pro Arg Ala Leu Glu Gly
     40                  45                  50 tgg ctc cac cca gag gac aga gga caa gca gaa gag gca gag gag gag     240
Trp Leu His Pro Glu Asp Arg Gly Gln Ala Glu Glu Ala Glu Glu Glu
 55                  60                  65                  70 ctg gaa atc agg ttc aat gct ccc ttc gat gtt ggc atc aag ctg tca     288
Leu Glu Ile Arg Phe Asn Ala Pro Phe Asp Val Gly Ile Lys Leu Ser
                 75                  80                  85 gga gct cag tac cag cag cat ggc cgg gcc ctg gga aag ttt ctt cag     336
Gly Ala Gln Tyr Gln Gln His Gly Arg Ala Leu Gly Lys Phe Leu Gln
```

```
                  90                  95                 100
gat atc ctc tgg gaa gag gtc aaa gag gcg cca gct aac aag           378
Asp Ile Leu Trp Glu Glu Val Lys Glu Ala Pro Ala Asn Lys
        105                 110                 115 taaccactga caggactggt ccctgtactt tcctcctaag caagaactca catccagctt  438
ctgcctcctc tgcaactccc agcactctcc tgctgactta caaataaatg ttcaagctgt  498
```

<210> SEQ ID NO 15
<211> LENGTH: 508
<212> TYPE: DNA
<213> ORGANISM: Homo sapiens
<220> FEATURE:
<221> NAME/KEY: CDS
<222> LOCATION: (34)...(378)
<223> OTHER INFORMATION: Base sequence of cDNA coding prepro-form of
      human endogenous peptides (27 amino acids) of growth hormone
      secretagogue

<400> SEQUENCE: 15

```
gcaggcccac ctgtctgcaa cccagctgag gcc atg ccc tcc cca                45
                                    Met Pro Ser Pro
                                     1 ggg acc gtc tgc agc ctc ctg ctc ctc ggc atg ctc tgg ctg gac ttg    93
Gly Thr Val Cys Ser Leu Leu Leu Leu Gly Met Leu Trp Leu Asp Leu
  5                  10                  15                  20 gcc atg gca ggc tcc agc ttc ctg agc cct gaa cac cag aga gtc cag   141
Ala Met Ala Gly Ser Ser Phe Leu Ser Pro Glu His Gln Arg Val Gln
                 25                  30                  35 aga aag gag tcg aag aag cca cca gcc aag ctg cag ccc cga gct cta   189
Arg Lys Glu Ser Lys Lys Pro Pro Ala Lys Leu Gln Pro Arg Ala Leu
             40                  45                  50 gca ggc tgg ctc cgc ccg gaa gat gga ggt caa gca gaa ggg gca gag   237
Ala Gly Trp Leu Arg Pro Glu Asp Gly Gly Gln Ala Glu Gly Ala Glu
         55                  60                  65 gat gaa ctg gaa gtc cgg ttc aac gcc ccc ttt gat gtt gga atc aag   285
Asp Glu Leu Glu Val Arg Phe Asn Ala Pro Phe Asp Val Gly Ile Lys
     70                  75                  80 ctg tca ggg gtt cag tac cag cag cac agc cag gcc ctg ggg aag ttt   333
Leu Ser Gly Val Gln Tyr Gln Gln His Ser Gln Ala Leu Gly Lys Phe
 85                  90                  95                 100 ctt cag gac atc ctc tgg gaa gag gcc aaa gag gcc cca gcc gac aag   381
Leu Gln Asp Ile Leu Trp Glu Glu Ala Lys Glu Ala Pro Ala Asp Lys
                105                 110                 115 tgatcgccca caagccttac tcacctctct ctaagtttag aagcgctcat ctggcttttc  441
gcttgcttct gcagcaactc ccacgactgt tgtacaagct caggaggcga ataaatgttc  501
aaactgt                                                           508
```

<210> SEQ ID NO 16
<211> LENGTH: 28
<212> TYPE: PRT
<213> ORGANISM: Sus scrofa (pig)
<220> FEATURE:
<223> OTHER INFORMATION: Amino acid sequence for porcine endogenous
      peptides of growth hormone secretagogue

<400> SEQUENCE: 16

```
Gly Ser Ser Phe Leu Ser Pro Glu His Gln Lys Val Gln Gln Arg Lys
 1               5                  10                  15

Glu Ser Lys Lys Pro Ala Ala Lys Leu Lys Pro Arg
            20                  25
```

<210> SEQ ID NO 17
<211> LENGTH: 27
<212> TYPE: PRT
<213> ORGANISM: Sus scrofa (pig)
<220> FEATURE:
<223> OTHER INFORMATION: Amino acid sequence for porcine endogenous
      peptides (27 amino acids) of growth hormone secretagogue

<400> SEQUENCE: 17

Gly Ser Ser Phe Leu Ser Pro Glu His Gln Lys Val Gln Arg Lys Glu
 1               5                  10                  15

Ser Lys Lys Pro Ala Ala Lys Leu Lys Pro Arg
            20                  25

<210> SEQ ID NO 18
<211> LENGTH: 118
<212> TYPE: PRT
<213> ORGANISM: Sus scrofa (pig)
<220> FEATURE:
<223> OTHER INFORMATION: Amino acid sequence for prepro-form of porcine
      endogenous peptides of growth hormone secretagogue

<400> SEQUENCE: 18

Met Pro Ser Thr Gly Thr Ile Cys Ser Leu Leu Leu Leu Ser Val Leu
 1               5                  10                  15

Leu Met Ala Asp Leu Ala Met Ala Gly Ser Ser Phe Leu Ser Pro Glu
            20                  25                  30

His Gln Lys Val Gln Gln Arg Lys Glu Ser Lys Lys Pro Ala Ala Lys
        35                  40                  45

Leu Lys Pro Arg Ala Leu Glu Gly Trp Leu Gly Pro Glu Asp Ser Gly
    50                  55                  60

Glu Val Glu Gly Thr Glu Asp Lys Leu Glu Ile Arg Phe Asn Ala Pro
65                  70                  75                  80

Cys Asp Val Gly Ile Lys Leu Ser Gly Ala Gln Ser Asp Gln His Gly
                85                  90                  95

Gln Pro Leu Gly Lys Phe Leu Gln Asp Ile Leu Trp Glu Glu Val Thr
            100                 105                 110

Glu Ala Pro Ala Asp Lys
        115

<210> SEQ ID NO 19
<211> LENGTH: 117
<212> TYPE: PRT
<213> ORGANISM: Sus scrofa (pig)
<220> FEATURE:
<223> OTHER INFORMATION: Amino acid sequence for prepro-form of porcine
      endogenous peptides (27 amino acids) of growth hormone
      secretagogue

<400> SEQUENCE: 19

Met Pro Ser Thr Gly Thr Ile Cys Ser Leu Leu Leu Leu Ser Val Leu
 1               5                  10                  15

Leu Met Ala Asp Leu Ala Met Ala Gly Ser Ser Phe Leu Ser Pro Glu
            20                  25                  30

His Gln Lys Val Gln Arg Lys Glu Ser Lys Lys Pro Ala Ala Lys Leu
        35                  40                  45

Lys Pro Arg Ala Leu Glu Gly Trp Leu Gly Pro Glu Asp Ser Gly Glu
    50                  55                  60

Val Glu Gly Thr Glu Asp Lys Leu Glu Ile Arg Phe Asn Ala Pro Cys
65                  70                  75                  80

Asp Val Gly Ile Lys Leu Ser Gly Ala Gln Ser Asp Gln His Gly Gln
                85                  90                  95

Pro Leu Gly Lys Phe Leu Gln Asp Ile Leu Trp Glu Val Thr Glu
            100                 105                 110

Ala Pro Ala Asp Lys
        115

<210> SEQ ID NO 20
<211> LENGTH: 494
<212> TYPE: DNA
<213> ORGANISM: Sus scrofa (pig)
<220> FEATURE:
<221> NAME/KEY: CDS
<222> LOCATION: (9)...(362)
<223> OTHER INFORMATION: Base sequence of cDNA coding prepro-form of
      porcine endogenous peptides of growth hormone secretagogue

<400> SEQUENCE: 20

```
ctgaggcc atg ccc tcc acg ggg acc att tgc agc ctg ctg ctc ctc          47
         Met Pro Ser Thr Gly Thr Ile Cys Ser Leu Leu Leu Leu
          1               5                  10 agc gtg ctc ctc atg gca gac ttg gcc atg gcg ggc tcc agc ttc ttg       95
Ser Val Leu Leu Met Ala Asp Leu Ala Met Ala Gly Ser Ser Phe Leu
    15                  20                  25 agc ccc gaa cac cag aaa gtg cag cag aga aag gag tcc aag aag cca      143
Ser Pro Glu His Gln Lys Val Gln Gln Arg Lys Glu Ser Lys Lys Pro
30                  35                  40                  45 gca gcc aaa ctg aag ccc cgg gcc ctg gaa ggc tgg ctc ggc cca gaa      191
Ala Ala Lys Leu Lys Pro Arg Ala Leu Glu Gly Trp Leu Gly Pro Glu
                50                  55                  60 gac agt ggt gag gtg gaa ggc acg gag gac aag ctg gaa atc cgg ttc      239
Asp Ser Gly Glu Val Glu Gly Thr Glu Asp Lys Leu Glu Ile Arg Phe
            65                  70                  75 aac gcc ccc tgt gat gtt ggg atc aag ttg tca ggg gct cag tcc gac      287
Asn Ala Pro Cys Asp Val Gly Ile Lys Leu Ser Gly Ala Gln Ser Asp
        80                  85                  90 cag cac ggc cag ccc ctg ggg aaa ttt ctc cag gac atc ctc tgg gaa      335
Gln His Gly Gln Pro Leu Gly Lys Phe Leu Gln Asp Ile Leu Trp Glu
    95                  100                 105 gag gtc act gag gcc ccg gcc gac aag tgattgtccc tgagaccagc            382
Glu Val Thr Glu Ala Pro Ala Asp Lys
110                 115 cacctctgtt ctcccagcct cctaagggct cacctggctt ccaggacgct tccactatca   442
cacccagctc tgagggatgc tagcctggga ggtgaataaa cattcagact gg           494
```

<210> SEQ ID NO 21
<211> LENGTH: 491
<212> TYPE: DNA
<213> ORGANISM: Sus scrofa (pig)
<220> FEATURE:
<221> NAME/KEY: CDS
<222> LOCATION: (9)...(359)
<223> OTHER INFORMATION: Base sequence of cDNA coding prepro-form of
      porcine endogenous peptides (27 amino acids) of growth hormone
      secretagogue

<400> SEQUENCE: 21

```
ctgaggcc atg ccc tcc acg ggg acc att tgc agc ctg ctg ctc ctc          47
         Met Pro Ser Thr Gly Thr Ile Cys Ser Leu Leu Leu Leu
          1               5                  10 agc gtg ctc ctc atg gca gac ttg gcc atg gcg ggc tcc agc ttc ttg       95
Ser Val Leu Leu Met Ala Asp Leu Ala Met Ala Gly Ser Ser Phe Leu
    15                  20                  25
```

```
agc ccc gaa cac cag aaa gtg cag aga aag gag tcc aag aag cca gca    143
Ser Pro Glu His Gln Lys Val Gln Arg Lys Glu Ser Lys Lys Pro Ala
 30              35                  40                  45 gcc aaa ctg aag ccc cgg gcc ctg gaa ggc tgg ctc ggc cca gaa gac    191
Ala Lys Leu Lys Pro Arg Ala Leu Glu Gly Trp Leu Gly Pro Glu Asp
                 50                  55                  60 agt ggt gag gtg gaa ggc acg gag gac aag ctg gaa atc cgg ttc aac    239
Ser Gly Glu Val Glu Gly Thr Glu Asp Lys Leu Glu Ile Arg Phe Asn
             65                  70                  75 gcc ccc tgt gat gtt ggg atc aag ttg tca ggg gct cag tcc gac cag    287
Ala Pro Cys Asp Val Gly Ile Lys Leu Ser Gly Ala Gln Ser Asp Gln
         80                  85                  90 cac ggc cag ccc ctg ggg aaa ttt ctc cag gac atc ctc tgg gaa gag    335
His Gly Gln Pro Leu Gly Lys Phe Leu Gln Asp Ile Leu Trp Glu Glu
     95                 100                 105 gtc act gag gcc ccg gcc gac aag tgattgtccc tgagaccagc               379
Val Thr Glu Ala Pro Ala Asp Lys
110             115 cacctctgtt ctcccagcct cctaagggct cacctggctt ccaggacgct tccactatca   439
cacccagctc tgagggatgc tagcctggga ggtgaataaa cattcagact gg           491

<210> SEQ ID NO 22
<211> LENGTH: 27
<212> TYPE: PRT
<213> ORGANISM: Bos taurus
<220> FEATURE:
<223> OTHER INFORMATION: Amino acid sequence for bovine endogenous
      peptides (27 amino acids) of growth hormone secretagogue

<400> SEQUENCE: 22

Gly Ser Ser Phe Leu Ser Pro Glu His Gln Glu Leu Gln Arg Lys Glu
  1               5                  10                  15

Ala Lys Lys Pro Ser Gly Arg Leu Lys Pro Arg
             20                  25

<210> SEQ ID NO 23
<211> LENGTH: 89
<212> TYPE: PRT
<213> ORGANISM: Bos taurus
<220> FEATURE:
<223> OTHER INFORMATION: Partial amino acid sequence for a prepro-form
      of bovine endogenous peptides (27 amino acids) of growth hormone
      secretagogue

<400> SEQUENCE: 23

Asp Leu Ala Met Ala Gly Ser Ser Phe Leu Ser Pro Glu His Gln Glu
  1               5                  10                  15

Leu Gln Arg Lys Glu Ala Lys Lys Pro Ser Gly Arg Leu Lys Pro Arg
             20                  25                  30

Thr Leu Glu Gly Gln Phe Asp Phe Glu Val Gly Ser Gln Ala Glu Gly
         35                  40                  45

Ala Glu Asp Glu Leu Glu Ile Arg Phe Asn Ala Phe Phe Asn Ile Gly
     50                  55                  60

Ile Lys Leu Ala Gly Ala Gln Ser Leu Gln His Gly Gln Thr Leu Gly
 65                  70                  75                  80

Lys Phe Leu Gln Asp Ile Leu Trp Glu
                 85

<210> SEQ ID NO 24
<211> LENGTH: 267
```

<212> TYPE: DNA
<213> ORGANISM: Bos taurus
<220> FEATURE:
<221> NAME/KEY: CDS
<222> LOCATION: (1)...(267)
<223> OTHER INFORMATION: Base sequence of cDNA coding prepro-form of
      bovine endogenous peptides (27 amino acids) of growth hormone
      secretagogue

<400> SEQUENCE: 24

```
gac ttg gcc atg gcg ggc tcc agc ttt ctg agc ccc gaa cat cag gaa    48
Asp Leu Ala Met Ala Gly Ser Ser Phe Leu Ser Pro Glu His Gln Glu
 1               5                  10                  15 ctg cag aga aag gaa gct aag aag cca tca ggc aga ctg aag ccc cgg    96
Leu Gln Arg Lys Glu Ala Lys Lys Pro Ser Gly Arg Leu Lys Pro Arg
             20                  25                  30 acc ctg gaa ggc cag ttt gac ccg gag gtg gga agt cag gcg gaa ggt   144
Thr Leu Glu Gly Gln Phe Asp Pro Glu Val Gly Ser Gln Ala Glu Gly
         35                  40                  45 gca gag gac gag ctg gaa atc cgg ttc aac gcc ccc ttt aac att ggg   192
Ala Glu Asp Glu Leu Glu Ile Arg Phe Asn Ala Pro Phe Asn Ile Gly
 50                  55                  60 atc aag cta gca ggg gct cag tcc ctc cag cat ggc cag acg ttg ggg   240
Ile Lys Leu Ala Gly Ala Gln Ser Leu Gln His Gly Gln Thr Leu Gly
 65                  70                  75                  80 aag ttt ctt cag gac atc ctc tgg gaa                               267
Lys Phe Leu Gln Asp Ile Leu Trp Glu
                 85
```

<210> SEQ ID NO 25
<211> LENGTH: 24
<212> TYPE: PRT
<213> ORGANISM: Gallus domesticus
<220> FEATURE:
<223> OTHER INFORMATION: Amino acid sequence for chicken endogenous
      peptides of growth hormone secretagogue

<400> SEQUENCE: 25

```
Gly Ser Ser Phe Leu Ser Pro Thr Tyr Lys Asn Ile Gln Gln Gln Lys
 1               5                  10                  15

Gly Thr Arg Lys Pro Thr Ala Arg
             20
```

<210> SEQ ID NO 26
<211> LENGTH: 21
<212> TYPE: PRT
<213> ORGANISM: Anguilla japonica
<220> FEATURE:
<221> NAME/KEY: AMIDATION
<222> LOCATION: 21
<223> OTHER INFORMATION: Amino acid sequence for eel endogenous peptides
      of growth hormone secretagogue

<400> SEQUENCE: 26

```
Gly Ser Ser Phe Leu Ser Pro Ser Gln Arg Pro Gln Gly Lys Asp Lys
 1               5                  10                  15

Lys Pro Pro Arg Val
             20
```

<210> SEQ ID NO 27
<211> LENGTH: 28
<212> TYPE: PRT
<213> ORGANISM: Rana cafesbeiana
<220> FEATURE:
<223> OTHER INFORMATION: Amino acid sequence for frog endogenous
      peptides of growth hormone secretagogue

```
<400> SEQUENCE: 27

Gly Leu Ser Phe Leu Ser Pro Ala Glu Met Gln Lys Ile Ala Glu Arg
 1               5                  10                  15

Gln Ser Gln Asn Lys Leu Arg His Gly Asn Met Arg
            20                  25

<210> SEQ ID NO 28
<211> LENGTH: 27
<212> TYPE: PRT
<213> ORGANISM: Xenopus laevis
<220> FEATURE:
<223> OTHER INFORMATION: Amino acid sequence for frog (Xenopus laevis)
      endogenous peptides of growth hormone secretagogue

<400> SEQUENCE: 28

Gly Leu Thr Phe Leu Ser Pro Ala Asp Met Gln Lys Ile Ala Glu Arg
 1               5                  10                  15

Gln Ser Gln Asn Lys Leu Arg His Gly Asn Met
            20                  25

<210> SEQ ID NO 29
<211> LENGTH: 23
<212> TYPE: PRT
<213> ORGANISM: Oncorhynchus mykiss
<220> FEATURE:
<221> NAME/KEY: AMIDATION
<222> LOCATION: 23
<223> OTHER INFORMATION: Amino acid sequence for rainbow trout
      endogenous peptides (23 amino acids) of growth hormone
      secretagogue

<400> SEQUENCE: 29

Gly Ser Ser Phe Leu Ser Pro Ser Gln Lys Pro Gln Val Arg Gln Gly
 1               5                  10                  15

Lys Gly Lys Pro Pro Arg Val
            20

<210> SEQ ID NO 30
<211> LENGTH: 20
<212> TYPE: PRT
<213> ORGANISM: Oncorhynchus mykiss
<220> FEATURE:
<221> NAME/KEY: AMIDATION
<222> LOCATION: 20
<223> OTHER INFORMATION: Amino acid sequence for rainbow trout
      endogenous peptides (20 amino acids) of growth hormone
      secretagogue

<400> SEQUENCE: 30

Gly Ser Ser Phe Leu Ser Pro Ser Gln Lys Pro Gln Gly Lys Gly Lys
 1               5                  10                  15

Pro Pro Arg Val
            20

<210> SEQ ID NO 31
<211> LENGTH: 28
<212> TYPE: PRT
<213> ORGANISM: Canis familiaris
<220> FEATURE:
<223> OTHER INFORMATION: Amino acid sequence for dog endogenous peptides
      of growth hormone secretagogue

<400> SEQUENCE: 31

Gly Ser Ser Phe Leu Ser Pro Glu His Gln Lys Leu Gln Gln Arg Lys
 1               5                  10                  15
```

Glu Ser Lys Lys Pro Pro Ala Lys Leu Gln Pro Arg
            20                  25

<210> SEQ ID NO 32
<211> LENGTH: 108
<212> TYPE: PRT
<213> ORGANISM: Anguilla japonica
<220> FEATURE:
<223> OTHER INFORMATION: Amino acid sequence for prepro-form of eel
      endogenous peptides of growth hormone secretagogue

<400> SEQUENCE: 32

Met Lys Arg Thr Ala Tyr Ile Ile Leu Leu Val Cys Val Leu Ala Leu
 1               5                  10                  15

Trp Met Asp Ser Val Gln Ala Gly Ser Ser Phe Leu Ser Pro Ser Gln
            20                  25                  30

Arg Pro Gln Gly Lys Asp Lys Lys Pro Pro Arg Val Gly Arg Arg Asp
        35                  40                  45

Ser Asp Gly Ile Leu Asp Leu Phe Met Arg Pro Pro Leu Gln Asp Glu
50                  55                  60

Asp Ile Arg His Ile Thr Phe Asn Thr Pro Phe Glu Ile Gly Ile Thr
65                  70                  75                  80

Met Thr Glu Glu Leu Phe Gln Gln Tyr Gly Glu Val Met Gln Lys Ile
                85                  90                  95

Met Gln Asp Leu Leu Met Asp Thr Pro Ala Lys Glu
            100                 105

<210> SEQ ID NO 33
<211> LENGTH: 114
<212> TYPE: PRT
<213> ORGANISM: Xenopus laevis
<220> FEATURE:
<223> OTHER INFORMATION: Amino acid sequence frog (Xenopus laevis)
      endogenous peptides of growth hormone secretagogue

<400> SEQUENCE: 33

Met Asn Phe Gly Lys Ala Ala Ile Phe Gly Val Val Leu Phe Cys Leu
 1               5                  10                  15

Leu Trp Thr Glu Gly Ala Gln Ala Gly Leu Thr Phe Leu Ser Pro Ala
            20                  25                  30

Asp Met Gln Lys Ile Ala Glu Arg Gln Ser Gln Asn Lys Leu Arg His
        35                  40                  45

Gly Asn Met Asn Arg Arg Gly Val Glu Asp Leu Ala Gly Glu Glu
50                  55                  60

Ile Gly Val Thr Phe Pro Leu Asp Met Lys Met Thr Gln Glu Gln Phe
65                  70                  75                  80

Gln Lys Gln Arg Ala Ala Val Gln Asp Phe Leu Tyr Ser Ser Leu Leu
                85                  90                  95

Ser Leu Gly Ser Val Gln Asp Thr Glu Asp Lys Asn Glu Asn Pro Gln
            100                 105                 110

Ser Gln

<210> SEQ ID NO 34
<211> LENGTH: 82
<212> TYPE: PRT
<213> ORGANISM: Oncorhynchus mykiss
<220> FEATURE:
<223> OTHER INFORMATION: Amino acid sequence for prepro-form of rainbow
      trout endogenous peptides (23 amino acids) of growth hormone
      secretagogue -continued

<400> SEQUENCE: 34

Met Ile Leu Met Leu Cys Thr Leu Ala Leu Trp Ala Lys Ser Val Ser
1               5                   10                  15

Ala Gly Ser Ser Phe Leu Ser Pro Ser Gln Lys Pro Gln Val Arg Gln
            20                  25                  30

Gly Lys Gly Lys Pro Pro Arg Val Gly Arg Arg Asp Ile Glu Ser Phe
        35                  40                  45

Ala Glu Leu Phe Glu Gly Pro Leu His Gln Glu Asp Lys His Asn Thr
    50                  55                  60

Ile Lys Ala Pro Phe Glu Met Gly Ile Thr Met Ser Glu Glu Glu Phe
65                  70                  75                  80

Gln Glu

<210> SEQ ID NO 35
<211> LENGTH: 99
<212> TYPE: PRT
<213> ORGANISM: Oncorhynchus mykiss
<220> FEATURE:
<223> OTHER INFORMATION: Amino acid sequence for prepro-form of rainbow
      trout endogenous peptides (20 amino acids) of growth hormone
      secretagogue

<400> SEQUENCE: 35

Met Ile Leu Met Leu Cys Thr Leu Ala Leu Trp Ala Lys Ser Val Ser
1               5                   10                  15

Ala Gly Ser Ser Phe Leu Ser Pro Ser Gln Lys Pro Gln Gly Lys Gly
            20                  25                  30

Lys Pro Pro Arg Val Gly Arg Arg Asp Ile Glu Ser Phe Ala Glu Leu
        35                  40                  45

Phe Glu Gly Pro Leu His Gln Glu Asp Lys His Asn Thr Ile Lys Ala
    50                  55                  60

Pro Phe Glu Met Gly Ile Thr Met Ser Glu Glu Glu Phe Gln Glu Tyr
65                  70                  75                  80

Gly Ala Val Leu Gln Lys Ile Leu Gln Asp Val Leu Gly Asp Thr Ala
                85                  90                  95

Thr Ala Glu

<210> SEQ ID NO 36
<211> LENGTH: 503
<212> TYPE: DNA
<213> ORGANISM: Anguilla japonica
<220> FEATURE:
<221> NAME/KEY: CDS
<222> LOCATION: (66)...(389)
<223> OTHER INFORMATION: Base sequence of cDNA coding prepro-form of eel
      endogenous peptides of growth hormone secretagogue

<400> SEQUENCE: 36
tccaagaggc actgggtttc ctcttaaagt gcaaaactcc actgtgagct tcagacatga    60 ggcag atg aaa cgc acc gca tac atc atc ctg ctg gtc tgc gtc ctg       107
      Met Lys Arg Thr Ala Tyr Ile Ile Leu Leu Val Cys Val Leu
      1               5                   10 gcg ctg tgg atg gac tct gtc cag gct ggc tcc agc ttc ctc agc ccc     155
Ala Leu Trp Met Asp Ser Val Gln Ala Gly Ser Ser Phe Leu Ser Pro
15                  20                  25                  30 tca cag aga ccg cag ggg aag gat aag aag cct ccc agg gtt ggc aga     203
Ser Gln Arg Pro Gln Gly Lys Asp Lys Lys Pro Pro Arg Val Gly Arg
                35                  40                  45

```
cga gac tca gat ggg atc ctg gac ctg ttt atg agg ccc cca ttg cag      251
Arg Asp Ser Asp Gly Ile Leu Asp Leu Phe Met Arg Pro Pro Leu Gln
             50                  55                  60 gat gaa gac atc aga cac att acg ttt aac act cct ttt gag atc ggg      299
Asp Glu Asp Ile Arg His Ile Thr Phe Asn Thr Pro Phe Glu Ile Gly
         65                  70                  75 atc acc atg act gag gag ctg ttc cag caa tat gga gaa gtg atg cag      347
Ile Thr Met Thr Glu Glu Leu Phe Gln Gln Tyr Gly Glu Val Met Gln
     80                  85                  90 aag atc atg cag gat ttg ctg atg gac aca cct gcc aaa gag              389
Lys Ile Met Gln Asp Leu Leu Met Asp Thr Pro Ala Lys Glu
 95              100                 105 tgacaagagt ggatatgatc tggacttcat aaaaccctgc gtcccatata ttcctgcatt    449
attgcatgca taattcaacc aattgttaaa catttaataa aattttgcaa acgc          503

<210> SEQ ID NO 37
<211> LENGTH: 484
<212> TYPE: DNA
<213> ORGANISM: Xenopus laevis
<220> FEATURE:
<221> NAME/KEY: CDS
<222> LOCATION: (47)...(388)
<223> OTHER INFORMATION: Base sequence of cDNA coding prepro-form of
      frog (Xenopus laevis) endogenous peptides of growth hormone
      secretagogue

<400> SEQUENCE: 37
tttcactttt atctcgcagg cggcaccggt gaccaggacc ttcagg                   46 atg aat ttt ggt aaa gcc gcc atc ttt ggg gtt gtc ttg ttc tgc ctg      94
Met Asn Phe Gly Lys Ala Ala Ile Phe Gly Val Val Leu Phe Cys Leu
 1               5                  10                  15 ctg tgg acg gag ggg gcc cag gct ggc ttg acc ttc ctg agt cca gcc      142
Leu Trp Thr Glu Gly Ala Gln Ala Gly Leu Thr Phe Leu Ser Pro Ala
             20                  25                  30 gac atg cag aag att gcg gag agg caa tca cag aat aag ctg aga cac      190
Asp Met Gln Lys Ile Ala Glu Arg Gln Ser Gln Asn Lys Leu Arg His
         35                  40                  45 ggc aat atg aat cgc agg ggt gtg gag gat gac ctg gcc ggg gag gag      238
Gly Asn Met Asn Arg Arg Gly Val Glu Asp Asp Leu Ala Gly Glu Glu
     50                  55                  60 atc ggg gtg acc ttc cct ctg gat atg aag atg acg cag gag cag ttc      286
Ile Gly Val Thr Phe Pro Leu Asp Met Lys Met Thr Gln Glu Gln Phe
 65                  70                  75                  80 cag aag cag agg gct gcg gtg cag gac ttc ctg tac tcc tcc ctc ctc      334
Gln Lys Gln Arg Ala Ala Val Gln Asp Phe Leu Tyr Ser Ser Leu Leu
                 85                  90                  95 tct ctc ggg tca gtg cag gat aca gaa gac aag aat gaa aat cct cag      382
Ser Leu Gly Ser Val Gln Asp Thr Glu Asp Lys Asn Glu Asn Pro Gln
             100                 105                 110 agc caa                                                              388
Ser Gln tgagaatgat gaaatccgc tcgtctctga tgccctccc cgatctgtgt                  438
gtctttatta tctctgtgta acccagaaat aaatcttatt tatggc                    484

<210> SEQ ID NO 38
<211> LENGTH: 462
<212> TYPE: DNA
<213> ORGANISM: Oncorhynchus mykiss
<220> FEATURE:
<221> NAME/KEY: CDS
<222> LOCATION: (12)...(257)
<223> OTHER INFORMATION: Base sequence of cDNA coding prepro-form of
      rainbow trout endogenous peptides (23 amino acids) of growth
      hormone secretagogue
```

<400> SEQUENCE: 38

```
tcacaggtct c atg ata ctg atg ctg tgt act ctg gct ctg tgg gcc          47
             Met Ile Leu Met Leu Cys Thr Leu Ala Leu Trp Ala
               1               5                  10 aag tca gtc agt gct ggc tcc agc ttc ctc agc ccc tcc cag aaa cca       95
Lys Ser Val Ser Ala Gly Ser Ser Phe Leu Ser Pro Ser Gln Lys Pro
             15                  20                  25 cag gta aga cag ggt aaa ggg aag ccc cct cga gtt ggt cgg cga gac      143
Gln Val Arg Gln Gly Lys Gly Lys Pro Pro Arg Val Gly Arg Arg Asp
         30                  35                  40 att gag agc ttt gct gag ctg ttt gag ggt ccc ctt cac cag gaa gac      191
Ile Glu Ser Phe Ala Glu Leu Phe Glu Gly Pro Leu His Gln Glu Asp
 45                  50                  55                  60 aaa cac aat acg atc aag gct cct ttt gag atg ggc atc acc atg agt      239
Lys His Asn Thr Ile Lys Ala Pro Phe Glu Met Gly Ile Thr Met Ser
                 65                  70                  75 gag gag gag ttc cag gag tatggtgccg tgctgcagaa gatcctgcag             287
Glu Glu Glu Phe Gln Glu
                 80 gacgtcctgg gagacactgc cactgcagaa tgatcacaac ttggcataga cacggaatac   347 aaagaacctc cattccctgt tctccaactt tcctttctca acttgtctta tacccaatgt   407 actgtgtgaa catcgtttga attgtaaaag atgaataaaa taaccgcggc cgcta        462
```

<210> SEQ ID NO 39
<211> LENGTH: 453
<212> TYPE: DNA
<213> ORGANISM: Oncorhynchus mykiss
<220> FEATURE:
<221> NAME/KEY: CDS
<222> LOCATION: (12)...(308)
<223> OTHER INFORMATION: Base sequence of cDNA coding prepro-form of rainbow trout endogenous peptides (20 amino acids) of growth hormone secretagogue

<400> SEQUENCE: 39

```
tcacaggtct c atg ata ctg atg ctg tgt act ctg gct ctg tgg gcc          47
             Met Ile Leu Met Leu Cys Thr Leu Ala Leu Trp Ala
               1               5                  10 aag tca gtc agt gct ggc tcc agc ttc ctc agc ccc tcc cag aaa cca       95
Lys Ser Val Ser Ala Gly Ser Ser Phe Leu Ser Pro Ser Gln Lys Pro
             15                  20                  25 cag ggt aaa ggg aag ccc cct cga gtt ggt cgg cga gac att gag agc     143
Gln Gly Lys Gly Lys Pro Pro Arg Val Gly Arg Arg Asp Ile Glu Ser
         30                  35                  40 ttt gct gag ctg ttt gag ggt ccc ctt cac cag gaa gac aaa cac aat     191
Phe Ala Glu Leu Phe Glu Gly Pro Leu His Gln Glu Asp Lys His Asn
 45                  50                  55                  60 acg atc aag gct cct ttt gag atg ggc atc acc atg agt gag gag gag     239
Thr Ile Lys Ala Pro Phe Glu Met Gly Ile Thr Met Ser Glu Glu Glu
                 65                  70                  75 ttc cag gag tat ggt gcc gtg ctg cag aag atc ctg cag gac gtc ctg     287
Phe Gln Glu Tyr Gly Ala Val Leu Gln Lys Ile Leu Gln Asp Val Leu
                 80                  85                  90 gga gac act gcc act gca gaa tgatcacaac ttggcataga cacggaatac       338
Gly Asp Thr Ala Thr Ala Glu
             95 aaagaacctc cattccctgt tctccaactt tcctttctca acttgtctta tacccaatgt  398 actgtgtgaa catcgtttga attgtaaaag atgaataaaa taacactgct tcctt        453
```

```
<210> SEQ ID NO 40
<211> LENGTH: 28
<212> TYPE: PRT
<213> ORGANISM: Rattus norvegicus
<220> FEATURE:
<221> NAME/KEY: Residue
<222> LOCATION: (3)
<223> OTHER INFORMATION: Xaa = Ser
<220> FEATURE:
<223> OTHER INFORMATION: Amino acid sequence of the purified ghrelin
      derived from rat was determined by a peptide
      sequencer.

<400> SEQUENCE: 40

Gly Ser Xaa Phe Leu Ser Pro Glu His Gln Lys Ala Gln Gln Arg Lys
 1               5                  10                  15

Glu Ser Lys Lys Pro Pro Ala Lys Leu Gln Pro Arg
            20                  25

<210> SEQ ID NO 41
<211> LENGTH: 21
<212> TYPE: DNA
<213> ORGANISM: Artificial Sequence
<220> FEATURE:
<223> OTHER INFORMATION: Sense primer

<400> SEQUENCE: 41
ttgagcccag agcaccagaa a                                              21

<210> SEQ ID NO 42
<211> LENGTH: 22
<212> TYPE: DNA
<213> ORGANISM: Artificial Sequence
<220> FEATURE:
<223> OTHER INFORMATION: Antisense primer

<400> SEQUENCE: 42
agttgcagag gaggcagaag ct                                             22

<210> SEQ ID NO 43
<211> LENGTH: 27
<212> TYPE: PRT
<213> ORGANISM: Rattus norvegicus
<220> FEATURE:
<221> NAME/KEY: Residue
<222> LOCATION: (3)
<223> OTHER INFORMATION: Xaa = any amino acid
<220> FEATURE:
<223> OTHER INFORMATION: Amino acid sequence wherein in rat ghrelin
      consisting of 28 amino acids, glutamine 13 or 14 was deleted.

<400> SEQUENCE: 43

Gly Ser Xaa Phe Leu Ser Pro Glu His Gln Lys Ala Gln Arg Lys Glu
 1               5                  10                  15

Ser Lys Lys Pro Pro Ala Lys Leu Gln Pro Arg
            20                  25
```